US009816105B2

(12) United States Patent
Broglie et al.

(10) Patent No.: US 9,816,105 B2
(45) Date of Patent: Nov. 14, 2017

(54) COMPOSITIONS AND METHODS FOR INSECTICIDAL CONTROL OF STINKBUGS

(71) Applicants: PIONEER HI BRED INTERNATIONAL INC, Johnston, IA (US); E I DU PONT DE NEMOURS AND COMPANY, Wilmington, DE (US)

(72) Inventors: Karen E. Broglie, Landenberg, PA (US); David Charles Cerf, Palo Alto, CA (US); Rafael Herrmann, Wilmington, DE (US); Albert L. Lu, Newark, DE (US); Brian McGonigle, Wilmington, DE (US); James Kevin Presnail, Des Moines, IA (US)

(73) Assignees: PIONEER HI-BRED INTERNATIONAL, INC., Johnston, IA (US); E. I. DU PONT DE NEMOURS AND COMPANY, Wilmington, DE (US)

( * ) Notice: Subject to any disclaimer, the term of this patent is extended or adjusted under 35 U.S.C. 154(b) by 227 days.

(21) Appl. No.: 14/525,482

(22) Filed: Oct. 28, 2014

(65) Prior Publication Data

US 2015/0052643 A1 Feb. 19, 2015

Related U.S. Application Data

(63) Continuation of application No. 13/152,795, filed on Jun. 3, 2011, now Pat. No. 8,872,001.

(60) Provisional application No. 61/351,405, filed on Jun. 4, 2010.

(51) Int. Cl.

| | |
|---|---|
| ***C12N 15/82*** | (2006.01) |
| ***A01H 5/00*** | (2006.01) |
| ***A01N 57/16*** | (2006.01) |
| ***A01N 65/00*** | (2009.01) |
| ***C12N 15/113*** | (2010.01) |
| ***A01N 65/44*** | (2009.01) |

(52) U.S. Cl.

CPC ......... *C12N 15/8286* (2013.01); *A01N 57/16* (2013.01); *A01N 65/00* (2013.01); *A01N 65/44* (2013.01); *C12N 15/113* (2013.01); *C12N 15/8218* (2013.01); *C12N 2310/14* (2013.01); *C12N 2310/531* (2013.01)

(58) Field of Classification Search

None

See application file for complete search history.

(56) References Cited

U.S. PATENT DOCUMENTS

| | | | |
|---|---|---|---|
| 7,560,542 | B2 | 7/2009 | Anderson et al. |
| 7,745,391 | B2 | 6/2010 | Mintz et al. |
| 8,067,671 | B2 | 11/2011 | Boukharov et al. |
| 8,080,413 | B2 | 12/2011 | Li |
| 8,143,476 | B2 | 3/2012 | Meyer et al. |
| 2003/0150017 | A1 | 8/2003 | Mesa et al. |
| 2005/0095199 | A1 | 5/2005 | Whyard et al. |
| 2006/0021087 | A1 | 1/2006 | Baum et al. |
| 2006/0075515 | A1 | 4/2006 | Luethy et al. |
| 2006/0200878 | A1 | 9/2006 | Lutfiyya et al. |
| 2006/0272049 | A1 | 11/2006 | Waterhouse et al. |
| 2007/0199100 | A1 | 8/2007 | Michaeli et al. |
| 2009/0188008 | A1 | 7/2009 | Lassner |
| 2009/0192116 | A1 | 7/2009 | Herrmann et al. |
| 2009/0192117 | A1 | 7/2009 | Herrmann et al. |
| 2009/0265818 | A1 | 10/2009 | Herrmann et al. |

FOREIGN PATENT DOCUMENTS

| | | | | |
|---|---|---|---|---|
| CN | 101215570 | A * | 7/2008 | ............. C12N 15/52 |
| EP | 1818405 | A3 | 3/2008 | |
| WO | 200137654 | A2 | 5/2001 | |
| WO | 2001034815 | A1 | 5/2001 | |
| WO | 2002000904 | A2 | 1/2002 | |
| WO | 2003052110 | A2 | 6/2003 | |
| WO | 2005049841 | A1 | 6/2005 | |
| WO | 2005077116 | A2 | 8/2005 | |
| WO | 2005110068 | A2 | 11/2005 | |
| WO | 2006044480 | A2 | 4/2006 | |
| WO | 2006045590 | A2 | 5/2006 | |
| WO | 2006047495 | A2 | 5/2006 | |
| WO | 2007003023 | A2 | 1/2007 | |
| WO | 2007087153 | A2 | 8/2007 | |
| WO | 2007095469 | A2 | 8/2007 | |

OTHER PUBLICATIONS

Thomas et al, 2001, Plant J., 25:417-425.*

(Continued)

*Primary Examiner* — Jason Deveau Rosen

(74) *Attorney, Agent, or Firm* — Pioneer Hi-Bred Int'l, Inc.

(57) ABSTRACT

Methods and compositions are provided which employ a silencing element that, when ingested by a pest, such as a *Pentatomidae* plant pest or a *N. viridula, Acrosternum hilare, Piezodorus guildini*, and/or *Halymorpha halys* plant pest, decrease the expression of a target sequence in the pest. In specific embodiments, the decrease in expression of the target sequence controls the pest and thereby the methods and compositions are capable of limiting damage to a plant. The present invention provides various target polynucleotides set forth in any one of SEQ ID NOS: 1-292 or 302-304 or active variants and fragments thereof, wherein a decrease in expression of one or more the sequences in the target pest controls the pest (i.e., has insecticidal activity). Further provided are silencing elements which when ingested by the pest decrease the level of the target polypeptide and thereby control the pest. In specific embodiment, the pest is *Pentatomidae*. Plants, plant part, bacteria and other host cells comprising the silencing elements or an active variant or fragment thereof of the invention are also provided.

31 Claims, 2 Drawing Sheets

(56) References Cited

OTHER PUBLICATIONS

Fourgoux-Nicol et al, 1999, Plant Molecular Biology 40 :857-872.*
Jagadeeswaran, G., et al, "Deep sequencing of small RNA libraries reveals dynamic regulation of conserved and novel microRNAs and microRNA-stars during silkworm development," BMC Genomics, 2010, vol. 11(52), pp. 1-18.
Sindhu, A., et al, "Effective and specific in planta RNAi in cyst nematodes: expression interference of four parasitism genes reduces parasitic success," Journal of Experiemental Botany, 2009, vol. 60(1), pp. 315-324.
Tomoyasu, Y., et al, "Exploring systemic RNA interference in insects: a genome-wide survey for RNAi genes in Tribolium," Genome Biology, 2008, vol. 9(1), pp. R10-R10.22.
Zhang, B., et al, "Plant microRNA: A small regulatory molecule with big impact," Developmental Biology, 2006, vol. 289, pp. 3-16.
Zhang, Y., et al, "Insect-Specific microRNA Involved in the Development of the Silkworm Bombyx mori," PLoS ONE, 2009, vol. 4(3), e4677, pp. 1-7.
Agrawal, N., et al, "siRNA-Directed Silencing of Transgene Expressed in Cultured Insect Cells", Biochemical and Biophysical Research Communications, 2004, pp. 428-434, vol. 320, No. 2, Elsevier Science Publishers Ltd., United Kingdom.
Atkinson, H.J. et al, "Engineering Plants for Nematode Resistance," Ann. Rev. Phytopathol, 2003, pp. 615-639, vol. 41.
Boutla, A. , et al, "Induction of RNA Interference in Caenorhabditis Elegans by RNAs Derived From Plants Exhibiting Post-Transcriptional Gene Silencing", Nucleic Acids Research, 2002, pp. 1688-1694, vol. 30, No. 7.
Thomas, et al, 2001, Plant J., 25:417-425.
International Search Report and Written Opinion for International Publication PCT/US2011/039042 dated Apr. 16, 2012.

* cited by examiner

Figure 1. 2nd instar SGSB feeding assays on soybean embryo tissue containing HP constructs
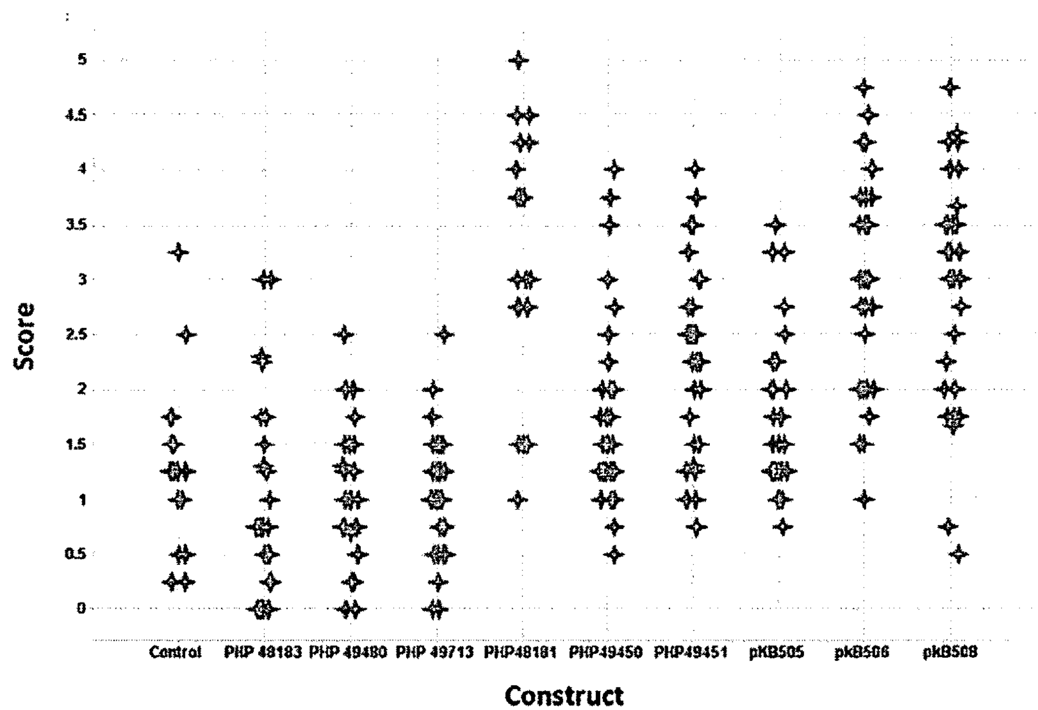

Figure 2. 2nd instar SGSB feeding assays on soybean embryo tissue containing amiRNA constructs
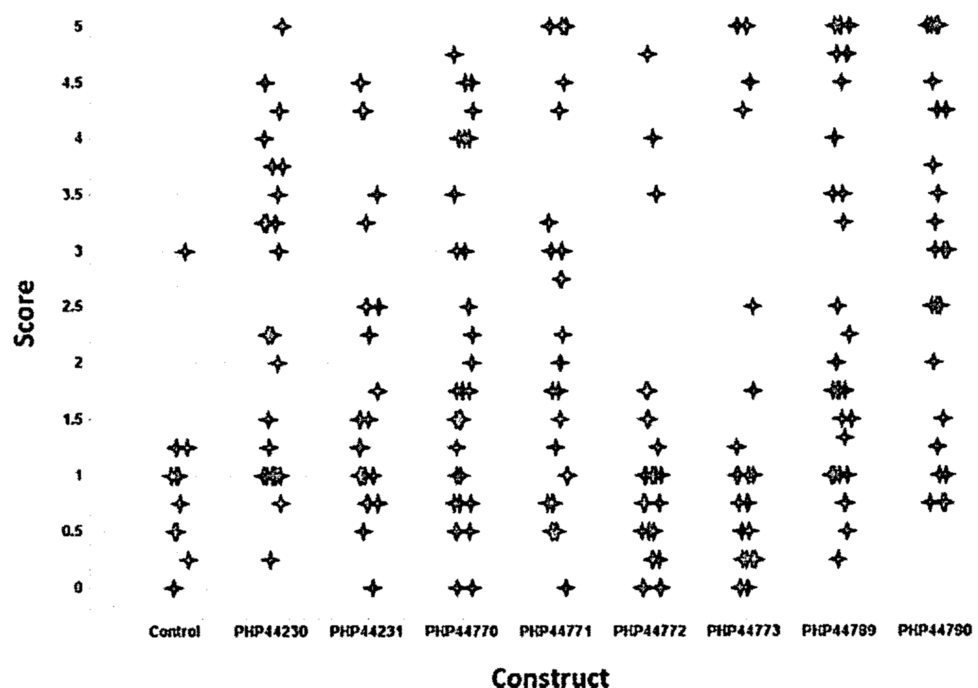

SEQUENCE LISTING

```
<160> NUMBER OF SEQ ID NOS: 346

<210> SEQ ID NO 1
<211> LENGTH: 272
<212> TYPE: DNA
<213> ORGANISM: Nezara viridula
```

<400> SEQUENCE: 1

```
gggtattaat ttttatttgt ttatccataa attagctctt ttaaaccaat tactttgatt     60

ttttcttgat agttatcatg ttagcgactt cattaacatt cactaatcag gaaagacagt    120

ttacgaaatc tgtatctaga ttgaagaaat tccgtatgat ttttaataca ttgaaaaaat    180

atggccatta atcgaattag aaaaacgttt ttctactaca acaataggcg cagactttcc    240

atttcgcttt gggagagggg aggtgaagaa cc                                  272
```

<210> SEQ ID NO 2
<211> LENGTH: 529
<212> TYPE: DNA
<213> ORGANISM: Nezara viridula
<220> FEATURE:
<221> NAME/KEY: misc_feature
<222> LOCATION: 476
<223> OTHER INFORMATION: n = A,T,C or G

<400> SEQUENCE: 2

```
gggtatcaat tatacatata aagtagcatt accttcctat ttacaaagaa aataaataca     60

agttgattca aattattgaa ctaaactatt tctttaatca ttagtaatat gctaaaaaaa    120

ttaacattac ttctgtaacg cattcaaaat ttaaaaaaac aaaagacagg atataacctt    180

tccagtagaa catataaaaa aaactagaga ccatatattt gctcctaatt ctctgatttt    240

aacgattatt tttttgtttt tcaggaaatt ccgtaaattt tgaaaaacac aaatccgtat    300

actttttgag ttattcggaa tttaattgta ccatccctcg taactttttt cctagcttct    360

tttcgttgaa gtatgttata tagataaatt tagaaggagt tgagaaattg attttagcga    420

agtttcattg aaatcggtac attcgtttag acgctacagt ctgtagcaac tcagantttt    480

tttccccgtt attttaaaag taaaaggcga ataataatgt cgatgaagc                529
```

<210> SEQ ID NO 3
<211> LENGTH: 574
<212> TYPE: DNA
<213> ORGANISM: Nezara viridula

<400> SEQUENCE: 3

```
ggggaaggag ctcaagattt accctgctct gcgagtttac tgagtggaag tttatcttct     60

tttccaagtt attcatcgac ttctagaaga tctctatcac tcaaacaagg gcgtaagtcc    120

actctatctc ccaaagacat taactcatca tcggtagatc agacggcaga agcacagtcc    180

actggaaaga gaactactca atccagtgat attgttgaaa atgttaaggc taactcattt    240

tcatcttctc gtaaaggaag acgatctctt agtataccaa atggtagttc ctttgaaaaa    300

aatcatttga tgcagtcatc agaatcaggt tccagtgatt tattgaatat taccaatgaa    360

aagcacaata gaagtgttga tacaaatcat ttctcatctc ccttaaatga cactttatct    420

aggagtaagt tcgttgattg taatattagt cagaaaggct taaatggttc atcttcagat    480

gtgtcagttt tttctctggg ttcttttaat tcttcttatc ataaaagtaa aagtgatggt    540

gatagtttat ctttatcaca agctactgat gtaa                                574
```

<210> SEQ ID NO 4
<211> LENGTH: 652
<212> TYPE: DNA
<213> ORGANISM: Nezara viridula

<400> SEQUENCE: 4

```
ggggattgga caagaggttt ctcgtttctc aatatgaaga tctttttttct cctttttgtt    60

gtggctgtca gccatgcgct tcctcacgat gaatgggaat tgtttaagat atcgcatggg   120

aagaagtaca aaacattagc agaagaacaa caccgaatga atattttcta tgacaacaag   180

cagttcatcg aaaatcataa taaaaatttt gaacaaggcc cggtctcttt cactctggaa   240

atgaaccgtt ttggagattt gatgaaccac gaattccgaa caatgatgaa cagatacaac   300

agtacaaaag cagctagaac tagacaagat tcatcaactt atatcagatc aaccgatgaa   360

gaagttcccg aatcttttga ctggaggcag gaaggagcgg tcacccctgt caaagatcaa   420

gcacactgtg gctcatgctg ggcttttagt actactggag ctcttgaagg acaacacttc   480

aggaagaccg gggaagtggt ttctctcagc gaacagaact tggtcgactg ttccagcatg   540

tacggcaaca atgggtgtca aggaggactc atggttgacg ctttcaagta cattgctgaa   600

aatggcggca tcgacactga agattcttat ccttatgaag gaagggacgg ca           652
```

<210> SEQ ID NO 5
<211> LENGTH: 75
<212> TYPE: DNA
<213> ORGANISM: Nezara viridula

<400> SEQUENCE: 5

```
gggggtgtaa taagacttcc tgaaagtccg ttttatcatt gaccttaata aatttaattt    60

aatcactgtt ttctg                                                      75
```

<210> SEQ ID NO 6
<211> LENGTH: 643
<212> TYPE: DNA
<213> ORGANISM: Nezara viridula

<400> SEQUENCE: 6

```
ggggagtctg ccagcgactt cttccccgcc atataccagc ggtacctact tgtacatagc    60

agtacataag tacataagta gaggcacctc ttgatgtaca gacactccat tcctagcaca   120

gaaagaagac ctcatcgctg aactgaaaat gtcgaaagat atttcgggca tcaagaagct   180

caaagtggag aggaccaagc aggaggagaa ggagtactgc atgtttacaa tacaatgtta   240

tcataattca taatttttat ataagtttga taagtaaaga attgtaattt tttttaaaac   300

aaaattgtgc ttaaaattta taaaattcag taatttaaac tgtataaagc tgatatgatt   360

taaagaaatc ttgggacctg aatcgacaaa tttctagcca tttaatgcca ataacttaaa   420

taatcttatc gaatgatatg ttattataga ttttttttta aatttatgat tatgaagtta   480

ccctccattc aaactaacat tagattataa acaaaatatt ttacagtttt gtaataaaga   540

tcttgaacaa taaaccataa atctttattt gtagaaaata aaaagagctt cactaacttt   600

tattgtaagc aaaagaaaat tataacaaag aacatgttac att                      643
```

<210> SEQ ID NO 7
<211> LENGTH: 542
<212> TYPE: DNA
<213> ORGANISM: Nezara viridula

<400> SEQUENCE: 7

```
ggggacagtt cttcgtccgt ttaggttaac actcgccatg aagatcggtt tgtgtgcgta    60

cagtgggtac aaaatttacc ctggacatgg gaagaccatg gtcaaagctg atgggaagac   120

ctttacattt ttaaactcaa aatgtgaagc ttcccattta atgaggagaa atcctcgtaa   180

agttacttgg accgttttat acagacggaa gcataagaaa ggtcaggagg aagaacagag   240
```

```
taagaaaaga actagaagga cccagaagtt tcagagggct attgttggtg catccctttc    300

agatatcatg gccaaaagaa acatgaaacc tgaagttagg aaagcccaga gagaacaggc    360

aattagggct gccaaggagc agaagagggc gaccaaggct gccaaaaaaa cctgaaaaag    420

cagctcccaa ggttaaacag ccttcaaaac agaaggccac caaggttcaa cagaaatctg    480

ctccaagagt tggaggaaag cgataatttt tttttgtatt ttaaataaat acgttttatt    540

at                                                                   542
```

<210> SEQ ID NO 8
<211> LENGTH: 676
<212> TYPE: DNA
<213> ORGANISM: Nezara viridula

<400> SEQUENCE: 8

```
gggaagcagt ggtatcaacg cagagtggcc attacggccg ggaagcagtg gtatcaacgc     60

agagtggcca ttacggccgg ggaatattaa ttttatgtaa actttaactc atatttattc    120

tcagaaaatt ttgtattcca gtcaataaat aaacaactca tttcaacaat tgacatgaga    180

atgagaacaa ctgattatcg aaacgttgct aaaatataat tctatattta tttaatgatc    240

atcaatatac ttgaaacatc attaagaata tattaaacaa ttatatttat tattgttagt    300

tataacaaat ctttgtatcc aaaattaaaa gaaattagtt gacccgagtg aataatacgt    360

atagtgtatt gattagtgaa agaaataaga taatgctatg tattatgtga cggagaaaaa    420

attttctttt tctccatcaa taacaaaatg cattcacaag tttacaaatt acaataggat    480

gcatctttgc gaataattgt gtttttatat gaatagttgt tttgtttttt tttcagtgtc    540

atggataaga tccgaatttt catgcaaatg catatttttt tttttcaaaa acatgagtcg    600

atatctttac gaaacaagtc attctattat tattttattt tttttttttt agcatttatt    660

tataacatta ctattg                                                    676
```

<210> SEQ ID NO 9
<211> LENGTH: 606
<212> TYPE: DNA
<213> ORGANISM: Nezara viridula

<400> SEQUENCE: 9

```
gggggtcagt ctaacgttgg acgccatgaa gagatcttcg gaagtttgct tactcagccc     60

actggattcc ggtctatgta tgagactggt aagctcagct gatgattcta cggcattcaa    120

gtcttccggt gtcttcaaga cattggacct tatcctcaaa gaagacacag atggaactat    180

cgaaaaggct cgaggaatct acaatttcaa agtcaaaaat aaagaaggaa aggaagctat    240

atggactgta aacgcttcga ctggtaaagg ttctgttaca ttcaatggaa aggaaaagcc    300

agatgtaaca tttattatta acgatgaaga tgtcattgat ctgttgtctg gtaaactcaa    360

tccacagaaa gcctactttc agggaaaaat aaaaatcaca gggaacatgg gtatggctat    420

gaaaatcaca ggattgttga aaagagcagg tagtaaaatg gataacctca aagctaagtt    480

gtaaacagaa cagttaagac tgaatatgtg tgaaacaaag taagttaata gtgaatggca    540

tcatatgaat ataaatatat gtatatataa ttgtaatgtt ttgttgataa ttatatttag    600

ttaacc                                                               606
```

<210> SEQ ID NO 10
<211> LENGTH: 656
<212> TYPE: DNA

<213> ORGANISM: Nezara viridula

<400> SEQUENCE: 10

```
gggggtcagt gcctcagctg caatcatgtc ctcagttcta tacttggtac tcctcttcgg     60
ggcagccgtg tctgccaagc acgtcctccc ttcttacgtg aagacttgct caaggaatga    120
ccccaacctg agtgagtgcg cactgaagag gggcaaggag atcataccca agatcattaa    180
aggagaccca agtataagac ttccagtact ggacccgatg atgctggaca aagttggtat    240
cagtaccact ggtcgcgcca atgggggagg actccaactc acttgctaca aatgtatcgt    300
ctacgggctc tcaaacgcag tactccagga catcaaaatt gacttggaca agaagcacat    360
cgccttgaag atcttcgttc cacaattatc tgtcgcaggc aaatatgatg tcaatggcaa    420
gctattgctt ttcccaatca ccggcaatgg acaggctaac atcactctgc ttgatttgaa    480
agctgaggcc gccctcgact ggaagcttat caagaggaaa ggaagcgaat acgctcacat    540
ctcaagggac agggtagact tcacagcatc aaggcttaag ctctccctaa ctggcctctt    600
cggtggagac aaagcactca gtgacaacat gaaccagatc ctcaacgata actgga        656
```

<210> SEQ ID NO 11
<211> LENGTH: 688
<212> TYPE: DNA
<213> ORGANISM: Nezara viridula

<400> SEQUENCE: 11

```
ggggcatcag aaccagccat gttcacagct tggtctcttt gcgccatcct cttcgccgct     60
gtcttcagcg caggagctgc acccttcgat gacgatgagg atatcctagt cgacaaggtg    120
aaggacatca ttacccacat caacaacttc atcgaagatc ataacttaga gcacctcgcc    180
cttcccaaca tcgggctgct tccgatcgac cctctcaagc tgagacaagg acggcttggc    240
aagttctcca ccatcgaatt acaggatgtc accttcatca atcagactac gatgactgat    300
gggtccgtcc tgttcaactt cgacctctta cttgggctga aggagttccg gttcgaatac    360
gactttaccc tttatgctcc tttcttattc aaccataatg ggcatttcac cctctcgcct    420
ctacgaaact ccattcaggt atccggtaaa gttgccatca aggataagac atgcgacgcc    480
agcctcggca acgtcagagt tgccgagtac ggccacttca agatcgacct ccagccgaac    540
aacatgcctt atgccacgca gataaccgaa gacctcatga atttcgttac ccctctggtc    600
ttacctatta caaacaaagt catggaaata gcagcttatt taccacctgt aaacagggtg    660
ttgtcaggac tggtttgcaa agtcatag                                       688
```

<210> SEQ ID NO 12
<211> LENGTH: 681
<212> TYPE: DNA
<213> ORGANISM: Nezara viridula

<400> SEQUENCE: 12

```
gggctaatca atttataaga cttattagct attgattccc agtttcttga atttcctttt     60
tctataattt ttgtccatat atcacttggc aaaaaattct cttaattttt tttctgcaga    120
ttgctgttga agtgctcatc aaagaatgtt actttcaatc tttctgtagc attttccatt    180
cattgtttcc agagcccttt ggcctcctgt ttttatgtaa tgaactgttc actgcattaa    240
atattcatta taactcctac cctttcccat tttcatttag aagtttaata ttttcaacat    300
tcaataacac atatctaaca ccattagtta agtagtccgt acagttccat tatgtcatta    360
tatagcttcc tattgacacc catcactcac ttagttttat ttaattctgc tatagtagtt    420
```

```
aggtaactat caaaattatc ttgtactttt ttttcttttg gtattgctga aaaatctatt    480

acgacttcac atttctccaa atcttctgtc atcttatctc tgtgtgttta aatcttaaac    540

attgtttaca agaaacattg tttccaagat taatatattg tttaacgaaa ggattattgg    600

cccaaatgat aatgtacttc ctataggtat tgtggttgac aggttgcctt caccatgact    660

tcgagctttt atacccatct c                                              681


<210> SEQ ID NO 13
<211> LENGTH: 674
<212> TYPE: DNA
<213> ORGANISM: Nezara viridula

<400> SEQUENCE: 13

ggggagctga taaaaaataa tcgttcaagt caactcacca acttgcagca aaatgccctc     60

aaatcaaatt ttgagtattg ttagaaatta tgcttctgct gccgctgcaa aatctattaa    120

accacctgtt caagtatttg gattagaagg tcgttatgcc acagcacttt attctgctgc    180

agtgaaattg aaacaactag atgttgtaga aaaggattta aaaaatatac agagtacatt    240

gaaaaatgat accaaacttc gaacttttat tgaaaatcca accattaaga ggaatctgaa    300

gatcgatgct ttcaaggatg tgtcaaataa aattaagttg agtgcaccat ccacaaacct    360

tcttggtctt ttagctgaga atggtaggct caatagactt gaccaagttt tgaatgcttt    420

ttctacaatt atggctggcc acagaggtga tcttcgatgt gaggttacga ctgcaaagcc    480

attggatgag gaaacaaaaa aacaactaga gactgtattg aaagcatttg ctaaaaaggg    540

tgaaaatatt atttcggagc tgaaggttga accagctatc attggtggaa tgatcgtcag    600

tattggtgat aactatgttg acatgagtgt ttctagcaag attaagaagt atacagatat    660

catcacagag gctg                                                      674


<210> SEQ ID NO 14
<211> LENGTH: 687
<212> TYPE: DNA
<213> ORGANISM: Nezara viridula

<400> SEQUENCE: 14

actcaaaatg atagcacttt gtgatttatt ctatatgtca tccaatcttt aatttactgg     60

acgattgcta aaataagttt cagaaatatt tgtctgtaat aacattaatt gctcaattat    120

agaaataaag ctactaatta gcctataata tctaacatat atctaaaaaa ttagatatat    180

gttgaaccct aagtattgta aacatcagca tgttatacaa taaattaata acagaaaaca    240

ttcttacttc taaacagaat gaaaatatag agtacttgtg atttagccgg tcgccttcgg    300

acctaccttc ttatcttgtg ttatctcttc gtatcgctca tctctgctta gttacttgtg    360

cgttcttctt gttattcaat tattttcagt tttttttgt tttgttattt tttatttaaa    420

atggttacaa taacacttta ggaattactg tcttcggaag aagactatat tatatattag    480

acaggtcaac taaaaaaatt ggagggtcta aaaaagttgt tgaaatagac ggaagtcttt    540

tttctaaacg aaaaaatcat gtagggagag tgctctcgga ataatggatg tttggcagag    600

tttgtcgaga aacagatgag tgtttcattg taaaaataaa agaaacgcaa caattctatt    660

tactaattga taatatctct cttctat                                        687


<210> SEQ ID NO 15
<211> LENGTH: 494
<212> TYPE: DNA
```

<213> ORGANISM: Nezara viridula

<400> SEQUENCE: 15

```
ggggttaatg ttataatcta atatttgaat tttatggagt aataaatggt actgtagaaa     60
atgaattcta aatttttaag ataaaataat agactgtcga atagtacttc ttaaccttaa    120
catttaaaat ccaagtatat tataacagta atataggtaa tatatttgga atcaaataca    180
agttttataa tattaactca ttttattata aatgaattaa tattagaaaa ataaataaat    240
cctattattt ctaaaaggag ttttttttt atcggtacgt cataacttcg tcaattcctc    300
atcaaatcca acgattgacc gctcattttg aagatattct gctcctacac atgtgaaaaa    360
tagtccaatc tccccgaaat ttctggaaaa aaagttatgg aggaaaagaa actttatttg    420
cgaataactc aaaaagtatg catttttgtt tctggattgt acccacgata attacaaaga    480
ttactaaatt acct                                                       494
```

<210> SEQ ID NO 16
<211> LENGTH: 100
<212> TYPE: DNA
<213> ORGANISM: Nezara viridula

<400> SEQUENCE: 16

```
ggggtcagag ttgggtagag aaactctaaa acaaatagaa aatactaaaa ggcgtttaca     60
attaatgaaa atagcagaaa agaaagtgta agcagaaacc                          100
```

<210> SEQ ID NO 17
<211> LENGTH: 693
<212> TYPE: DNA
<213> ORGANISM: Nezara viridula

<400> SEQUENCE: 17

```
gggtggaaat atgtagtagg aacaaaagtc agttaagtag tatgctctct gcaatcttgg     60
actataccag caataaaaac tttatcatta gagataaaaa agatatatca tttttttcta    120
aagctatgga agtttgtagt aaactcaaag ataaggatct tctctacagg cttcatgaat    180
tattgttgac cggaaacaat tataatttga tcggagattc atttagtgaa tcggtgtatt    240
accgttattt ttttttattt gcttactgat actgaagaac ttagtaaagt aatggaattc    300
tatgatgacc ttgtaccaaa cgtttatgtt ccagagccat cagtgaccaa tgctatattg    360
aaagctgttt gtaacaacat ggcatgggac cttcttccca agctttggcc agacatacta    420
ttgtttgagc agtatgaagt ttccggtgtc ctggaaaaata ttttagatat tgcatctcaa    480
aatgaaggca agaatttgat ggaagggatg tctaaaattg catggtctgc atgggagaag    540
atagaaggaa taaagaggga gcgatccaac tttcaatggt ctgcgagtgc attgggaaac    600
attattctca ttttgttgaa atctggtgaa aaagctaagg cgaatttggt tatgaataaa    660
ttaattcaac taggaagttc tgccatgaat gaa                                  693
```

<210> SEQ ID NO 18
<211> LENGTH: 654
<212> TYPE: DNA
<213> ORGANISM: Nezara viridula

<400> SEQUENCE: 18

```
ggggaggtta tgtgactgtg ttacatcgag tttgatattg ttttcattgt gaagtgttga     60
ttagttctgt attacttcga agtttaaaga attattaata tactttagaa atgttgaatt    120
ttggttataa tgctagaaga tatatttatg ttttcatatt tactatgcct cttacttagt    180
```

```
actgatgtta cataggaaaa tgagagttaa aaaatatttg cctgatgtgt acatttgtgg    240

aagaaaattt aattctagaa aatggctgct ctgtttgacc caaatgacag aagcaggtaa    300

gttcatgaaa ttggtatttt ggtcaaatgt caaggcaaga tgccactgat cttttaatgg    360

gagaaaagga gggtggcgta tttcttgtcc gtgatagtat ctcaattcat ggtgattatg    420

ttctttgtgt aagggaagat agtaaagtaa gccattatat tatcaacaaa attcagcaga    480

atgatcaaat taagtacaga attggtgatc aaacatttaa tgatttgccc agttagctat    540

ctttctataa attgcactat ttagatacta cacctctaat tcgaccagca ccaaagagag    600

ttgaaaaagt gatagctaaa tttgacttca atggaagtga tcaagatgat ttac          654


<210> SEQ ID NO 19
<211> LENGTH: 635
<212> TYPE: DNA
<213> ORGANISM: Nezara viridula

<400> SEQUENCE: 19

ggggtttgca cctaatccaa tgtttggatt ctttattatg agagtaccaa tgttgcaaat     60

cagagatcca gaacttattc gacttatact tacaaaggaa ttttcacatt ttcgagacag    120

gatgtttatt aaattaagtg aaaaagatat tctcaatcaa catctgttca atctggaagg    180

cgaaaggtgg agagccttac gtgtgaaact caccccaaca tttacaagtg ggaaaatgaa    240

agctatgttc ccactctttg tcaattgtgc tgaggccttt gaatctttga tcgtgtcaaa    300

aattggtagt gacgtagaca tcaaagaatt agtaggtcga cttacgacag atattatctg    360

cagctgtgct tttggacttg atgctaatac aatcgaagag ccagatcata agctaaggca    420

aatcccagcc caacttacta aaatggggtt tattgataaa gtgataatag caatcatgca    480

agctatgcca caagttgcca gcaaatttaa agccaggttc actcctaaag agcttgagga    540

ctatattgta ggtcttgtag aaaacacatt ggagtataga gaaaagaata atattaaaag    600

aaatgatttc ctagatttat taattgagct gaaga                               635


<210> SEQ ID NO 20
<211> LENGTH: 682
<212> TYPE: DNA
<213> ORGANISM: Nezara viridula

<400> SEQUENCE: 20

ggggttcctt agcaggtttt cttgagtttt cattaaaaaa aaaaaaaagc actagtaagg     60

aaaacaataa tataaactat atatacattt ataaaactat atactgtcgc tattttgcta    120

atacatctat ttttaattaa caatatatat tttttaaata tttctgcctc tctatcaaag    180

atataacgaa gttttaagtg tctagatggt cagataccaa tttcgattaa ttttatcaat    240

actttttctt acggatgcgc aagtgtattt tcttagatat gctaatattt cagaaactgt    300

cagttcgatt tggcccaaat ttggattaaa gatgggcatt ataaaatagt gggtaaaaaa    360

aaaatcatac aatttttat taattctatc ttaaaattta cttgaaatgg agtattggat    420

atcagaagaa ttcataatcg agaaaatgaa aatacattcc acaagacaaa aaggacataa    480

atactaattt aaggtaatag gttattaatg ttattatgtt tgaaataatg gagcacgcca    540

tttttctaat tattatcata tacatgtaaa tgtaagaatc agtagaagaa aagaaaaaca    600

tttagatggt caaaaaacac ttggtcatta tcgcttcgaa taacgatttt taaatattta    660

taaaaaaaca tttttttat at                                              682
```

<210> SEQ ID NO 21
<211> LENGTH: 688
<212> TYPE: DNA
<213> ORGANISM: Nezara viridula
<220> FEATURE:
<221> NAME/KEY: misc_feature
<222> LOCATION: 587, 600
<223> OTHER INFORMATION: n = A,T,C or G

<400> SEQUENCE: 21

```
ggggccgttg tttctggttc agcatactct actaaatcta agcttaacgc agccgaaagc     60

aaagaaaaca aacaatcgaa agaaacctcc aacaagggat attccaagaa agccactgga    120

tacccagcct atggtgttta tggtggaggc gcttatgccg aatccggcta tgacaagaaa    180

tccaaatcag cttcttccaa caaggctagc cgtaccctaa acaaggaaga ttccacaaaa    240

gtaaccagct caagtgttgt agctccagga gttattgccc cagcagtcgt ttctagttca    300

ggatgctcca ccaaatctaa gcttaacgca gctgaaaaga aagaaaacaa acaatcaaaa    360

gaaacctcca acaaaggata ctcaaagaaa gccactggat acccagtata tggtgtttct    420

ggtggagccg cttatgctga atcaggctat gaccagaaat ccaaatcagc ttcttccaac    480

aaggctagcc gtaccctcaa caaggaagat tccacaaaag ttaccagctc tggtgttgta    540

gctccaggaa ttgttgcacc cgccgtcatt ggtagctcag gatattncaa aaaatctaan    600

gttaacgccg ccgcaagcac agaaaacaaa caatctcaag aatcctctaa caagggatac    660

tcgaaacagg ccactggata tccaggct                                       688
```

<210> SEQ ID NO 22
<211> LENGTH: 121
<212> TYPE: DNA
<213> ORGANISM: Nezara viridula

<400> SEQUENCE: 22

```
ggggatacaa aaacaaatgt aataacaaca aaaatacttt tatttgacga caaatatatt     60

aatgaaataa taaaaaaaca ctttgagaag atatgtacat ataaaacatc aaaatgaaat    120

t                                                                    121
```

<210> SEQ ID NO 23
<211> LENGTH: 678
<212> TYPE: DNA
<213> ORGANISM: Nezara viridula

<400> SEQUENCE: 23

```
ggggatttct ttgaatttat ctaattatgt ttggccctct agaattttct ccaactgtca     60

aagaaatatc cgatcaatat ggaaaaattg aaagatatga agtcggttgt cttttatgct    120

ccagtacctt taacttccca tctgaaaagg atgtatgttt aggtcacatt tttgaatctc    180

ataaaataat aatagcagat gttcaccaga tagggaattt aaaaaagtat ttagaatttt    240

ggaaacaaca attttcagaa gctcccatta cagaattctg ttcaactatt gttgcagata    300

taaaaaaaga tggtttacct cttaaagaca aagagtactt tttattatca gatgtgcacg    360

ataaggataa atttattcga gaaaaacttc aaacagaatt gcttgaaagt gccttagatc    420

aacaaaaatt agagagagag gacacaaatt atagtcatgg ttgtctcttt tgtcgtcaga    480

ttatagagcc cacaagatct gaatatttga ttcacctttc aacacagcac aatttacaat    540

tagggaaacc agaaaacctc gtttatgttg atgaactaat tgaaatcttg gaacaaaaaa    600

tggaaaagtt gcaatgcatt ttttgtgaac gaactttcaa agacagaaat gtcctcaaag    660
```

```
agcatatgag aaaaaaga                                                678

<210> SEQ ID NO 24
<211> LENGTH: 103
<212> TYPE: DNA
<213> ORGANISM: Nezara viridula

<400> SEQUENCE: 24

ggggggtcaa cggcgggggg gcggggtggc cgaataggct aaagcgtgag taacagcacc    60

gctagttgcc tggcaaccgg ataacagaga tttgagacga tag                     103

<210> SEQ ID NO 25
<211> LENGTH: 613
<212> TYPE: DNA
<213> ORGANISM: Nezara viridula
<220> FEATURE:
<221> NAME/KEY: misc_feature
<222> LOCATION: 489
<223> OTHER INFORMATION: n = A,T,C or G

<400> SEQUENCE: 25

agtccaataa gggtgctaca tttttttttt gatcggacaa gggggcttat aaacatcttt    60

agatacctga aaagagtacc atgaaaaaaa aaatgaaaac cactgtctta ttaaacctag   120

acagcagtaa tgtaaagatt gatattcata actggtcttt aaaaagtttg acaacaaaat   180

atgtctattt gtgaaatttt ctaaaggttt ttttcacaaa atcaaagctg gtgaggttgg   240

tccattgtga ttctcaaaat ttataatttt caaatataca acaatttaag aatttttttaa   300

aaaagttaat aaatggatgt atttttttcac cctgttaaaa gtttaacgta aatctttatt   360

gttataattt tttttttga ctgatttact atcttaattt tgatgaatca aattataatt   420

ttaattttat atattattgt aaagttgaaa ttgtagaagt tgcctttaaa agaataaaat   480

aatattttnt tccttcttaa cccaaaaaca attgttattt agataattag attatcattc   540

gatatgataa atgaaaaaga ttatttagga aaaaatatgt tacgatattg ttaaactact   600

aaattttaca aat                                                      613

<210> SEQ ID NO 26
<211> LENGTH: 682
<212> TYPE: DNA
<213> ORGANISM: Nezara viridula

<400> SEQUENCE: 26

gggatgctaa aacatcctgc taatcgttac agaattttaa ttatacgaca tttttaaaat    60

acagtattca cctatgttcg tctaattact ataacaggaa ataaataaat taaatttagt   120

ttttaaaaag tgcagacaat tttagagatt aatacaaaag aaagtttaaa atgaacttag   180

taacggcacg gctgtctttt cggttgatta aaaaactttt ctaacgttct gttcccatct   240

caaatttcca atgatagggt agtacaatta tggttcggaa tttaattaaa gattaattta   300

tttaagaaag taccaattat tttatgtact ttatttgttg acatttttat agtacaatta   360

taaaagaaat cgtctaattt tgaatctaaa ctattcaaag ttatccttat tagtgtccag   420

tttaaaaccc tccctcactt agctaaatat atatttgtta taataagtat gtgtacttat   480

tttatgaata atgttaatta ataataagtt attaagtttt atatttgaaa atttcatagt   540

ttaaaggttt ttttctccaa aaatcgcata ttcatttagg atttcatcat tttattttaa   600

aaactccgtt tttggaattt acaactgtct gactaaattc cgtaataatt tactaactcc   660
```

gtacctgaaa ttatactgtt aa 682

<210> SEQ ID NO 27
<211> LENGTH: 51
<212> TYPE: DNA
<213> ORGANISM: Nezara viridula

<400> SEQUENCE: 27
ggggtggagg tctgatgcac cccagtgtca tgaagctgtt aatggtaaaa c 51

<210> SEQ ID NO 28
<211> LENGTH: 636
<212> TYPE: DNA
<213> ORGANISM: Nezara viridula

<400> SEQUENCE: 28
ggggagatca gtagcgatgc acatctattc ctttgcgatt gtagttcttt tggcaggctg 60
cggcctcgcc ggtaaatgtg gtagctacgt ccagccggcc gtctaccaaa cgtatggtcc 120
agttgccgct ggtagcagtg gatactcgac cagctctaaa cttaacgccg cagaaagctc 180
agaagccgca caatcccaag aatcctccaa caaaggatac tccaagtatg gttccggata 240
cccaacttac ggtttgtacg gaggcggtgc ttacgccgaa tctggttatg atcagagctc 300
caaatcagct tcatcatcca aagctagccg ttcccttaac aaggaagatt ccgccagtgc 360
ttacaactca ggatttgctg caccaggctt ctatggccca gcagttgttg gaggctcagg 420
ttattctacc agttccaaac ttaatgcagc agaaagctca gaaaactctc aatcccaaga 480
atcatccaac aaaggatact ccaaacaagg ttccggatac ccagtctatg gcctttacgg 540
aggtggtgct tatgctgaat ctggttacga ccagagctcc aaatcagctt catcatccaa 600
agctagccgt tccctgaaca aagaagattc cgccag 636

<210> SEQ ID NO 29
<211> LENGTH: 364
<212> TYPE: DNA
<213> ORGANISM: Nezara viridula

<400> SEQUENCE: 29
ggggagttca gttttttcca ccaaaatgaa gctctacatc gccgtcctct gcatcgttct 60
catccaggga gtccatgtta attgccagag cagttacttg gactcggcca tgagtactat 120
caacagtgct taccagcaat accgcagcgg aacactgttg aggaacctcc tacagactgc 180
cagggaatac ctcaactatg ccgttatcag actgaaccag ttgcagaact tcatcagcac 240
cttgcaggtc ccggcattgc cttcgatacc gcagcccaca gtcccaggca ggatttggca 300
acagtgggct ggacgctaat tgtttcatgt acggtcaaat tataataaat tgtttataat 360
catc 364

<210> SEQ ID NO 30
<211> LENGTH: 683
<212> TYPE: DNA
<213> ORGANISM: Nezara viridula

<400> SEQUENCE: 30
ggggagtttg aataatttca atctcatcta aaggattatt taatgtgaat gatttgtgtc 60
agtttttact tttaactgcg gcatatagcc tgctgcagtt aatgcgggaa ggtttacctt 120
attatgtctg actgggaaca aagattgctc agcctggaaa aactggacag gtcatcgcca 180
gagctctggc cagagccgat acctggggtg acagaatatg ctgctcgcaa tgctctttct 240

```
agttcctctg ttccaaagaa cattgaatca ctccagagtc agtttactga ggatgactat    300

aagctgctaa attattacag tactctttct aaagaatctc tgattcaaga attaaagaag    360

cttcatgacc aggcctataa attaggtctt gaagaagcca aggaaatgac tagaggaaga    420

tttttgaaca tactgtctac cagaaaaaag taatggtttg taaatgctgc catgcttctg    480

aatggttcca tcatattctg atccagaaga aggaagttgt agcgaatgga gtaggtataa    540

aagtgagtca ataaggacaa gaagggctaa tttaatgtat ttttccaaat atttttgtaa    600

ttgcagaata gaagatttat gtgaagaaat gaatttaagt tttgttgtt gtaactgtct    660

gttatagttc cttcagtccc aaa                                            683
```

<210> SEQ ID NO 31
<211> LENGTH: 672
<212> TYPE: DNA
<213> ORGANISM: Nezara viridula

<400> SEQUENCE: 31

```
ggggagcaat agtagaatta tgcgcgtcat atgtgcaact gaatagtgat gctagttagt     60

tttaattgta tatattatga tgtgaagtaa ttatgtagcc cgtaggaacg ataaggactt    120

aattaattaa gtttgggacc tgatatcttc ctaagggatt agtgcattta agaattaaat    180

ggcggctgaa gaaaaatggt attttaccaa ggaacaatta gcaaatactc caagcagaaa    240

atgtggcttc gatgcggata aggaattgtc tagcagacag caagcagcaa atttcattca    300

agatatgggc caacggttac tagttactca gctatgcatt aatactgcga ttgtatatat    360

gcatcgtttc tatatgttcc attcgtttac acggtttcac cgaaatgcga tggctgcagc    420

tgcattattc ctagcagcta aagttgagga acaacccaga aagcttgaac atgttatcaa    480

agtggcccag atttgtcttc acagggagca acctccactt gacatcaagt ccgaggttta    540

tatggagcaa gctcaagaac tcgttgtgaa tgaaaatata cttctccaga cccttggatt    600

tgatgtcgca atagatcacc ctcatacaca tgttgtaaga tgttgtcatc tagtcagagc    660

aagcaaagat ct                                                        672
```

<210> SEQ ID NO 32
<211> LENGTH: 664
<212> TYPE: DNA
<213> ORGANISM: Nezara viridula

<400> SEQUENCE: 32

```
ggggattgaa tgtttgatag cacgttgtga ctccttgtac cggtactttt tgataataag     60

attcaaaatg agtgtaataa ttaagaatgc tttaagaatt cctgctctta aatcggctgg    120

aaaacttttc ggtacaaatt ccactgttaa tgtcaccaaa atccaagcta ccaggagtat    180

ctggaacttg tcgcaatctc aggaaacttt tcatcataag tgccgcaaac acaatttttg    240

tcaatgttct tctttaagaa gtttacacac tcgaggagag aaagaacttg ctgattttct    300

tgtggaggaa atatcagctg aaagaaagtt acaaaaaagt aagaaattac cttctgaaat    360

tgatgggttt aaaattgtaa ttgaaggatc tgaaatcagc cttgtaacga aaaatggtga    420

tgaaacaatt gaagtaaact tcaatgtcaa tcattctgtc gataccgacc cagttgaacc    480

tgaaattgaa cctacaatgg acaaacctga acttggcgag atgaaatcta gacctacttt    540

tgaagttgaa accaataggg cagggcagac actgggcttc acatgttcaa ctgtatcacc    600

ttctcaccag caaggccagc aagaagaaag ttacaatgat ctatttctta ttgatgaagt    660
```

tgtt 664

<210> SEQ ID NO 33
<211> LENGTH: 394
<212> TYPE: DNA
<213> ORGANISM: Nezara viridula

<400> SEQUENCE: 33
gggggatgtt ggaactggct attatttgaa tatgaatatt gaaagtgcca gagactattt 60
caaaaggaag gtaacttttg tcaccgaaca aatggaaaag attcagaata ttgggctaga 120
aaagagtaaa ataagagaag ctattatgga tgtgatggag atgaagattc aggctcaatt 180
agctacacag agagcggtcc aaaatactat agcgaaaacg tgagaaatga tgagagctgt 240
catacgaaaa atttatgttt cttatattaa cgcttgtatt tataatttac taatgttttc 300
acagagtttt gtatccataa atacctgtta ttaaatatgg aaattatatt ttagttctaa 360
cttttttttt ataaataaat acattttgtt atgt 394

<210> SEQ ID NO 34
<211> LENGTH: 634
<212> TYPE: DNA
<213> ORGANISM: Nezara viridula
<220> FEATURE:
<221> NAME/KEY: misc_feature
<222> LOCATION: 462
<223> OTHER INFORMATION: n = A,T,C or G

<400> SEQUENCE: 34
gggggaagaa attgagagaa tggttaatga tgccgagaaa tacaaggctg aagatgataa 60
gcagaaagct gtcattcaag ctaagaacac tctggagtcc tattgtttca atatgaaatc 120
tactgtagag gatgaaaaac tgaaagacaa aatttccgat tctgataaaa ctacaatttt 180
ggagaaatgt aatgaagtta ttcgctggct cgatgctaat cagttagctg aaaaagaaga 240
attcgaacat aagcaaaagg aattggaagc catatgcaat cctattatta ctaaattgta 300
ccaaagtggt ggtatgcccg gaggaatgcc aggtggtatg cctggtggtt tcccaggcgg 360
tgcccctcct aatgctggtg gtgctgctgg acctaccatt gaagaagttg attaaacatt 420
ccatgcgaat aaacacacaa ataatacatt gtataattaa tnctagttga attgcaattt 480
ttttttcctt tctagtcaag agaccttcaa atggccttgt atttttgttt aaaaatttaa 540
tgttaataat gtaactttta caagtatttt gtttatttat aattttttta tatgttctgt 600
cattggtatc aatgaattat attagagtta ctat 634

<210> SEQ ID NO 35
<211> LENGTH: 491
<212> TYPE: DNA
<213> ORGANISM: Nezara viridula

<400> SEQUENCE: 35
ggggaattta tcttaggtcc aagatgaggg ttatccttgc agtcatccta ttcgctggag 60
tggcccttgc caggcccgac ggctacacca ccaagtacga caacatcgac ctcgacgaaa 120
tcctcaacaa cgacaggctc taccagaagt acttccagtg ccacaccaac aaggggaagt 180
gcactcctga cggcaagcag ttgaaggaca tcctccctga cgccctgaag agcaagtgcg 240
ccaagtgtaa cgagaggcag aagaagggag cagagaaggt gttcaagcac ctcctcgaca 300
agaagcccaa cgattacaag accctcgaga agatctacga ccctcagggt acctacaggg 360
cccagtacaa gagcgaagcc gagaagaagg gaatcaaaat ataaaaatat ctgtgataaa 420
cttgtatgaa tgatgtgtgt ttgtttttgt ttgtaaattg ttatttaatt aataaataat 480
atgtttataa g 491

<210> SEQ ID NO 36
<211> LENGTH: 663
<212> TYPE: DNA
<213> ORGANISM: Nezara viridula

<400> SEQUENCE: 36
gggcaataaa gctcgttatc acttggtatt cgacattatt atttctcttg ttgccactct 60
tacacggcgt cggactaaga ttaaattttg aaaaatagcc cattgctgaa atgatgaaca 120
tttcgatcgc taacaatatg caggtccgat ttttattttt tgagatatgt caatccaaat 180
gcaaaaacac tttagttaat cgactccagc tgattttact cgagcgttac acatcggata 240
tctgacggct caatctaatt cactctctac aaaaaaaaat attattacta atcaaattaa 300
taatatgcaa taaatttgaa atcagagata catcctcaat tcttaaaata atattttaac 360
atattctttc tattatgagg cttgcgtttg atattcaaaa tattacaaga aataattttg 420
tggaagatgg aaattaatat gtagataatt gttgatattt cataataccg acataaccta 480
accttgttat taaactttaa ctagctgata aaatgtcggg tattaattaa ataatatcga 540
caacccgcaa gtaaaaaacg cgtctaaaga agttttaatt taaaaatata gtgaaaataa 600
ttttattcag cctacgttcc gacctaacta tacaggtctt catcaggact atggtcagga 660
aac 663

<210> SEQ ID NO 37
<211> LENGTH: 548
<212> TYPE: DNA
<213> ORGANISM: Nezara viridula

<400> SEQUENCE: 37
ggggacagct cgcccagctg gaagagggtc aacatggatt cgcaagaact agaccacagc 60
gagctgagga gtcgcctcta ctccatatcc tccctcatct tgcccatctt catcctcctc 120
tacgtggggt ggaggttggc caacaagagg ttcatcgaac tcgcagaaaa gataccaggt 180
cctccgggtc ttccgatcat aggaaacgtt ctcgaactgc gagggacgcc caacgaaata 240
tttgaaaacc tatattcgaa gagtgaaata tatccagatg tcgccagagt gtgggcggga 300
ccaagattac tggtttttct tacaaatcca gcagacattg agattgtcct cagtagccat 360
gatcatttgg acaagtctgc cgaatatgat tttttgagac catggttagg aaatggactt 420
ctagtaagca caggagagaa atggcgatca catagaaaga taatagctcc aacatttcat 480
ctgaatgttc ttcgcagctt tatggaaaga tttaacagaa attcaaaaaa aacattagaa 540
agactaac 548

<210> SEQ ID NO 38
<211> LENGTH: 598
<212> TYPE: DNA
<213> ORGANISM: Nezara viridula

<400> SEQUENCE: 38
ggggattcgt gtatcagttt gcaatacaag ctacttttaa atttaatatc atcactggtg 60
tttttaaatt tcaatcataa attactttaa tacacaagtt atttgaagtt gttttaattt 120
atttcaggcc acataaatat ttaataaaat atgtctgggg accaaaaaga aagaaaaagg 180
aaggaaagta tcttagattt gtcaaaatat ttagacaaag ctatcagagt caaattttct 240
ggcggaagag aagctgctgg tgtattaaag ggatatgatc cacttctgaa tttggtttta 300
gatgatacaa cagaatatat gagagacccc gatgaccctt ataagttaac tgatgaaaca 360
aggatgcttg gtttggttgt gtgccgtgga acatcggttg ttcttatatg tccagttgat 420
ggtatggaga gtataccaaa ccctttcgtt ccacaagaat cataaataat ggactaattc 480
taagtttaag aagattaagt tctttcctac ttatgaaaat gaaaagaatt tactttattt 540
aggtttaaaa aactgtttgt ttataaacat gtatatatat taaaaatctc cattttta 598

<210> SEQ ID NO 39
<211> LENGTH: 689
<212> TYPE: DNA
<213> ORGANISM: Nezara viridula

<400> SEQUENCE: 39
gggattaaaa aaagaaattg attattttat tttttattaa ttataagaac attaattaca 60
atttcagcta ataactgaat aagaatatga ataggtcttg aactaaacat aatatcattt 120
attcctttaa ttttacaaaa aaaatagtaa atcaagatcc gaggcagcta taatttactt 180
tctaattcaa agaattagaa gaattatcct atttataata attacaatta atttattaaa 240
attattaaat tattcaaatt ttattaatat attaattaca attagaattc taataaaatt 300
gggagctgca ccatttcata agtgaatacc tgaaattata acaaaaataa gatgaataaa 360
atgtataatt ttaataacat gacaaaaaat agccccatta ataataattt gtaatttaaa 420
tagaagtaga atattaatta aattatcaat tatttgatca gttggagttg gaagaatcgg 480
aggaattaac caatcatcat tacgaaaatt aatagcatat tcatcaatta accatttagg 540
atgaatacta gccattaata aaaaaaatta atttatgatt agtatattga ataatttata 600
gaataattat ctttataatt tgtctaatat ttaataatta taaattatta ttcttaaatc 660
aaattagcag atccaatata aataatcca 689

<210> SEQ ID NO 40
<211> LENGTH: 662
<212> TYPE: DNA
<213> ORGANISM: Nezara viridula

<400> SEQUENCE: 40
ggggagttga ggtttggcaa ccgacttgtt tagagatcct gcaagaaaat gagagctacg 60
tactgcttaa tcctagctgc tgcagttctt gcagtggctg cagctcacac ttaccatctc 120
ggaaattgcc ccatcgtaga acctatgtct ggttttcaga tgtcaaagtt tttaggttta 180
tggtatgcca tccagaagac ttcaacaggt agcagatgct tgacatacaa cttcactctt 240
ggggaagagc caggcgaata caacttggag caagtttctg aacatccagt cttaggagta 300
gcatcagttg acaacaaata ccattacaca ggacatttaa aggccaattc tgacgttcca 360
tccaaaatga cagtgaaatt tcctttaagt gttgctggaa catcaagttt cacagtcttc 420
atgacagatt acgaaactta tgctggaatt tacacgtgcc aaaaactacc tgcagctaat 480
agaagatcag ctaccatcct ttctaggacg aagacattgg ataagatggt gattgataag 540
attcgttccc gtctgtctaa cttcggtgtc aacccatacg acctcagcat cattgaccat 600
gctaaatgcc cagcagaaac caaccttaat ttcaacatcg acaaggaaac cttctcacct 660
ca 662

<210> SEQ ID NO 41
<211> LENGTH: 628
<212> TYPE: DNA
<213> ORGANISM: Nezara viridula

<400> SEQUENCE: 41

```
gggctaacaa gaagaaaaat aagtcagcga agtctaaaca gacagctgaa caaaataaat     60

ctaaacagcc tgccgagcaa aataaatcac cacccagaac tagaagcaaa tcaaacacca    120

caaaaacagc tccaactgca ccaaatacca cagccagcaa taattttgat cttggtagta    180

actcacctaa caagcctccg gtacctcaag gttttactga ccccgagccg ccccctattt    240

ttgtctctaa aattgaaaat tttatatcat tcgttcaaga aattgccaat cttatcggac    300

aaaccagttt ccgctgtttt tctagggtta atgacattaa gattaacacg agctctaaag    360

aaaattataa aactctgata aattatttta caactaaaaa atatgaattt cactgttacc    420

aactgagaca agaaaaggca tatcgggtgg tattgagagg cttgcactca accactccca    480

tatccgttat caaatctgat ctagaggaaa taggacataa cgttaggcat atagcatgcg    540

tcctacatcc aacgcaaaaa tatccattgc cactgttttt cgttgatttg gagcctgcaa    600

gcaataacat tgacatattt caagttaa                                        628
```

<210> SEQ ID NO 42
<211> LENGTH: 70
<212> TYPE: DNA
<213> ORGANISM: Nezara viridula

<400> SEQUENCE: 42

```
gggtcagtaa aaagccaagc ttatctctaa tctccaaaat taaaattttt attaaactat     60

ttactgaacc                                                            70
```

<210> SEQ ID NO 43
<211> LENGTH: 685
<212> TYPE: DNA
<213> ORGANISM: Nezara viridula

<400> SEQUENCE: 43

```
ggggacacca caggacatcg ccatggtagc taagatatta ttggtttcac tgggccttat     60

agggttgact tttggcagcc atttacaaga ttctaggcaa ttcctatacc agcagcagca    120

acaacaacaa cctgccagac agtatgttgc atcacaatac caccaacttc ctgcggccac    180

ccatctactt ccgaacaatg tcaatgatgg tgtaaggtat ggacagcagt cacttgtgta    240

cgtaatgcct cagggttcac agtacctcta cgaggaaggc gctgaacagc cacagcaagc    300

tcaacctggt ggagcttatg ttgaatcttt cttcaatttg gtcaataatc catcaggata    360

tcatcaagca gcaagtgacc aaaagcctgt ccatcagcaa cctgctctgc cttctggagc    420

tgaaaaacct gaaaggcttc aggcagagcg accaagtttg ccaacccagg cagctcagca    480

gcagcactac ctccaacagc tggctgctca agaacagata caatatcttc aacaggaggc    540

acaacgacat aagtttatgg ctttgtcttc tcagcctcaa tatttccagc aacaacaaca    600

acgaccagct gctgcagcac cacacaatct cttctactac agtttccctc agcagcaact    660

tcagcagtat gcccaagccg ataaa                                           685
```

<210> SEQ ID NO 44
<211> LENGTH: 669
<212> TYPE: DNA
<213> ORGANISM: Nezara viridula

<400> SEQUENCE: 44
gggggtttct cagagtagtg gttccaggcc tctgattaag aatacataga tgaagacagc 60
acgtccccgt tcttgaaaaa atcacttctt caaatgtgga ttcaactgaa gaaaatgttt 120
tgattcattt gagatttgtt catcaattcc atttatatca atgccacttt ttccaaaaac 180
attttcaagc agtgtacttc ataatttcta agtatcgtct tcaagaaggt ggtacaaatc 240
tgctacatac ctaaaaaaat aaatagatat cagttattgt ttcattataa taaattgtta 300
tattagataa gtttttaaaa attacaaatt ctttataaat aaatacattt aaatactttg 360
ttgttctata caaaaggctt ttttaaaatt tatttttgta taaaacagca ttgagttagt 420
aagtatgatt tttgaaattt ttatttcaat tttgcattat ccagttccaa ttactaccag 480
aaagttagtt atatacagtt ttctttattt ttaagaatca attttctagt tattagaaat 540
ttttaagtag aatattcaac atagtaggac aaatctactt tcttattgtt ctagatctct 600
cagatcgatt gcatttgttg tatgattgag caacatttta ttataagcag aaatattata 660
aatgacaaa 669

<210> SEQ ID NO 45
<211> LENGTH: 134
<212> TYPE: DNA
<213> ORGANISM: Nezara viridula

<400> SEQUENCE: 45
ggggagtgtt gaagggaccg tccgtctggg ttgtgagtag tgttctcgtc gccgttctca 60
tcaccattat aattcggaag atggcagagg tggccaagag tgtgaatgaa gtcatggaat 120
cagttacaac agtt 134

<210> SEQ ID NO 46
<211> LENGTH: 225
<212> TYPE: DNA
<213> ORGANISM: Nezara viridula

<400> SEQUENCE: 46
gggggtcgca aaaggagtaa tgaactatgc aaggtgatag cccatatatg gtaagaagaa 60
tgtgtacccg aaaaatggaa gtgatcccac agagtgaaat gaaaatattt ttttattatc 120
ctgggactgt tgtccccttta ggacaaatta catatacaaa ataaatgccc gtattgccat 180
acataaaatt aattatttac aattattatt aaaattaaga ttttg 225

<210> SEQ ID NO 47
<211> LENGTH: 664
<212> TYPE: DNA
<213> ORGANISM: Nezara viridula
<220> FEATURE:
<221> NAME/KEY: misc_feature
<222> LOCATION: 557, 610
<223> OTHER INFORMATION: n = A,T,C or G

<400> SEQUENCE: 47
gggggcagtc gagtgtgaca tgcccgcctg agactttatg ctggcaggcc cgagtatgac 60
tgtgcttaaa ttgccccaga tggaagagcg caagtcgccc gaagcggcca aagggatcag 120
cttcagcgtg gctgcgttgc ttgcggactc gaggaggagt cctagccccg aagaagagga 180
tgactcagcg gaagaggaat tggacgtgtg cagggacaag agcccggagc cggggtacag 240
ccagcagcag cggctggtgc tcagccccgc cagtggcccc atcaggccca ctcccttcac 300
cgccttcgct gcggccgccg cagctgccta tgccggtctg ccgccgcaca cggcctcctg 360

```
gccggtccac cacttcccag gagggccagt cttcccgccc ttccatggcg gtctctcttc    420

ttctccaggt aatagatctc tcaatgttca gttatatata ctcatgtatt gtggtggtca    480

taattaaggc agaacgaatg attggaaggt tcgcggaatc atatgctaac taacgggtag    540

ttcttgttta ctaacangat aactacccgt attacgaaac ttccgtgtat aggtggaaag    600

aaataagtan gatcattata acatcctcca atgaattaaa atagagaata agtgataaaa    660

gttg                                                                 664
```

<210> SEQ ID NO 48
<211> LENGTH: 452
<212> TYPE: DNA
<213> ORGANISM: Nezara viridula

<400> SEQUENCE: 48

```
gggggctctt gctaggtcgc gtgttgttga agtattgtgt gggacatcaa atttatttta     60

ttttgattaa aaatttagta aaatgagtag atttttcgct actgggtcgg actctgagtc    120

tgaaacctct tctgaagagg agcagattgt gaaacaaact gccactttta cgttcagtga    180

tgatgaagaa gatacaaaaa gggtggttcg ctcagcaaaa gaaaagcgct atgaagaact    240

taccaatctt atcaagcaga ttcgaaattt caaaaagatc aaagacatga gcagtatgtt    300

aaatagtttt gaagatttaa tgagagctta tcaaaaagcc caaccagtta tcaataagga    360

agaaaatggt caaactccga agttttatct gcgttgtctt gttgaggtgg aagatttcat    420

caatgaaatg tgggaagata gagagggaag ga                                  452
```

<210> SEQ ID NO 49
<211> LENGTH: 275
<212> TYPE: DNA
<213> ORGANISM: Nezara viridula

<400> SEQUENCE: 49

```
gggcaaccat cttatgttca aacaacgcca tatgatccat ttagacaagt atttcctgca     60

gtcgaccgaa caactttcaa gaaaaaataa gaagaaagca agaaaagacc aaaatgcagc    120

ctatttatct caacgaaata atcccaattc agtttgatga ctggattttt gtatttatat    180

actcatattg agacatacct acataacaaa atttgacaaa atctgaaatt atttgctccc    240

aaaagtaaat taaacaaata ttctgaaaac aaaag                               275
```

<210> SEQ ID NO 50
<211> LENGTH: 569
<212> TYPE: DNA
<213> ORGANISM: Nezara viridula

<400> SEQUENCE: 50

```
gggcgggaag tggagcgaca atattatcct ccgaattcta ctgatgtaga aaagcttggg     60

ttaagacggt aaatgtcttt gaagccaaag acaaaacata aaaaaactga gcgagtttcc    120

ttgaaacaac atgagcggaa tatttatttt aaaaaatgta tcataatatc atagtcgctc    180

caaccgcacc ttgataacct gtatattacc tcctacttcc ccattcctta tctttaatga    240

cataaacata gaaggaatta aaaccagtct tatatattat acttatacat tatagagcct    300

tcttcttggt tagagatcaa tcaacattat tgattagggg tacaatcctt gagcgtgatc    360

ttggtgcaat cagctctctg tactgttggc ctgaaacttc gtaagtatct tcatctcatt    420

gtgaactaca aatattttat tttcgaatta ttgaaattgg agcgtttgaa agcaagtaat    480
```

```
tcctagtata agaagttgtg aatacccatt ttttcccact tgaaccgtaa gataatataa    540

tcataaaatg aataaaaaga aaaaaaaaa                                      569


<210> SEQ ID NO 51
<211> LENGTH: 586
<212> TYPE: DNA
<213> ORGANISM: Nezara viridula
<220> FEATURE:
<221> NAME/KEY: misc_feature
<222> LOCATION: 534
<223> OTHER INFORMATION: n = A,T,C or G

<400> SEQUENCE: 51

gggggattca gtcgccggct tccatacaaa tattcaagaa acaaaaatgt ctttagacga     60

gaacttcaac actgctgctg aagatgtcaa agcactccag ggaactccag atgaccaaga    120

attattggaa atttatgcac ttttcaaaca agggactgta ggagactgta atacttccaa    180

accagggatg ttcgatttta agggaaaagc taaatgggag gcttggaatg ccaagaaagg    240

cacagcccaa gatgcagcaa aggagagcta catcgaaaaa gtcaaaactt taattgggaa    300

atatggaaag aagtagacat tttgagtaaa gcctaacatt tattttttat taataattta    360

tgatttgctg ctcaaaattt gattttattt tttacattaa tgtaagcaaa catttacaac    420

attcaagaat atttgaacca aaggttgtgc aatttatgta tataatatat atacatataa    480

ggtatttctt ttataatttt tcataaattt atatttgtta aaaaatttga aganagtttt    540

gtaaaatgat tttttaatac atttatatgg atagttgaat attata                   586


<210> SEQ ID NO 52
<211> LENGTH: 633
<212> TYPE: DNA
<213> ORGANISM: Nezara viridula
<220> FEATURE:
<221> NAME/KEY: misc_feature
<222> LOCATION: 555
<223> OTHER INFORMATION: n = A,T,C or G

<400> SEQUENCE: 52

gggcttcacc ccttacaacg cataagctgc acgtgtgttg ggacagtctt ctgcttacat     60

tctggtttac caacatcggc gtgaacatta aacctggagc gttactagta tgagctccaa    120

tacctgttat agatgtaacc ggactgggca tttcgctaga gaatgcccaa atggtggtgg    180

aggaggaggt ggaggtggat ttggaggtcg tggtcgagac aaatgttata aatgtaatcg    240

ttatggtcac tttgcaaggg attgtaaaga agatcaagac agatgttaca gatgcaatgg    300

agtgggacac attgctaagg actgtcaaca aagtgctgat gagccttctt gttacaactg    360

caacaaaact gggcacatag ctagggaatg tcccgaacaa agagatggtt ctagaggtgg    420

gttcacctca gcttgttata attgtaacaa aactgggcac atggcccgag catgtcctga    480

tggatctagg tcctgttaca gttgtgggaa gacaggacac attagtcgtg actgcgataa    540

gaatgactga atganttgtc aaaattaagc aagttatata tttgtttttg taaggggcaa    600

ctttttcttt tcctttttta ctattacacc ttg                                 633


<210> SEQ ID NO 53
<211> LENGTH: 535
<212> TYPE: DNA
<213> ORGANISM: Nezara viridula

<400> SEQUENCE: 53

ggggaaaagt gacaaacaaa cgaatgggtt ccataaggct cagagaaaca gatgaagata     60
```

```
tagcagatct tttatccatg caatggatgg aatatgctca tatttatttg ataaatatta    120

ctcctccata ccgcagtttg atattaacgg aactgaatga agctttaagt tttcagtcat    180

attttggagg aaatcagata actgcagctg ataaagctgt tttcagagct ttaagacaca    240

taatggtgat gttttattat taatttacta taaacttatc tttggagatt tttctttata    300

tatgtatgtt atatgggcca tttcgaaatt ttgatcacat ttgggcatta tttttttaga    360

aaaaagaaat ttgagaaata gtgttttttg gcttcttaac aatctttata gtttgagaag    420

gagttgcggt caaataaata aaaaaattaa aatatataaa ttattttaat ttttgccgac    480

gtttcgaccc actttgcagg tcgtcttcag ggctacaaaa gatacaaaca tgttg         535
```

<210> SEQ ID NO 54
<211> LENGTH: 686
<212> TYPE: DNA
<213> ORGANISM: Nezara viridula

<400> SEQUENCE: 54

```
gggggcagtc gagggtgaga tggcggacaa ggccgcacct tttcatcatg ggccaaaatc     60

cttctcttct atgtatgttt ttacgcttgc cttatgggct ttttctcagc cctcctcgcc    120

ctgttcttcc agactctcga tttcagagca ccgaagtggc aacttaaaag ttcattgatt    180

ggcgataacc caggattggg gttcaggcca atgccaccag aatctcatgt agaaagtaca    240

cttgtctggt ataaaatcag cgataataat tacgcaacgt ggacgacaaa actggatgac    300

ttcctaaagc catacagaga gccagattca caatgggaag cattaaagca aaattgtgac    360

tataatgaca cacctgattc tccagataaa gtatgcaagg tagacatcag ttcatggtca    420

ccttgtgtca aagaaaacaa ttacaactac cataatgctg ctccatgtat tttccttaaa    480

ctcaacaaga tatttggttg gatgcctgag ttctacaatg atactgaaaa gttaccagaa    540

aacatgccaa cagatcttaa aaatcatatc aaggcagaaa aaacaagtca tgcagcagaa    600

ttgagtagat taaatacagt atgggtgtct tgtgaaggag agaatccagc agatgttgaa    660

aatgttggtt cgatacaata tattcc                                         686
```

<210> SEQ ID NO 55
<211> LENGTH: 50
<212> TYPE: DNA
<213> ORGANISM: Nezara viridula

<400> SEQUENCE: 55

```
gggggaggt ctggttcacc catgtgtcag gttaattcat acgaaatccc                 50
```

<210> SEQ ID NO 56
<211> LENGTH: 666
<212> TYPE: DNA
<213> ORGANISM: Nezara viridula

<400> SEQUENCE: 56

```
ggggaggacg actatacttt ttatattttt tttttaatcg cacgattttt attttaaatt     60

tgaaaacgta tttttcctat taatttcatt ttcctggaat acgaatgagt gtgatattaa    120

aaaataattt ccttatttcc tttgcaataa ctgttaatgt cataaataca gagataaacg    180

gactagttat ttattttgga aattaaattg tcttgaaggc agactacaaa caattgcagg    240

ctcgcaaacg gtttctcata aaaaacataa tatcaatttt tttaaattta tgtttaatat    300

gcatgttgta tcgatcagat atgaaaaaaa ataaaaatat tattaaaata gatataattc    360
```

```
taatatttat ttttgtattt atttatttga gtgtgttttc ttcataaatt gaagtttccc    420

tcagccaaat tccttcccca gtcgtttcat ccacttctcc ctgcctatcg cattctccta    480

cgtcaatcct cggctctata ctctctgcca caacatctct ccatatgacg agcctttcct    540

ctctttttcc tatcctcggt ctcccagtca aatgtcgttt tgggaagcag ttcgctatta    600

gcccttttc tatgctcata ccactttaat ctcctttctt ccattatctc ttatatatta     660

atctta                                                               666


<210> SEQ ID NO 57
<211> LENGTH: 586
<212> TYPE: DNA
<213> ORGANISM: Nezara viridula

<400> SEQUENCE: 57

gggctcctcc tctctcgatc atagagacct caagtcgacg aaatgagaca tgtattcaat     60

gatagtaata caattaccat caggttgtgt ggatgcgtac cctatgcctt gcgttatctc    120

gaaaatagta cgttttggac ttaaaaacgc aggatccgat agttccggag gaactattcg    180

ggtcttgctg tacgcatcaa aatcttcaag gtccaatttg ttccgcatcg atctatagac    240

ctaccaccgt cccagtattg aagcctagca aaatgtttgt atcgacttta cttattttag    300

aaagaaaaac aaaagcggag aatacgattt gcttaccccc cgtgaaattc tgaatccaac    360

ggtaccccat tcatggtatt tgagcatgac aggagcttat atttggtaca aaaccgattt    420

cgagccttac tgtaataata tatgtacgga tttaagccca atatgaaaat attcttctct    480

gtttttggta ataataactt ccgattaaca acaattgatt tatttgttgt attttcaagt    540

ctataaaatg gacttaataa acaagaaaaa tgtaatttat ccacgg                   586


<210> SEQ ID NO 58
<211> LENGTH: 431
<212> TYPE: DNA
<213> ORGANISM: Nezara viridula

<400> SEQUENCE: 58

gggggaacgt gaactttttc gactaggatt tagtcgcaat gtctttttttc aatttttttct   60

ctcaagttgt gccttctgtc aaggcccaag atgacgaaga agagctggta gatccgcaag    120

tggtcctcaa ggagcaatgt ggtgagaaat gctcgaatta taaagataaa ttagactctt    180

gtaatggaag agttagctca agatcacaga ccaccgaaac ttgctttgaa gaactcattg    240

acttcgttca ttgtgttgat cactgcgtag ccaaagacat attttccaag ctgaagtgaa    300

tgtttctaaa aaggattgtt tttaaatttg tagctttaat tgttagtcat atgtacatat    360

aattctgtgt tttaagttaa acaattgttg aaataataaa ttcattagct cagctgagtt    420

attgtttatt t                                                         431


<210> SEQ ID NO 59
<211> LENGTH: 606
<212> TYPE: DNA
<213> ORGANISM: Nezara viridula

<400> SEQUENCE: 59

gggggtctta cgaaagttga gttgtagtta tttttatctt ctctgagaaa ataatgtctt     60

gcaaaacatt attcagtaac aaactttact ccagactgat aagtcttcct ggtataaata    120

tgagccaatc ttcttattcc actggtttgg gagatctggg tagtggtgca ggacaggggg    180

gtggagatgg aggatcagta agacaggctg gaggtagctt tggaaaaaga gaagctggat    240
```

```
tagaaggaga atattttaac agattaaaac aacaacagct tgaacaattg aagagcagca    300

tgcacgatga cgtaaagttt catgaagaac aaatcaagag acatcaaggt gctattgaaa    360

aaataaaaag ccgtatcaac agtgcagaat aaatttagta tttattttac accaataaag    420

ttagcaatgt tagatttaaa agatattgct ggcctattga tattgaagtt ttgggattta    480

tcaatatatt atatcctcat ttattatatg tggaaaattt atatattgga gaaaaaaata    540

cgtagtatat aattttacag agcttttaaa tgatattatg aaacatttgt atttcattaa    600

gtattg                                                               606
```

```
<210> SEQ ID NO 60
<211> LENGTH: 615
<212> TYPE: DNA
<213> ORGANISM: Nezara viridula

<400> SEQUENCE: 60

gggggttgtc ctttcgtgta gtggcatcgt tccagatggt ggtcaattca aaaatccaga     60

aggccggagg agctgagcct gatgcttttg aggcatctat tgctcaagca ctcttagact    120

tggagatgaa tagtgatttg aaggctcaat taagagaact tcatatcact aaagcaaagg    180

aactagattt ggctggaaag aaatctatca ttatctatgt tccaatgcct caattgaaga    240

atttccaaaa aatccagatt aggcttgtca gagaactgga gaaaaagttt tctggaaaac    300

acgttgtgtt cgttggagat aggaaaatcc ttccaaaacc tactaggaaa tcgagaactc    360

agagtaaaca aaaaaggcca aggagtcgaa ctcttacatc tgtttatgat gagattctgg    420

aagatatggt gtttccagct gaaattgttg gtaaaagaat ccgtgtaagg actgatggca    480

aacagatcat caaggttcat cttgacagat tacaacaggt caatatcgag aacaagattg    540

acacattcac atcaatttat aagaaactga cagggcagag aagttacttt tgagttccca    600

caaccctatc tctaa                                                     615
```

```
<210> SEQ ID NO 61
<211> LENGTH: 517
<212> TYPE: DNA
<213> ORGANISM: Nezara viridula

<400> SEQUENCE: 61

ggggagtcct agcatgtgct catagcaggc gggtcggagt gtgctctcga gagattacga     60

tgccgtcgtc ctgttcctgg atatttcctc tgctcttctg ccttcatcta gccctagcga    120

aagttcaata taaaacaaaa tgcagcgacg acacaatgga ggtagaactt cggcgcaccg    180

atgacatcaa cgctatttac ctcgaaggac tcaagcatta tccagatcca gcctgtaagc    240

ctgtattatt cggacatcag gcagtattca ggttgtcttt gaatgacgta ttcaaatgtg    300

gcataacaag ggtcatcaac caagcaaatg gcttaagaac attttaccat agaataataa    360

ttgaaacaga taataaagat gcacccaaag aagcaattca agtcaaatgt ttgcaagctg    420

gaaatcacac catctttaaa agaaacgtac tgcctgctgg atttcaagag cccatagatt    480

tggatattac tacatcctta acagggcgtg cccctca                              517
```

```
<210> SEQ ID NO 62
<211> LENGTH: 631
<212> TYPE: DNA
<213> ORGANISM: Nezara viridula

<400> SEQUENCE: 62
```

gggggtgtca tttatttcaa tgatggtgtt tgctgtcatc tcaaccatgt tgttgttagt 60
cagtttgatt ctatattgca aaaattcagt gcaagaagta aaacgtttgg catttataaa 120
tggttatgtt gattcaatgg tatgcacata cttttatggc tatttgaaaa aaataattcc 180
tgatcaagga actggaacag gaggtttata tgacaaaata atgatctaca aagaaaaaca 240
aaaccttacc aacaaagatt ttccgtttca taaaatcttc attattatat gtgcatccgg 300
atttgttcca cctacccttg aaaagataga taacaaacgg atcgaagcta gaaagcactt 360
agatccgttg gttttaaata atgctggaat aaatggtcga cgttatacga cagctgtata 420
caaggtcaag taccgcaatt taaaggatca cattactgtt gccatggagg gtactcctcc 480
attacttact ctgtcggacg cttctgcaga agatccagaa ctaaaaaata acaagaaaca 540
aatcattgaa atgttttata aaagattatc aaagaaattg gctgaaaatg cagaatttgc 600
aaattcttat gaggttgtat tttacaatga t 631

<210> SEQ ID NO 63
<211> LENGTH: 572
<212> TYPE: DNA
<213> ORGANISM: Nezara viridula

<400> SEQUENCE: 63
ggggtggtgt ggaaaggtga ttagagggtg ttaatacgtt aatagaatat ctatttgatt 60
aaacttgtgt attgtttata ttgttattag ttactttgtt gtatgtgaaa agtgcaacta 120
gttaatgttt aaagcattaa taggatacat atatatttga ccaaacttgt atagtgttta 180
tttgatcaaa cttttgcagt gaagcccttt acagtttagt gccaggtgtg aggtgcaatt 240
tggcttctta ataaaaatta attttcccga ggatatcacc agtacagagt tgcctgttgt 300
gtatattctt tctgaattat ggatgaactg cagggagaag tggatgaatt gaagcgacag 360
cttgagtttg agaggcataa ggctgaagtg gctagattaa ggcaacaaaa tgaagatcta 420
agagtttacc aagttcttga tgagtgtgaa gggtcagatg ttgatgataa cgtagaacat 480
cattcagaag tagaatttga cataagcgac aatgaaattg aagctatgct ggaagaaggt 540
tttgaaaaag gagtaaaaac aaaggacgaa tc 572

<210> SEQ ID NO 64
<211> LENGTH: 70
<212> TYPE: DNA
<213> ORGANISM: Nezara viridula

<400> SEQUENCE: 64 gggggggggag gtacgatgtg tccctgtgtc atgtactgta catcgattct gtgtacaaca 60
ataaagtgcg 70

<210> SEQ ID NO 65
<211> LENGTH: 621
<212> TYPE: DNA
<213> ORGANISM: Nezara viridula
<220> FEATURE:
<221> NAME/KEY: misc_feature
<222> LOCATION: 547, 548
<223> OTHER INFORMATION: n = A,T,C or G

<400> SEQUENCE: 65
ggggaagtaa cagctgatac tacagacacg gcagcttgaa tgatgtgtct catcagtttt 60
atttatttct gttaattaag gtgaattcgc gatggcagta acattgtggg gattgttaga 120
ggcttcgata ttgttcctca atgccgtttg tgttcttcat gaagaaagat ttttagcaaa 180

```
aatgggatgg tggagagcac caagtataca aggctttggt gaaaaaccta ctctgaaaag    240

ccaatgctta catttaatgc attctatcag aacagttacg aggataccgt tgattttcat    300

caatatagta gtgattttag taaaacttat tttgggttga tacacttttg actccattcc    360

ttgaatcctc taaaatgtct gtgaaaaagt tcatagatat tggtgccaat ttattagatt    420

caatgtatca aggtatttac catggaaaga gcaaacatga acccgatttg tccgatgttc    480

tgacccgtgc atggggcaat ggtctggata agattatttt aactggtgta agtttgaaag    540

aaagtannaa actttagatt ttacagacac tgatagccga ttgtattgca ctgtgggctg    600

ccatccaact aattgcgatg a                                              621
```

```
<210> SEQ ID NO 66
<211> LENGTH: 577
<212> TYPE: DNA
<213> ORGANISM: Nezara viridula

<400> SEQUENCE: 66

ggggagaacc cgtcaccaat tggtaaggta tatcagtcct tacgctttct cgaataattg     60

tcagtatcca gtgtgatcta caattattaa cacatctaca atggcatcca atcaagtacg    120

ccaaaatttc catgctgact ctgaagaggc tatcaacaaa caaataaata tggaactatt    180

tgccagctat gcttacatgt ctatggctta ttattttgat agagatgatg tagctttaga    240

aggtttcaca aaatatttca agcatgcttc tgaggaagaa agagaacatg caatgaagtt    300

gatgacttat ttaaacaaaa gaggaggaag agttatcttt tctccaattg ctgctccaag    360

tacaaatgac tggggatctg ctgagaaagc tgtcgaagca tctcttcagc ttgagaaaga    420

tgttaatatg agcttgttga atcttcatgg tgttgcatca tctcatggag atgctaacct    480

ctgtgatttt atcgaaaatg aattcttgca agaacaagtt gactcaatta aatctcttgg    540

agatctgctc actaatgttc gtcgtgtcaa ggaagga                             577
```

```
<210> SEQ ID NO 67
<211> LENGTH: 544
<212> TYPE: DNA
<213> ORGANISM: Nezara viridula

<400> SEQUENCE: 67

gggtcagtcc tctcgtggct atcgttgtgt tctgttctct ctccatctct ctctcatctt     60

ctcgtctctc tacgctctct gttcaagtct caggctccgc cttttctacc gtcctctctg    120

cctgcgccac gacttgcttc acaactattg atatttataa gttcgcagta tcgtaaacct    180

attccattac tgttatggcg ttacttttaa aatatataga tgacatacaa gaaatatttg    240

acacaaatgg agacccacgg acgagggact ggccattgat gtcttctcct ttgccgaccg    300

ccatgatctg catgagctac atctacctgg tcaaggttgt tggccccaag ttgatggaga    360

acaggaagcc cttccagctg agacatgtcc tcatattcta taatctgttc caagtgatct    420

tctcggcgtg gctcttctac gaggtgagtc ccgtttagca accacttagc ttttagtttt    480

ggttacagga tcctacaata agctacataa tgacttttca atacttgtac tgatataaat    540

ctca                                                                 544
```

```
<210> SEQ ID NO 68
<211> LENGTH: 314
<212> TYPE: DNA
<213> ORGANISM: Nezara viridula
<220> FEATURE:
```

<221> NAME/KEY: misc_feature
<222> LOCATION: 297
<223> OTHER INFORMATION: n = A,T,C or G

<400> SEQUENCE: 68

```
aactgggcaa aaagaaggag caaacttagt aactggtggt tcaagagttt ggtaatgcag     60

gatattttgt tgcgccaacc atcttttctg aagttactga tgacatgacg attgcccggg    120

aggagatttt tggaccagtt caacaaattt tgaaattcaa atctctcgat gaggttatac    180

acagggcaaa tgattccaat tatggtttag ctggagcagt attttcaaat aacattaata    240

atataaacac cattatccaa ggtcttcggg caggaactgt ttgggttaac acctatnata    300

caataactgc ccag                                                      314
```

<210> SEQ ID NO 69
<211> LENGTH: 573
<212> TYPE: DNA
<213> ORGANISM: Nezara viridula
<220> FEATURE:
<221> NAME/KEY: misc_feature
<222> LOCATION: 78
<223> OTHER INFORMATION: n = A,T,C or G

<400> SEQUENCE: 69

```
gatcgtggcg gctgttcggg tcaatgtcga gcagcgggac gaagacaact gagtagccaa     60

tgattaatta ttgaactngg cgaatagagc gccatcaaat gtgccaagac aaacacagtc    120

tttcctatcg aatgcagttt cgaagttaat aaaataagaa tttttcttta cgagaccatg    180

ttcgaaaaac attggttgat taattatttt tctttttga tttattattt ccatggcagc     240

tgtgaaaagt gttaagtgca attttgagaa tttcaccgga acgctaattt ttctctccat    300

attgtgtcta aagtgctaag ttatactgca attataagta tgaacattcc tttgtgaata    360

attggtggaa actccaaaat tacaccggtg aaaattccaa gctttcaatc gcatttttcc    420

tttaatatga tttttgcact tacactatga acaggttcca tacatttttt aaagcgtatt    480

tgtatcaaat ttttaattat ttttgcatta ttatatgaat ttgtgtgatg taattatgat    540

gtaacttgtg cctttataaa cgattatacc acc                                 573
```

<210> SEQ ID NO 70
<211> LENGTH: 578
<212> TYPE: DNA
<213> ORGANISM: Nezara viridula

<400> SEQUENCE: 70

```
ggggagacga ttctgagctg ggttgttgta attgttggga ttgattagta cataactgtt     60

accatgaggg aaattgttca cattcaggca ggacaatgcg gcaaccagat tggtgccaag    120

ttctgggaaa tcatcacaga tgagcatggc attgacccca ctggctcata ccacggtgat    180

tctgatcttc agcttgaaag aatcaatgtt tactataacg aagcgtcagg tggaaagtat    240

gtacctagag caattttggt tgatctggaa cccgggacca tggactcagt acgttcagga    300

ccttttggac aaatctttcg acctgacaac ttcgtttttg gccaaccagg tgcaggaaac    360

aactgggcta aaggccatta cacagaagga gctgaactcg ttgattcggt tcttgatgtg    420

gttcgcaaag aggctgaatc atgtgattgt cttcagggtt ttcaactgac tcattccctt    480

ggaggtggca ctggttctgg aatgggaacc ctgttaattt ccaaaattcg tgaagagtat    540

cctgacagaa tcatgaatac ttattcagtt gtaccatc                            578
```

<210> SEQ ID NO 71
<211> LENGTH: 527
<212> TYPE: DNA
<213> ORGANISM: Nezara viridula

<400> SEQUENCE: 71
gggcaacaag ggacacctat agcagaatca ccattaacat ctatgaatag ataccttcat 60
tggagatgat acaaatgggt cacggtgatg gatcttttta ctaaagcagc aatggtatac 120
atgatccagg agcggtggtt ggaagcaatg ttaggagccc aaaggacata gttccaattt 180
tatggtgtgc ctgaccgcat tgcatcggat gggggcaagg aattcaacaa tgccaccatt 240
ctagtagaag cgaaaggttt ggagatcaca tagcacatta acacccaaag agtagagagt 300
atattgaacg ttgcaaagca cgctaagtga cctgcaaata caccaactga taaaaggact 360
agagccagat gtagtgaaga caaaagcagt cacagcatat aatcagtcta ttgtgttttt 420
tgtttttgtc cacccccttgc tcgccttcta ggttatacgg gtattttctc gggcatcagt 480
atatgatttt attggtgtaa tattaaagtc tgatgacagt tcactcc 527

<210> SEQ ID NO 72
<211> LENGTH: 575
<212> TYPE: DNA
<213> ORGANISM: Nezara viridula

<400> SEQUENCE: 72
gggggattgg gggaacgtgt gtgaaatgtg ttgtgtaaaa tttatgtatt gatttttata 60 ttttttagt taaaataaca gacaatttgc caaaatgggg aacgttaatg catctagtca 120
aaaaagtacc tcggacgcat ttgctgcatt tgaaccagaa aatgttgttc ctttagtgga 180
tgaaaagttg gaaaatccag ggtctatgga agagctgcac aaaaaatgta aagatatatt 240
tcctgtaaat tttgaaggag ctaaaatagc tgtccaaaaa ggtctgagca atcatttcca 300
aatttctcat tccttaaata tgagttcttt ggcaccatct ggttatcgat ttggtgctac 360
atatgtcgga acaaaacaat atggccctgg tgaagcatat cctgtgttag tgggtgacat 420
agatccagtc ggaaatctta atgcgaacat ttatcataag tttaatgaca acataattgg 480
gaaaattcaa gcccaggtac aaagtagccg ttgtacagca tcacagtacg ttttagatta 540
cagaggtagt aattacacag ctacagttac gtttg 575

<210> SEQ ID NO 73
<211> LENGTH: 117
<212> TYPE: DNA
<213> ORGANISM: Nezara viridula

<400> SEQUENCE: 73
ggggcccact cgtcggtctg ggaggcgatc ttgtgtccag cttctttgtg ttgtgtcagt 60
cctaaatcgg gtctttttag ccttcacagt cagtgttcat cgccgtacgt catatat 117

<210> SEQ ID NO 74
<211> LENGTH: 301
<212> TYPE: DNA
<213> ORGANISM: Nezara viridula

<400> SEQUENCE: 74
gggggctact gtatctatta tataacttgt gtccattata taattaaata atcgttgatt 60
cctcttttga aaaaatggaa gatttaaaga aatattaata aataaatatt tttttatgat 120
atctcaatga tttttgactc catataattt tgtgccatga gccttatatg tacacttttg 180

```
ttttccttaa ttggattttg tgatatctta accttattta tgtcactcat ccatatgagt    240

attttcattt acacagctat aaatatatct attatgaaaa ctattttact aataaaattt    300

t                                                                    301
```

<210> SEQ ID NO 75
<211> LENGTH: 615
<212> TYPE: DNA
<213> ORGANISM: Nezara viridula

<400> SEQUENCE: 75

```
ggggacaaga cttcttcaag atgaaagctg cactctgcct taccactctt ctcgctgttg     60

tctgcctttc ttgggcggca actccggaat acaaagctaa agttgttaca gcaattagtg    120

cttgctcaaa agaatacaat gctgaactaa aggatattct ggaaatcata aaacaaaata    180

aacttccaga aaccaaggat caaaagtgca ttattggttg cttctttgag aaaatggact    240

atgtgacgga tcacaaagtt gattgggaga aggttaaggc aatgaaccca cagaaatatg    300

acaccccctga tttggtagaa aaaatcaacc aagttactga cacttgtgct aaagttgtga    360

ctgaaggatc aaccgacatt tgcgagttag gtgtcccagc aataaaatgc ttgaaggagg    420

aagcagataa ggtcggattg ccaaaaccag aagtaaagtt tgataaacac tgatgccctg    480

atgatgaaaa ttttatcgat aaaggacaat aatacactct gggatacata cttaatctac    540

aaaagccaaa ttaacattta acgttaatgc catttagaaa tagttctttt attttgtgtg    600

tgctatcctg tataa                                                     615
```

<210> SEQ ID NO 76
<211> LENGTH: 403
<212> TYPE: DNA
<213> ORGANISM: Nezara viridula

<400> SEQUENCE: 76

```
aaaagaaatg atttattcta attagaatag aaagtaatga tgtattcatt gtttctgata     60

tgttgttttg tgactgttgg aagtgcaaca tcgatcagtg aacttctctt tccaactcat    120

aataaatgtg gttgttttta ttatgagcaa tgccccaaac ttcatgtacc taactgtact    180

attgaagatg aaaattatga ggatctttgt ctacaaaatt ctgcatcttc aaactctcct    240

gagatatgca acaagtggtt tctggaaggt tttaataaac agttaatctc agaaaatggg    300

actctcaaga tatcaatttc gttctcttct gccttattcc agaaaattcc tcttagtgtt    360

catctctttt atcaaaatca gtgcttggat attaacaata ata                     403
```

<210> SEQ ID NO 77
<211> LENGTH: 514
<212> TYPE: DNA
<213> ORGANISM: Nezara viridula

<400> SEQUENCE: 77

```
ggggtaccga aaatttatta cttcatcgaa aggtgccccc catgaaaatt caagaccccg     60

tcaaaatgtg cccccctcaa aaattttgat ggcgttcctt gccccttgaa accccccttct    120

ggacacctct gcgtatcatt acacacatta tttcacggtc tgttgtttaa tgtactactc    180

aaacagtaaa ccgatcgatt gagctggcag gaaattaaaa gtaactacct atgcgtgtag    240

aaaaaaccat ctgtattagg aaggcattga taaagggata gaggcgaagg aggaagattg    300

ttgttgatta ggaatggcaa gtgtttgaat ctaatcggaa aggaaagatt gaactcagaa    360

aatatagaat taaaatcact attccattgc aaaatggttg tgattttaat ttataaaaaa    420
```

```
tataaagtga ttcatgagat taaaatcttt agattagttg agcgttgctt ttagcttggg    480

attgagtttg gcaacatagc gatattctag tata                                514


<210> SEQ ID NO 78
<211> LENGTH: 326
<212> TYPE: DNA
<213> ORGANISM: Nezara viridula

<400> SEQUENCE: 78

tttaatatat tcttatttgt tatttctaat ggtaagtatt aagttctgat taatgtataa     60

ttttttgtt tggtgttgca taccgtaaag atgtaaagat cattggccac ataatatggt    120

attatggaaa tttattgctt gccaagataa caggataacc aaccatagct tagtaaccta    180

tcccttggag gccaagtcaa tgtacttccc ttcacttggg tttacgagca ttgaggaatc    240

ggtctagata catggattat ggctcttttc agggtcacca ggtgcacaaa tacttgcatt    300

tcttcaatga aacagattgt acatac                                         326


<210> SEQ ID NO 79
<211> LENGTH: 341
<212> TYPE: DNA
<213> ORGANISM: Nezara viridula
<220> FEATURE:
<221> NAME/KEY: misc_feature
<222> LOCATION: 304
<223> OTHER INFORMATION: n = A,T,C or G

<400> SEQUENCE: 79

ggggaacgca acacttcttg aggaaagcgc tcaactgctc ggaccaaaga ttgtttgtgg     60

ttttccaact tagggtatgc tctgtggcat gccatccttt ccagttcggt ccaaagccga    120

taagctaggt cagggcctcc tgagggccaa tccgagacag agatgaactc tggaatgttc    180

ctttgcagcc actgctgagt tgacctggcc ttgtgagctt gagcggaatc ctgctggaaa    240

acctaatgac ttccagcaaa cggagtatca tttagatgct tgacaacaag ttccaaaata    300

tcancctgat agtgtttagc agctgtttta actccttttt c                        341


<210> SEQ ID NO 80
<211> LENGTH: 615
<212> TYPE: DNA
<213> ORGANISM: Nezara viridula

<400> SEQUENCE: 80

tgttcatgaa gactatagat cacaaaagaa tgacattgct ttattacgtt tagatgaaga     60

tgttgttttc actgataaaa taagacctat ttgcctacca caacctgcta gcctaagatc    120

ttctactttt gatagaaaat atccatttgt agttggctgg ggtgaaacca gtctcgaggg    180

tccttcttca gacattcttt tacaagtaca agttcctgta gttgacaatg atagctgtaa    240

aaaagcttat gcaaaacacg gagctatcat aactgagagc caactttgtg ctggagaaaa    300

gaaaggaggc aaggattctt gtaggggaga ttctggagga cctttaatgc taccacagaa    360

tggatcatat taccaaattg gtattatctc ttttggttat aagtgtgctg aaccaggata    420

cccaggggtg tatgctcgtg ttacgtctta ccttgattgg atcaaaaata atatggaata    480

agattacatt ttgttttaat tttaccaaat agcacaaaca tatctgtgaa actgcaaaaa    540

gtgtattaag tgcaattttg tgaattttta tgggtattcc tccaatgata atttatctct    600

ctttctttgt ggagc                                                     615
```

<210> SEQ ID NO 81
<211> LENGTH: 53
<212> TYPE: DNA
<213> ORGANISM: Nezara viridula

<400> SEQUENCE: 81
ggggtggagg tctgatgcac cccagtgtca tgaaactgtt aatggtaaaa cag 53

<210> SEQ ID NO 82
<211> LENGTH: 604
<212> TYPE: DNA
<213> ORGANISM: Nezara viridula
<220> FEATURE:
<221> NAME/KEY: misc_feature
<222> LOCATION: 467
<223> OTHER INFORMATION: n = A,T,C or G

<400> SEQUENCE: 82
tgatgacatt ccattaagta ttttatttga cttatattgt ttcatgacta tttaaaaaat 60
aaaaataaaa taattcatta tttttaaaaa ctgcattgta ataattcata tttatattca 120
cttcttttgc atatgattca tgatagtatt tattattaaa taaaatagga atacaagtat 180
tttacttaat agggttataa aattgtaatg aaatatttgg aatttgaaag aaatttttaa 240
taataagttc tacaataaaa tttacttaca tgttttatgt aatagaaaat aattatgtgt 300
aatggagctc aatatttatg tgtaaataaa taacttaagt ccagtcagtc cttaagaatt 360
taaaattttg ttgtagtatt tagtatttgg aaatatcaca aagatgcaga attaaagaaa 420
aagaagaaaa gttgggagaa ttttcataat tgagacaaaa agaaggntaa atgaagagaa 480
gagataagaa aaaaaaaaga acttgaatag tgattaaaga gagataattt aaaataaaac 540
atcatgtaag taaaatcaaa aagctgaaaa cattcattac atatgttttt tctacaaata 600
tttt 604

<210> SEQ ID NO 83
<211> LENGTH: 623
<212> TYPE: DNA
<213> ORGANISM: Nezara viridula

<400> SEQUENCE: 83
cggccggggg agttaaaaga cacatgttct atatatcatg cctctttgct attctttcgt 60
tgaaaatgaa aattgataga atgccgtgat aagtagtcac tgttgctagc tttacttcaa 120
aatttgaatt cgaatatgtc ctacagcatc attctcagtc atttgagtag gttcccacta 180
ttctcttact caagaggata tagtgtcatt accagccaaa atgtgaaaaa tatccctgtg 240
agtttcagat attattcatc tggtggaagg aggcctaatt ttttctccca atttatagaa 300
aatgttaggc aagacttggc aaaaagtaaa gagatgaaag aaagtttgaa aaagtttagg 360
gaagaagcgc agaaattaga acaatccgaa gctttacaga aagcaagatg attgttgttg 420
cagagccaag tttcatactg ttgaatcaga agcatcgaaa ggtggtgaag ttttcaagga 480
gaaattggac cacattaaag ataaagtcag tgatgtgctg gaggaagcag caaaatcaga 540
aatcgggaaa aaagtcagct gggagcagaa attggaaaga ctgcgagggg agctgctgaa 600
acattatcag aaacaggaca gca 623

<210> SEQ ID NO 84
<211> LENGTH: 637
<212> TYPE: DNA
<213> ORGANISM: Nezara viridula
<220> FEATURE:
<221> NAME/KEY: misc_feature
<222> LOCATION: 7, 29, 30
<223> OTHER INFORMATION: n = A,T,C or G

<400> SEQUENCE: 84

```
ggggagngta ataaggaagg ttttgaatnn tgtgaacttt gccttattca aaataattta     60

aggaaatgtc tttatcaaat attttgggaa gaagccttaa tgtcttaaaa aataaaagtt    120

tttgtagtgt aatacctggt aaaacttctt cgttattgaa gtatcctgct gtttcttctg    180

tatcatgtct taacttccat aaaatatcaa atgaaaaacg aattgcccct tcagaaccca    240

aggtaaaact gactgatgca gtacgacatt tttccataac ccaacctaaa ctttctggac    300

atggtgacca ttccaaactg tgggtctatg aacgatatgt gtcagcagca ttactgggta    360

ttgttcctct tggtttaatg atgccgaaca tactctttga tctcttgatt gcagtagcca    420

gtgtcatgca tatacattgg ggtattgaag ctattgttat agactacatc cgcccaatca    480

tttttggtaa tttgatatca aaattagcgg tctactttgt ctatctcctt tcaatattta    540

ccttggttgg tcttttgaat cttactttca acaattgtgg ccttgctaat agcatcaagc    600

ttctttggag aataagcaaa caagaataga agtaata                             637
```

<210> SEQ ID NO 85
<211> LENGTH: 638
<212> TYPE: DNA
<213> ORGANISM: Nezara viridula

<400> SEQUENCE: 85

```
gggctgttct aagattttgg gcgagcgagg agagtgagtt cgggcgcgct cgtattcctt     60

tggttcttcc attacaacca ttctttgtta cgatctttta tttctccttt agttaattat    120

taaattcttt catattctat atttaacaat tctttaaatc ggagatcaat gtgaaatggt    180

taattatttc aaataaaaaa aattaaaggt actttagaag aagaaatagt gaaattagcc    240

atatgaggcc tgtttgagaa cataaatcag aataaaacta cattttatta taaaatgctt    300

aatttaacac tgataagatg aatttaatca aaactttaat gtggtttttc tagaaaatcg    360

taaacatgtg tttactccaa tatataaagt ggcatttcca gttagccaat tttgacgaaa    420

aatttgccgt aacatcccca gcttataaaa acctcaaata tgcaatttca cttttataag    480

atttcggttt tttgagctag actgttaata cccacacaga cagaccattt tgcgggactt    540

ggttatttgg actcagggga cttcaaaacg agtatttcca ttgaaaagtg agattggaaa    600

attttcacga tcacaatact ttcttttact atacattt                            638
```

<210> SEQ ID NO 86
<211> LENGTH: 444
<212> TYPE: DNA
<213> ORGANISM: Nezara viridula

<400> SEQUENCE: 86

```
gggggcagtg gattttctga aaagatggct gcttcgttgg gtcgccaata tctcaggaag     60

tttaattctt ccaaaactct ttttaagagc ttccttcagc ctctgctgta gctggagatc    120

atggtgctgg tgttaaactt tggcgtaatg tgagttattt tgctggcttc ccttctgttt    180

tgttatgcat gttaaatgca tatttggctc atattcgtca tgaacatgca agaccagaat    240

ttaagaaata tgatcattta agagtgcgta ataagaaatt cccttgggga gatggaaacc    300

gttccctgtt tcacaaccca cacaccaacg ccttaccaga tggttatgaa gcgtaactag    360
```

```
tttaaaaata gtaaacagca tgtatgtaat taaactgaaa tcattatgtt atcatttata    420

agaataaatt taagggttaa taac                                           444


<210> SEQ ID NO 87
<211> LENGTH: 69
<212> TYPE: DNA
<213> ORGANISM: Nezara viridula

<400> SEQUENCE: 87

ggagggggag gtacgatgtg tccctgtgtc atgtactgta catcgattct gtgtacaaca     60

ataaaatgc                                                             69


<210> SEQ ID NO 88
<211> LENGTH: 652
<212> TYPE: DNA
<213> ORGANISM: Nezara viridula

<400> SEQUENCE: 88

ggggaaacca aagtatggct ggagtacggc aaaatgtctc tggaacaaac agcatgtgaa     60

gatttaaagg cttttgaaag aaggcttact gaagttattt catgcctaca acccgcgact    120

ttaagatgga gaattctctt agcaatcata tcaacatgta cagcaattgg agcttggtat    180

tggttgacag accctcatac atcagatgtt tctttcaccc aaagtctcat taatcatcca    240

ttcttctcta catctagcat aattttagtt ttgctactaa tgtctggtat acacaaaaga    300

gtaattgctc catcgataat aactgcaagg accaggatag tattgactga ttttaatatg    360

tcttgtgatg acactggaaa gcttattttg aagcctagac cagctcaatc atgacatgaa    420

tagaaatagt cagcaaatgt acataattaa gaattggtta tggtgaggct gtcattgaaa    480

gtggaagaca cttagctcct ttttttgtta gaacagagtg ggaaagaatg tttaattatt    540

tctttttgag ttgtatttta tatttgaagt aattttttat ggtactcgct tcctttttat    600

aaagattgtt gggataactt agtgtcttct atttgtcaag ataataatga ac            652


<210> SEQ ID NO 89
<211> LENGTH: 340
<212> TYPE: DNA
<213> ORGANISM: Nezara viridula
<220> FEATURE:
<221> NAME/KEY: misc_feature
<222> LOCATION: 14
<223> OTHER INFORMATION: n = A,T,C or G

<400> SEQUENCE: 89

ggggacagtc agtngcaaat atgatccaac agctggtagt cctcttctcc ttggtggccg     60

cctcttacgg cttcttcttc cctccgggac tcctcggcaa cggcaccaac cctctggctc    120

ccttcctagg ctgaggattg gttcattctt ttacacttaa actaatttca aattgaagta    180

actatgaaga taaaagtaca atgaattgta cccaaactta caacttttaa gttttcaact    240

atgaaatcaa atgcaactct agctgtattt catttacttg tgtattatac caaattaatt    300

ttttagatat tatataatga ataaacattt ataaaacgcc                          340


<210> SEQ ID NO 90
<211> LENGTH: 492
<212> TYPE: DNA
<213> ORGANISM: Nezara viridula

<400> SEQUENCE: 90

gggggagcca ccggtaactt ctcttcttat tgcatttgtg tgtgtatgtt ccattgttaa     60
```

```
tccggcttat gtggtacttt gttgcacgaa ccagtgaaaa agatactttt aggcaagacg    120

ttcattcccg aacaggtctt cgatgaatat ttaaatggtt tagccgaatc agaattcagg    180

ggtgatcatt acgaccttct aaagcacaac tgcaataact tttcagacaa tctcagtcgc    240

tttctcgtcg gcaacggaat accagaatac attttgaaac tacctgagga aatacttagc    300

acgccatttg gacagagatt tcaaggattg attgaacaga tcagccagaa ttctccgaac    360

ttgcagccta cccaacggag agccgcctca cctgaattct accaattgaa ttcagatatt    420

gaagctgcta gacatcattc ttctcttctg agggaaaaac gtaatgctct gtgtgaaaaa    480

ttagcaaagc at                                                         492
```

<210> SEQ ID NO 91
<211> LENGTH: 503
<212> TYPE: DNA
<213> ORGANISM: Nezara viridula

<400> SEQUENCE: 91

```
aattattcag tatcctggat aaacatagtc gactgtatat aaatcaaaat gtatatttta     60

gattttaatt gttttattta ttttcttttt tcagatgatt cattaagttt ttttaacata    120

aataattgaa tcatactaaa tttctgaaga gtgccgagtt tatgaatgta cttttaaata    180

atgggctgta ttatgattga aacaagtatg agcctataac taaagaaata taccatcatt    240

tttgaagtaa cttgatgcat ctcaattttc taactttcca caagaataaa aaaaactagt    300

caatatttat ttataactat aaaatatatg tattttattt ggattcatta tattaattta    360

aattgtgtta aattaatatt tctttaggat gttttgaata aaatgatgtg tatatcttga    420

tttctacagc tatgatatat taatgatctc atttattaac aaaagtaatt cttttcaaat    480

ataaatttca taaatctcca taa                                            503
```

<210> SEQ ID NO 92
<211> LENGTH: 647
<212> TYPE: DNA
<213> ORGANISM: Nezara viridula

<400> SEQUENCE: 92

```
ggggaaaaac gttggtcatt cttggggtgg cttagttgtt tattgaaatt atttctttta     60

aaatggcaat gccaagaagt tatggtggct tatctgatta cagaaccgtt cctgcacctt    120

cttttagtcc atattctgaa aatggaggga gtgtagtagc tgtagctggc gatgacttcg    180

caattatagc atctgataca cgtttaagta caggttttca aatttatacc agaaaccagt    240

caaaattatt taaattgtct gacaaaacaa ttcttggtag tactggttgt tggtgtgatg    300

ttctttctct tactaggctt gttcaaaccc ggataaaaat gtatcagtac gatcataata    360

aagttatgtc cactccagca gttgcccaaa tgctctctgt actactttat tataaacgct    420

ttttcccata ctatgtagcc aatattcttg ctggaataga tgataatggt aaaggagtgg    480

tttacagtta cgatccaatc ggtcatcatg aaagctcaaa attcagagct ggaggaacag    540

ctggagcttt attacaacca ctgttagaca atcagctcgg tatgttgaat caagaaaatg    600

ttcaagacaa aacatacact ttggaaaaag cccatgcaat tgtaaaa                  647
```

<210> SEQ ID NO 93
<211> LENGTH: 648
<212> TYPE: DNA
<213> ORGANISM: Nezara viridula

<400> SEQUENCE: 93

```
ggggtgtagt ggtagctgat ttatatgtat gtagttggtg tctttaacca tgattagaat     60
tttatttttt atctatagct gtgcttcatt attgagtgct agtagtcttc atcgaggata    120
taattttgtc ggaacagcca gtgaaactga tggtatattt gttaatgtta tttctgatat    180
caatcagtat ataaaagaca ataagtttga tgttcacaaa ctcatggaca ttcctataaa    240
tttaccattc acctctgtga gtttatctaa tggacaaatg agagacttct cttctattga    300
acttcataag tcttctattt taccacaaag tgaacgcagg ctgtattgga ctctaggagt    360
aggtttggaa aatttttcat tacaatacga cttcaaatca gatttttttg atgtttttaa    420
gaattcaggt agtctgaaac tgacagttcc aaaaaaataat attcttttaa gtggcacgat    480
agatatatca ttgccaaaat gttcgacagc aattgagatt gtgacttata tggattttcc    540
tgatgttaaa gttgaagtgc aaccttggag cgtaaaaaat ttcttttttta aaaatttact    600
agaatttgta gtaaatcata gtaaaactct agtaagccct gcattaaa                 648
```

<210> SEQ ID NO 94
<211> LENGTH: 550
<212> TYPE: DNA
<213> ORGANISM: Nezara viridula

<400> SEQUENCE: 94

```
ggggcactaa cttagtcttc gtgagtgcca gcttcttctt aaggtaattc accatggctg     60
agaaacccac aaaagaaaag gcggaaaaga agcctaagga gaaagtagaa aagaagccta    120
aaaagactat tgaaaaacct actgaaccag ctaagccaaa aaaatctaag cgaatgatta    180
ggaaaaaacc cgggcgtttg tatgctaaag cggttttcac agggtttcag agaggtcaaa    240
gaaatcagaa tgaaaatact gccctgctgg ctgtagaagg atgtaaaaca caggaagaca    300
gcaagtttta tgtcggaaag aagtgtgtgt ttgtttttaa ggctaaaaat cgaactaggg    360
ttcctggccc cgtaaaaaag aagaccaagg ttcgcgccat ttggggtaaa gtaaccagga    420
cccatggctg ctctggagca gtaagggcca agtccaagtc taatctcccg gccactgcca    480
tgggcaggag aattagaatt atgctgtatc cttctttgat ttaattttga aaataaattt    540
ttattatttc                                                           550
```

<210> SEQ ID NO 95
<211> LENGTH: 568
<212> TYPE: DNA
<213> ORGANISM: Nezara viridula

<400> SEQUENCE: 95

```
gggggttata gaggcggcac tggttagctg tatcacgttg ttatccactt tattttttta     60
cagataggaa aaaagaattt tgatagtgtg taatatttat cgagaaaaat ggctcaaagc    120
aagttgaatg atttagccgg acgttttagt caaaacccca aaggtgtcgg attaggttta    180
aaactattag cttttgccgg tgctacagct tatggagtaa gtcaatctat gtatactgtt    240
gaaggtggtc accgagcaat catatttagt aggcttagtg gagttcagaa agaagtctac    300
tccgagggtc ttcactttag gataccttgg tttcagtatc cagttgttta cgatatcaga    360
tcaagaccaa ggaaaatttc atcacctact ggatccaagg atttgcagat ggttaatatt    420
tccctcaggg tactgtctag accagactcg attaagttgc cttttgtgta caggcaactt    480
ggtttagatt atgatgagaa agttctacca tcaatttgta atgaagttct caaatcggtt    540
gttgctaaat tcaatgcttc tcaactga                                       568
```

```
<210> SEQ ID NO 96
<211> LENGTH: 544
<212> TYPE: DNA
<213> ORGANISM: Nezara viridula

<400> SEQUENCE: 96

gggggatata tttgatagtg ggaagagggt ttcgttattg aaataatgaa atgttcacta      60

ttttaatcgt gtagttcatc ttattttaaa atggcatttt ctttattacc aagaagattc     120

ttgaagtttc tctggaatga agaaagtgtt agaaggatat ctgttagctc tgtgaggttt     180

aatgaagatg aatctaacaa aaaatcatca gctgctgata agttacattc acttttacag     240

gatattatta aggatgaaac actaattaaa gaaaatatag taaaggcaac tgctgagcct     300

gttattgtgc cggtaaaaaa gaaacgtcct gagaaaccaa agaatttggg tgaaaaaatt     360

gttgattcgg caaaagaagt tgccaaaggt ttagaaggaa agcctgaaga aacagaagcg     420

caacttcttc atcgggtact ttttaaaaac aagcctctta cagaaagtgt tacaaaagct     480

gctgcaaacg atacattgaa ggagcttctt tcaggaatgg atgttgaaag aactccaaca     540

gtac                                                                  544

<210> SEQ ID NO 97
<211> LENGTH: 115
<212> TYPE: DNA
<213> ORGANISM: Nezara viridula

<400> SEQUENCE: 97

gggcgagtgt gaagaaaaag acatagactt tgttaaaact tctgatagcg gaatagataa      60

agaatatgac ctaccttccc ttccaacatt ggtttattac agaaacaaat tcagg          115

<210> SEQ ID NO 98
<211> LENGTH: 344
<212> TYPE: DNA
<213> ORGANISM: Nezara viridula

<400> SEQUENCE: 98

ggggagactc ggtgccaggc gtgttgttat aaacttttta gtccgtgtat agtgaagtgt      60

gtaggcatat caatacatat tttatgttat ttatagttat tagtacttaa aattttacca     120

agagagtgat agtacctata aatttcgttt caccatgtct aagcgtaaca cagaagatga     180

taaaccaatt cctgatattg tttttgattc caattcgaag actacttaca aaaagggaca     240

gtttttagga aagggtggtt ttgctaaatg ctatgaatta agagaagtaa ctaccaatgg     300

aatatttgct gggaagattg tatccaaacg acttcttacc aatc                      344

<210> SEQ ID NO 99
<211> LENGTH: 359
<212> TYPE: DNA
<213> ORGANISM: Nezara viridula

<400> SEQUENCE: 99

gggggtagta cgagatttca cgtgaagtta ttttcaggct taaaattttt actcccggtt      60

atatcttaaa cgatgtgata tagatgtaat gtcaattatt ttggtttcag atttagattt     120

agtattcaaa ttataggtga ttcgaatgtt attgaaaaaa gtggtgataa aggaacatat     180

agttgagggg cagtgtcggc acggtgttat tgagttttgt gttcagtcgt atttatatag     240

cccgggtgta atgtatcatt catacaattt tcagttcgcg gaaatgtttt aacctgtagt     300
```

```
tgtgtatact gatttctatg tgcttttaac tgttgtaaat tagaacttag gagtgtgta     359


<210> SEQ ID NO 100
<211> LENGTH: 640
<212> TYPE: DNA
<213> ORGANISM: Nezara viridula
<220> FEATURE:
<221> NAME/KEY: misc_feature
<222> LOCATION: 577
<223> OTHER INFORMATION: n = A,T,C or G

<400> SEQUENCE: 100

ggggagtgtc agtgtagtgt agtgtcgtga tcgggcttca tcatcatcaa caacactacc      60

acgcctgcgc atcattagcc tgcgcatcac ataataaccg acgcggaggc tggtcagaag     120

aagaggggag gaggtgcgac ttgaactggc ggaggcgtca ggagctcata cccagggcca     180

agttgagaca gccttctccg gaatattcca agtggggcga ttcaggaaag ccagtaagac     240

acacagttag tttttgtggc aaaattggac cgcagtcgtc atcaaaccag tgtcagaaac     300

agccggcaca aaggcacggt gatcgacaaa aggagaaaga acgattttgc accctgagaa     360

gggagccacg aagggagagg atggatcgga tgtatgacag caccgagagc ggctacgatg     420

gaggctccca agagaacatt cttgatgagc cacactatga atccatcaaa aatatcaaca     480

taaaaccgga aattcaaaaa gaacatattt acgaaagaat gaatggaaaa aaaaagaaaa     540

agaaacaaca gaatctcaaa ataataaaac agagganagt gaaaaaaagt aggccgaaaa     600

ataaatacga cgagacaaaa acggtaccaa atgggaataa                           640


<210> SEQ ID NO 101
<211> LENGTH: 680
<212> TYPE: DNA
<213> ORGANISM: Nezara viridula

<400> SEQUENCE: 101

ggggactggg atgaaacctt tcatggaggt gcaatttgta ttttgtttga ttgtgcttgt      60

tgattaaacg tcatttcttt acgatatgaa taaaagaaaa agagaagata gtatgtcgga     120

agactgtatg atggaagttc aggttagtaa aaatgcctgt tcaagttcag gagagtcagt     180

tatgcctcag tgtttaagga tgttggatga aataatgagg agtggaccag ctgaattagt     240

tgaacgtagc ttaaaccctc ttggtgcttc tccattggga aatcatgtga aacgtgttac     300

aggatatgaa atagcagaat tagatgaatt tacagcaacg gttgactcaa ggcttaaaca     360

aaccgttatg actaaaataa ttactatatc tgatcaaatg aaatttcttc gtcaacagct     420

agtaaacgct gtccaagatg cacaagaaag ttcggcctta aaccatacac catgcaattt     480

ccgcaaagtg cctggaaatg tatattatct gtatcagaga ccttctggcc agaactattt     540

ttccttattg tctcctgcag attggaacga aaaaccaccc caccagttct gtggttcata     600

tctttatgag catgattata catggaaaaa aatatgaatc ttgacttgtt tcttttaata     660

tgaataattt taataaaaaa                                                  680


<210> SEQ ID NO 102
<211> LENGTH: 610
<212> TYPE: DNA
<213> ORGANISM: Nezara viridula
<220> FEATURE:
<221> NAME/KEY: misc_feature
<222> LOCATION: 38
<223> OTHER INFORMATION: n = A,T,C or G

<400> SEQUENCE: 102
```

gggggtatta atgtggagat attttatttc aaaagagntc tgtttgttta tgttcagtga 60
tttgagaagt aatacaggtt tgattccatt ctatttttct ttttttttct ttaatatttt 120
aattgaaggt ctgaaaaaaa gtgttgtgta tctgtgtgtg ttggaataaa atgtcttcat 180
aagttcctca aattttaaaa ttattttatt cttgtatgtt cctatattct tcttggaaaa 240
tattatcaaa taaataagaa attgatcttt caactccatt gttatttaag actacgatac 300
agccctggaa tgtaattata gattctttca attttttttt gtttttttcct tggttgaatt 360 aatgatgctg tgatagtttg tctaacttcc cttttcttca cctatgatta ttatatgtga 420
ttaaaaaagt taccttgatt tagcctaatt ctatttgtat agatataaat atgttattaa 480
tgtgaattat tgaattgatt tcttaatcat taaaatgatt atgtgcaata atattgtatc 540
tgagattttc ttctaatggt aagtttattg atcacctggt ttacccgtag aacatagaat 600
atagtagatt 610

<210> SEQ ID NO 103
<211> LENGTH: 272
<212> TYPE: DNA
<213> ORGANISM: Nezara viridula

<400> SEQUENCE: 103
gggtattaat ttttatttgt ttatccataa attagctctt ttaaaccaat tactttgatt 60
ttttcttgat agttatcatg ttagcgactt cattaacatt cactaatcag gaaagacagt 120
ttacgaaatc tgtatctaga ttgaagaaat tccgtatgat ttttaataca ttgaaaaaat 180
atggccatta atcgaattag aaaaacgttt ttctactaca acaataggcg cagactttcc 240
atttcgcttt gggagagggg aggtgaagaa cc 272

<210> SEQ ID NO 104
<211> LENGTH: 618
<212> TYPE: DNA
<213> ORGANISM: Nezara viridula

<400> SEQUENCE: 104
ggggacaggc catgttgatc atgaaggctg tcgctgtgat tcttcttgtc gtcttggccg 60
cgtcttgtca tgctttctca atcagtggct tcttcggatc tgtctcaaac cacgccaagg 120
aaaatatcga gcaaaagaaa acccaggtca caaacaacat cgatctcatg catggacaca 180
tgaaggactt caagcaggct tcacttaatg gtgacgtcct tggggctgtt cagttgtcat 240
ccaagaactc agtgaacatg gcaaaaacta tggctgagca agcaatacaa aatactgtta 300
aatacgctca tgatgcagtt gaagacctaa agtatctaat tcccttcaaa ccgtcaaaga 360
aaccacctag catgggcaaa gtacctaaac caacaacagg accaccaaaa tattccattg 420
tttctgaaaa taataataaa ccaacaaaag gaaaaggaac tcctgcttca cacaaaactt 480
tggaatggaa agccggtttt aattccaaag ttacgataag taccgaagga acgattaatg 540
caactagagt acctcctgaa caaaaaatgc ctaatccttc aaaagaatca acagctaaac 600
tagaaatgtc tcttacta 618

<210> SEQ ID NO 105
<211> LENGTH: 675
<212> TYPE: DNA
<213> ORGANISM: Nezara viridula
<220> FEATURE:
<221> NAME/KEY: misc_feature
<222> LOCATION: 483

<223> OTHER INFORMATION: n = A,T,C or G

<400> SEQUENCE: 105

```
ggggaagtat gttttctgta gtgaaccaat gtagttaacg ttcaagagtg ttagttttaa     60
aatagcagtt aggattttct tttttctttc tttttttgt atggaaatga gatttcatcg    120
aagaagacac ttccaaatca actttattgg ttcttgacaa atccagtgta tatctttaaa    180
actgattttc atgtcaagcc tcaaaacact ttcacttcat tgtaaccaaa aagtaaggcc    240
cagtttgaga tggtttaaat ggcctttcaa gttcaagaaa caactagtga agaagagcgg    300
ataaagattg attgggaaac aactgaaaaa gatattttgt ctcaaccgtc tgctgttgaa    360
attgaagtaa atgaaaatct caacagcaac ttaaataaca gtcataaagt tgttgactac    420
agtaaaccga ttgttgataa catctcaaat cacactgaga ggttctttct tgttggtgaa    480
gantcaacat gtgttggaaa gaaaggcgac gaaaatgggg tatgtaatgg agtttatttt    540
cagaatgtta ataccaatga agtagatgat ccaggtgaga caaatgattg tgttcagtta    600
aatccaataa aggacacatt cactaatatg aaacttccat ctgtgccagt aaaagaaaat    660
aaggattgta ccatt                                                    675
```

<210> SEQ ID NO 106
<211> LENGTH: 653
<212> TYPE: DNA
<213> ORGANISM: Nezara viridula

<400> SEQUENCE: 106

```
ggggaatgtg tgtttactac cgccagttgc ttgtgttgaa cttgaatttg tatgtcattt     60
ttttagtatg aattatggag gtaacttcaa ttggaaatga agaaatacaa ttagctggta    120
atctgaaata tgttcagttt aagtctgact taaagaactt aatagaaagg gaaattctag    180
cagatgggtg gcaatcctcc gctgaagcat ttgataaaat cttccccaag aaaaggtact    240
tgcctagttt caagaaggca tttcatggtg ctattttagc tggttttgaa gaaagtctag    300
atgaaatgtt gggagatgtt ttgcctaaac agtgggatat tttatatcaa gaaaaatatg    360
acaatcatca tgatgggaag gatacttctc ggctgactta tagtaaaatg gcattaaatg    420
atttgaaatt aaaacaaaaa gctgctgtag aatctgttat agaattaaaa ctgaaaaaaa    480
ttgaagaaat taaacaaagt atatatatta agaaattaga agtaataaag aaatcatctg    540
aattgcaagc cattaaacaa aaatggaaaa aaaactgtgg aatattagaa gacttgaaaa    600
aaatgagttt ctaagttaca ttaccaatac atgagaacct atttatttat ata          653
```

<210> SEQ ID NO 107
<211> LENGTH: 398
<212> TYPE: DNA
<213> ORGANISM: Nezara viridula
<220> FEATURE:
<221> NAME/KEY: misc_feature
<222> LOCATION: 176
<223> OTHER INFORMATION: n = A,T,C or G

<400> SEQUENCE: 107

```
ggggactcta gttagtgact aagtttaata ttttattaaa atgaccaaga aaaggaggaa     60
tggaggaaga tccaaacatg gtaggggtca cgtgcaagca gtccgttgca ccaactgtgc    120
ccgttgcgtg ccaaaagata aggctatcaa gaaattcgtt attcgtaata tcgtanaagc    180
tgcagctgtg agggatatca cagatgctag cgtttactct tcgtaccagt tgccgaagct    240
ctatgccaaa ctacattatt gtgtgtcatg tgctatccac tctaaagtag tgcgtaatcg    300
```

ttctaaggct gagagaagaa ttaggacacc tcctcagcgt aacttcccaa gggatatgat 360
gcgtcaaggt ggaccccaga taaggaagta atcttttc 398

<210> SEQ ID NO 108
<211> LENGTH: 607
<212> TYPE: DNA
<213> ORGANISM: Nezara viridula
<220> FEATURE:
<221> NAME/KEY: misc_feature
<222> LOCATION: 455
<223> OTHER INFORMATION: n = A,T,C or G

<400> SEQUENCE: 108
ggggaatgtt gtggtgtgct gacatagata ttagtccatt tgatttggaa atttactctg 60
atttagctat aggagcaggt acgggtagta gtgcagcatt ttctgtctgt gttgctgcag 120
ctgtatataa ttatattagg ttaaaagcat ttcaaaagtt tggctgtggt gaatttaata 180
tttccagcag tccattcaag cctcatatga tggaattatc tcagcattat aatggatttt 240
ctccaaagga taaagacata gtgaataaat gggcattttg tgtggaaaaa attaatcatt 300
ccactccttc gggtattgat aacactattt gtacctttgg aaatgccgtt ttaatgaatg 360
ctgctggtga aaaagatgaa aaacgttcta tagaactatt agataatctt ccagccttcc 420
gggtgctgat agttaattca ggtgtaccaa gatcnactgc tgacatggta aagaaagttt 480
caaccttgct tgaaatttgt cctgaaagca actcaatcca tttcttgaat caatggatgt 540
aatcgctatg aaatttcttg aatatgctca agaaataaaa aaagcaactg aaaaattgga 600
tgttttg 607

<210> SEQ ID NO 109
<211> LENGTH: 53
<212> TYPE: DNA
<213> ORGANISM: Nezara viridula

<400> SEQUENCE: 109
ggggttcggt atcggtttcg ctggaaagat gaccgaactt gatcatttag agc 53

<210> SEQ ID NO 110
<211> LENGTH: 652
<212> TYPE: DNA
<213> ORGANISM: Nezara viridula
<220> FEATURE:
<221> NAME/KEY: misc_feature
<222> LOCATION: 399
<223> OTHER INFORMATION: n = A,T,C or G

<400> SEQUENCE: 110
ggggagttat catctctcca cagcccgcgg cactacagtt ccccgcttaa cagttctcta 60
taggatcaga ggtggtgcgc tctatctgtc gacccgcgca tgctgtactc gtccctcttc 120
ggggcctttc ttcttcgaac tcgccggctg gaaggtcctc gctcctcgct ccgtacagga 180
tctctttagt ctctcttaaa acaatcaagt gttttttatt agtgttccat aatgagtgat 240
acagcagctg aaaccaagga aactcaggct gcaagctcac ctgagaagaa ggaggtggtg 300
tgcgagcgaa agccagcagc tgctgctgaa aaagaaacca aggaagaaaa gaagacagaa 360
gataaaccag aaacaaatgg acacagcaaa accgaagant ctaccgaaga aaaacctgta 420
gaaaatggag atgcaactga tgtgtgctca ttgccacaga agaggaaatc tgaagttggt 480
agtggggaat ccactgagaa gtcagctgaa ggtgcaagtc ctgaaaagaa ggctaaacta 540

```
gaagagaaag ttgaaaatgg tgaagctgaa gcaaaagctt aaaaccattt aattcaaatt    600

aatctagact gttatacagt gttatgttta caaaatgcag catttgtaat at            652


<210> SEQ ID NO 111
<211> LENGTH: 575
<212> TYPE: DNA
<213> ORGANISM: Nezara viridula

<400> SEQUENCE: 111

ggggacgctt tatctcattg gtacttggaa gtcacgtttc tcgtaaacct tctcttatag     60

gttatattta tttcttacag ttctgttcaa actaattctt tcagatatga aacctttaat    120

gttacacggc catgaaaggg ccatcaccca aatcaagtac aatagagaag gggacttatt    180

attctcttca gccaaagatc actgtcctaa tgtttggtat tctcttaatg gcgaaaggct    240

aggtaacttc attggacata ttggtgctgt atggtgtctt gacatcaact gggaaagcac    300

taagtttatg tctggtgttg ctgataacac cctaaaatta tgggactgtt ctaatggtgt    360

agagattgga aatattaaca ccaaatcaac tgtgaggaca tgtgtcttca gttattcagg    420

caacttggct gcttattcca ctgatactca gaggaaacaa atttgtgaaa tcaatgtaat    480

tgactgtagg attagtgact cgtttggttc cgaaccaata ctgtgtatac cagtaccaga    540

gtcaaaggtg acggcattat tttggggccc tctgg                               575


<210> SEQ ID NO 112
<211> LENGTH: 169
<212> TYPE: DNA
<213> ORGANISM: Nezara viridula

<400> SEQUENCE: 112

ggggctgcct attaaagata atttatggct taatttacac cttcccttag ggaaaatact     60

aggtcaagtt cttgtttaat ggtgatcatt ttacctgtgt tcagttgatc acttaaaaaa    120

aagagtttat ttattaattt tttatcctga ttatagccga gtgttatac                169


<210> SEQ ID NO 113
<211> LENGTH: 636
<212> TYPE: DNA
<213> ORGANISM: Nezara viridula

<400> SEQUENCE: 113

gggggataga aacattcttc aagttcaaag tgagaaagaa aggcaagaaa gtaaagaagc     60

agtaggcgct cggctaatca ggaggttgag tatgcggccc acgcaagaag aattggaaga    120

gaggaatatt ttaaaaaaac aaacagctgc tgaagaaaag aagctcaaag aagaaaagaa    180

gcgtatgctg ctgcgaaaac tcagttttag gccaactgtt gaagaactga aggaaaagaa    240

gatcatacgc ttcaatgact acatagaagt gacccaggct catgactacg atcggcgcgc    300

agacaagcca tggactcgac tgacaccaaa agataaggct gccatccgaa aggaactcaa    360

cgaatttaag tcctctgaaa tggaggtcca ccaagaaagt agacatctta ctaggtttca    420

taggccatga catttggcag caaaagccgt gtctagttgt acagtgttat ctaccatgct    480

attgtatata ccacagtcgc taagctacct gcaccgtatt agagcctcga caaatttttt    540

tactgtttgt aactttgttt gtatatattt tatatatata tgaaaatata taaataatat    600

aacatatggt accattccat aattagggat ggttaa                              636


<210> SEQ ID NO 114
<211> LENGTH: 450
```

<212> TYPE: DNA
<213> ORGANISM: Nezara viridula
<220> FEATURE:
<221> NAME/KEY: misc_feature
<222> LOCATION: 414
<223> OTHER INFORMATION: n = A,T,C or G

<400> SEQUENCE: 114
gggcagactg agattttatt tatatttatc ttatgcagta tacaattcga gggtgagagc 60
aattacagtt tttcataaaa ataaaaaaaa caaacaaaaa taacttgtca ttttgatgat 120
ccaataaaaa taacttagta aatatcattt ttatggtatg aatttaaaaa atgtattaat 180
tgtaaaatat ttaatttgtc aattcactta atagaaatac ttggatccat ttttatttgt 240
cagctttcac cagtgctgta atgttataaa tgtgatctgt tcaaaggaga tttccattgg 300
aaatgtatta ttattttttt atttttcttt cttttttttg tttaatttac agcatgtatg 360
ttgctgtcaa tataaattgc cgttgttcga aaccttcaaa gtcttgatgt agcnacaatt 420
ttttattaat aaaattggat ttgaaaatct 450

<210> SEQ ID NO 115
<211> LENGTH: 467
<212> TYPE: DNA
<213> ORGANISM: Nezara viridula

<400> SEQUENCE: 115
gggcaccaat cttacccatt cacatctcgt tagcaagcag ccaccaccac aatgccaaca 60
ctgcaataat acacttacag ccagtcacaa gttacaggaa tgttattttt acatatcaaa 120
tctaaatagt gtaggactta cacctataat atcaaacatt ttaagttatg acgaagacag 180
tataatgtta gtgttagatt tcttaaaatc aaacaatttg ttaaataaaa tttaaaattg 240
atgcagagac cgttgatata atatgagaag gagttgatcg gggggtgcgg tcaaattaat 300
actaaattaa actattatta ttaaaaaaca ctttattcag aaatattaca atttgtcaca 360
gttaaggaca cttataatag agttcagaga ttgcattcat accgtatata caaaaaatata 420 aataaataaa gtaataacaa aagaataaga agaaagaaca aaagagc 467

<210> SEQ ID NO 116
<211> LENGTH: 363
<212> TYPE: DNA
<213> ORGANISM: Nezara viridula

<400> SEQUENCE: 116
ggggatccat aggatccgca taacacttac ttctaaaaac atgaagtcgt tagagaaagt 60
gtgtgctgat ctaataaatg gagctaagaa ggaaaatctc cgtgtcaagg gacccatcag 120
gatgcccatc aaaattctga ggattacgac tcgtaaaacc ccttgcggag aaggttctaa 180
gacttgggat cgattccaaa tgaggatcca caagagggtt atcgatcttc attctccttc 240
tgaagttgtg aaacagataa cttcaatttc tcttgaacct ggtgttgaag tggaagtcac 300
cattgccgaa taattacttt gtttttatta tgtgataatt atataaaaaa aattatataa 360
tag 363

<210> SEQ ID NO 117
<211> LENGTH: 632
<212> TYPE: DNA
<213> ORGANISM: Nezara viridula

<400> SEQUENCE: 117
gggcagaggg aaagttaaaa gtatttagaa aatgccacta tcacttagtg tacatagata 60
aactagggtt acataggttc ttgatagaat tgaatttatt actatggtat aaccctcttg 120
taaactttca tatcaaactg ttttaccagt gcatacacca cacctcactt cacttataaa 180
taagtagcta tttaaaaaaa aaaatgtttt tattatttta taattttccc ttctgatagt 240
tttactgtca tataacatgt attaaaacat aaaatctcct tattttctat tcctataaaa 300
aaaagaaaaa aaaaaagaaa ttgtaaataa gaaggatgca tttgttcatt ccatttatta 360
gttgttaatc aggtgctatt tcagtttttta ttttagaagc attagtttac ggatgttgta 420
tttctcattt tagctcttat gtgtcatact gctggttgtt ctcccataaa aatctaactg 480
tgcatttaaa ttaatcataa tagctatggc taaggccttt taaatttaaa caaaagataa 540
gttaagtgta ttatgtaata tgtattgtag aagaagcatg aatatcttat aagagaacaa 600
taaattattt tattttaata tagtttactt tc 632

<210> SEQ ID NO 118
<211> LENGTH: 690
<212> TYPE: DNA
<213> ORGANISM: Nezara viridula
<220> FEATURE:
<221> NAME/KEY: misc_feature
<222> LOCATION: 627
<223> OTHER INFORMATION: n = A,T,C or G

<400> SEQUENCE: 118
gggtgttgat gagtggctga cggtgatgaa gttctcaatc cctgttgtac tgctagatga 60
gacattgaag tttgttgcaa ggaagatcgc cgatgttcaa ccttcaatcc agataagata 120
ctgagaggga ccaccaagac attcaaaaga gggtttatgt gcttctagta gaataaataa 180
aatgcctata tttaaaatct cataggatga tcacaaattg tataaaagag gtgtatagaa 240
cccatttgtc ctattacgcg gagaaatgtc atttcctatc tagtctattt tggttctcga 300
tttttaacct attagaatta tattttttat aatttttttg attattttat tagatttttt 360
ttatatatac acatcctttt tcaacataca acgcctctaa ccaataacat tttattaga 420 ttcttataaa ccgtcacatt tgatggaacc caacagctgg ctgaagggtg tctattcttt 480
aatactaaca tgtcgcgtga ttttcattca cctctcatta tacctgtaca ttctcaatta 540
atattaattt aatcttcatc taatattact ttacattctg tggtcttcct tttttataaa 600
agattatatc aaaatttcac tagtagncta taaatatttt atttattttc tgttgtatat 660
atgaaaatac tgtacattca cttatgtatc 690

<210> SEQ ID NO 119
<211> LENGTH: 690
<212> TYPE: DNA
<213> ORGANISM: Nezara viridula

<400> SEQUENCE: 119
ggggaagtta taagttgtta cagtatccaa agattctctt actatgtatg tttacgattt 60
gccatacaat gaaagaaagc aaatttgcag aattttggat ttgaataaag cttgggagca 120
attaggtgga agttacatga aatttgatgt gacaacttta aagcattttg aggaagcacc 180
ttcaagaaat cactctccaa ctgatgaatt attaacttca tggggtactc ggaatcataa 240
tgttttggaa ctgttcgtat tgctttctaa aatgcagcac tatcaggcta tgaatgtact 300
caaagatttt gttgatgtaa agtatcatcg gctcatatat gaaggagaag aaaatttgtc 360
taagatattg gaggataaag gaaatccttt tggtcaaaat accagtgcat cagtcgggaa 420

```
ttataaaaaa gaggaagtaa atggaaactt aaatattaat cgaaaaggac aagacattcc    480

acctgataag gatatgcaga aaaataaaat gtttataaat gagaaaatag ttaacaaaaa    540

agaaactgat cttggtgtcg aaggcctttt gagaatggaa aatggacagt ctaaattgga    600

tgaaaatact cgtgatagtt cgagtctatt gatttcatat gctgaactag aacgagctac    660

tggttcttgg gacaaaaaga atattttagg                                      690


<210> SEQ ID NO 120
<211> LENGTH: 250
<212> TYPE: DNA
<213> ORGANISM: Nezara viridula

<400> SEQUENCE: 120

gggacatgtg ttattgtttc acaagattca attatccttc ttcgtaagga ataaaggtca     60

ttgactggtc tcgcatagac tatgtaacta cataactata taatggtata gttattgatt    120

agttatttat tatttactct tacttcagtg gggaacgttg aacattagag acagattaat    180

gtttgaggca ccttagaaaa taaaaataaa gctaagacaa tttttgagta aaaacataaa    240

cgttttaaag                                                            250


<210> SEQ ID NO 121
<211> LENGTH: 138
<212> TYPE: DNA
<213> ORGANISM: Nezara viridula

<400> SEQUENCE: 121

gggcaaaggg aacaattaca aaaacaagaa cccttaccat cagtagctac agaatgtgat     60

agccaccaac catttttgat ggattcaact atgttaatcc ctagtgaagt caagtctgaa    120

aagaagaaag atgatccg                                                   138


<210> SEQ ID NO 122
<211> LENGTH: 363
<212> TYPE: DNA
<213> ORGANISM: Nezara viridula
<220> FEATURE:
<221> NAME/KEY: misc_feature
<222> LOCATION: 65, 243, 340
<223> OTHER INFORMATION: n = A,T,C or G

<400> SEQUENCE: 122

aaataccggt tttgagactg gtttttcaac cgtcataacc tacattattt gcctcttaca     60

ttgangcaag gactaacaat tttttttca tcgaacaatt tttgaaagat ttcttataaa    120

taaaacattt ctttttatat tttcactgtt actacttctt tgactagtga gttaaatata    180

acatatttaa aacatcagtg gattctccaa aaattttatt aatcagcttt tttatacaat    240

gcngtatcag tatgtttaaa ataattctac atttaatact tttatggtat accataacta    300

cggcttcaaa atataagttg atacggaaaa gcgattggtn attaaaaaaa aaactttata    360

aac                                                                   363


<210> SEQ ID NO 123
<211> LENGTH: 547
<212> TYPE: DNA
<213> ORGANISM: Nezara viridula

<400> SEQUENCE: 123

gggggagtgc aagatgtggg tctccactac ttttctcgtg gtagcttttt ttcacgcctc     60
```

```
tgtgtctcag tactttaacg atgctgagga acaacggaat ttcgcgaaag aggaagttga    120

ccgagatgac gatggtgtta tcgtagtgat aaacgacgat cctgaaccaa atgacggatg    180

gaaacccgat gaggaagatc ctcttcaagc tggacctccg ccggagtata tgaacatgca    240

agcaccacct tcggactact tggaagaaca aagaccacca caggactatt tcgaagtgca    300

aagaccagag ccggattact tggaattgca aggaccatca ccatttgaat atgtttaagg    360

taaaattgaa gaagaaaact tcaacaagaa tgtaaataag aacttaagtg ctggaagtaa    420

ttgttttttc ttgatctccg ccatctactg agacttcaca cccaccgtta tgattcttca    480

tgttttacaa ttttttcccc atcacctcca atttgtcttt ccttaataaa caagttatac    540

attgtag                                                              547
```

<210> SEQ ID NO 124
<211> LENGTH: 575
<212> TYPE: DNA
<213> ORGANISM: Nezara viridula
<220> FEATURE:
<221> NAME/KEY: misc_feature
<222> LOCATION: 470
<223> OTHER INFORMATION: n = A,T,C or G

<400> SEQUENCE: 124

```
ggggagttga gcataatgaa gtctctttca gtttgctttc tggctgtact gctaatacaa     60

gcatcgtcag gcagacctaa tgatgacagt ggtgagtacg aagaacatga agagcattca    120

ttcgtttaca gctcaactaa tcctggtcgg gtacagagca cgcaaacaat cataggaaga    180

ccaccctttc agccaatgag ctttggcttc ggcaacccag ggcggcagaa cttcgggaat    240

atgttcggca ccggaggatt cggcggtttc cccagtttta gacccttacc aggcttccca    300

cctcttggac aaatgagccc aggtggtttc ggcggagtaa caggacagtc tttccagcta    360

caacacccag gaggatttgg acagatcagt ggattcactg gtccatcatc cgcaggaaat    420

gctgcctttg ctagttctag ttccggaagc ccaggtggtt cgaatagccn actaatcata    480

aaaccaggag gaggcttagc attcgcaagt tcgagctcaa gtagcccagg aagtaaccaa    540

gtttcaatca gtacgcagac ctcgagttcg acaga                               575
```

<210> SEQ ID NO 125
<211> LENGTH: 482
<212> TYPE: DNA
<213> ORGANISM: Nezara viridula

<400> SEQUENCE: 125

```
gggggcacct catcaccagc tattttagca tctgtttatg taatagaaaa attaattttt     60

tgagaaaaaa tcctctgaca ttattgataa cataacatcg caaattataa taaatattaa    120

agtaaatgag tgagtaaata tttacatcac tttagaattc gattgaatcg gacttacaaa    180

gttttggaaa taagccattg gtatactaaa acaattgagg ggtcaagtag ataaagagaa    240

gaagtaatat ttctgaattc ttaggaaaat gaattcaaat gactttcatc tattacaaga    300

tcaatgttta ttggcgatgg accaaatttg aagatggaaa gaagaaatat taatgatatc    360

aaacttgtaa aattttacca taaagtttgc cattatccat aattcaattt ttcctaaaaa    420

tgcactcatt cccataaccc atcaattatt gttaaattga agggcaaaaa aactactttt    480

tt                                                                   482
```

<210> SEQ ID NO 126
<211> LENGTH: 535

<212> TYPE: DNA
<213> ORGANISM: Nezara viridula

<400> SEQUENCE: 126

```
gggataagag agtgcaacaa gttctggtaa ggttaaatgt agtaacttca tgtactaact     60

taaaacagta caactttaga tgttaggtgt taaatgttgt agtcaattct atgattttct    120

acaggaattc gtacaattta aaaattattc tatgaattaa ttctaaaata aaaagtcgat    180

tttttcatag aggaactgat ttcaaaaggg ttgccataac acaagtttat ttattttacc    240

cataaatagc aagggaaata gctaaacatg gattattttt aagaattgca aatattttta    300

ttatgactgt agatttatta taacttttaa tttttaaaat aattatctag tctatatact    360

ccattagaat aagttgtctt tgtgatgtaa aactaatttt aagaataggt ttatgtcaat    420

aaggatgtac ttacgttata ttagtaggta ttgaatataa tagattctgt ataattacct    480

aatagaataa gttcagtgct attgtatctg ttaacaataa atgtgaattt attat         535
```

<210> SEQ ID NO 127
<211> LENGTH: 94
<212> TYPE: DNA
<213> ORGANISM: Nezara viridula

<400> SEQUENCE: 127

```
ggggttcatt gaactgttaa gtggtaaagt taatcatata acatatatta attcttattt     60

atattgtcat ttgtcttata cctctcgaat gttt                                 94
```

<210> SEQ ID NO 128
<211> LENGTH: 70
<212> TYPE: DNA
<213> ORGANISM: Nezara viridula

<400> SEQUENCE: 128

```
gggcatctat agaaatattc ttacttatca gaatcttacc tctaaatata aataaacaaa     60

gaagaagtgg                                                            70
```

<210> SEQ ID NO 129
<211> LENGTH: 688
<212> TYPE: DNA
<213> ORGANISM: Nezara viridula

<400> SEQUENCE: 129

```
gggggactta tcaaacgttg atgaagacta attatactca cggattacat ctgtgagttg     60

acaaacatat atttgtcacc ctaatgtact taccacttta ttaggttttc taaacaactt    120

gaaaacaaat ttttctcttg ctttaactat gacattgttt caatttcgat ggctgcgtcg    180

acttataagg agtaatacca agcccattcc aatggataaa gcagagttat ggaaagaacg    240

tctttcagtt gcttatatgt ttgtttcatt aaatatcctt ggtactataa tttattttta    300

ttacaaagga aaacctgatt tagctgaata ttatggtctt aaaactgagg aagagataaa    360

caaaaaacca gcaatatatt atgcagagct cttaggaatt aaaaaaacac atgttataag    420

gtataaaggg tttcaaaaag tagaagaatt tgattatgaa aaaccagcag acagtgaaaa    480

agtgaaaact gatacagagt agaatttttg ttctttttat ttataattag tgttatattt    540

aaaaaaatgg taagccagtg tcaattgtaa atctctaaat acaataatac tgttagtaaa    600

ggacaattcc ataaataaat aaatgtatct atcaatacag atatttttat tatttttaca    660

tatatttgtt attaattgca ttaaataa                                       688
```

<210> SEQ ID NO 130
<211> LENGTH: 214
<212> TYPE: DNA
<213> ORGANISM: Nezara viridula

<400> SEQUENCE: 130

```
gggccaccat catacgatag acgtgtaatt tctggaggca gtggtccaga gtctaagcca     60

actaaggtca tacctgatga tgaaggtagt gatgatgatt ccatcgactg gggcagtggt    120

tcagagtcta gttcggaatc gagtgatgat gaaggacagt accaatcgat cagagaaaga    180

tttttgaaaa aaacaacaga tcgagaagaa gaag                                214
```

<210> SEQ ID NO 131
<211> LENGTH: 496
<212> TYPE: DNA
<213> ORGANISM: Nezara viridula

<400> SEQUENCE: 131

```
ggggaatgaa tgagaatcgt taagagctag tcaatccttt aactgttatg tttcatctca     60

agcaaatgaa ttccttgtac ttatgttcat tgttaccctc attaccacag gctacaggtg    120

atacaggaag taaactgcag tatactcact gtcgattgtg cagcttagaa gaaaattgcg    180

gtgttctttt gcccaaagag attaatgcaa cagttctcat ggaaccaatt gtgtttgaac    240

ttatgtatga attgacaagg tttcaggatg ttatcaatag ctgccaaaat gaattagagt    300

cttcttactt agtgaattat gtatttaaat tatgtaacac tgtgaatcgt tgtttaaaaa    360

atttgccagt aaagggacag ccttcagata ttgctgagca acgattgtta cttttccata    420

ctgctaaaac gtttctacat tcatcaatga agattcttgg tttacagcct cttaataaaa    480

tgtagatttt actcag                                                    496
```

<210> SEQ ID NO 132
<211> LENGTH: 632
<212> TYPE: DNA
<213> ORGANISM: Nezara viridula
<220> FEATURE:
<221> NAME/KEY: misc_feature
<222> LOCATION: 122
<223> OTHER INFORMATION: n = A,T,C or G

<400> SEQUENCE: 132

```
gggagatgtt cctttaatga aatggacagc ctttatgctc ggagagcaaa actgaatcgg     60

actgcaagag cacatatggc taatgaagca ggcgttactt aggcgtagga aaaaaaaaaa    120

anttattttc ttagattact ggtttaattt ctttaatagc tttttaatgt aggtactggc    180

aaatcgaaaa aaattgccaa gaggttagca gcacataaaa tgtggatgag actgaaagac    240

ttaccctgcg aaagcaacac cattcattac ggcttggatg atgaagatga ggtatgcgta    300

attaaattgt ttatctacta ttatcttttt ttaaaaatgc ttgatttaaa tttatgattg    360

attattagtt atacttgtgt agttaattac aaattaatta atatagtaat tagtttttta    420

ctgatttttt ctattttaat ttattttatt ggctcgattt aagttttata gctggctata    480

aaaaatacca agtttctata ctcagtaaga atatatttta tgggcattgg aaatccaggc    540

tattcccaaa ctcgttatga acctataaaa ggaattaaag gtattccttt attcatcatt    600

ggattgttga tagtttgctt ttgggatcaa tg                                  632
```

<210> SEQ ID NO 133
<211> LENGTH: 422

<212> TYPE: DNA
<213> ORGANISM: Nezara viridula

<400> SEQUENCE: 133
ggggattggt tgatgaaata ttctacctgt tgacagtatg gttggggtat tgctctgttt 60
tcatcagtaa ttttacgttt catctgcaaa atagttttta tttgcataag aaatgaacat 120
cgaacataaa atgaaactct ttttgctgtt gttattccct tctctatgtg cctctcattt 180
ttgtccatcg aggcattact ggagtaaagc tcatagtaaa tgcttggaat gtaaacagtg 240
ccatgtaaca cttattcctt gtacagctaa gatgaattca atttgtgcca atatccatga 300
aaaaaatcac cacttccaaa aatatcgtat tcaatttttt gatgatggga atgaagatga 360
gcttgacaaa caagtagatt ctacagggca catacacaaa gatgatctgt atcttccaca 420
tg 422

<210> SEQ ID NO 134
<211> LENGTH: 134
<212> TYPE: DNA
<213> ORGANISM: Nezara viridula

<400> SEQUENCE: 134
gggcccctga tgtcgatata atccgaaaag ttacaaaaag tcaggcaact ggaacactat 60
ctcaaatttg atatcatttt cataaaaagc gcccccccaa aacatcatag tcgaccctga 120
tatcgattta atcc 134

<210> SEQ ID NO 135
<211> LENGTH: 68
<212> TYPE: DNA
<213> ORGANISM: Nezara viridula

<400> SEQUENCE: 135 ggggggggagg tacgatgtgt ccctgtgtca tgtactgtac atcgattctg tgtacaacaa 60
taaaatac 68

<210> SEQ ID NO 136
<211> LENGTH: 82
<212> TYPE: DNA
<213> ORGANISM: Nezara viridula

<400> SEQUENCE: 136
tatataaaac ctgcaaatga aattaaacca gaagaatttc gattactaga tgtagataat 60
cgtacagtat taccaataaa ta 82

<210> SEQ ID NO 137
<211> LENGTH: 691
<212> TYPE: DNA
<213> ORGANISM: Nezara viridula
<220> FEATURE:
<221> NAME/KEY: misc_feature
<222> LOCATION: 532
<223> OTHER INFORMATION: n = A,T,C or G

<400> SEQUENCE: 137
ggggtaattt aggtaaaaat cagtaagaat aaatgcattg attcacttat ttgaaaatta 60
aataagaatt aaataaactt ttgaaataga acaattcaat cgttgccctt taagtaagat 120
aagcggttcc atattcgttt gtaagaacaa aggaattgat agattagctg tcaaagctta 180
tagatcgatt gagatgtatc ttccaactct taaggtgatg acttattcaa agttttttct 240

```
tacagaaagt aatgaagctt ttcaaattta attaaaactt ttttctcttc agatagtcaa    300

tataaaaagt ccataacaat caatttataa tatagaggta tatcttcata cccaatcgta    360

atttattctt ccctttttt tattattatt tacaggcttt gctgaccttt tatttctttt    420

attattttat attatatttc tattatagtt taataaatta tttatttatg aatagatgta    480

cgagcttgta aagttttaag taggcttttg attaaacata ccatacaatg gnacgaaatt    540

tttaataagc tacaaaacaa agcaaaaaga tgaatgaaat aagttgaaaa aagtcctgga    600

atgtcctaaa cgaatattag taaaaatttt acatttatca tgtatgtaag attgcatgtg    660

cttgtagcat gtgttagaaa taaattattt c                                   691
```

```
<210> SEQ ID NO 138
<211> LENGTH: 172
<212> TYPE: DNA
<213> ORGANISM: Nezara viridula

<400> SEQUENCE: 138

ggggcattca agtcctgtaa agttacatca acagggacaa gatctaaatg atataaaaac     60

cacttaatta taaatccata cactaagttt aatcaaaatc gttggagcca ttttgaaaaa    120

atcttaaaaa tgtttttaat cgattctgtt aagtgtcatt tcagattatc cc            172
```

```
<210> SEQ ID NO 139
<211> LENGTH: 645
<212> TYPE: DNA
<213> ORGANISM: Nezara viridula

<400> SEQUENCE: 139

gggtgtattc atatataatt tttcaatttc aaaaattggg tgtttgttgg atggttcaac     60

tttattaata ttgaaaaaca aaattggcgc ataaagctag ttgatcttcc aaaaatatgg    120

aacctaggtt tcagtaatag gatttggtgt cattaagttg tatcaattga tgcattttac    180

ccatctctaa aatattaaca taaaaattcc aatagataca tactattgct ttagaaatat    240

atttaaacat attaaatgtg ataatatttt cttaatatat gttttttttt tctttcttgt    300

tttattcatg cgtgtatttt aatgttttaa caaatataaa tattttagat agataaatat    360

ttttgatagc gtgtgatatt gatgaactga ctagaaaata tttaattatt ttatgatctt    420

atttgagtta ttagacctta atttcgaaca cattttagga aaaaaaaaca tttataaaga    480

aaaaaaaaaa aggaaaagaa atgagtaaac tgaaaacagt ttaaagttta atttaacttt    540

atcatgtgtc aataatacca tgatatattg ttatattcat gatatattgt tatatcaaat    600

aaaaagttat atagacttat aaagcattat aatacatgta tgaaa                    645
```

```
<210> SEQ ID NO 140
<211> LENGTH: 23
<212> TYPE: DNA
<213> ORGANISM: Nezara viridula

<400> SEQUENCE: 140

aatcaaggtg tggactgaaa att                                             23
```

```
<210> SEQ ID NO 141
<211> LENGTH: 19
<212> TYPE: RNA
<213> ORGANISM: Nezara viridula

<400> SEQUENCE: 141

ucaaggugug gacugaaaa                                                  19
```

<210> SEQ ID NO 142
<211> LENGTH: 19
<212> TYPE: RNA
<213> ORGANISM: Nezara viridula

<400> SEQUENCE: 142
uuuucagucc acaccuuga 19

<210> SEQ ID NO 143
<211> LENGTH: 23
<212> TYPE: DNA
<213> ORGANISM: Nezara viridula

<400> SEQUENCE: 143
aattggttgc tacatattct ctt 23

<210> SEQ ID NO 144
<211> LENGTH: 19
<212> TYPE: RNA
<213> ORGANISM: Nezara viridula

<400> SEQUENCE: 144
uugguugcua cauauucuc 19

<210> SEQ ID NO 145
<211> LENGTH: 19
<212> TYPE: RNA
<213> ORGANISM: Nezara viridula

<400> SEQUENCE: 145
gagaauaugu agcaaccaa 19

<210> SEQ ID NO 146
<211> LENGTH: 23
<212> TYPE: DNA
<213> ORGANISM: Nezara viridula

<400> SEQUENCE: 146
aagaacgtct taggatgcat att 23

<210> SEQ ID NO 147
<211> LENGTH: 19
<212> TYPE: RNA
<213> ORGANISM: Nezara viridula

<400> SEQUENCE: 147
gaacgucuua ggaugcaua 19

<210> SEQ ID NO 148
<211> LENGTH: 19
<212> TYPE: RNA
<213> ORGANISM: Nezara viridula

<400> SEQUENCE: 148
uaugcauccu aagacguuc 19

<210> SEQ ID NO 149
<211> LENGTH: 23
<212> TYPE: DNA
<213> ORGANISM: Nezara viridula

<400> SEQUENCE: 149
aagcaagcac ctaccttcac att 23

<210> SEQ ID NO 150
<211> LENGTH: 19
<212> TYPE: RNA
<213> ORGANISM: Nezara viridula

<400> SEQUENCE: 150
gcaagcaccu accuucaca 19

<210> SEQ ID NO 151
<211> LENGTH: 19
<212> TYPE: RNA
<213> ORGANISM: Nezara viridula

<400> SEQUENCE: 151
ugugaaggua ggugcuugc 19

<210> SEQ ID NO 152
<211> LENGTH: 23
<212> TYPE: DNA
<213> ORGANISM: Nezara viridula

<400> SEQUENCE: 152
aaaccaaggt agctgtggat ctt 23

<210> SEQ ID NO 153
<211> LENGTH: 19
<212> TYPE: RNA
<213> ORGANISM: Nezara viridula

<400> SEQUENCE: 153
accaagguag cuguggauc 19

<210> SEQ ID NO 154
<211> LENGTH: 19
<212> TYPE: RNA
<213> ORGANISM: Nezara viridula

<400> SEQUENCE: 154
gauccacagc uaccuuggu 19

<210> SEQ ID NO 155
<211> LENGTH: 23
<212> TYPE: DNA
<213> ORGANISM: Nezara viridula

<400> SEQUENCE: 155
aataatggat gtggtggcgg att 23

<210> SEQ ID NO 156
<211> LENGTH: 19
<212> TYPE: RNA
<213> ORGANISM: Nezara viridula

<400> SEQUENCE: 156
uaauggaugu gguggcgga 19

<210> SEQ ID NO 157
<211> LENGTH: 19
<212> TYPE: RNA
<213> ORGANISM: Nezara viridula

<400> SEQUENCE: 157
uccgccacca cauccauua 19

<210> SEQ ID NO 158
<211> LENGTH: 23
<212> TYPE: DNA
<213> ORGANISM: Nezara viridula

<400> SEQUENCE: 158
aaaaggatac cactttggac ttt 23

<210> SEQ ID NO 159
<211> LENGTH: 19
<212> TYPE: RNA
<213> ORGANISM: Nezara viridula

<400> SEQUENCE: 159
aaggauacca cuuuggacu 19

<210> SEQ ID NO 160
<211> LENGTH: 19
<212> TYPE: RNA
<213> ORGANISM: Nezara viridula

<400> SEQUENCE: 160
aguccaaagu gguauccuu 19

<210> SEQ ID NO 161
<211> LENGTH: 23
<212> TYPE: DNA
<213> ORGANISM: Nezara viridula

<400> SEQUENCE: 161
aaaggatacc actttggact ttt 23

<210> SEQ ID NO 162
<211> LENGTH: 19
<212> TYPE: RNA
<213> ORGANISM: Nezara viridula

<400> SEQUENCE: 162
aggauaccac uuuggacuu 19

<210> SEQ ID NO 163
<211> LENGTH: 19
<212> TYPE: RNA
<213> ORGANISM: Nezara viridula

<400> SEQUENCE: 163
aaguccaaag ugguauccu 19

<210> SEQ ID NO 164
<211> LENGTH: 23
<212> TYPE: DNA
<213> ORGANISM: Nezara viridula

<400> SEQUENCE: 164
aaaccaagac ccagactgga gtt 23

<210> SEQ ID NO 165
<211> LENGTH: 19
<212> TYPE: RNA
<213> ORGANISM: Nezara viridula

<400> SEQUENCE: 165
accaagaccc agacuggag 19

<210> SEQ ID NO 166
<211> LENGTH: 19
<212> TYPE: RNA
<213> ORGANISM: Nezara viridula

<400> SEQUENCE: 166
cuccagucug ggucuuggu 19

<210> SEQ ID NO 167
<211> LENGTH: 23
<212> TYPE: DNA
<213> ORGANISM: Nezara viridula

<400> SEQUENCE: 167
aagacccaga ctggagttga att 23

<210> SEQ ID NO 168
<211> LENGTH: 19
<212> TYPE: RNA
<213> ORGANISM: Nezara viridula

<400> SEQUENCE: 168
gacccagacu ggaguugaa 19

<210> SEQ ID NO 169
<211> LENGTH: 19
<212> TYPE: RNA
<213> ORGANISM: Nezara viridula

<400> SEQUENCE: 169
uucaacucca gucuggguc 19

<210> SEQ ID NO 170
<211> LENGTH: 23
<212> TYPE: DNA
<213> ORGANISM: Nezara viridula

<400> SEQUENCE: 170
aaccaagaaa ctgggaaagt gtt 23

<210> SEQ ID NO 171
<211> LENGTH: 19
<212> TYPE: RNA
<213> ORGANISM: Nezara viridula

<400> SEQUENCE: 171
ccaagaaacu gggaaagug 19

<210> SEQ ID NO 172
<211> LENGTH: 19
<212> TYPE: RNA
<213> ORGANISM: Nezara viridula

<400> SEQUENCE: 172
cacuuuccca guuucuugg 19

<210> SEQ ID NO 173
<211> LENGTH: 23
<212> TYPE: DNA
<213> ORGANISM: Nezara viridula

<400> SEQUENCE: 173
aactgggaaa gtgttcggaa att 23

<210> SEQ ID NO 174
<211> LENGTH: 19
<212> TYPE: RNA
<213> ORGANISM: Nezara viridula

<400> SEQUENCE: 174
cugggaaagu guucggaaa 19

<210> SEQ ID NO 175
<211> LENGTH: 19
<212> TYPE: RNA
<213> ORGANISM: Nezara viridula

<400> SEQUENCE: 175
uuuccgaaca cuuucccag 19

<210> SEQ ID NO 176
<211> LENGTH: 23
<212> TYPE: DNA
<213> ORGANISM: Nezara viridula

<400> SEQUENCE: 176
aactgaaatt gccctcactg att 23

<210> SEQ ID NO 177
<211> LENGTH: 19
<212> TYPE: RNA
<213> ORGANISM: Nezara viridula

<400> SEQUENCE: 177
cugaaauugc ccucacuga 19

<210> SEQ ID NO 178
<211> LENGTH: 19
<212> TYPE: RNA
<213> ORGANISM: Nezara viridula

<400> SEQUENCE: 178
ucagugaggg caauuucag 19

<210> SEQ ID NO 179
<211> LENGTH: 23
<212> TYPE: DNA
<213> ORGANISM: Nezara viridula

<400> SEQUENCE: 179
aagctttctt gtgatacctc att 23

<210> SEQ ID NO 180
<211> LENGTH: 19
<212> TYPE: RNA
<213> ORGANISM: Nezara viridula

<400> SEQUENCE: 180
gcuuucuugu gauaccuca 19

<210> SEQ ID NO 181
<211> LENGTH: 19
<212> TYPE: RNA

<213> ORGANISM: Nezara viridula

<400> SEQUENCE: 181
ugagguauca caagaaagc 19

<210> SEQ ID NO 182
<211> LENGTH: 23
<212> TYPE: DNA
<213> ORGANISM: Nezara viridula

<400> SEQUENCE: 182
aatgatacgt gtgctttgaa ctt 23

<210> SEQ ID NO 183
<211> LENGTH: 19
<212> TYPE: RNA
<213> ORGANISM: Nezara viridula

<400> SEQUENCE: 183
ugauacgugu gcuuugaac 19

<210> SEQ ID NO 184
<211> LENGTH: 19
<212> TYPE: RNA
<213> ORGANISM: Nezara viridula

<400> SEQUENCE: 184
guucaaagca cacguauca 19

<210> SEQ ID NO 185
<211> LENGTH: 23
<212> TYPE: DNA
<213> ORGANISM: Nezara viridula

<400> SEQUENCE: 185
aagcattaat gatggacgtg ttt 23

<210> SEQ ID NO 186
<211> LENGTH: 19
<212> TYPE: RNA
<213> ORGANISM: Nezara viridula

<400> SEQUENCE: 186
gcauuaauga uggacgugu 19

<210> SEQ ID NO 187
<211> LENGTH: 19
<212> TYPE: RNA
<213> ORGANISM: Nezara viridula

<400> SEQUENCE: 187
acacguccau cauuaaugc 19

<210> SEQ ID NO 188
<211> LENGTH: 23
<212> TYPE: DNA
<213> ORGANISM: Nezara viridula

<400> SEQUENCE: 188
aaaactttct caaagaacca gtt 23

<210> SEQ ID NO 189
<211> LENGTH: 19

<212> TYPE: RNA
<213> ORGANISM: Nezara viridula

<400> SEQUENCE: 189
aacuuucuca aagaaccag 19

<210> SEQ ID NO 190
<211> LENGTH: 19
<212> TYPE: RNA
<213> ORGANISM: Nezara viridula

<400> SEQUENCE: 190
cugguucuuu gagaaaguu 19

<210> SEQ ID NO 191
<211> LENGTH: 23
<212> TYPE: DNA
<213> ORGANISM: Nezara viridula

<400> SEQUENCE: 191
aaagaaccag ttccaaatgc att 23

<210> SEQ ID NO 192
<211> LENGTH: 19
<212> TYPE: RNA
<213> ORGANISM: Nezara viridula

<400> SEQUENCE: 192
agaaccaguu ccaaaugca 19

<210> SEQ ID NO 193
<211> LENGTH: 19
<212> TYPE: RNA
<213> ORGANISM: Nezara viridula

<400> SEQUENCE: 193
ugcauuugga acugguucu 19

<210> SEQ ID NO 194
<211> LENGTH: 23
<212> TYPE: DNA
<213> ORGANISM: Nezara viridula

<400> SEQUENCE: 194
aatgcattcc cttcaatctc att 23

<210> SEQ ID NO 195
<211> LENGTH: 19
<212> TYPE: RNA
<213> ORGANISM: Nezara viridula

<400> SEQUENCE: 195
ugcauucccu ucaaucuca 19

<210> SEQ ID NO 196
<211> LENGTH: 19
<212> TYPE: RNA
<213> ORGANISM: Nezara viridula

<400> SEQUENCE: 196
ugagauugaa gggaaugca 19

<210> SEQ ID NO 197

<211> LENGTH: 23
<212> TYPE: DNA
<213> ORGANISM: Nezara viridula

<400> SEQUENCE: 197
aacctctcct cgtctggagt ctt 23

<210> SEQ ID NO 198
<211> LENGTH: 19
<212> TYPE: RNA
<213> ORGANISM: Nezara viridula

<400> SEQUENCE: 198
ccucuccucg ucuggaguc 19

<210> SEQ ID NO 199
<211> LENGTH: 19
<212> TYPE: RNA
<213> ORGANISM: Nezara viridula

<400> SEQUENCE: 199
gacuccagac gaggagagg 19

<210> SEQ ID NO 200
<211> LENGTH: 23
<212> TYPE: DNA
<213> ORGANISM: Nezara viridula

<400> SEQUENCE: 200
aaagaattca cctggtccta ctt 23

<210> SEQ ID NO 201
<211> LENGTH: 19
<212> TYPE: RNA
<213> ORGANISM: Nezara viridula

<400> SEQUENCE: 201
agaauucacc ugguccuac 19

<210> SEQ ID NO 202
<211> LENGTH: 19
<212> TYPE: RNA
<213> ORGANISM: Nezara viridula

<400> SEQUENCE: 202
guaggaccag gugaauucu 19

<210> SEQ ID NO 203
<211> LENGTH: 23
<212> TYPE: DNA
<213> ORGANISM: Nezara viridula

<400> SEQUENCE: 203
aattctggaa gaaatggacc att 23

<210> SEQ ID NO 204
<211> LENGTH: 19
<212> TYPE: RNA
<213> ORGANISM: Nezara viridula

<400> SEQUENCE: 204
uucuggaaga aauggacca 19

<210> SEQ ID NO 205
<211> LENGTH: 19
<212> TYPE: RNA
<213> ORGANISM: Nezara viridula

<400> SEQUENCE: 205 uggucauuu cuuccagaa 19

<210> SEQ ID NO 206
<211> LENGTH: 23
<212> TYPE: DNA
<213> ORGANISM: Nezara viridula

<400> SEQUENCE: 206
aacgtctaga aatggtgaga gtt 23

<210> SEQ ID NO 207
<211> LENGTH: 19
<212> TYPE: RNA
<213> ORGANISM: Nezara viridula

<400> SEQUENCE: 207
cgucuagaaa uggugagag 19

<210> SEQ ID NO 208
<211> LENGTH: 19
<212> TYPE: RNA
<213> ORGANISM: Nezara viridula

<400> SEQUENCE: 208
cucucaccau uucuagacg 19

<210> SEQ ID NO 209
<211> LENGTH: 23
<212> TYPE: DNA
<213> ORGANISM: Nezara viridula

<400> SEQUENCE: 209
aataagaaac acgaagcagg ctt 23

<210> SEQ ID NO 210
<211> LENGTH: 19
<212> TYPE: RNA
<213> ORGANISM: Nezara viridula

<400> SEQUENCE: 210
uaagaaacac gaagcaggc 19

<210> SEQ ID NO 211
<211> LENGTH: 19
<212> TYPE: RNA
<213> ORGANISM: Nezara viridula

<400> SEQUENCE: 211
gccugcuucg uguuucuua 19

<210> SEQ ID NO 212
<211> LENGTH: 23
<212> TYPE: DNA
<213> ORGANISM: Nezara viridula

<400> SEQUENCE: 212
aaatgaagag ccatttaggc ttt 23

<210> SEQ ID NO 213
<211> LENGTH: 19
<212> TYPE: RNA
<213> ORGANISM: Nezara viridula

<400> SEQUENCE: 213
augaagagcc auuuaggcu 19

<210> SEQ ID NO 214
<211> LENGTH: 19
<212> TYPE: RNA
<213> ORGANISM: Nezara viridula

<400> SEQUENCE: 214
agccuaaaug gcucuucau 19

<210> SEQ ID NO 215
<211> LENGTH: 23
<212> TYPE: DNA
<213> ORGANISM: Nezara viridula

<400> SEQUENCE: 215
aacttcgaac catctccccg gtt 23

<210> SEQ ID NO 216
<211> LENGTH: 19
<212> TYPE: RNA
<213> ORGANISM: Nezara viridula

<400> SEQUENCE: 216
cuucgaacca ucuccccgg 19

<210> SEQ ID NO 217
<211> LENGTH: 19
<212> TYPE: RNA
<213> ORGANISM: Nezara viridula

<400> SEQUENCE: 217
ccggggagau gguucgaag 19

<210> SEQ ID NO 218
<211> LENGTH: 23
<212> TYPE: DNA
<213> ORGANISM: Nezara viridula

<400> SEQUENCE: 218
aagcttcctt cactacaaat gtt 23

<210> SEQ ID NO 219
<211> LENGTH: 19
<212> TYPE: RNA
<213> ORGANISM: Nezara viridula

<400> SEQUENCE: 219
gcuuccuuca cuacaaaug 19

<210> SEQ ID NO 220
<211> LENGTH: 19
<212> TYPE: RNA
<213> ORGANISM: Nezara viridula

<400> SEQUENCE: 220
cauuuguagu gaaggaagc 19

<210> SEQ ID NO 221
<211> LENGTH: 23
<212> TYPE: DNA
<213> ORGANISM: Nezara viridula

<400> SEQUENCE: 221
aaggttcagc tccggggatc ttt 23

<210> SEQ ID NO 222
<211> LENGTH: 19
<212> TYPE: RNA
<213> ORGANISM: Nezara viridula

<400> SEQUENCE: 222
gguucagcuc cggggaucu 19

<210> SEQ ID NO 223
<211> LENGTH: 19
<212> TYPE: RNA
<213> ORGANISM: Nezara viridula

<400> SEQUENCE: 223
agauccccgg agcugaacc 19

<210> SEQ ID NO 224
<211> LENGTH: 23
<212> TYPE: DNA
<213> ORGANISM: Nezara viridula

<400> SEQUENCE: 224
aatcgacgac caaaatactg att 23

<210> SEQ ID NO 225
<211> LENGTH: 19
<212> TYPE: RNA
<213> ORGANISM: Nezara viridula

<400> SEQUENCE: 225
ucgacgacca aaauacuga 19

<210> SEQ ID NO 226
<211> LENGTH: 19
<212> TYPE: RNA
<213> ORGANISM: Nezara viridula

<400> SEQUENCE: 226
ucaguauuuu ggucgucga 19

<210> SEQ ID NO 227
<211> LENGTH: 23
<212> TYPE: DNA
<213> ORGANISM: Nezara viridula

<400> SEQUENCE: 227
aatacttcag agtacggcgt att 23

<210> SEQ ID NO 228
<211> LENGTH: 19
<212> TYPE: RNA
<213> ORGANISM: Nezara viridula

<400> SEQUENCE: 228
uacuucagag uacggcgua 19

<210> SEQ ID NO 229
<211> LENGTH: 19
<212> TYPE: RNA
<213> ORGANISM: Nezara viridula

<400> SEQUENCE: 229
uacgccguac ucugaagua 19

<210> SEQ ID NO 230
<211> LENGTH: 23
<212> TYPE: DNA
<213> ORGANISM: Nezara viridula

<400> SEQUENCE: 230
aaaatgagag ctacgtactg ctt 23

<210> SEQ ID NO 231
<211> LENGTH: 19
<212> TYPE: RNA
<213> ORGANISM: Nezara viridula

<400> SEQUENCE: 231
aaugagagcu acguacugc 19

<210> SEQ ID NO 232
<211> LENGTH: 19
<212> TYPE: RNA
<213> ORGANISM: Nezara viridula

<400> SEQUENCE: 232
gcaguacgua gcucucauu 19

<210> SEQ ID NO 233
<211> LENGTH: 23
<212> TYPE: DNA
<213> ORGANISM: Nezara viridula

<400> SEQUENCE: 233
aaataccatt acacaggaca ttt 23

<210> SEQ ID NO 234
<211> LENGTH: 19
<212> TYPE: RNA
<213> ORGANISM: Nezara viridula

<400> SEQUENCE: 234
auaccauuac acaggacau 19

<210> SEQ ID NO 235
<211> LENGTH: 19
<212> TYPE: RNA
<213> ORGANISM: Nezara viridula

<400> SEQUENCE: 235
auguccugug uaaugguau 19

<210> SEQ ID NO 236
<211> LENGTH: 23
<212> TYPE: DNA
<213> ORGANISM: Nezara viridula

<400> SEQUENCE: 236
aagtgttgct ggaacatcaa gtt 23

<210> SEQ ID NO 237
<211> LENGTH: 19
<212> TYPE: RNA
<213> ORGANISM: Nezara viridula

<400> SEQUENCE: 237
guguugcugg aacaucaag 19

<210> SEQ ID NO 238
<211> LENGTH: 19
<212> TYPE: RNA
<213> ORGANISM: Nezara viridula

<400> SEQUENCE: 238
cuugauguuc cagcaacac 19

<210> SEQ ID NO 239
<211> LENGTH: 23
<212> TYPE: DNA
<213> ORGANISM: Nezara viridula

<400> SEQUENCE: 239
aatgcccagc agaaaccaac ctt 23

<210> SEQ ID NO 240
<211> LENGTH: 19
<212> TYPE: RNA
<213> ORGANISM: Nezara viridula

<400> SEQUENCE: 240
ugcccagcag aaaccaacc 19

<210> SEQ ID NO 241
<211> LENGTH: 19
<212> TYPE: RNA
<213> ORGANISM: Nezara viridula

<400> SEQUENCE: 241
gguugguuuc ugcugggca 19

<210> SEQ ID NO 242
<211> LENGTH: 23
<212> TYPE: DNA
<213> ORGANISM: Nezara viridula

<400> SEQUENCE: 242
aaataccaca gccagcaata att 23

<210> SEQ ID NO 243
<211> LENGTH: 19
<212> TYPE: RNA
<213> ORGANISM: Nezara viridula

<400> SEQUENCE: 243
auaccacagc cagcaauaa 19

<210> SEQ ID NO 244
<211> LENGTH: 19
<212> TYPE: RNA
<213> ORGANISM: Nezara viridula

<400> SEQUENCE: 244
uuauugcugg cugugguau 19

<210> SEQ ID NO 245
<211> LENGTH: 23
<212> TYPE: DNA
<213> ORGANISM: Nezara viridula

<400> SEQUENCE: 245
aataccacag ccagcaataa ttt 23

<210> SEQ ID NO 246
<211> LENGTH: 19
<212> TYPE: RNA
<213> ORGANISM: Nezara viridula

<400> SEQUENCE: 246
uaccacagcc agcaauaau 19

<210> SEQ ID NO 247
<211> LENGTH: 19
<212> TYPE: RNA
<213> ORGANISM: Nezara viridula

<400> SEQUENCE: 247
auuauugcug gcugguggua 19

<210> SEQ ID NO 248
<211> LENGTH: 23
<212> TYPE: DNA
<213> ORGANISM: Nezara viridula

<400> SEQUENCE: 248
aagcctccgg tacctcaagg ttt 23

<210> SEQ ID NO 249
<211> LENGTH: 19
<212> TYPE: RNA
<213> ORGANISM: Nezara viridula

<400> SEQUENCE: 249
gccuccggua ccucaaggu 19

<210> SEQ ID NO 250
<211> LENGTH: 19
<212> TYPE: RNA
<213> ORGANISM: Nezara viridula

<400> SEQUENCE: 250
accuugaggu accggaggc 19

<210> SEQ ID NO 251
<211> LENGTH: 23
<212> TYPE: DNA
<213> ORGANISM: Nezara viridula

<400> SEQUENCE: 251
aatcttatcg gacaaaccag ttt 23

<210> SEQ ID NO 252
<211> LENGTH: 19
<212> TYPE: RNA
<213> ORGANISM: Nezara viridula

<400> SEQUENCE: 252
ucuuaucgga caaaccagu 19

<210> SEQ ID NO 253
<211> LENGTH: 19
<212> TYPE: RNA
<213> ORGANISM: Nezara viridula

<400> SEQUENCE: 253
acugguuugu ccgauaaga 19

<210> SEQ ID NO 254
<211> LENGTH: 23
<212> TYPE: DNA
<213> ORGANISM: Nezara viridula

<400> SEQUENCE: 254
aaaaatatcc attgccactg ttt 23

<210> SEQ ID NO 255
<211> LENGTH: 19
<212> TYPE: RNA
<213> ORGANISM: Nezara viridula

<400> SEQUENCE: 255
aaauauccau ugccacugu 19

<210> SEQ ID NO 256
<211> LENGTH: 19
<212> TYPE: RNA
<213> ORGANISM: Nezara viridula

<400> SEQUENCE: 256
acaguggcaa uggauauuu 19

<210> SEQ ID NO 257
<211> LENGTH: 23
<212> TYPE: DNA
<213> ORGANISM: Nezara viridula

<400> SEQUENCE: 257
aaaatatcca ttgccactgt ttt 23

<210> SEQ ID NO 258
<211> LENGTH: 19
<212> TYPE: RNA
<213> ORGANISM: Nezara viridula

<400> SEQUENCE: 258
aauauccauu gccacuguu 19

<210> SEQ ID NO 259
<211> LENGTH: 19
<212> TYPE: RNA
<213> ORGANISM: Nezara viridula

<400> SEQUENCE: 259
aacaguggca auggauauu 19

<210> SEQ ID NO 260
<211> LENGTH: 23
<212> TYPE: DNA

<213> ORGANISM: Nezara viridula

<400> SEQUENCE: 260
aaatatccat tgccactgtt ttt 23

<210> SEQ ID NO 261
<211> LENGTH: 19
<212> TYPE: RNA
<213> ORGANISM: Nezara viridula

<400> SEQUENCE: 261
auauccauug ccacuguuu 19

<210> SEQ ID NO 262
<211> LENGTH: 19
<212> TYPE: RNA
<213> ORGANISM: Nezara viridula

<400> SEQUENCE: 262
aaacaguggc aauggauau 19

<210> SEQ ID NO 263
<211> LENGTH: 23
<212> TYPE: DNA
<213> ORGANISM: Nezara viridula

<400> SEQUENCE: 263
aaggatggga tgtgttccga gtt 23

<210> SEQ ID NO 264
<211> LENGTH: 19
<212> TYPE: RNA
<213> ORGANISM: Nezara viridula

<400> SEQUENCE: 264
ggaugggaug uguuccgag 19

<210> SEQ ID NO 265
<211> LENGTH: 19
<212> TYPE: RNA
<213> ORGANISM: Nezara viridula

<400> SEQUENCE: 265
cucggaacac aucccaucc 19

<210> SEQ ID NO 266
<211> LENGTH: 23
<212> TYPE: DNA
<213> ORGANISM: Nezara viridula

<400> SEQUENCE: 266
aagatggggg gatgatgtac gtt 23

<210> SEQ ID NO 267
<211> LENGTH: 19
<212> TYPE: RNA
<213> ORGANISM: Nezara viridula

<400> SEQUENCE: 267 gauggggga ugauguacg 19

<210> SEQ ID NO 268
<211> LENGTH: 19

<212> TYPE: RNA
<213> ORGANISM: Nezara viridula

<400> SEQUENCE: 268
cguacaucau ccccccauc 19

<210> SEQ ID NO 269
<211> LENGTH: 23
<212> TYPE: DNA
<213> ORGANISM: Nezara viridula

<400> SEQUENCE: 269
aagaacatcc acaggagaac ctt 23

<210> SEQ ID NO 270
<211> LENGTH: 19
<212> TYPE: RNA
<213> ORGANISM: Nezara viridula

<400> SEQUENCE: 270
gaacauccac aggagaacc 19

<210> SEQ ID NO 271
<211> LENGTH: 19
<212> TYPE: RNA
<213> ORGANISM: Nezara viridula

<400> SEQUENCE: 271
gguucuccug uggauguuc 19

<210> SEQ ID NO 272
<211> LENGTH: 23
<212> TYPE: DNA
<213> ORGANISM: Nezara viridula

<400> SEQUENCE: 272
aagactctat taatatccag ctt 23

<210> SEQ ID NO 273
<211> LENGTH: 19
<212> TYPE: RNA
<213> ORGANISM: Nezara viridula

<400> SEQUENCE: 273
gacucuauua auauccagc 19

<210> SEQ ID NO 274
<211> LENGTH: 19
<212> TYPE: RNA
<213> ORGANISM: Nezara viridula

<400> SEQUENCE: 274
gcuggauauu aauagaguc 19

<210> SEQ ID NO 275
<211> LENGTH: 23
<212> TYPE: DNA
<213> ORGANISM: Nezara viridula

<400> SEQUENCE: 275
aaatggaaag ctgggcagaa ctt 23

<210> SEQ ID NO 276

<211> LENGTH: 19
<212> TYPE: RNA
<213> ORGANISM: Nezara viridula

<400> SEQUENCE: 276
auggaaagcu gggcagaac 19

<210> SEQ ID NO 277
<211> LENGTH: 19
<212> TYPE: RNA
<213> ORGANISM: Nezara viridula

<400> SEQUENCE: 277
guucugccca gcuuuccau 19

<210> SEQ ID NO 278
<211> LENGTH: 1053
<212> TYPE: DNA
<213> ORGANISM: Nezara viridula

<400> SEQUENCE: 278
ggaaatatgt agtaggaaca aaagtcagtt aagtagtatg ctctctgcaa tcttggacta 60
taccagcaat aaaaacttta tcattagaga taaaaaagat atatcatttt tttctaaagc 120
tatggaagtt tgtagtaaac tcaaagataa ggatcttctc tacaggcttc atgaattatt 180
gttgaccgga aacaattata atttgatcgg agattcattt agtgaatcgg tgtattaccg 240
ttattttttt ttatttgctt actgatactg aagaacttag taaagtaatg gaattctatg 300
atgaccttgt accaaacgtt tatgttccag agccatcagt gaccaatgct atattgaaag 360
ctgtttgtaa caacatggca tgggaccttc ttcccaagct ttggccagac atactattgt 420
ttgagcagta tgaagtttcc ggtgtcctgg aaaatatttt agatattgca tctcaaaatg 480
aaggcaagaa tttgatggaa gggatgtcta aaattgcatg gtctgcatgg gagaagatag 540
aaggaataaa gagggagcga tccaactttc aatggtctgc gagtgcattg ggaaacatta 600
ttctcatttt gttgaaatct ggtgaaaaag ctaaggcgaa tttggttatg aataaattaa 660
ttcaactagg aagttctgcc atgaatgaac caaaaataga ggctttgagt ctctacgtgg 720
acagttgcat agaaagttca tcaccagatg tagcaattaa atgcattcaa tattgcaacg 780
atattggatt tacggaaacc acagagtttg ctaggcgaat caattcttct atcgagctca 840
acccaaggca atatgaaaaa ttaacatcta ttgtaggcga agattgtctg aaagttgaaa 900
agaaaaaaga tcaaagtagt tgaaattgtt tttagacttt taataaatgt ataattttac 960
attgttagtt aatatttgca tagttttctt gtaatataat cactagttca actgttttat 1020
tctaatttaa gagaataaaa gttttacatt tcc 1053

<210> SEQ ID NO 279
<211> LENGTH: 861
<212> TYPE: DNA
<213> ORGANISM: Nezara viridula

<400> SEQUENCE: 279
agtttgaata atttcaatct catctaaagg attatttaat gtgaatgatt tgtgtcagtt 60
tttactttta actgcggcat atagcctgct gcagttaatg cgggaaggtt taccttatta 120
tgtctgactg ggaacaaaga ttgctcagcc tggaaaaact ggacaggtca tcgccagagc 180
tctggccaga gccgatacct ggggtgacag aatatgctgc tcgcaatgct ctttctagtt 240
cctctgttcc aaagaacatt gaatcactcc agagtcagtt tactgaggat gactataagc 300

```
tgctaaatta ttacagtact ctttctaaag aatctctgat tcaagaatta aagaagcttc    360

atgaccaggc ctataaatta ggtcttgaag aagccaagga aatgactaga ggaagatttt    420

tgaacatact gtctaccaga aaaaagtaat ggtttgtaaa tgctgccatg cttctgaatg    480

gttccatcat attctgatcc agaagaagga agttgtagcg aatggagtag gtataaaagt    540

gagtcaataa ggacaagaag ggctaattta atgtattttt ccaaatattt ttgtaattgc    600

agaatagaag atttatgtga agaaatgaat ttaagttttt gttgttgtaa ctgtctgtta    660

tagttccttc agtcccaaat attttgttgg cttctaatca agctcttgta tttattaatt    720

ttctttttca attcaattaa ttaaagtgtt gctaaaaagt tgataatatt aaagtaaatt    780

tagtttattt ttatttccca gaattaatta tttattattg ttatctgtac taagaataaa    840

aaatatgtta attgttctcc g                                              861
```

<210> SEQ ID NO 280
<211> LENGTH: 992
<212> TYPE: DNA
<213> ORGANISM: Nezara viridula

<400> SEQUENCE: 280

```
gaagaaattg agagaatggt taatgatgcc gagaaataca aggctgaaga tgataagcag     60

aaagctgtca ttcaagctaa gaacactctg gagtcctatt gtttcaatat gaaatctact    120

gtagaggatg aaaaactgaa agacaaaatt tccgattctg ataaaactac aatttttggag    180

aaatgtaatg aagttattcg ctggctcgat gctaatcagt tagctgaaaa agaagaattc    240

gaacataagc aaaaggaatt ggaagccata tgcaatccta ttattactaa attgtaccaa    300

agtggtggta tgcccggagg aatgccaggt ggtatgcctg gtggtttccc aggcggtgcc    360

cctcctaatg ctggtggtgc tgctggacct accattgaag aagttgatta aacattccat    420

gcgaataaac acacaaataa tacattgtat aattaatgct agttgaattg caattttttt    480

ttcctttcta gtcaagagac cttcaaatgg ccttgtattt ttgtttaaaa atttaatgtt    540

aataatgtaa cttttacaag tattttgttt atttataatt tttttatatg ttctgtcatt    600

ggtatcaatg aattatatta gagttactat taactaatgt ttttaaataa aaatatagcc    660

tgtagaggaa tacttgatgt aaatgtatac agtattaaat gagccatata atttttattt    720

aaattccatt tttttaattt atatattgat aaattgcatt ttgtgtgtta tacttgcctc    780

attgaattta tgttaatgaa tattttttat agttaaaaaa aaaggctgat tccaatttaa    840

gttttatttt gaagaagaat tttgtaccct tgtttgataa atcttgtgaa tcttgttatg    900

gttaaacatc ttttggtaac cacccctttgg ttgtattcaa aattgtgaat gaaacatttt    960

cggcacaaaa ttaataaaat taattattcc ac                                  992
```

<210> SEQ ID NO 281
<211> LENGTH: 858
<212> TYPE: DNA
<213> ORGANISM: Nezara viridula

<400> SEQUENCE: 281

```
agtgtccgcc ctcttcatct cctgtcttgt atcatcacat catccttccc cttctctcgc     60

tgagtcaact tacgccaaac cgtcatccag cggtaggaag cgagaggctg ccctagattg    120

tatgctaggc tctctcaccg agaacatgtc caggcaagga gtcacaacga cacagaaagg    180

ctgctgttca gcttgcgaca aacccattgt cggccaggta atcacagcac taggcaagac    240
```

```
atggcatcca gaacactttg tctgcacaca ctgcaaccag gagcttggaa caagaaactt    300

ctttgagagg gatggtcacc cctactgtga gccagattac cacaacctct tcagtcctcg    360

atgtgcctac tgcaacggcc ctatcttaga taaatgtgtc acagccttgg aaaaaacatg    420

gcatacggaa catttctttt gtgctcagtg tggtaaacag tttggggaag aggggttcca    480

tgagaaagat ggtcgaccct attgtcggga cgattacttt gaaatgtttg ctccaaaatg    540

tggcggctgt tcccgcccaa taatggagaa ctatatttca gccctctcaa tgcagtggca    600

tcaagactgt tttgtctgca gggattgccg gaagcccgtc acagggaaga ccttttatgc    660

catggaagga aagcctgtct gtccgaaatg tgtcggagtg gacgaggaag aagaagactg    720

aagattcggc aaaaactaat acctctatat taaatgcttt tttatagaac cacgcgaatc    780

ataaccacca tcctaccaac tctgtattta tatttgtata gaaaataaaa gttttttttt    840

ttttttttta ttaattag                                                  858
```

<210> SEQ ID NO 282
<211> LENGTH: 643
<212> TYPE: DNA
<213> ORGANISM: Nezara viridula

<400> SEQUENCE: 282

```
gggtgcctag ggtgcccctt cctggagcag gtggtggaat tggttcagca agacctgcgg     60

gacgtggagt tccagctcct ggtacaccag ctgcacctgg tctccaaggt ccagttcgtg    120

gtgtaggtgg cccatctgca caagttatga ctccagcggg gcgtggagga caagtttctg    180

ctcctcctca gatgcgtgct ccacccccag gaatgccccc aatgatggga gctccaccaa    240

tgatgaacat ggcaccagga atggcgatgg gaagaggtgg accacctcct caaatgggtg    300

ctcctccagc tccaccaatg cgaggtcccc caccaggaat gatgagaggt ccccctcctt    360

tttaagaaga aagaaaattt tgttaccttc cttctgtaat ttttttttaa gtttgaaatt    420

tacaaagcca atggatggct aagattaatt tctgactttt ttttggatac ataccattta    480

tttatgtaaa tgtgctcatg tatgtatata tttatctatg cattttggaa aaagaatatt    540

tgtactaaat tatttgataa ataattgtag taattatact taaacactct ggtctttatt    600

taataaacca ttgttttttt attaattgta ataaatttgt ttt                      643
```

<210> SEQ ID NO 283
<211> LENGTH: 792
<212> TYPE: DNA
<213> ORGANISM: Nezara viridula

<400> SEQUENCE: 283

```
attgaggttt cagtttctgc acagtccagt gactttggtt tcgatcggga tttatatctc     60

tattatggac aatttgggtc aacaaacacc tcatcaaaat aatcattcaa atgatacaga    120

aatgaacaat tttatggacg tatccagaat gagtaccatg tggccttatc cacatcctga    180

caggttttca caatacaggg atttctttca tgaacctcag caaggagtag tttctgggaa    240

tgaaacaaca aataatgtta gccaagtatt aacaaacaat tccacacagc aacattcttt    300

agtgaatact atgcctgtta tgggaacttt acaaacagta ttaactcaag gtttgccaaa    360

ccaaaatgct aatgctaatg ttgttaattt aaatcatact ccacagaatt tacccagtac    420

tattcagact tccataaata gccttccaaa tgccaccaac tctaccagtc aaggacaaga    480

gcaatctacc cagatattaa caagaatgag gttgcaagat ttggtgagag aagtagatcc    540

taatgaacaa ttagacgaag atgttgaaga tgtattatta caaatggcag atgattttgt    600
```

```
tgactcagca attacagctg gttgtcttct tgccaagcac agaaaatcaa ctactgtaga    660

agttaaggat cttcagctac atttagaaag aaattggaat atgtggatac ctggttttgg    720

aacagatgaa ttgcgacctt acaaacgtgc atctgttaca gaagctcata aacaaagact    780

tacgcttatc ac                                                        792
```

<210> SEQ ID NO 284
<211> LENGTH: 536
<212> TYPE: DNA
<213> ORGANISM: Nezara viridula

<400> SEQUENCE: 284

```
gaaatatgta gtaggaacaa aagtcagtta agtagtatgc tctctgcaat cttggactat     60

accagcaata aaaactttat cattagagat aaaaaagata tatcattttt ttctaaagct    120

atggaagttt gtagtaaact caaagataag gatcttctct acaggcttca tgaattattg    180

ttgaccggaa acaattataa tttgatcgga gattcattta gtgaatcggt gtattaccgt    240

tatttttttt tatttgctta ctgatactga agaacttagt aaagtaatgg aattctatga    300

tgaccttgta ccaaacgttt atgttccaga gccatcagtg accaatgcta tattgaaagc    360

tgtttgtaac aacatggcat gggaccttct tcccaagctt tggccagaca tactattgtt    420

tgagcagtat gaagtttccg gtgtcctgga aaatatttta gatattgcat ctcaaaatga    480

aggcaagaat ttgatggaag ggatgtctaa aattgcatgg tctgcatggg agaaga        536
```

<210> SEQ ID NO 285
<211> LENGTH: 605
<212> TYPE: DNA
<213> ORGANISM: Nezara viridula

<400> SEQUENCE: 285

```
tgcggcatat agcctgctgc agttaatgcg ggaaggttta ccttattatg tctgactggg     60

aacaaagatt gctcagcctg gaaaaactgg acaggtcatc gccagagctc tggccagagc    120

cgatacctgg ggtgacagaa tatgctgctc gcaatgctct ttctagttcc tctgttccaa    180

agaacattga atcactccag agtcagttta ctgaggatga ctataagctg ctaaattatt    240

acagtactct ttctaaagaa tctctgattc aagaattaaa gaagcttcat gaccaggcct    300

ataaattagg tcttgaagaa gccaaggaaa tgactagagg aagatttttg aacatactgt    360

ctaccagaaa aaagtaatgg tttgtaaatg ctgccatgct tctgaatggt tccatcatat    420

tctgatccag aagaaggaag ttgtagcgaa tggagtaggt ataaaagtga gtcaataagg    480

acaagaaggg ctaatttaat gtatttttcc aaatattttt gtaattgcag aatagaagat    540

ttatgtgaag aaatgaattt aagtttttgt tgttgtaact gtctgttata gttccttcag    600

tccca                                                                605
```

<210> SEQ ID NO 286
<211> LENGTH: 762
<212> TYPE: DNA
<213> ORGANISM: Nezara viridula

<400> SEQUENCE: 286

```
tgcggcatat agcctgctgc agttaatgcg ggaaggttta ccttattatg tctgactggg     60

aacaaagatt gctcagcctg gaaaaactgg acaggtcatc gccagagctc tggccagagc    120

cgatacctgg ggtgacagaa tatgctgctc gcaatgctct ttctagttcc tctgttccaa    180
```

```
agaacattga atcactccag agtcagttta ctgaggatga ctataagctg ctaaattatt    240

acagtactct ttctaaagaa tctctgattc aagaattaaa gaagcttcat gaccaggcct    300

ataaattagg tcttgaagaa gccaaggaaa tgactagagg aagatttttg aacatactgt    360

ctaccagaaa aaagtaatgg tttgtaaatg ctgccatgct tctgaatggt tccatcatat    420

tctgatccag aagaaggaag ttgtagcgaa tggagtaggt ataaaagtga gtcaataagg    480

acaagaaggg ctaatttaat gtatttttcc aaatattttt gtaattgcag aatagaagat    540

ttatgtgaag aaatgaattt aagtttttgt tgttgtaact gtctgttata gttccttcag    600

tcccaaatat tttgttggct tctaatcaag ctcttgtatt tattaatttt ctttttcaat    660

tcaattaatt aaagtgttgc taaaaagttg ataatattaa agtaaattta gtttattttt    720

atttcccaga attaattatt tattattgtt atctgtacta ag                       762


<210> SEQ ID NO 287
<211> LENGTH: 367
<212> TYPE: DNA
<213> ORGANISM: Nezara viridula

<400> SEQUENCE: 287

tgcggcatat agcctgctgc agttaatgcg ggaaggttta ccttattatg tctgactggg     60

aacaaagatt gctcagcctg gaaaaactgg acaggtcatc gccagagctc tggccagagc    120

cgatacctgg ggtgacagaa tatgctgctc gcaatgctct ttctagttcc tctgttccaa    180

agaacattga atcactccag agtcagttta ctgaggatga ctataagctg ctaaattatt    240

acagtactct ttctaaagaa tctctgattc aagaattaaa gaagcttcat gaccaggcct    300

ataaattagg tcttgaagaa gccaaggaaa tgactagagg aagatttttg aacatactgt    360

ctaccag                                                              367


<210> SEQ ID NO 288
<211> LENGTH: 485
<212> TYPE: DNA
<213> ORGANISM: Nezara viridula

<400> SEQUENCE: 288

tgccgagaaa tacaaggctg aagatgataa gcagaaagct gtcattcaag ctaagaacac     60

tctggagtcc tattgtttca atatgaaatc tactgtagag gatgaaaaac tgaaagacaa    120

aatttccgat tctgataaaa ctacaatttt ggagaaatgt aatgaagtta ttcgctggct    180

cgatgctaat cagttagctg aaaaagaaga attcgaacat aagcaaaagg aattggaagc    240

catatgcaat cctattatta ctaaattgta ccaaagtggt ggtatgcccg gaggaatgcc    300

aggtggtatg cctggtggtt tcccaggcgg tgcccctcct aatgctggtg gtgctgctgg    360

acctaccatt gaagaagttg attaaacatt ccatgcgaat aaacacacaa ataatacatt    420

gtataattaa tgctagttga attgcaattt ttttttcctt tctagtcaag agaccttcaa    480

atggc                                                                485


<210> SEQ ID NO 289
<211> LENGTH: 451
<212> TYPE: DNA
<213> ORGANISM: Nezara viridula

<400> SEQUENCE: 289

ctagtcaaga gaccttcaaa tggccttgta tttttgttta aaaatttaat gttaataatg     60

taacttttac aagtattttg tttatttata attttttat atgttctgtc attggtatca    120
```

atgaattata ttagagttac tattaactaa tgtttttaaa taaaaatata gcctgtagag 180
gaatacttga tgtaaatgta tacagtatta aatgagccat ataattttta tttaaattcc 240 attttttaa tttatatatt gataaattgc attttgtgtg ttatacttgc ctcattgaat 300
ttatgttaat gaatattttt tatagttaaa aaaaaaggct gattccaatt taagttttat 360
tttgaagaag aattttgtac ccttgtttga taaatcttgt gaatcttgtt atggttaaac 420
atcttttggt aaccaccctt tggttgtatt c 451

<210> SEQ ID NO 290
<211> LENGTH: 799
<212> TYPE: DNA
<213> ORGANISM: Nezara viridula

<400> SEQUENCE: 290
gtgtccgccc tcttcatctc ctgtcttgta tcatcacatc atccttcccc ttctctcgct 60
gagtcaactt acgccaaacc gtcatccagc ggtaggaagc gagaggctgc cctagattgt 120
atgctaggct ctctcaccga gaacatgtcc aggcaaggag tcacaacgac acagaaaggc 180
tgctgttcag cttgcgacaa acccattgtc ggccaggtaa tcacagcact aggcaagaca 240
tggcatccag aacactttgt ctgcacacac tgcaaccagg agcttggaac aagaaacttc 300
tttgagaggg atggtcaccc ctactgtgag ccagattacc acaacctctt cagtcctcga 360
tgtgcctact gcaacggccc tatcttagat aaatgtgtca cagccttgga aaaaacatgg 420
catacggaac atttcttttg tgctcagtgt ggtaaacagt ttggggaaga ggggttccat 480
gagaaagatg gtcgacccta ttgtcgggac gattactttg aaatgtttgc tccaaaatgt 540
ggcggctgtt cccgcccaat aatggagaac tatatttcag ccctctcaat gcagtggcat 600
caagactgtt ttgtctgcag ggattgccgg aagcccgtca cagggaagac cttttatgcc 660
atggaaggaa agcctgtctg tccgaaatgt gtcggagtgg acgaggaaga agaagactga 720
agattcggca aaaactaata cctctatatt aaatgctttt ttatagaacc acgcgaatca 780
taaccaccat cctaccaac 799

<210> SEQ ID NO 291
<211> LENGTH: 576
<212> TYPE: DNA
<213> ORGANISM: Nezara viridula

<400> SEQUENCE: 291
ttcctggagc aggtggtgga attggttcag caagacctgc gggacgtgga gttccagctc 60
ctggtacacc agctgcacct ggtctccaag gtccagttcg tggtgtaggt ggcccatctg 120
cacaagttat gactccagcg gggcgtggag gacaagtttc tgctcctcct cagatgcgtg 180
ctccaccccc aggaatgccc ccaatgatgg gagctccacc aatgatgaac atggcaccag 240
gaatggcgat gggaagaggt ggaccacctc ctcaaatggg tgctcctcca gctccaccaa 300
tgcgaggtcc cccaccagga atgatgagag gtccccctcc tttttaagaa gaaagaaaat 360
tttgttacct tccttctgta attttttttt aagtttgaaa tttacaaagc caatggatgg 420
ctaagattaa tttctgactt ttttttggat acataccatt tatttatgta aatgtgctca 480
tgtatgtata tatttatcta tgcattttgg aaaaagaata tttgtactaa attatttgat 540
aaataattgt agtaattata cttaaacact ctggtc 576

<210> SEQ ID NO 292

<211> LENGTH: 782
<212> TYPE: DNA
<213> ORGANISM: Nezara viridula

<400> SEQUENCE: 292

```
gaggtttcag tttctgcaca gtccagtgac tttggtttcg atcgggattt atatctctat     60
tatggacaat ttgggtcaac aaacacctca tcaaaataat cattcaaatg atacagaaat    120
gaacaatttt atggacgtat ccagaatgag taccatgtgg ccttatccac atcctgacag    180
gttttcacaa tacagggatt tctttcatga acctcagcaa ggagtagttt ctgggaatga    240
aacaacaaat aatgttagcc aagtattaac aaacaattcc acacagcaac attctttagt    300
gaatactatg cctgttatgg gaactttaca aacagtatta actcaaggtt tgccaaacca    360
aaatgctaat gctaatgttg ttaatttaaa tcatactcca cagaatttac ccagtactat    420
tcagacttcc ataaatagcc ttccaaatgc caccaactct accagtcaag gacaagagca    480
atctacccag atattaacaa gaatgaggtt gcaagatttg gtgagagaag tagatcctaa    540
tgaacaatta gacgaagatg ttgaagatgt attattacaa atggcagatg attttgttga    600
ctcagcaatt acagctggtt gtcttcttgc caagcacaga aaatcaacta ctgtagaagt    660
taaggatctt cagctacatt tagaaagaaa ttggaatatg tggatacctg gttttggaac    720
agatgaattg cgaccttaca aacgtgcatc tgttacagaa gctcataaac aaagacttac    780
gc                                                                   782
```

<210> SEQ ID NO 293
<211> LENGTH: 1358
<212> TYPE: DNA
<213> ORGANISM: Artificial Sequence
<220> FEATURE:
<223> OTHER INFORMATION: PHP49713 Haripin RNA Construct without promoter

<400> SEQUENCE: 293

```
ggaaatatgt agtaggaaca aaagtcagtt aagtagtatg ctctctgcaa tcttggacta     60
taccagcaat aaaaacttta tcattagaga taaaaaagat atatcatttt tttctaaagc    120
tatggaagtt tgtagtaaac tcaaagataa ggatcttctc tacaggcttc atgaattatt    180
gttgaccgga aacaattata atttgatcgg agattcattt agtgaatcgg tgtattaccg    240
ttattttttt ttatttgctt actgatactg aagaacttag taaagtaatg gaattctatg    300
atgaccttgt accaaacgtt tatgttccag agccatcagt gaccaatgct atattgaaag    360
ctgtttgtaa caacatggca tgggaccttc ttcccaagct ttggccagac atactattgt    420
ttgagcagta tgaagtttcc ggtgtcctgg aaaatatttt agatattgca tctcaaaatg    480
aaggcaagaa tttgatggaa gggatgtcta aaattgcatg gtctgcatgg gagaagcaac    540
tttattatac aaagttgata gatatcggtc cgagatccat caggtaagtt tctgcttcta    600
cctttgatat atatataata attatcatta attagtagta atataatatt tcaaatattt    660
ttttcaaaat aaaagaatgt agtatatagc aattgctttt ctgtagttta taagtgtgta    720
tattttaatt tataactttt ctaatatatg accaaaacat ggtgatgtgc aggtccatgg    780
tggagctcga ccgatatcta tcaactttgt ataataaagt tgcttctccc atgcagacca    840
tgcaatttta gacatccctt ccatcaaatt cttgccttca ttttgagatg caatatctaa    900
aatattttcc aggacaccgg aaacttcata ctgctcaaac aatagtatgt ctggccaaag    960
cttgggaaga aggtcccatg ccatgttgtt acaaacagct ttcaatatag cattggtcac   1020
tgatggctct ggaacataaa cgtttggtac aaggtcatca tagaattcca ttactttact   1080
```

```
aagttcttca gtatcagtaa gcaaataaaa aaaaataacg gtaatacacc gattcactaa   1140

atgaatctcc gatcaaatta taattgtttc cggtcaacaa taattcatga agcctgtaga   1200

gaagatcctt atctttgagt ttactacaaa cttccatagc tttagaaaaa aatgatatat   1260

ctttttttatc tctaatgata aagtttttat tgctggtata gtccaagatt gcagagagca   1320

tactacttaa ctgacttttg ttcctactac atatttcc                           1358
```

<210> SEQ ID NO 294
<211> LENGTH: 1498
<212> TYPE: DNA
<213> ORGANISM: Artificial Sequence
<220> FEATURE:
<223> OTHER INFORMATION: PHP48181 Haripin RNA Construct without promoter

<400> SEQUENCE: 294

```
ctgcggcata tagcctgctg cagttaatgc gggaaggttt accttattat gtctgactgg     60

gaacaaagat tgctcagcct ggaaaaactg gacaggtcat cgccagagct ctggccagag    120

ccgatacctg ggtgacagga atatgctgct cgcaatgctc tttctagttc ctctgttcca    180

aagaacattg aatcactcca gagtcagttt actgaggatg actataagct gctaaattat    240

tacagtactc tttctaaaga atctctgatt caagaattaa agaagcttca tgaccaggcc    300

tataaattag gtcttgaaga agccaaggaa atgactagag gaagattttt gaacatactg    360

tctaccagaa aaaagtaatg gtttgtaaat gctgccatgc ttctgaatgg ttccatcata    420

ttctgatcca gaagaaggaa gttgtagcga atggagtagg tataaaagtg agtcaataag    480

gacaagaagg gctaatttaa tgtatttttc caaatatttt tgtaattgca gaatagaaga    540

tttatgtgaa gaaatgaatt taagtttttg ttgttgtaac tgtctgttat agttccttca    600

gtcccacaac tttattatac aaagttgata gatatcggtc cgagatccat caggtaagtt    660

tctgcttcta cctttgatat atatataata attatcatta attagtagta atataatatt    720

tcaaatattt ttttcaaaat aaaagaatgt agtatatagc aattgctttt ctgtagttta    780

taagtgtgta tattttaatt tataactttt ctaatatatg accaaaacat ggtgatgtgc    840

aggtccatgg tggagctcga ccgatatcta tcaactttgt ataataaagt tgtgggactg    900

aaggaactat aacagacagt tacaacaaca aaaacttaaa ttcatttctt cacataaatc    960

ttctattctg caattacaaa aatatttgga aaaatacatt aaattagccc ttcttgtcct   1020

tattgactca cttttatacc tactccattc gctacaactt ccttcttctg gatcagaata   1080

tgatggaacc attcagaagc atggcagcat ttacaaacca ttactttttt ctggtagaca   1140

gtatgttcaa aaatcttcct ctagtcattt ccttggcttc ttcaagacct aatttatagg   1200

cctggtcatg aagcttcttt aattcttgaa tcagagattc tttagaaaga gtactgtaat   1260

aatttagcag cttatagtca tcctcagtaa actgactctg gagtgattca atgttctttg   1320

gaacagagga actagaaaga gcattgcgag cagcatattc tgtcacccca ggtatcggct   1380

ctggccagag ctctggcgat gacctgtcca gtttttccag gctgagcaat ctttgttccc   1440

agtcagacat aataaggtaa accttcccgc attaactgca gcaggctata tgccgcag     1498
```

<210> SEQ ID NO 295
<211> LENGTH: 1813
<212> TYPE: DNA
<213> ORGANISM: Artificial Sequence
<220> FEATURE:
<223> OTHER INFORMATION: pKB505 Haripin RNA Construct without promoter

<400> SEQUENCE: 295
ctgcggcata tagcctgctg cagttaatgc gggaaggttt accttattat gtctgactgg 60
gaacaaagat tgctcagcct ggaaaaactg gacaggtcat cgccagagct ctggccagag 120
ccgatacctg ggtgacagaa atatgctgct cgcaatgctc tttctagttc ctctgttcca 180
aagaacattg aatcactcca gagtcagttt actgaggatg actataagct gctaaattat 240
tacagtactc tttctaaaga atctctgatt caagaattaa agaagcttca tgaccaggcc 300
tataaattag gtcttgaaga agccaaggaa atgactagag gaagattttt gaacatactg 360
tctaccagaa aaaagtaatg gtttgtaaat gctgccatgc ttctgaatgg ttccatcata 420
ttctgatcca gaagaaggaa gttgtagcga atggagtagg tataaaagtg agtcaataag 480
gacaagaagg gctaatttaa tgtatttttc caaatatttt tgtaattgca gaatagaaga 540
tttatgtgaa gaaatgaatt taagtttttg ttgttgtaac tgtctgttat agttccttca 600
gtcccaaata ttttgttggc ttctaatcaa gctcttgtat ttattaattt tctttttcaa 660
ttcaattaat taaagtgttg ctaaaaagtt gataatatta aagtaaattt agtttatttt 720
tatttcccag aattaattat ttattattgt tatctgtact aagcaacttt attatacaaa 780
gttggataga tatcggtccg agatccatca ggtaagtttc tgcttctacc tttgatatat 840
atataataat tatcattaat tagtagtaat ataatatttc aaatattttt ttcaaaataa 900
aagaatgtag tatatagcaa ttgcttttct gtagtttata agtgtgtata ttttaattta 960
taacttttct aatatatgac caaaacatgg tgatgtgcag gtccatggtg gagctcgacc 1020
gatatctatc aactttgtat aataaagttg cttagtacag ataacaataa taaataatta 1080
attctgggaa ataaaaataa actaaattta ctttaatatt atcaactttt tagcaacact 1140
ttaattaatt gaattgaaaa agaaaattaa taaatacaag agcttgatta gaagccaaca 1200
aaatatttgg gactgaagga actataacag acagttacaa caacaaaaac ttaaattcat 1260
ttcttcacat aaatcttcta ttctgcaatt acaaaaatat ttggaaaaat acattaaatt 1320
agcccttctt gtccttattg actcactttt atacctactc cattcgctac aacttccttc 1380
ttctggatca gaatatgatg gaaccattca gaagcatggc agcatttaca aaccattact 1440
tttttctggt agacagtatg ttcaaaaatc ttcctctagt catttccttg gcttcttcaa 1500
gacctaattt ataggcctgg tcatgaagct tctttaattc ttgaatcaga gattctttag 1560
aaagagtact gtaataattt agcagcttat agtcatcctc agtaaactga ctctggagtg 1620
attcaatgtt ctttggaaca gaggaactag aaagagcatt gcgagcagca tattctgtca 1680
ccccaggtat cggctctggc cagagctctg gcgatgacct gtccagtttt tccaggctga 1740
gcaatctttg ttcccagtca gacataataa ggtaaacctt cccgcattaa ctgcagcagg 1800
ctatatgccg cag 1813

<210> SEQ ID NO 296
<211> LENGTH: 1694
<212> TYPE: DNA
<213> ORGANISM: Artificial Sequence
<220> FEATURE:
<223> OTHER INFORMATION: pKB506 Haripin RNA Construct without promoter

<400> SEQUENCE: 296
gggtgattgc ggttacatca tgtacggaaa aataattcta atccttgatt taaatttgaa 60
cttgactatt tatttattct ttatttcatt ttgtaaatca ttttatgtat ctcctggcaa 120
gcaattttat ccaccttgca ccaacacctt cgggttccat aatcaaacca ccttaacttc 180

```
acaccatgct gtaactcaca ccgcccagca tctccaatgt gaaagaagct aaaatttaat    240

aaacaatcat acgaagcagt gacaaaatac cagatggtat taatgcttcg ataaaattaa    300

ttggaaagta taaaatggta gaaaataata aattataatt aatttaagta agataaaaaa    360

taattaaaaa ctaaaatgtt aaaattttaa aaaaattatt ttaaataata tttaaaaaca    420

ttaaaaatca ttttaaaaaa tttatttata gaacaattaa ataaatattt cagctaataa    480

aaaacaaaag cttacctagc cttagaagac aacttgtcca acaattagat gatacccatt    540

gcccttacgt tttctttaac atcaattatt gtttttgtca acaagctatc ttttagtttt    600

attttattgg taaaaaatat gtcgccttca agttgcatca tttaacacat ctcgtcatta    660

gaaaaataaa actcttccct aaacgattag tagaaaaaat cattcgataa taaataagaa    720

agaaaaatta gaaaaaaata acttcatttt aaaaaaatca ttaaggctat attttttaaa    780

tgactaattt tatatagact gtaactaaaa gtatacaatt tattatgcta tgtatcttaa    840

agaattactt ataaaaatct acggaagaat atcttacaaa gtgaaaaaca aatgagaaag    900

aatttagtgg gatgattatg attttatttg aaaattgaaa aaataattat taaagacttt    960

agtggagtaa gaaagctttc ctattagtct tttcttatcc ataaaaaaaa aaaaaaaaat   1020

ctagcgtgac agcttttcca tagattttaa taatgtaaaa tactggtagc agccgaccgt   1080

tcaggtaatg gacactgtgg tcctaacttg caacgggtgc gggcccaatt taataacgcc   1140

gtggtaacgg ataaagccaa gcgtgaagcg gtgaaggtac atctctgact ccgtcaagat   1200

tacgaaaccg tcaactacga aggactcccc gaaatatcat ctgtgtcata aacaccaagt   1260

cacaccatac atgggcacgc gtcacaatat gattggagaa cggttccacc gcatatgcta   1320

taaaatgccc ccacacccct cgaccctaat cgcacttcaa ttgcaatcaa attagttcat   1380

tctctttgcg cagttcccta cctctccttt caaggttcgt agatttcttc cgtttttttt   1440

tcttcttctt tattgtttgt tctacatcag catgatgttg atttgattgt gttttctatc   1500

gtttcatcga ttataaattt tcataatcag aagattcagc ttttattaat gcaagaacgt   1560

ccttaattga tgattttata accgtaaatt aggtctaatt agagtttttt tcataaagat   1620

tttcagatcc gtttacaaca agccttaatt gttgattctg tagtcgtaga ttaaggtttt   1680

tttcatgaac tact                                                     1694
```

```
<210> SEQ ID NO 297
<211> LENGTH: 1256
<212> TYPE: DNA
<213> ORGANISM: Artificial Sequence
<220> FEATURE:
<223> OTHER INFORMATION: PHP48183 Haripin RNA Construct without promoter
<220> FEATURE:
<221> NAME/KEY: misc_feature
<222> LOCATION: 432, 825
<223> OTHER INFORMATION: n = A,T,C or G

<400> SEQUENCE: 297

tgccgagaaa tacaaggctg aagatgataa gcagaaagct gtcattcaag ctaagaacac     60

tctggagtcc tattgtttca atatgaaatc tactgtagag gatgaaaaac tgaaagacaa    120

aatttccgat tctgataaaa ctacaatttt ggagaaatgt aatgaagtta ttcgctggct    180

cgatgctaat cagttagctg aaaaagaaga attcgaacat aagcaaaagg aattggaagc    240

catatgcaat cctattatta ctaaattgta ccaaagtggt ggtatgcccg gaggaatgcc    300

aggtggtatg cctggtggtt tcccaggcgg tgcccctcct aatgctggtg gtgctgctgg    360
```

```
acctaccatt gaagaagttg attaaacatt ccatgcgaat aaacacacaa ataatacatt    420

gtataattaa tnctagttga attgcaattt ttttttcctt tctagtcaag agaccttcaa    480

atggccaact ttattataca aagttgatag atatcggtcc gagatccatc aggtaagttt    540

ctgcttctac ctttgatata tatataataa ttatcattaa ttagtagtaa tataatattt    600

caaatatttt tttcaaaata aaagaatgta gtatatagca attgcttttc tgtagtttat    660

aagtgtgtat attttaattt ataacttttc taatatatga ccaaaacatg gtgatgtgca    720

ggtccatggt ggagctcgac cgatatctat caactttgta taataaagtt ggccatttga    780

aggtctcttg actagaaagg aaaaaaaaat tgcaattcaa ctagnattaa ttatacaatg    840

tattatttgt gtgtttattc gcatggaatg tttaatcaac ttcttcaatg gtaggtccag    900

cagcaccacc agcattagga ggggcaccgc ctgggaaacc accaggcata ccacctggca    960

ttcctccggg cataccacca ctttggtaca atttagtaat aataggattg catatggctt   1020

ccaattcctt ttgcttatgt tcgaattctt ctttttcagc taactgatta gcatcgagcc   1080

agcgaataac ttcattacat ttctccaaaa ttgtagtttt atcagaatcg gaaattttgt   1140

ctttcagttt ttcatcctct acagtagatt tcatattgaa acaataggac tccagagtgt   1200

tcttagcttg aatgacagct ttctgcttat catcttcagc cttgtatttc tcggca       1256
```

<210> SEQ ID NO 298
<211> LENGTH: 1188
<212> TYPE: DNA
<213> ORGANISM: Artificial Sequence
<220> FEATURE:
<223> OTHER INFORMATION: pKB508 Haripin RNA Construct without promoter

<400> SEQUENCE: 298

```
ctagtcaaga gaccttcaaa tggccttgta tttttgttta aaaatttaat gttaataatg     60

taacttttac aagtattttg tttatttata atttttttat atgttctgtc attggtatca    120

atgaattata ttagagttac tattaactaa tgtttttaaa taaaaatata gcctgtagag    180

gaatacttga tgtaaatgta tacagtatta aatgagccat ataattttta tttaaattcc    240

atttttttaa tttatatatt gataaattgc attttgtgtg ttatacttgc ctcattgaat    300

ttatgttaat gaatattttt tatagttaaa aaaaaaggct gattccaatt taagttttat    360

tttgaagaag aattttgtac ccttgtttga taaatcttgt gaatcttgtt atggttaaac    420

atcttttggt aaccaccctt tggttgtatt ccaactttat tatacaaagt tgatagatat    480

cggtccgaga tccatcaggt aagtttctgc ttctaccttt gatatatata taataattat    540

cattaattag tagtaatata atatttcaaa tatttttttc aaaataaaag aatgtagtat    600

atagcaattg cttttctgta gtttataagt gtgtatattt taatttataa cttttctaat    660

atatgaccaa aacatggtga tgtgcaggtc catggtggag ctcgaccgat atctatcaac    720

tttgtataat aaagttggaa tacaaccaaa gggtggttac caaaagatgt ttaaccataa    780

caagattcac aagatttatc aaacaagggt acaaaattct tcttcaaaat aaaacttaaa    840

ttggaatcag cctttttttt taactataaa aaatattcat taacataaat tcaatgaggc    900

aagtataaca cacaaaatgc aatttatcaa tatataaatt aaaaaaatgg aatttaaata    960

aaaattatat ggctcattta atactgtata catttacatc aagtattcct ctacaggcta   1020

tatttttatt taaaaacatt agttaatagt aactctaata taattcattg ataccaatga   1080

cagaacatat aaaaaaatta taaataaaca aaatacttgt aaaagttaca ttattaacat   1140

taaattttta aacaaaaata caaggccatt tgaaggtctc ttgactag                1188
```

<210> SEQ ID NO 299
<211> LENGTH: 1882
<212> TYPE: DNA
<213> ORGANISM: Artificial Sequence
<220> FEATURE:
<223> OTHER INFORMATION: PHP49450 Haripin RNA Construct without promoter

<400> SEQUENCE: 299

```
gtgtccgccc tcttcatctc ctgtcttgta tcatcacatc atccttcccc ttctctcgct     60

gagtcaactt acgccaaacc gtcatccagc ggtaggaagc gagaggctgc cctagattgt    120

atgctaggct ctctcaccga gaacatgtcc aggcaaggag tcacaacgac acagaaaggc    180

tgctgttcag cttgcgacaa acccattgtc ggccaggtaa tcacagcact aggcaagaca    240

tggcatccag aacactttgt ctgcacacac tgcaaccagg agcttggaac aagaaacttc    300

tttgagaggg atggtcaccc ctactgtgag ccagattacc acaacctctt cagtcctcga    360

tgtgcctact gcaacggccc tatcttagat aaatgtgtca cagccttgga aaaaacatgg    420

catacggaac atttcttttg tgctcagtgt ggtaaacagt ttggggaaga ggggttccat    480

gagaaagatg gtcgacccta ttgtcgggac gattactttg aaatgtttgc tccaaaatgt    540

ggcggctgtt cccgcccaat aatggagaac tatatttcag ccctctcaat gcagtggcat    600

caagactgtt ttgtctgcag ggattgccgg aagcccgtca cagggaagac cttttatgcc    660

atggaaggaa acctgtctgt ccgaaatgtg tcggagtgga cgaggaagaa gaagactgaa    720

gattcggcaa aaactaatac ctctatatta aatgcttttt tatagaacca cgcgaatcat    780

aaccaccatc ctaccaacca actttattat acaaagttga tagatatcgg tccgagatcc    840

atcaggtaag tttctgcttc tacctttgat atatatataa taattatcat taattagtag    900

taatataata tttcaaatat ttttttcaaa ataaaagaat gtagtatata gcaattgctt    960

ttctgtagtt tataagtgtg tatattttaa tttataactt ttctaatata tgaccaaaac   1020

atggtgatgt gcaggtccat ggtggagctc gaccgatatc tatcaacttt gtataataaa   1080

gttggttggt aggatggtgg ttatgattcg cgtggttcta taaaaaagca tttaatatag   1140

aggtattagt ttttgccgaa tcttcagtct tcttcttcct cgtccactcc gacacatttc   1200

ggacagacag gtttccttcc atggcataaa aggtcttccc tgtgacgggc ttccggcaat   1260

ccctgcagac aaaacagtct tgatgccact gcattgagag ggctgaaata tagttctcca   1320

ttattgggcg ggaacagccg ccacattttg gagcaaacat ttcaaagtaa tcgtcccgac   1380

aatagggtcg accatctttc tcatggaacc cctcttcccc aaactgttta ccacactgag   1440

cacaaaagaa atgttccgta tgccatgttt tttccaaggc tgtgacacat ttatctaaga   1500

tagggccgtt gcagtaggca catcgaggac tgaagaggtt gtggtaatct ggctcacagt   1560

aggggtgacc atccctctca aagaagtttc ttgttccaag ctcctggttg cagtgtgtgc   1620

agacaaagtg ttctggatgc catgtcttgc ctagtgctgt gattacctgg ccgacaatgg   1680

gtttgtcgca agctgaacag cagcctttct gtgtcgttgt gactccttgc ctggacatgt   1740

tctcggtgag agagcctagc atacaatcta gggcagcctc tcgcttccta ccgctggatg   1800

acggtttggc gtaagttgac tcagcgagag aaggggaagg atgatgtgat gatacaagac   1860

aggagatgaa gagggcggac ac                                            1882
```

<210> SEQ ID NO 300
<211> LENGTH: 1438
<212> TYPE: DNA

<213> ORGANISM: Artificial Sequence
<220> FEATURE:
<223> OTHER INFORMATION: PHP49451 Haripin RNA Construct without promoter

<400> SEQUENCE: 300

```
ttcctggagc aggtggtgga attggttcag caagacctgc gggacgtgga gttccagctc     60
ctggtacacc agctgcacct ggtctccaag gtccagttcg tggtgtaggt ggcccatctg    120
cacaagttat gactccagcg gggcgtggag gacaagtttc tgctcctcct cagatgcgtg    180
ctccaccccc aggaatgccc ccaatgatgg gagctccacc aatgatgaac atggcaccag    240
gaatggcgat gggaagaggt ggaccacctc ctcaaatggg tgctcctcca gctccaccaa    300
tgcgaggtcc cccaccagga atgatgagag gtccccctcc tttttaagaa gaaagaaaat    360
tttgttacct tccttctgta attttttttt aagtttgaaa tttacaaagc caatggatgg    420
ctaagattaa tttctgactt ttttttggat acataccatt tatttatgta aatgtgctca    480
tgtatgtata tatttatcta tgcattttgg aaaaagaata tttgtactaa attatttgat    540
aaataattgt agtaattata cttaaacact ctggtccaac tttattatac aaagttgata    600
gatatcggtc cgagatccat caggtaagtt tctgcttcta cctttgatat atatataata    660
attatcatta attagtagta atataatatt tcaaatattt ttttcaaaat aaaagaatgt    720
agtatatagc aattgctttt ctgtagttta taagtgtgta tattttaatt tataactttt    780
ctaatatatg accaaaacat ggtgatgtgc aggtccatgg tggagctcga ccgatatcta    840
tcaactttgt ataataaagt tggaccagag tgtttaagta taattactac aattatttat    900
caaataattt agtacaaata ttcttttttcc aaaatgcata gataaatata tacatacatg    960
agcacattta cataaataaa tggtatgtat ccaaaaaaaa gtcagaaatt aatcttagcc   1020
atccattggc tttgtaaatt tcaaacttaa aaaaaaatta cagaaggaag gtaacaaaat   1080
tttctttctt cttaaaaagg agggggacct ctcatcattc ctggtggggg acctcgcatt   1140
ggtggagctg gaggagcacc catttgagga ggtggtccac ctcttcccat cgccattcct   1200
ggtgccatgt tcatcattgg tggagctccc atcattgggg gcattcctgg gggtggagca   1260
cgcatctgag gaggagcaga aacttgtcct ccacgccccg ctggagtcat aacttgtgca   1320
gatgggccac ctacaccacg aactggacct tggagaccag gtgcagctgg tgtaccagga   1380
gctggaactc cacgtcccgc aggtcttgct gaaccaattc caccacctgc tccaggaa     1438
```

<210> SEQ ID NO 301
<211> LENGTH: 1850
<212> TYPE: DNA
<213> ORGANISM: Artificial Sequence
<220> FEATURE:
<223> OTHER INFORMATION: PHP49480 Haripin RNA Construct without promoter

<400> SEQUENCE: 301

```
gaggtttcag tttctgcaca gtccagtgac tttggtttcg atcgggattt atatctctat     60
tatggacaat ttgggtcaac aaacacctca tcaaaataat cattcaaatg atacagaaat    120
gaacaatttt atggacgtat ccagaatgag taccatgtgg ccttatccac atcctgacag    180
gttttcacaa tacagggatt tctttcatga acctcagcaa ggagtagttt ctgggaatga    240
aacaacaaat aatgttagcc aagtattaac aaacaattcc acacagcaac attctttagt    300
gaatactatg cctgttatgg gaactttaca aacagtatta actcaaggtt tgccaaacca    360
aaatgctaat gctaatgttg ttaatttaaa tcatactcca cagaatttac ccagtactat    420
tcagacttcc ataaatagcc ttccaaatgc caccaactct accagtcaag gacaagagca    480
```

```
atctacccag atattaacaa gaatgaggtt gcaagatttg gtgagagaag tagatcctaa    540

tgaacaatta gacgaagatg ttgaagatgt attattacaa atggcagatg attttgttga    600

ctcagcaatt acagctggtt gtcttcttgc caagcacaga aaatcaacta ctgtagaagt    660

taaggatctt cagctacatt tagaaagaaa ttggaatatg tggatacctg gttttggaac    720

agatgaattg cgaccttaca aacgtgcatc tgttacagaa gctcataaac aaagacttac    780

gccaacttta ttatacaaag ttgatagata tcggtccgag atccatcagg taagtttctg    840

cttctacctt tgatatatat ataataatta tcattaatta gtagtaatat aatatttcaa    900

atattttttt caaaataaaa gaatgtagta tatagcaatt gcttttctgt agtttataag    960

tgtgtatatt ttaatttata acttttctaa tatatgacca aaacatggtg atgtgcaggt   1020

ccatggtgga gctcgaccga tatctatcaa ctttgtataa taaagttggc gtaagtcttt   1080

gtttatgagc ttctgtaaca gatgcacgtt tgtaaggtcg caattcatct gttccaaaac   1140

caggtatcca catattccaa tttctttcta aatgtagctg aagatcctta acttctacag   1200

tagttgattt tctgtgcttg gcaagaagac aaccagctgt aattgctgag tcaacaaaat   1260

catctgccat ttgtaataat acatcttcaa catcttcgtc taattgttca ttaggatcta   1320

cttctctcac caaatcttgc aacctcattc ttgttaatat ctgggtagat tgctcttgtc   1380

cttgactggt agagttggtg gcatttggaa ggctatttat ggaagtctga atagtactgg   1440

gtaaattctg tggagtatga tttaaattaa caacattagc attagcattt tggtttggca   1500

aaccttgagt taatactgtt tgtaaagttc ccataacagg catagtattc actaaagaat   1560

gttgctgtgt ggaattgttt gttaatactt ggctaacatt atttgttgtt tcattcccag   1620

aaactactcc ttgctgaggt tcatgaaaga aatccctgta ttgtgaaaac ctgtcaggat   1680

gtggataagg ccacatggta ctcattctgg atacgtccat aaaattgttc atttctgtat   1740

catttgaatg attattttga tgaggtgttt gttgacccaa attgtccata atagagatat   1800

aaatcccgat cgaaaccaaa gtcactggac tgtgcagaaa ctgaaacctc              1850
```

<210> SEQ ID NO 302
<211> LENGTH: 643
<212> TYPE: DNA
<213> ORGANISM: Nezara viridula

<400> SEQUENCE: 302

```
cagagtgaaa tcgctccact gagagtgtcg gtctcttgtc gctccgtttg atcgctcgta     60

cgtacgcggt attatatacg ggccgagtgt ggcgttggac atggtactta catcgaacat    120

ctttaaagga ctttctgttt aagagaggag gagaggagga cacatggcga ccctgcggcc    180

gcacttcgtc acccacaacg gccccccaga cctgtccgac gatggcactg acgatgaggg    240

gacgccgctc acccacgata tctatggcgg aagtacaagg actgttcagg agacaaaagg    300

atgggatgtg ttccgagttc ttcccccaaa aacagattcg ggttcgatgg aaaaccaagc    360

atgtcttgaa ttcactgtga gaattttaaa aattatagca tacctggtta cgttcactat    420

tgtcctcacc agtggtgtat tggctaagct gtcagttctc ttcatcactt cccaactgcg    480

acctgatagg gtggtcagtt attgtaataa ggacttggga agggataagc aattcgtagt    540

gaacttacca cccgaagaac gagtggcctg gtcatggtgc ttactatttg cttttgcaat    600

tcctgaagtt ggaacattca ttaggtccct gagaatatgt atc                      643
```

<210> SEQ ID NO 303

<211> LENGTH: 1219
<212> TYPE: DNA
<213> ORGANISM: Nezara viridula

<400> SEQUENCE: 303
aggttatgtg actgtgttac atcgagtttg atattgtttt cattgtgaag tgttgattag 60
ttctgtatta cttcgaagtt taaagaatta ttaatatact ttagaaatgt tgaattttgg 120
ttataatgct agaagatata tttatgtttt catatttact atgcctctta cttagtactg 180
atgttacata ggaaaatgag agttaaaaaa tatttgcctg atgtgtacat ttgtggaaga 240
aaatttaatt ctagaaaatg gctgctctgt ttgacccaaa tgacagaagc aggtaagttc 300
atgaaattgg tattttggtc aaatgtcaag gcaagatgcc actgatcttt taatgggaga 360
aaaggagggt ggcgtatttc ttgtccgtga tagtatctca attcatggtg attatgttct 420
ttgtgtaagg gaagatagta aagtaagcca ttatattatc aacaaaattc agcagaatga 480
tcaaattaag tacagaattg gtgatcaaac atttaatgat ttgcccagtt agctatcttt 540
ctataaattg cactatttag atactacacc tctaattcga ccagcaccaa agagagttga 600
aaaagtgata gctaaatttg acttcaatgg aagtgatcaa gatgatttac cgtttaagaa 660
aggtgatatt ttaacaatta tttctaaaga tgaagatcag tggtggacag ccaaaaacag 720
tgctggttta atgggatcaa taccagttcc ctatattcaa aagtataatg accaagatgt 780
actagcagat cttggttctt catttgttga taatagtcct cctagtggaa gtcatgtaga 840
acctataaga agatctaatg ttcagaggaa gcttcctgcg tttgcgaaag taaaacaggc 900
cagagctcca aatgcttatg acaagacagc tttaaagcta gaaattggtg aaataataaa 960
agttacaaaa atgaatttaa atggacagtg ggaaggtgaa cttaagggaa aaactggaca 1020
ttttccgttt actcatgttg aattcataga taatgaaatg tgaatgctgc aattttttta 1080
acaaatagta caaacataat tcatggctat tgttcattat tggtgctcta atgaaaattt 1140
tattaatgca cttctgctat ttataaaaca tattattatt ttttgtaaag cattaaactt 1200
atgttattca atttacagc 1219

<210> SEQ ID NO 304
<211> LENGTH: 1470
<212> TYPE: DNA
<213> ORGANISM: Nezara viridula

<400> SEQUENCE: 304
actcaaaatg atagcacttt gtgatttatt ctatatgtca tccaatcttt aatttactgg 60
acgattgcta aaataagttt cagaaatatt tgtctgtaat aacattaatt gctcaattat 120
agaaataaag ctactaatta gcctataata tctaacatat atctaaaaaa ttagatatat 180
gttgaaccct aagtattgta aacatcagca tgttatacaa taaattaata acagaaaaca 240
ttcttacttc taaacagaat gaaaatatag agtacttgtg atttagccgg tcgccttcgg 300
acctaccttc ttatcttgtg ttatctcttc gtatcgctca tctctgctta gttacttgtg 360
cgttcttctt gttattcaat tattttcagt tttttttgt tttgttattt tttatttaaa 420
atggttacaa taacacttta ggaattactg tcttcggaag aagactatat tatatattag 480
acaggtcaac taaaaaaatt ggagggtcta aaaaagttgt tgaaatagac ggaagtcttt 540
tttctaaacg aaaaaatcat gtagggagag tgctctcgga ataatggatg tttggcagag 600
tttgtcgaga aacagatgag tgtttcattg taaaaataaa agaaacgcaa caattctatt 660
tactaattga taatatctct cttctatatt atcttctaaa aataatatag aagaaagaaa 720

```
cactatatat tctgactgtt ggagaggata taaaacctaa gaactaaata aagcgaacta    780

aaaccatttc caggtgaatc actggtatag ctttgtcgat ccacactcaa cacatagaac    840

tattatgggg ctcagctaag tggaggaata aaatatatcg aggaactgcg atgctactcc    900

gggattcata tatttagcta ctgcagtaca caaaatcata tttatgtgaa tttttgtggc    960

gatgggtgca cagagaagag acgtgttcct cgctatttta actagcatta agctattttg   1020

tcttccaaaa tgaataaaat gttgtaaaat aaaagagttt tgttattatt acatttctgt   1080

ttgtttattt caatttccat aattataaat aaggaggtag gtgttatcag tgttcagatt   1140

ataaataatg atggatagca gtacgtggtg accagttaac tcacaagtgc caaatatagc   1200

actggtttaa ctgtttgtga tctgaggtag aagaattaat aagaagtcta catattctcc   1260

caccataagt taatataatc acctagtgtg tatcttcaat tagaacttca gaaggaagat   1320

ccagcaataa tgagatgagc ataattttag ttgaaatgga agaaataggc gaagcctatc   1380

aaaaatcaaa ctttattttc taatgatgta gatatgggca gataatttgt ttagggaaga   1440

ggttcatgga tcaattacgt aatttgtatg                                    1470
```

<210> SEQ ID NO 305
<211> LENGTH: 21
<212> TYPE: DNA
<213> ORGANISM: Nezara viridula

<400> SEQUENCE: 305

```
taagtaccat gtccaacgcc a                                               21
```

<210> SEQ ID NO 306
<211> LENGTH: 21
<212> TYPE: DNA
<213> ORGANISM: Nezara viridula

<400> SEQUENCE: 306

```
tattacaata actgaccacc c                                               21
```

<210> SEQ ID NO 307
<211> LENGTH: 21
<212> TYPE: DNA
<213> ORGANISM: Nezara viridula

<400> SEQUENCE: 307

```
tcctactaca tatttccacc c                                               21
```

<210> SEQ ID NO 308
<211> LENGTH: 21
<212> TYPE: DNA
<213> ORGANISM: Nezara viridula

<400> SEQUENCE: 308

```
tattccttct atcttctccc a                                               21
```

<210> SEQ ID NO 309
<211> LENGTH: 21
<212> TYPE: DNA
<213> ORGANISM: Nezara viridula

<400> SEQUENCE: 309

```
taaagtatat taataattct t                                               21
```

<210> SEQ ID NO 310

<211> LENGTH: 21
<212> TYPE: DNA
<213> ORGANISM: Nezara viridula

<400> SEQUENCE: 310
ttactatctt cccttacaca a 21

<210> SEQ ID NO 311
<211> LENGTH: 21
<212> TYPE: DNA
<213> ORGANISM: Nezara viridula

<400> SEQUENCE: 311
tacgaagaga taacacaaga t 21

<210> SEQ ID NO 312
<211> LENGTH: 21
<212> TYPE: DNA
<213> ORGANISM: Nezara viridula

<400> SEQUENCE: 312
taacaaaaca aaaaaaaact g 21

<210> SEQ ID NO 313
<211> LENGTH: 21
<212> TYPE: DNA
<213> ORGANISM: Nezara viridula

<400> SEQUENCE: 313
tggcgttgga ctaggtactt t 21

<210> SEQ ID NO 314
<211> LENGTH: 21
<212> TYPE: DNA
<213> ORGANISM: Nezara viridula

<400> SEQUENCE: 314
gggtggtcag tatttgtaat t 21

<210> SEQ ID NO 315
<211> LENGTH: 21
<212> TYPE: DNA
<213> ORGANISM: Nezara viridula

<400> SEQUENCE: 315
gggtggaaat aattagtagg t 21

<210> SEQ ID NO 316
<211> LENGTH: 21
<212> TYPE: DNA
<213> ORGANISM: Nezara viridula

<400> SEQUENCE: 316
tgggagaaga tcaaaggaat t 21

<210> SEQ ID NO 317
<211> LENGTH: 21
<212> TYPE: DNA
<213> ORGANISM: Nezara viridula

<400> SEQUENCE: 317
aagaattatt ataatacttt t 21

<210> SEQ ID NO 318
<211> LENGTH: 21
<212> TYPE: DNA
<213> ORGANISM: Nezara viridula

<400> SEQUENCE: 318
ttgtgtaagg gttgatagta t 21

<210> SEQ ID NO 319
<211> LENGTH: 21
<212> TYPE: DNA
<213> ORGANISM: Nezara viridula

<400> SEQUENCE: 319
atcttgtgtt aaatcttcgt t 21

<210> SEQ ID NO 320
<211> LENGTH: 21
<212> TYPE: DNA
<213> ORGANISM: Nezara viridula

<400> SEQUENCE: 320
cagttttttt tgcttttgtt t 21

<210> SEQ ID NO 321
<211> LENGTH: 976
<212> TYPE: DNA
<213> ORGANISM: Artificial Sequence
<220> FEATURE:
<223> OTHER INFORMATION: amiRNA precursor sequence #1 for
inv1c.pk005.h23.f

<400> SEQUENCE: 321
ctaggtaaac catggttcta gctagctagg gtttgggtag tgagtgtaat aaagttgcaa 60
agtttttggt taggttacgt tttgacctta ttattatagt tcaaagggaa acattaatta 120
aaggggatta tgaagtggcg ttggactagg tacttttgag gatcttactg ggtgaattga 180
gctgcttagc tatggatccc acagttctac ccatcaataa gtgcttttgt ggtagtcttg 240
tggcttccat atctggggag cttcatttgc ctttatagta ttaaccttct aagtaccatg 300
tccaacgcca cacccttctc ttcttttctc tcataataat ttaaatttgt tatagactct 360
aaactttaaa tgtttttttt gaagtttttc cgtttttctc ttttgccatg atcccgttct 420
tgctgtggag taaccttgtc cgaggtatgt gcatgattag atccatactt aatttgtgtg 480
catcacgaag gtgaggttga aatgaacttt gctttttttga ccttttagga aagttctttt 540
gttgcagtaa tcaattttaa ttagttttaa ttgacactat tacttttatt gtcatctttg 600
ttagttttat tgttgaattg agtgcatatt tcgtaggaaa ttctcttacc taacattttt 660
tatacagatc tatgctcttg gctcttgccc ttactcttgg ccttgtgttg gttatttgtc 720
tacatattta ttgactggtc gatgagacat gtcacaattc ttgggcttat ttgttggtct 780
aataaaagga gtgcttattg aaagatcaag acggagattc ggttttatat aaataaacta 840
aagatgacat attagtgtgt tgatgtctct tcaggataat ttttgtttga aataatatgg 900
taatgtcttg tctaaatttg tgtacataat tcttactgat tttttggatt gttggatttt 960
tataaacaaa tctgtt 976

<210> SEQ ID NO 322
<211> LENGTH: 977
<212> TYPE: DNA
<213> ORGANISM: Artificial Sequence
<220> FEATURE:
<223> OTHER INFORMATION: amiRNA precursor sequence #2 for
      inv1c.pk005.h23.f

<400> SEQUENCE: 322

```
ctaggtaaac catggattct agctagctag ggtttgggta gtgagtgtaa taaagttgca     60

aagtttttgg ttaggttacg ttttgacctt attattatag ttcaaaggga aacattaatt    120

aaaggggatt atgaaggggt ggtcagtatt tgtaatttga ggatcttact gggtgaattg    180

agctgcttag ctatggatcc cacagttcta cccatcaata agtgcttttg tggtagtctt    240

gtggcttcca tatctgggga gcttcatttg cctttatagt attaaccttc tattacaata    300

actgaccacc ccacccttct cttcttttct ctcataataa tttaaatttg ttatagactc    360

taaactttaa atgttttttt tgaagttttt ccgtttttct cttttgccat gatcccgttc    420

ttgctgtgga gtaaccttgt ccgaggtatg tgcatgatta gatccatact taatttgtgt    480

gcatcacgaa ggtgaggttg aaatgaactt tgctttttttg acctttttagg aaagttcttt   540

tgttgcagta atcaatttta attagtttta attgacacta ttacttttat tgtcatcttt    600

gttagtttta ttgttgaatt gagtgcatat ttcgtaggaa attctcttac ctaacatttt    660

ttatacagat ctatgctctt ggctcttgcc cttactcttg gccttgtgtt ggttatttgt    720

ctacatattt attgactggt cgatgagaca tgtcacaatt cttgggctta tttgttggtc    780

taataaaagg agtgcttatt gaaagatcaa gacggagatt cggttttata taaataaact    840

aaagatgaca tattagtgtg ttgatgtctc ttcaggataa tttttgtttg aaataatatg    900

gtaatgtctt gtctaaattt gtgtacataa ttcttactga ttttttggat tgttggattt    960

ttataaacaa atctgtt                                                   977
```

<210> SEQ ID NO 323
<211> LENGTH: 966
<212> TYPE: DNA
<213> ORGANISM: Artificial Sequence
<220> FEATURE:
<223> OTHER INFORMATION: amiRNA precursor sequence #1 for
      inv1c.pk004.e6.f:fis

<400> SEQUENCE: 323

```
ctaggttcta gctagctagg gtttgggtag tgagtgtaat aaagttgcaa agtttttggt     60

taggttacgt tttgacctta ttattatagt tcaaagggaa acattaatta aaggggatta    120

tgaaggggtg gaaataatta gtaggttgag gatcttactg ggtgaattga gctgcttagc    180

tatggatccc acagttctac ccatcaataa gtgcttttgt ggtagtcttg tggcttccat    240

atctggggag cttcatttgc ctttatagta ttaaccttct cctactacat atttccaccc    300

caccccttctc ttcttttctc tcataataat ttaaatttgt tatagactct aaactttaaa   360

tgtttttttt gaagtttttc cgtttttctc ttttgccatg atcccgttct tgctgtggag    420

taaccttgtc cgaggtatgt gcatgattag atccatactt aatttgtgtg catcacgaag    480

gtgaggttga aatgaacttt gctttttttga cctttttagga aagttctttt gttgcagtaa  540

tcaattttaa ttagttttaa ttgacactat tacttttatt gtcatctttg ttagttttat    600

tgttgaattg agtgcatatt tcgtaggaaa ttctcttacc taacattttt tatacagatc    660

tatgctcttg gctcttgccc ttactcttgg ccttgtgttg gttatttgtc tacatattta    720

ttgactggtc gatgagacat gtcacaattc ttgggcttat ttgttggtct aataaaagga    780

gtgcttattg aaagatcaag acggagattc ggttttatat aaataaacta aagatgacat    840
```

```
attagtgtgt tgatgtctct tcaggataat ttttgtttga aataatatgg taatgtcttg    900

tctaaatttg tgtacataat tcttactgat tttttggatt gttggatttt tataaacaaa    960

tctgtt                                                               966
```

<210> SEQ ID NO 324
<211> LENGTH: 966
<212> TYPE: DNA
<213> ORGANISM: Artificial Sequence
<220> FEATURE:
<223> OTHER INFORMATION: amiRNA precursor sequence #2 for inv1c.pk004.e6.f:fis

<400> SEQUENCE: 324

```
ctaggttcta gctagctagg gtttgggtag tgagtgtaat aaagttgcaa agtttttggt     60

taggttacgt tttgacctta ttattatagt tcaaagggaa acattaatta aaggggatta    120

tgaagtggga gaagatcaaa ggaatttgag gatcttactg ggtgaattga gctgcttagc    180

tatggatccc acagttctac ccatcaataa gtgcttttgt ggtagtcttg tggcttccat    240

atctggggag cttcatttgc ctttatagta ttaaccttct attccttcta tcttctccca    300

caccccttctc ttcttttctc tcataataat ttaaatttgt tatagactct aaactttaaa   360

tgtttttttt gaagtttttc cgtttttctc ttttgccatg atcccgttct tgctgtggag    420

taaccttgtc cgaggtatgt gcatgattag atccatactt aatttgtgtg catcacgaag    480

gtgaggttga aatgaacttt gctttttga cctttagga aagttctttt gttgcagtaa      540

tcaattttaa ttagttttaa ttgacactat tacttttatt gtcatctttg ttagttttat    600

tgttgaattg agtgcatatt tcgtaggaaa ttctcttacc taacattttt tatacagatc    660

tatgctcttg gctcttgccc ttactcttgg ccttgtgttg gttatttgtc tacatattta    720

ttgactggtc gatgagacat gtcacaattc ttgggcttat ttgttggtct aataaaagga    780

gtgcttattg aaagatcaag acggagattc ggtttatat aaataaacta aagatgacat     840

attagtgtgt tgatgtctct tcaggataat ttttgtttga aataatatgg taatgtcttg    900

tctaaatttg tgtacataat tcttactgat tttttggatt gttggatttt tataaacaaa    960

tctgtt                                                               966
```

<210> SEQ ID NO 325
<211> LENGTH: 966
<212> TYPE: DNA
<213> ORGANISM: Artificial Sequence
<220> FEATURE:
<223> OTHER INFORMATION: amiRNA precursor sequence #1 for inv1c.pk004.e11.f:fis

<400> SEQUENCE: 325

```
ctaggttcta gctagctagg gtttgggtag tgagtgtaat aaagttgcaa agtttttggt     60

taggttacgt tttgacctta ttattatagt tcaaagggaa acattaatta aaggggatta    120

tgaagaagaa ttattataat actttttgag gatcttactg ggtgaattga gctgcttagc    180

tatggatccc acagttctac ccatcaataa gtgcttttgt ggtagtcttg tggcttccat    240

atctggggag cttcatttgc ctttatagta ttaaccttct aaagtatatt aataattctt    300

cacccttctc ttcttttctc tcataataat ttaaatttgt tatagactct aaactttaaa    360

tgtttttttt gaagtttttc cgtttttctc ttttgccatg atcccgttct tgctgtggag    420

taaccttgtc cgaggtatgt gcatgattag atccatactt aatttgtgtg catcacgaag    480

gtgaggttga aatgaacttt gctttttga cctttagga aagttctttt gttgcagtaa      540
```

```
tcaattttaa ttagttttaa ttgacactat tacttttatt gtcatctttg ttagttttat    600

tgttgaattg agtgcatatt tcgtaggaaa ttctcttacc taacattttt tatacagatc    660

tatgctcttg gctcttgccc ttactcttgg ccttgtgttg gttatttgtc tacatattta    720

ttgactggtc gatgagacat gtcacaattc ttgggcttat ttgttggtct aataaaagga    780

gtgcttattg aaagatcaag acggagattc ggttttatat aaataaacta aagatgacat    840

attagtgtgt tgatgtctct tcaggataat ttttgtttga aataatatgg taatgtcttg    900

tctaaatttg tgtacataat tcttactgat tttttggatt gttggatttt tataaacaaa    960

tctgtt                                                               966
```

```
<210> SEQ ID NO 326
<211> LENGTH: 966
<212> TYPE: DNA
<213> ORGANISM: Artificial Sequence
<220> FEATURE:
<223> OTHER INFORMATION: amiRNA precursor sequence #2 for
      inv1c.pk004.e11.f:fis

<400> SEQUENCE: 326

ctaggttcta gctagctagg gtttgggtag tgagtgtaat aaagttgcaa agtttttggt     60

taggttacgt tttgacctta ttattatagt tcaaagggaa acattaatta aaggggatta    120

tgaagttgtg taagggttga tagtattgag gatcttactg ggtgaattga gctgcttagc    180

tatggatccc acagttctac ccatcaataa gtgcttttgt ggtagtcttg tggcttccat    240

atctggggag cttcatttgc ctttatagta ttaaccttct tactatcttc ccttacacaa    300

cacccttctc ttcttttctc tcataataat ttaaatttgt tatagactct aaactttaaa    360

tgtttttttt gaagttttc cgtttttctc ttttgccatg atcccgttct tgctgtggag    420

taaccttgtc cgaggtatgt gcatgattag atccatactt aatttgtgtg catcacgaag    480

gtgaggttga aatgaacttt gctttttga cctttagga aagttctttt gttgcagtaa    540

tcaattttaa ttagttttaa ttgacactat tacttttatt gtcatctttg ttagttttat    600

tgttgaattg agtgcatatt tcgtaggaaa ttctcttacc taacattttt tatacagatc    660

tatgctcttg gctcttgccc ttactcttgg ccttgtgttg gttatttgtc tacatattta    720

ttgactggtc gatgagacat gtcacaattc ttgggcttat ttgttggtct aataaaagga    780

gtgcttattg aaagatcaag acggagattc ggttttatat aaataaacta aagatgacat    840

attagtgtgt tgatgtctct tcaggataat ttttgtttga aataatatgg taatgtcttg    900

tctaaatttg tgtacataat tcttactgat tttttggatt gttggatttt tataaacaaa    960

tctgtt                                                               966
```

```
<210> SEQ ID NO 327
<211> LENGTH: 966
<212> TYPE: DNA
<213> ORGANISM: Artificial Sequence
<220> FEATURE:
<223> OTHER INFORMATION: amiRNA precursor sequence #1 for
      inv1c.pk004.d17.f:fis

<400> SEQUENCE: 327

ctaggttcta gctagctagg gtttgggtag tgagtgtaat aaagttgcaa agtttttggt     60

taggttacgt tttgacctta ttattatagt tcaaagggaa acattaatta aaggggatta    120

tgaagatctt gtgttaaatc ttcgtttgag gatcttactg ggtgaattga gctgcttagc    180
```

```
tatggatccc acagttctac ccatcaataa gtgcttttgt ggtagtcttg tggcttccat    240

atctggggag cttcatttgc ctttatagta ttaaccttct acgaagagat aacacaagat    300

caccccttctc ttcttttctc tcataataat ttaaatttgt tatagactct aaactttaaa    360

tgttttttttt gaagtttttc cgtttttctc ttttgccatg atcccgttct tgctgtggag    420

taaccttgtc cgaggtatgt gcatgattag atccatactt aatttgtgtg catcacgaag    480

gtgaggttga aatgaacttt gctttttga cctttagga aagttctttt gttgcagtaa    540

tcaattttaa ttagttttaa ttgacactat tacttttatt gtcatctttg ttagttttat    600

tgttgaattg agtgcatatt tcgtaggaaa ttctcttacc taacattttt tatacagatc    660

tatgctcttg gctcttgccc ttactcttgg ccttgtgttg gttatttgtc tacatattta    720

ttgactggtc gatgagacat gtcacaattc ttgggcttat ttgttggtct aataaaagga    780

gtgcttattg aaagatcaag acggagattc ggttttatat aaataaacta aagatgacat    840

attagtgtgt tgatgtctct tcaggataat ttttgtttga aataatatgg taatgtcttg    900

tctaaatttg tgtacataat tcttactgat tttttggatt gttggatttt tataaacaaa    960

tctgtt                                                               966
```

<210> SEQ ID NO 328
<211> LENGTH: 966
<212> TYPE: DNA
<213> ORGANISM: Artificial Sequence
<220> FEATURE:
<223> OTHER INFORMATION: amiRNA precursor sequence #2 for inv1c.pk004.d17.f:fis

<400> SEQUENCE: 328

```
ctaggttcta gctagctagg gtttgggtag tgagtgtaat aaagttgcaa agtttttggt     60

taggttacgt tttgacctta ttattatagt tcaaagggaa acattaatta aaggggatta    120

tgaagcagtt ttttttgctt ttgttttgag gatcttactg ggtgaattga gctgcttagc    180

tatggatccc acagttctac ccatcaataa gtgcttttgt ggtagtcttg tggcttccat    240

atctggggag cttcatttgc ctttatagta ttaaccttct aacaaaacaa aaaaaaactg    300

caccccttctc ttcttttctc tcataataat ttaaatttgt tatagactct aaactttaaa    360

tgttttttttt gaagtttttc cgtttttctc ttttgccatg atcccgttct tgctgtggag    420

taaccttgtc cgaggtatgt gcatgattag atccatactt aatttgtgtg catcacgaag    480

gtgaggttga aatgaacttt gctttttga cctttagga aagttctttt gttgcagtaa    540

tcaattttaa ttagttttaa ttgacactat tacttttatt gtcatctttg ttagttttat    600

tgttgaattg agtgcatatt tcgtaggaaa ttctcttacc taacattttt tatacagatc    660

tatgctcttg gctcttgccc ttactcttgg ccttgtgttg gttatttgtc tacatattta    720

ttgactggtc gatgagacat gtcacaattc ttgggcttat ttgttggtct aataaaagga    780

gtgcttattg aaagatcaag acggagattc ggttttatat aaataaacta aagatgacat    840

attagtgtgt tgatgtctct tcaggataat ttttgtttga aataatatgg taatgtcttg    900

tctaaatttg tgtacataat tcttactgat tttttggatt gttggatttt tataaacaaa    960

tctgtt                                                               966
```

<210> SEQ ID NO 329
<211> LENGTH: 3236
<212> TYPE: DNA
<213> ORGANISM: Artificial Sequence
<220> FEATURE:

<223> OTHER INFORMATION: PHP44230 amiRNA precursor expression construct

<400> SEQUENCE: 329

```
ccgggtgatt gcggttacat catgtacgga aaaataattc taatccttga tttaaatttg     60
aacttgacta tttatttatt ctttatttca ttttgtaaat cattttatgt atctcctggc    120
aagcaatttt atccaccttg caccaacacc ttcgggttcc ataatcaaac caccttaact    180
tcacaccatg ctgtaactca caccgcccag catctccaat gtgaaagaag ctaaaattta    240
ataaacaatc atacgaagca gtgacaaaat accagatggt attaatgctt cgataaaatt    300
aattggaaag tataaaatgg tagaaaataa taaattataa ttaatttaag taagataaaa    360
aataattaaa aactaaaatg ttaaaatttt aaaaaaatta ttttaaataa tatttaaaaa    420
cattaaaaat cattttaaaa aatttattta tagaacaatt aaataaatat ttcagctaat    480
aaaaaacaaa agcttaccta gccttagaag acaacttgtc caacaattag atgataccca    540
ttgcccttac gttttcttta acatcaatta ttgtttttgt caacaagcta tcttttagtt    600
ttattttatt ggtaaaaaat atgtcgcctt caagttgcat catttaacac atctcgtcat    660
tagaaaaata aaactcttcc ctaaacgatt agtagaaaaa atcattcgat aataaataag    720
aaagaaaaat tagaaaaaaa taacttcatt ttaaaaaaat cattaaggct atatttttta    780
aatgactaat tttatataga ctgtaactaa aagtatacaa tttattatgc tatgtatctt    840
aaagaattac ttataaaaat ctacggaaga atatcttaca aagtgaaaaa caaatgagaa    900
agaatttagt gggatgatta tgattttatt tgaaaattga aaaaataatt attaaagact    960
ttagtggagt aagaaagctt tcctattagt cttttcttat ccataaaaaa aaaaaaaaaa   1020
atctagcgtg acagcttttc catagatttt aataatgtaa aatactggta gcagccgacc   1080
gttcaggtaa tggacactgt ggtcctaact tgcaacgggt gcgggcccaa tttaataacg   1140
ccgtggtaac ggataaagcc aagcgtgaag cggtgaaggt acatctctga ctccgtcaag   1200
attacgaaac cgtcaactac gaaggactcc ccgaaatatc atctgtgtca taaacaccaa   1260
gtcacaccat acatgggcac gcgtcacaat atgattggag aacggttcca ccgcatatgc   1320
tataaaatgc ccccacaccc ctcgacccta atcgcacttc aattgcaatc aaattagttc   1380
attctctttg cgcagttccc tacctctcct ttcaaggttc gtagatttct tccgtttttt   1440
tttcttcttc tttattgttt gttctacatc agcatgatgt tgatttgatt gtgttttcta   1500
tcgtttcatc gattataaat tttcataatc agaagattca gcttttatta atgcaagaac   1560
gtccttaatt gatgatttta taaccgtaaa ttaggtctaa ttagagtttt tttcataaag   1620
attttcagat ccgtttacaa caagccttaa ttgttgattc tgtagtcgta gattaaggtt   1680
tttttcatga actacttcag atccgttaaa caacagcctt atttgttgat acttcagtcg   1740
tttttcaaga aattgttcag atccgttgat aaaagcctta ttcgttgatt ctgtatggta   1800
tttcaagaga tattgctcag gtcctttagc aactacctta tttgttgatt ctgtggccat   1860
agattaggat tttttttcac gaaattgctt cttgaaatta cgtgatggat tttgattctg   1920
atttatcttg tgattgttga ctctacagca gatcctaggt aaaccatggt tctagctagc   1980
tagggtttgg gtagtgagtg taataaagtt gcaaagtttt tggttaggtt acgttttgac   2040
cttattatta tagttcaaag ggaaacatta attaaagggg attatgaagt ggcgttggac   2100
taggtacttt tgaggatctt actgggtgaa ttgagctgct tagctatgga tcccacagtt   2160
ctacccatca ataagtgctt ttgtggtagt cttgtggctt ccatatctgg ggagcttcat   2220
ttgcctttat agtattaacc ttctaagtac catgtccaac gccacaccct tctcttcttt   2280
```

```
tctctcataa taatttaaat ttgttataga ctctaaactt taaatgtttt ttttgaagtt   2340

tttccgtttt tctcttttgc catgatcccg ttcttgctgt ggagtaacct tgtccgaggt   2400

atgtgcatga ttagatccat acttaatttg tgtgcatcac gaaggtgagg ttgaaatgaa   2460

ctttgctttt ttgacctttt aggaaagttc ttttgttgca gtaatcaatt ttaattagtt   2520

ttaattgaca ctattacttt tattgtcatc tttgttagtt ttattgttga attgagtgca   2580

tatttcgtag gaaattctct tacctaacat tttttataca gatctatgct cttggctctt   2640

gcccttactc ttggccttgt gttggttatt tgtctacata tttattgact ggtcgatgag   2700

acatgtcaca attcttgggc ttatttgttg gtctaataaa aggagtgctt attgaaagat   2760

caagacggag attcggtttt atataaataa actaaagatg acatattagt gtgttgatgt   2820

ctcttcagga taatttttgt ttgaaataat atggtaatgt cttgtctaaa tttgtgtaca   2880

taattcttac tgattttttg gattgttgga tttttataaa caaatctgtt aacagatctc   2940

ttctcccggg taactgtacc taaagaagga gtgcgtcgaa gcagatcgtt caaacatttg   3000

gcaataaagt ttcttaagat tgaatcctgt tgccggtctt gcgatgatta tcatataatt   3060

tctgttgaat tacgttaagc atgtaataat taacatgtaa tgcatgacgt tatttatgag   3120

atgggttttt atgattagag tcccgcaatt atacatttaa tacgcgatag aaaacaaaat   3180

atagcgcgca aactaggata aattatcgcg cgcggtgtca tctatgttac tagatc       3236
```

<210> SEQ ID NO 330
<211> LENGTH: 3237
<212> TYPE: DNA
<213> ORGANISM: Artificial Sequence
<220> FEATURE:
<223> OTHER INFORMATION: PHP44231 amiRNA precursor expression construct

<400> SEQUENCE: 330

```
ccgggtgatt gcggttacat catgtacgga aaaataattc taatccttga tttaaatttg     60

aacttgacta tttatttatt ctttatttca ttttgtaaat cattttatgt atctcctggc    120

aagcaatttt atccaccttg caccaacacc ttcgggttcc ataatcaaac caccttaact    180

tcacaccatg ctgtaactca caccgcccag catctccaat gtgaaagaag ctaaaattta    240

ataaacaatc atacgaagca gtgacaaaat accagatggt attaatgctt cgataaaatt    300

aattggaaag tataaaatgg tagaaaataa taaattataa ttaatttaag taagataaaa    360

aataattaaa aactaaaatg ttaaaatttt aaaaaaatta ttttaaataa tatttaaaaa    420

cattaaaaat cattttaaaa aatttattta tagaacaatt aaataaatat ttcagctaat    480

aaaaaacaaa agcttaccta gccttagaag acaacttgtc caacaattag atgataccca    540

ttgcccttac gttttcttta acatcaatta ttgtttttgt caacaagcta tcttttagtt    600

ttattttatt ggtaaaaaat atgtcgcctt caagttgcat catttaacac atctcgtcat    660

tagaaaaata aaactcttcc ctaaacgatt agtagaaaaa atcattcgat aataaataag    720

aaagaaaaat tagaaaaaaa taacttcatt ttaaaaaaat cattaaggct atattttta    780

aatgactaat tttatataga ctgtaactaa aagtatacaa tttattatgc tatgtatctt    840

aaagaattac ttataaaaat ctacggaaga atatcttaca aagtgaaaaa caaatgagaa    900

agaatttagt gggatgatta tgattttatt tgaaaattga aaaaataatt attaaagact    960

ttagtggagt aagaaagctt tcctattagt cttttcttat ccataaaaaa aaaaaaaaaa   1020

atctagcgtg acagcttttc catagatttt aataatgtaa aatactggta gcagccgacc   1080
```

```
gttcaggtaa tggacactgt ggtcctaact tgcaacgggt gcgggcccaa tttaataacg   1140

ccgtggtaac ggataaagcc aagcgtgaag cggtgaaggt acatctctga ctccgtcaag   1200

attacgaaac cgtcaactac gaaggactcc ccgaaatatc atctgtgtca taaacaccaa   1260

gtcacaccat acatgggcac gcgtcacaat atgattggag aacggttcca ccgcatatgc   1320

tataaaatgc ccccacaccc ctcgacccta atcgcacttc aattgcaatc aaattagttc   1380

attctctttg cgcagttccc tacctctcct ttcaaggttc gtagatttct tccgtttttt   1440

tttcttcttc tttattgttt gttctacatc agcatgatgt tgatttgatt gtgttttcta   1500

tcgtttcatc gattataaat tttcataatc agaagattca gcttttatta atgcaagaac   1560

gtccttaatt gatgatttta taaccgtaaa ttaggtctaa ttagagtttt tttcataaag   1620

attttcagat ccgtttacaa caagccttaa ttgttgattc tgtagtcgta gattaaggtt   1680

tttttcatga actacttcag atccgttaaa caacagcctt atttgttgat acttcagtcg   1740

tttttcaaga aattgttcag atccgttgat aaaagcctta ttcgttgatt ctgtatggta   1800

tttcaagaga tattgctcag gtcctttagc aactacctta tttgttgatt ctgtggccat   1860

agattaggat tttttttcac gaaattgctt cttgaaatta cgtgatggat tttgattctg   1920

atttatcttg tgattgttga ctctacagca gatcctaggt aaaccatgga ttctagctag   1980

ctagggtttg ggtagtgagt gtaataaagt tgcaaagttt ttggttaggt tacgttttga   2040

ccttattatt atagttcaaa gggaaacatt aattaaaggg gattatgaag ggtggtcag    2100

tatttgtaat ttgaggatct tactgggtga attgagctgc ttagctatgg atcccacagt   2160

tctacccatc aataagtgct tttgtggtag tcttgtggct tccatatctg gggagcttca   2220

tttgccttta tagtattaac cttctattac aataactgac caccccaccc ttctcttctt   2280

ttctctcata ataatttaaa tttgttatag actctaaact ttaaatgttt tttttgaagt   2340

ttttccgttt ttctcttttg ccatgatccc gttcttgctg tggagtaacc ttgtccgagg   2400

tatgtgcatg attagatcca tacttaattt gtgtgcatca cgaaggtgag gttgaaatga   2460

actttgcttt tttgaccttt taggaaagtt cttttgttgc agtaatcaat tttaattagt   2520

tttaattgac actattactt ttattgtcat ctttgttagt tttattgttg aattgagtgc   2580

atatttcgta ggaaattctc ttacctaaca ttttttatac agatctatgc tcttggctct   2640

tgcccttact cttggccttg tgttggttat ttgtctacat atttattgac tggtcgatga   2700

gacatgtcac aattcttggg cttatttgtt ggtctaataa aaggagtgct tattgaaaga   2760

tcaagacgga gattcggttt tatataaata aactaaagat gacatattag tgtgttgatg   2820

tctcttcagg ataattttg tttgaaataa tatggtaatg tcttgtctaa atttgtgtac    2880

ataattctta ctgatttttt ggattgttgg atttttataa acaaatctgt taacagatct   2940

cttctcccgg gtaactgtac ctaaagaagg agtgcgtcga agcagatcgt tcaaacattt   3000

ggcaataaag tttcttaaga ttgaatcctg ttgccggtct tgcgatgatt atcatataat   3060

ttctgttgaa ttacgttaag catgtaataa ttaacatgta atgcatgacg ttatttatga   3120

gatgggtttt tatgattaga gtcccgcaat tatacattta atacgcgata gaaaacaaaa   3180

tatagcgcgc aaactaggat aaattatcgc gcgcggtgtc atctatgtta ctagatc      3237
```

```
<210> SEQ ID NO 331
<211> LENGTH: 3226
<212> TYPE: DNA
<213> ORGANISM: Artificial Sequence
<220> FEATURE:
<223> OTHER INFORMATION: PHP44770 amiRNA precursor expression construct
```

<400> SEQUENCE: 331

```
ccgggtgatt gcggttacat catgtacgga aaaataattc taatccttga tttaaatttg     60
aacttgacta tttatttatt ctttatttca ttttgtaaat cattttatgt atctcctggc    120
aagcaatttt atccaccttg caccaacacc ttcgggttcc ataatcaaac caccttaact    180
tcacaccatg ctgtaactca caccgcccag catctccaat gtgaaagaag ctaaaattta    240
ataaacaatc atacgaagca gtgacaaaat accagatggt attaatgctt cgataaaatt    300
aattggaaag tataaaatgg tagaaaataa taaattataa ttaatttaag taagataaaa    360
aataattaaa aactaaaatg ttaaaatttt aaaaaaatta ttttaaataa tatttaaaaa    420
cattaaaaat cattttaaaa aatttattta tagaacaatt aaataaatat ttcagctaat    480
aaaaaacaaa agcttaccta gccttagaag acaacttgtc caacaattag atgataccca    540
ttgcccttac gttttcttta acatcaatta ttgtttttgt caacaagcta tcttttagtt    600
ttattttatt ggtaaaaaat atgtcgcctt caagttgcat catttaacac atctcgtcat    660
tagaaaaata aaactcttcc ctaaacgatt agtagaaaaa atcattcgat aataaataag    720
aaagaaaaat tagaaaaaaa taacttcatt ttaaaaaaat cattaaggct atattttta    780
aatgactaat tttatataga ctgtaactaa aagtatacaa tttattatgc tatgtatctt    840
aaagaattac ttataaaaat ctacggaaga atatcttaca aagtgaaaaa caaatgagaa    900
agaatttagt gggatgatta tgattttatt tgaaaattga aaaaataatt attaaagact    960
ttagtggagt aagaaagctt tcctattagt cttttcttat ccataaaaaa aaaaaaaaaa   1020
atctagcgtg acagcttttc catagatttt aataatgtaa aatactggta gcagccgacc   1080
gttcaggtaa tggacactgt ggtcctaact tgcaacgggt gcgggcccaa tttaataacg   1140
ccgtggtaac ggataaagcc aagcgtgaag cggtgaaggt acatctctga ctccgtcaag   1200
attacgaaac cgtcaactac gaaggactcc ccgaaatatc atctgtgtca taaacaccaa   1260
gtcacaccat acatgggcac gcgtcacaat atgattggag aacggttcca ccgcatatgc   1320
tataaaatgc ccccacaccc ctcgacccta atcgcacttc aattgcaatc aaattagttc   1380
attctctttg cgcagttccc tacctctcct ttcaaggttc gtagatttct tccgtttttt   1440
tttcttcttc tttattgttt gttctacatc agcatgatgt tgatttgatt gtgttttcta   1500
tcgtttcatc gattataaat tttcataatc agaagattca gcttttatta atgcaagaac   1560
gtccttaatt gatgatttta taaccgtaaa ttaggtctaa ttagagtttt tttcataaag   1620
attttcagat ccgtttacaa caagccttaa ttgttgattc tgtagtcgta gattaaggtt   1680
tttttcatga actacttcag atccgttaaa caacagcctt atttgttgat acttcagtcg   1740
tttttcaaga aattgttcag atccgttgat aaaagcctta ttcgttgatt ctgtatggta   1800
tttcaagaga tattgctcag gtcctttagc aactacctta tttgttgatt ctgtggccat   1860
agattaggat ttttttcac gaaattgctt cttgaaatta cgtgatggat tttgattctg   1920
atttatcttg tgattgttga ctctacagca gatcctaggt tctagctagc tagggtttgg   1980
gtagtgagtg taataaagtt gcaaagtttt tggttaggtt acgttttgac cttattatta   2040
tagttcaaag ggaaacatta attaaagggg attatgaagg ggtggaaata attagtaggt   2100
tgaggatctt actgggtgaa ttgagctgct tagctatgga tcccacagtt ctacccatca   2160
ataagtgctt ttgtggtagt cttgtggctt ccatatctgg ggagcttcat ttgcctttat   2220
agtattaacc ttctcctact acatatttcc accccaccct tctcttcttt tctctcataa   2280
```

```
taatttaaat ttgttataga ctctaaactt taaatgtttt ttttgaagtt tttccgtttt   2340

tctcttttgc catgatcccg ttcttgctgt ggagtaacct tgtccgaggt atgtgcatga   2400

ttagatccat acttaatttg tgtgcatcac gaaggtgagg ttgaaatgaa ctttgctttt   2460

ttgacctttt aggaaagttc ttttgttgca gtaatcaatt ttaattagtt ttaattgaca   2520

ctattacttt tattgtcatc tttgttagtt ttattgttga attgagtgca tatttcgtag   2580

gaaattctct tacctaacat tttttataca gatctatgct cttggctctt gcccttactc   2640

ttggccttgt gttggttatt tgtctacata tttattgact ggtcgatgag acatgtcaca   2700

attcttgggc ttatttgttg gtctaataaa aggagtgctt attgaaagat caagacggag   2760

attcggtttt atataaataa actaaagatg acatattagt gtgttgatgt ctcttcagga   2820

taatttttgt ttgaaataat atggtaatgt cttgtctaaa tttgtgtaca taattcttac   2880

tgattttttg gattgttgga tttttataaa caaatctgtt aacagatctc ttctcccggg   2940

taactgtacc taaagaagga gtgcgtcgaa gcagatcgtt caaacatttg gcaataaagt   3000

ttcttaagat tgaatcctgt tgccggtctt gcgatgatta tcatataatt tctgttgaat   3060

tacgttaagc atgtaataat taacatgtaa tgcatgacgt tatttatgag atgggttttt   3120

atgattagag tcccgcaatt atacatttaa tacgcgatag aaaacaaaat atagcgcgca   3180

aactaggata aattatcgcg cgcggtgtca tctatgttac tagatc                  3226
```

<210> SEQ ID NO 332
<211> LENGTH: 3226
<212> TYPE: DNA
<213> ORGANISM: Artificial Sequence
<220> FEATURE:
<223> OTHER INFORMATION: PHP44771 amiRNA precursor expression construct

<400> SEQUENCE: 332

```
ccgggtgatt gcggttacat catgtacgga aaaataattc taatccttga tttaaatttg     60

aacttgacta tttatttatt ctttatttca ttttgtaaat cattttatgt atctcctggc    120

aagcaatttt atccaccttg caccaacacc ttcgggttcc ataatcaaac caccttaact    180

tcacaccatg ctgtaactca caccgcccag catctccaat gtgaaagaag ctaaaattta    240

ataaacaatc atacgaagca gtgacaaaat accagatggt attaatgctt cgataaaatt    300

aattggaaag tataaaatgg tagaaaaataa taaattataa ttaatttaag taagataaaa    360

aataattaaa aactaaaatg ttaaaatttt aaaaaaatta ttttaaataa tatttaaaaa    420

cattaaaaat catttttaaaa aatttattta tagaacaatt aaataaatat ttcagctaat    480

aaaaaacaaa agcttaccta gccttagaag acaacttgtc caacaattag atgataccca    540

ttgcccttac gttttcttta acatcaatta ttgtttttgt caacaagcta tcttttagtt    600

ttattttatt ggtaaaaaat atgtcgcctt caagttgcat catttaacac atctcgtcat    660

tagaaaaata aaactcttcc ctaaacgatt agtagaaaaa atcattcgat aataaataag    720

aaagaaaaat tagaaaaaaa taacttcatt ttaaaaaaat cattaaggct atatttttta    780

aatgactaat tttatataga ctgtaactaa aagtatacaa tttattatgc tatgtatctt    840

aaagaattac ttataaaaat ctacggaaga atatcttaca aagtgaaaaa caaatgagaa    900

agaatttagt gggatgatta tgattttatt tgaaaattga aaaaataatt attaaagact    960

ttagtggagt aagaaagctt tcctattagt cttttcttat ccataaaaaa aaaaaaaaaa   1020

atctagcgtg acagcttttc catagatttt aataatgtaa aatactggta gcagccgacc   1080

gttcaggtaa tggacactgt ggtcctaact tgcaacgggt gcgggcccaa tttaataacg   1140
```

```
ccgtggtaac ggataaagcc aagcgtgaag cggtgaaggt acatctctga ctccgtcaag   1200

attacgaaac cgtcaactac gaaggactcc ccgaaatatc atctgtgtca taaacaccaa   1260

gtcacaccat acatgggcac gcgtcacaat atgattggag aacggttcca ccgcatatgc   1320

tataaaatgc ccccacaccc ctcgacccta atcgcacttc aattgcaatc aaattagttc   1380

attctctttg cgcagttccc tacctctcct ttcaaggttc gtagatttct tccgtttttt   1440

tttcttcttc tttattgttt gttctacatc agcatgatgt tgatttgatt gtgttttcta   1500

tcgtttcatc gattataaat tttcataatc agaagattca gcttttatta atgcaagaac   1560

gtccttaatt gatgatttta taaccgtaaa ttaggtctaa ttagagtttt tttcataaag   1620

attttcagat ccgtttacaa caagccttaa ttgttgattc tgtagtcgta gattaaggtt   1680

tttttcatga actacttcag atccgttaaa caacagcctt atttgttgat acttcagtcg   1740

tttttcaaga aattgttcag atccgttgat aaaagcctta ttcgttgatt ctgtatggta   1800

tttcaagaga tattgctcag gtcctttagc aactacctta tttgttgatt ctgtggccat   1860

agattaggat ttttttcac gaaattgctt cttgaaatta cgtgatggat tttgattctg   1920

atttatcttg tgattgttga ctctacagca gatcctaggt tctagctagc tagggtttgg   1980

gtagtgagtg taataaagtt gcaaagtttt tggttaggtt acgttttgac cttattatta   2040

tagttcaaag ggaaacatta attaaagggg attatgaagt gggagaagat caaaggaatt   2100

tgaggatctt actgggtgaa ttgagctgct tagctatgga tcccacagtt ctacccatca   2160

ataagtgctt ttgtggtagt cttgtggctt ccatatctgg ggagcttcat ttgcctttat   2220

agtattaacc ttctattcct tctatcttct cccacacct tctcttcttt tctctcataa   2280

taatttaaat ttgttataga ctctaaactt taaatgtttt ttttgaagtt tttccgtttt   2340

tctcttttgc catgatcccg ttcttgctgt ggagtaacct tgtccgaggt atgtgcatga   2400

ttagatccat acttaatttg tgtgcatcac gaaggtgagg ttgaaatgaa ctttgctttt   2460

ttgacctttt aggaaagttc ttttgttgca gtaatcaatt ttaattagtt ttaattgaca   2520

ctattacttt tattgtcatc tttgttagtt ttattgttga attgagtgca tatttcgtag   2580

gaaattctct tacctaacat tttttataca gatctatgct cttggctctt gcccttactc   2640

ttggccttgt gttggttatt tgtctacata tttattgact ggtcgatgag acatgtcaca   2700

attcttgggc ttatttgttg gtctaataaa aggagtgctt attgaaagat caagacggag   2760

attcggtttt atataaataa actaaagatg acatattagt gtgttgatgt ctcttcagga   2820

taatttttgt ttgaaataat atggtaatgt cttgtctaaa tttgtgtaca taattcttac   2880

tgatttttttg gattgttgga tttttataaa caaatctgtt aacagatctc ttctcccggg   2940

taactgtacc taaagaagga gtgcgtcgaa gcagatcgtt caaacatttg gcaataaagt   3000

ttcttaagat tgaatcctgt tgccggtctt gcgatgatta tcatataatt tctgttgaat   3060

tacgttaagc atgtaataat taacatgtaa tgcatgacgt tatttatgag atgggttttt   3120

atgattagag tcccgcaatt atacatttaa tacgcgatag aaaacaaaat atagcgcgca   3180

aactaggata aattatcgcg cgcggtgtca tctatgttac tagatc                 3226
```

<210> SEQ ID NO 333
<211> LENGTH: 3226
<212> TYPE: DNA
<213> ORGANISM: Artificial Sequence
<220> FEATURE:
<223> OTHER INFORMATION: PHP44772 amiRNA precursor expression construct

<400> SEQUENCE: 333

```
ccgggtgatt gcggttacat catgtacgga aaaataattc taatccttga tttaaatttg      60
aacttgacta tttatttatt ctttatttca ttttgtaaat cattttatgt atctcctggc     120
aagcaatttt atccaccttg caccaacacc ttcgggttcc ataatcaaac caccttaact     180
tcacaccatg ctgtaactca caccgcccag catctccaat gtgaaagaag ctaaaattta     240
ataaacaatc atacgaagca gtgacaaaat accagatggt attaatgctt cgataaaatt     300
aattggaaag tataaaatgg tagaaaataa taaattataa ttaatttaag taagataaaa     360
aataattaaa aactaaaatg ttaaaatttt aaaaaaatta ttttaaataa tatttaaaaa     420
cattaaaaat cattttaaaa aatttattta tagaacaatt aaataaatat ttcagctaat     480
aaaaaacaaa agcttaccta gccttagaag acaacttgtc caacaattag atgataccca     540
ttgcccttac gttttcttta acatcaatta ttgtttttgt caacaagcta tcttttagtt     600
ttattttatt ggtaaaaaat atgtcgcctt caagttgcat catttaacac atctcgtcat     660
tagaaaaata aaactcttcc ctaaacgatt agtagaaaaa atcattcgat aataaataag     720
aaagaaaaat tagaaaaaaa taacttcatt ttaaaaaaat cattaaggct atattttta     780
aatgactaat tttatataga ctgtaactaa aagtatacaa tttattatgc tatgtatctt     840
aaagaattac ttataaaaat ctacggaaga atatcttaca aagtgaaaaa caaatgagaa     900
agaatttagt gggatgatta tgattttatt tgaaaattga aaaaataatt attaaagact     960
ttagtggagt aagaaagctt tcctattagt cttttcttat ccataaaaaa aaaaaaaaaa    1020
atctagcgtg acagcttttc catagatttt aataatgtaa aatactggta gcagccgacc    1080
gttcaggtaa tggacactgt ggtcctaact tgcaacgggt gcgggcccaa tttaataacg    1140
ccgtggtaac ggataaagcc aagcgtgaag cggtgaaggt acatctctga ctccgtcaag    1200
attacgaaac cgtcaactac gaaggactcc ccgaaatatc atctgtgtca taaacaccaa    1260
gtcacaccat acatgggcac gcgtcacaat atgattggag aacggttcca ccgcatatgc    1320
tataaaatgc ccccacaccc ctcgacccta atcgcacttc aattgcaatc aaattagttc    1380
attctctttg cgcagttccc tacctctcct ttcaaggttc gtagatttct tccgtttttt    1440
tttcttcttc tttattgttt gttctacatc agcatgatgt tgatttgatt gtgttttcta    1500
tcgtttcatc gattataaat tttcataatc agaagattca gcttttatta atgcaagaac    1560
gtccttaatt gatgatttta taaccgtaaa ttaggtctaa ttagagtttt tttcataaag    1620
attttcagat ccgtttacaa caagccttaa ttgttgattc tgtagtcgta gattaaggtt    1680
tttttcatga actacttcag atccgttaaa caacagcctt atttgttgat acttcagtcg    1740
tttttcaaga aattgttcag atccgttgat aaaagcctta ttcgttgatt ctgtatggta    1800
tttcaagaga tattgctcag gtcctttagc aactacctta tttgttgatt ctgtggccat    1860
agattaggat ttttttcac gaaattgctt cttgaaatta cgtgatggat tttgattctg    1920
atttatcttg tgattgttga ctctacagca gatcctaggt tctagctagc tagggtttgg    1980
gtagtgagtg taataaagtt gcaaagtttt tggttaggtt acgttttgac cttattatta    2040
tagttcaaag ggaaacatta attaaagggg attatgaaga agaattatta taatactttt    2100
tgaggatctt actgggtgaa ttgagctgct tagctatgga tcccacagtt ctacccatca    2160
ataagtgctt ttgtggtagt cttgtggctt ccatatctgg ggagcttcat ttgcctttat    2220
agtattaacc ttctaaagta tattaataat tcttcaccct tctcttcttt tctctcataa    2280
taatttaaat ttgttataga ctctaaactt taaatgtttt ttttgaagtt tttccgtttt    2340
```

```
tctcttttgc catgatcccg ttcttgctgt ggagtaacct tgtccgaggt atgtgcatga   2400

ttagatccat acttaatttg tgtgcatcac gaaggtgagg ttgaaatgaa ctttgctttt   2460

ttgacctttt aggaaagttc ttttgttgca gtaatcaatt ttaattagtt ttaattgaca   2520

ctattacttt tattgtcatc tttgttagtt ttattgttga attgagtgca tatttcgtag   2580

gaaattctct tacctaacat tttttataca gatctatgct cttggctctt gcccttactc   2640

ttggccttgt gttggttatt tgtctacata tttattgact ggtcgatgag acatgtcaca   2700

attcttgggc ttatttgttg gtctaataaa aggagtgctt attgaaagat caagacggag   2760

attcggtttt atataaataa actaaagatg acatattagt gtgttgatgt ctcttcagga   2820

taatttttgt ttgaaataat atggtaatgt cttgtctaaa tttgtgtaca taattcttac   2880

tgatttttttg gattgttgga tttttataaa caaatctgtt aacagatctc ttctcccggg   2940

taactgtacc taaagaagga gtgcgtcgaa gcagatcgtt caaacatttg gcaataaagt   3000

ttcttaagat tgaatcctgt tgccggtctt gcgatgatta tcatataatt tctgttgaat   3060

tacgttaagc atgtaataat taacatgtaa tgcatgacgt tatttatgag atgggttttt   3120

atgattagag tcccgcaatt atacatttaa tacgcgatag aaaacaaaat atagcgcgca   3180

aactaggata aattatcgcg cgcggtgtca tctatgttac tagatc                  3226
```

<210> SEQ ID NO 334
<211> LENGTH: 3226
<212> TYPE: DNA
<213> ORGANISM: Artificial Sequence
<220> FEATURE:
<223> OTHER INFORMATION: PHP44773 amiRNA precursor expression construct

<400> SEQUENCE: 334

```
ccgggtgatt gcggttacat catgtacgga aaaataattc taatccttga tttaaatttg     60

aacttgacta tttatttatt ctttatttca ttttgtaaat cattttatgt atctcctggc    120

aagcaatttt atccaccttg caccaacacc ttcgggttcc ataatcaaac caccttaact    180

tcacaccatg ctgtaactca caccgcccag catctccaat gtgaaagaag ctaaaattta    240

ataaacaatc atacgaagca gtgacaaaat accagatggt attaatgctt cgataaaatt    300

aattggaaag tataaaatgg tagaaaataa taaattataa ttaatttaag taagataaaa    360

aataattaaa aactaaaatg ttaaaatttt aaaaaaatta ttttaaataa tatttaaaaa    420

cattaaaaat cattttaaaa aatttattta tagaacaatt aaataaatat ttcagctaat    480

aaaaaacaaa agcttaccta gccttagaag acaacttgtc caacaattag atgataccca    540

ttgcccttac gttttcttta acatcaatta ttgtttttgt caacaagcta tcttttagtt    600

ttattttatt ggtaaaaaat atgtcgcctt caagttgcat catttaacac atctcgtcat    660

tagaaaaata aaactcttcc ctaaacgatt agtagaaaaa atcattcgat aataaataag    720

aaagaaaaat tagaaaaaaa taacttcatt ttaaaaaaat cattaaggct atattttta    780

aatgactaat tttatataga ctgtaactaa aagtatacaa tttattatgc tatgtatctt    840

aaagaattac ttataaaaat ctacggaaga atatcttaca aagtgaaaaa caaatgagaa    900

agaatttagt gggatgatta tgattttatt tgaaaattga aaaaataatt attaaagact    960

ttagtggagt aagaaagctt tcctattagt cttttcttat ccataaaaaa aaaaaaaaaa   1020

atctagcgtg acagcttttc catagatttt aataatgtaa aatactggta gcagccgacc   1080

gttcaggtaa tggacactgt ggtcctaact tgcaacgggt gcgggcccaa tttaataacg   1140
```

```
ccgtggtaac ggataaagcc aagcgtgaag cggtgaaggt acatctctga ctccgtcaag   1200
attacgaaac cgtcaactac gaaggactcc ccgaaatatc atctgtgtca taaacaccaa   1260
gtcacaccat acatgggcac gcgtcacaat atgattggag aacggttcca ccgcatatgc   1320
tataaaatgc ccccacaccc ctcgacccta atcgcacttc aattgcaatc aaattagttc   1380
attctctttg cgcagttccc tacctctcct ttcaaggttc gtagatttct tccgtttttt   1440
tttcttcttc tttattgttt gttctacatc agcatgatgt tgatttgatt gtgttttcta   1500
tcgtttcatc gattataaat tttcataatc agaagattca gcttttatta atgcaagaac   1560
gtccttaatt gatgatttta taaccgtaaa ttaggtctaa ttagagtttt tttcataaag   1620
attttcagat ccgtttacaa caagccttaa ttgttgattc tgtagtcgta gattaaggtt   1680
tttttcatga actacttcag atccgttaaa caacagcctt atttgttgat acttcagtcg   1740
tttttcaaga aattgttcag atccgttgat aaaagcctta ttcgttgatt ctgtatggta   1800
tttcaagaga tattgctcag gtcctttagc aactacctta tttgttgatt ctgtggccat   1860
agattaggat ttttttcac gaaattgctt cttgaaatta cgtgatggat tttgattctg   1920
atttatcttg tgattgttga ctctacagca gatcctaggt tctagctagc tagggtttgg   1980
gtagtgagtg taataaagtt gcaaagtttt tggttaggtt acgttttgac cttattatta   2040
tagttcaaag ggaaacatta attaaagggg attatgaagt tgtgtaaggg ttgatagtat   2100
tgaggatctt actgggtgaa ttgagctgct tagctatgga tcccacagtt ctacccatca   2160
ataagtgctt ttgtggtagt cttgtggctt ccatatctgg ggagcttcat ttgcctttat   2220
agtattaacc ttcttactat cttcccttac acaacaccct tctcttcttt tctctcataa   2280
taatttaaat ttgttataga ctctaaactt taaatgtttt ttttgaagtt tttccgtttt   2340
tctcttttgc catgatcccg ttcttgctgt ggagtaacct tgtccgaggt atgtgcatga   2400
ttagatccat acttaatttg tgtgcatcac gaaggtgagg ttgaaatgaa ctttgctttt   2460
ttgacctttt aggaaagttc ttttgttgca gtaatcaatt ttaattagtt ttaattgaca   2520
ctattacttt tattgtcatc tttgttagtt ttattgttga attgagtgca tatttcgtag   2580
gaaattctct tacctaacat tttttataca gatctatgct cttggctctt gcccttactc   2640
ttggccttgt gttggttatt tgtctacata tttattgact ggtcgatgag acatgtcaca   2700
attcttgggc ttatttgttg gtctaataaa aggagtgctt attgaaagat caagacggag   2760
attcggtttt atataaataa actaaagatg acatattagt gtgttgatgt ctcttcagga   2820
taatttttgt ttgaaataat atggtaatgt cttgtctaaa tttgtgtaca taattcttac   2880
tgatttttttg gattgttgga tttttataaa caaatctgtt aacagatctc ttctcccggg   2940
taactgtacc taaagaagga gtgcgtcgaa gcagatcgtt caaacatttg gcaataaagt   3000
ttcttaagat tgaatcctgt tgccggtctt gcgatgatta tcatataatt tctgttgaat   3060
tacgttaagc atgtaataat taacatgtaa tgcatgacgt tatttatgag atgggttttt   3120
atgattagag tcccgcaatt atacatttaa tacgcgatag aaaacaaaat atagcgcgca   3180
aactaggata aattatcgcg cgcggtgtca tctatgttac tagatc                  3226
```

<210> SEQ ID NO 335
<211> LENGTH: 3226
<212> TYPE: DNA
<213> ORGANISM: Artificial Sequence
<220> FEATURE:
<223> OTHER INFORMATION: PHP44789 amiRNA precursor expression construct

<400> SEQUENCE: 335

```
ccgggtgatt gcggttacat catgtacgga aaaataattc taatccttga tttaaatttg     60
aacttgacta tttatttatt ctttatttca ttttgtaaat cattttatgt atctcctggc    120
aagcaatttt atccaccttg caccaacacc ttcgggttcc ataatcaaac caccttaact    180
tcacaccatg ctgtaactca caccgcccag catctccaat gtgaaagaag ctaaaattta    240
ataaacaatc atacgaagca gtgacaaaat accagatggt attaatgctt cgataaaatt    300
aattggaaag tataaaatgg tagaaaataa taaattataa ttaatttaag taagataaaa    360
aataattaaa aactaaaatg ttaaaatttt aaaaaaatta ttttaaataa tatttaaaaa    420
cattaaaaat cattttaaaa aatttattta tagaacaatt aaataaatat ttcagctaat    480
aaaaaacaaa agcttaccta gccttagaag acaacttgtc caacaattag atgataccca    540
ttgcccttac gttttcttta acatcaatta ttgtttttgt caacaagcta tcttttagtt    600
ttattttatt ggtaaaaaat atgtcgcctt caagttgcat catttaacac atctcgtcat    660
tagaaaaata aaactcttcc ctaaacgatt agtagaaaaa atcattcgat aataaataag    720
aaagaaaaat tagaaaaaaa taacttcatt ttaaaaaaat cattaaggct atattttta    780
aatgactaat tttatataga ctgtaactaa aagtatacaa tttattatgc tatgtatctt    840
aaagaattac ttataaaaat ctacggaaga atatcttaca aagtgaaaaa caaatgagaa    900
agaatttagt gggatgatta tgattttatt tgaaaattga aaaaataatt attaaagact    960
ttagtggagt aagaaagctt tcctattagt cttttcttat ccataaaaaa aaaaaaaaaa   1020
atctagcgtg acagcttttc catagatttt aataatgtaa aatactggta gcagccgacc   1080
gttcaggtaa tggacactgt ggtcctaact tgcaacgggt gcgggcccaa tttaataacg   1140
ccgtggtaac ggataaagcc aagcgtgaag cggtgaaggt acatctctga ctccgtcaag   1200
attacgaaac cgtcaactac gaaggactcc ccgaaatatc atctgtgtca taaacaccaa   1260
gtcacaccat acatgggcac gcgtcacaat atgattggag aacggttcca ccgcatatgc   1320
tataaaatgc ccccacaccc ctcgacccta atcgcacttc aattgcaatc aaattagttc   1380
attctctttg cgcagttccc tacctctcct ttcaaggttc gtagatttct tccgtttttt   1440
tttcttcttc tttattgttt gttctacatc agcatgatgt tgatttgatt gtgttttcta   1500
tcgtttcatc gattataaat tttcataatc agaagattca gcttttatta atgcaagaac   1560
gtccttaatt gatgatttta taaccgtaaa ttaggtctaa ttagagtttt tttcataaag   1620
attttcagat ccgtttacaa caagccttaa ttgttgattc tgtagtcgta gattaaggtt   1680
tttttcatga actacttcag atccgttaaa caacagcctt atttgttgat acttcagtcg   1740
tttttcaaga aattgttcag atccgttgat aaaagcctta ttcgttgatt ctgtatggta   1800
tttcaagaga tattgctcag gtcctttagc aactacctta tttgttgatt ctgtggccat   1860
agattaggat ttttttcac gaaattgctt cttgaaatta cgtgatggat tttgattctg   1920
atttatcttg tgattgttga ctctacagca gatcctaggt tctagctagc tagggtttgg   1980
gtagtgagtg taataaagtt gcaaagtttt tggttaggtt acgttttgac cttattatta   2040
tagttcaaag ggaaacatta attaaagggg attatgaaga tcttgtgtta aatcttcgtt   2100
tgaggatctt actgggtgaa ttgagctgct tagctatgga tcccacagtt ctacccatca   2160
ataagtgctt ttgtggtagt cttgtggctt ccatatctgg ggagcttcat ttgcctttat   2220
agtattaacc ttctacgaag agataacaca agatcaccct tctcttcttt tctctcataa   2280
taatttaaat ttgttataga ctctaaactt taaatgtttt ttttgaagtt tttccgtttt   2340
```

```
tctcttttgc catgatcccg ttcttgctgt ggagtaacct tgtccgaggt atgtgcatga   2400
ttagatccat acttaatttg tgtgcatcac gaaggtgagg ttgaaatgaa ctttgctttt   2460
ttgacctttt aggaaagttc ttttgttgca gtaatcaatt ttaattagtt ttaattgaca   2520
ctattacttt tattgtcatc tttgttagtt ttattgttga attgagtgca tatttcgtag   2580
gaaattctct tacctaacat tttttataca gatctatgct cttggctctt gcccttactc   2640
ttggccttgt gttggttatt tgtctacata tttattgact ggtcgatgag acatgtcaca   2700
attcttgggc ttatttgttg gtctaataaa aggagtgctt attgaaagat caagacggag   2760
attcggtttt atataaataa actaaagatg acatattagt gtgttgatgt ctcttcagga   2820
taatttttgt ttgaaataat atggtaatgt cttgtctaaa tttgtgtaca taattcttac   2880
tgatttttttg gattgttgga tttttataaa caaatctgtt aacagatctc ttctcccggg  2940
taactgtacc taaagaagga gtgcgtcgaa gcagatcgtt caaacatttg gcaataaagt   3000
ttcttaagat tgaatcctgt tgccggtctt gcgatgatta tcatataatt tctgttgaat   3060
tacgttaagc atgtaataat taacatgtaa tgcatgacgt tatttatgag atgggttttt   3120
atgattagag tcccgcaatt atacatttaa tacgcgatag aaaacaaaat atagcgcgca   3180
aactaggata aattatcgcg cgcggtgtca tctatgttac tagatc                  3226
```

<210> SEQ ID NO 336
<211> LENGTH: 3226
<212> TYPE: DNA
<213> ORGANISM: Artificial Sequence
<220> FEATURE:
<223> OTHER INFORMATION: PHP44790 amiRNA precursor expression construct

<400> SEQUENCE: 336

```
ccgggtgatt gcggttacat catgtacgga aaaataattc taatccttga tttaaatttg     60
aacttgacta tttatttatt ctttatttca ttttgtaaat cattttatgt atctcctggc    120
aagcaatttt atccaccttg caccaacacc ttcgggttcc ataatcaaac caccttaact    180
tcacaccatg ctgtaactca caccgcccag catctccaat gtgaaagaag ctaaaattta    240
ataaacaatc atacgaagca gtgacaaaat accagatggt attaatgctt cgataaaatt    300
aattggaaag tataaaatgg tagaaaataa taaattataa ttaatttaag taagataaaa    360
aataattaaa aactaaaatg ttaaaatttt aaaaaaatta ttttaaataa tatttaaaaa    420
cattaaaaat cattttaaaa aatttattta tagaacaatt aaataaatat ttcagctaat    480
aaaaaacaaa agcttaccta gccttagaag acaacttgtc caacaattag atgataccca    540
ttgcccttac gttttcttta acatcaatta ttgtttttgt caacaagcta tcttttagtt    600
ttattttatt ggtaaaaaat atgtcgcctt caagttgcat catttaacac atctcgtcat    660
tagaaaaata aaactcttcc ctaaacgatt agtagaaaaa atcattcgat aataaataag    720
aaagaaaaat tagaaaaaaa taacttcatt ttaaaaaaat cattaaggct atattttttta   780
aatgactaat tttatataga ctgtaactaa aagtatacaa tttattatgc tatgtatctt    840
aaagaattac ttataaaaat ctacggaaga atatcttaca aagtgaaaaa caaatgagaa    900
agaatttagt gggatgatta tgattttatt tgaaaattga aaaaataatt attaaagact    960
ttagtggagt aagaaagctt tcctattagt cttttcttat ccataaaaaa aaaaaaaaaa   1020
atctagcgtg acagcttttc catagatttt aataatgtaa aatactggta gcagccgacc   1080
gttcaggtaa tggacactgt ggtcctaact tgcaacgggt gcgggcccaa tttaataacg   1140
ccgtggtaac ggataaagcc aagcgtgaag cggtgaaggt acatctctga ctccgtcaag   1200
```

```
attacgaaac cgtcaactac gaaggactcc ccgaaatatc atctgtgtca taaacaccaa   1260

gtcacaccat acatgggcac gcgtcacaat atgattggag aacggttcca ccgcatatgc   1320

tataaaatgc ccccacaccc ctcgacccta atcgcacttc aattgcaatc aaattagttc   1380

attctctttg cgcagttccc tacctctcct ttcaaggttc gtagatttct tccgtttttt   1440

tttcttcttc tttattgttt gttctacatc agcatgatgt tgatttgatt gtgttttcta   1500

tcgtttcatc gattataaat tttcataatc agaagattca gcttttatta atgcaagaac   1560

gtccttaatt gatgatttta taaccgtaaa ttaggtctaa ttagagtttt tttcataaag   1620

attttcagat ccgtttacaa caagccttaa ttgttgattc tgtagtcgta gattaaggtt   1680

tttttcatga actacttcag atccgttaaa caacagcctt atttgttgat acttcagtcg   1740

tttttcaaga aattgttcag atccgttgat aaaagcctta ttcgttgatt ctgtatggta   1800

tttcaagaga tattgctcag gtcctttagc aactacctta tttgttgatt ctgtggccat   1860

agattaggat ttttttcac gaaattgctt cttgaaatta cgtgatggat tttgattctg   1920

atttatcttg tgattgttga ctctacagca gatcctaggt tctagctagc tagggtttgg   1980

gtagtgagtg taataaagtt gcaaagtttt tggttaggtt acgttttgac cttattatta   2040

tagttcaaag ggaaacatta attaaagggg attatgaagc agttttttttt gcttttgttt   2100

tgaggatctt actgggtgaa ttgagctgct tagctatgga tcccacagtt ctacccatca   2160

ataagtgctt ttgtggtagt cttgtggctt ccatatctgg ggagcttcat ttgcctttat   2220

agtattaacc ttctaacaaa acaaaaaaaa actgcaccct tctcttcttt tctctcataa   2280

taatttaaat ttgttataga ctctaaactt taaatgtttt ttttgaagtt tttccgtttt   2340

tctcttttgc catgatcccg ttcttgctgt ggagtaacct tgtccgaggt atgtgcatga   2400

ttagatccat acttaatttg tgtgcatcac gaaggtgagg ttgaaatgaa ctttgctttt   2460

ttgacctttt aggaaagttc ttttgttgca gtaatcaatt ttaattagtt ttaattgaca   2520

ctattacttt tattgtcatc tttgttagtt ttattgttga attgagtgca tatttcgtag   2580

gaaattctct tacctaacat tttttataca gatctatgct cttggctctt gcccttactc   2640

ttggccttgt gttggttatt tgtctacata tttattgact ggtcgatgag acatgtcaca   2700

attcttgggc ttatttgttg gtctaataaa aggagtgctt attgaaagat caagacggag   2760

attcggtttt atataaataa actaaagatg acatattagt gtgttgatgt ctcttcagga   2820

taatttttgt ttgaaataat atggtaatgt cttgtctaaa tttgtgtaca taattcttac   2880

tgattttttg gattgttgga tttttataaa caaatctgtt aacagatctc ttctcccggg   2940

taactgtacc taaagaagga gtgcgtcgaa gcagatcgtt caaacatttg gcaataaagt   3000

ttcttaagat tgaatcctgt tgccggtctt gcgatgatta tcatataatt tctgttgaat   3060

tacgttaagc atgtaataat taacatgtaa tgcatgacgt tatttatgag atgggttttt   3120

atgattagag tcccgcaatt atacatttaa tacgcgatag aaaacaaaat atagcgcgca   3180

aactaggata aattatcgcg cgcggtgtca tctatgttac tagatc                  3226
```

```
<210> SEQ ID NO 337
<211> LENGTH: 21
<212> TYPE: DNA
<213> ORGANISM: Nezara viridula

<400> SEQUENCE: 337

tggcgttgga catggtactt a                                               21
```

<210> SEQ ID NO 338
<211> LENGTH: 21
<212> TYPE: DNA
<213> ORGANISM: Nezara viridula

<400> SEQUENCE: 338
gggtggtcag ttattgtaat a 21

<210> SEQ ID NO 339
<211> LENGTH: 21
<212> TYPE: DNA
<213> ORGANISM: Nezara viridula

<400> SEQUENCE: 339
gggtggaaat atgtagtagg a 21

<210> SEQ ID NO 340
<211> LENGTH: 21
<212> TYPE: DNA
<213> ORGANISM: Nezara viridula

<400> SEQUENCE: 340
tgggagaaga tagaaggaat a 21

<210> SEQ ID NO 341
<211> LENGTH: 21
<212> TYPE: DNA
<213> ORGANISM: Nezara viridula

<400> SEQUENCE: 341
aagaattatt aatatacttt a 21

<210> SEQ ID NO 342
<211> LENGTH: 21
<212> TYPE: DNA
<213> ORGANISM: Nezara viridula

<400> SEQUENCE: 342
ttgtgtaagg gaagatagta a 21

<210> SEQ ID NO 343
<211> LENGTH: 21
<212> TYPE: DNA
<213> ORGANISM: Nezara viridula

<400> SEQUENCE: 343
atcttgtgtt atctcttcgt a 21

<210> SEQ ID NO 344
<211> LENGTH: 21
<212> TYPE: DNA
<213> ORGANISM: Nezara viridula

<400> SEQUENCE: 344
cagttttttt ttgttttgtt a 21

<210> SEQ ID NO 345
<211> LENGTH: 21
<212> TYPE: DNA
<213> ORGANISM: Artificial Sequence
<220> FEATURE:
<223> OTHER INFORMATION: attB34 primer

<400> SEQUENCE: 345

```
caactttgta tagaaaagtt g                                                21


<210> SEQ ID NO 346
<211> LENGTH: 21
<212> TYPE: DNA
<213> ORGANISM: Artificial Sequence
<220> FEATURE:
<223> OTHER INFORMATION: attB3 primer

<400> SEQUENCE: 346

caactttgta taataaagtt g                                                21
```

COMPOSITIONS AND METHODS FOR INSECTICIDAL CONTROL OF STINKBUGS

CROSS-REFERENCE TO RELATED APPLICATION

This application is a continuation of U.S. Non Provisional application Ser. No. 13/152,795 filed Jun. 3, 2011 now granted as U.S. Pat. No. 8,872,001 which claims the benefit U.S. Provisional Application Ser. No. 61/351,405, filed Jun. 4, 2010; the contents of which are herein incorporated by reference in their entirety.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 20141028_3548USCNT_SeqList.txt, a creation date of Jun. 2, 2011 and a size of 195 KB. The sequence listing filed via EFS-Web is part of the specification and is hereby incorporated in its entirety by reference herein.

FIELD OF THE INVENTION

The present invention relates generally to methods of molecular biology and gene silencing to control pests.

BACKGROUND OF THE INVENTION

Insect pests are a serious problem in agriculture. They destroy millions of acres of staple crops such as corn, soybeans, peas, and cotton. Yearly, these pests cause over $100 billion dollars in crop damage in the U.S. alone. In an ongoing seasonal battle, farmers must apply billions of gallons of synthetic pesticides to combat these pests. Other methods employed in the past delivered insecticidal activity by microorganisms or genes derived from microorganisms expressed in transgenic plants. For example, certain species of microorganisms of the genus *Bacillus* are known to possess pesticidal activity against a broad range of insect pests including *Lepidoptera, Diptera, Coleoptera, Hemiptera*, and others. In fact, microbial pesticides, particularly those obtained from *Bacillus* strains, have played an important role in agriculture as alternatives to chemical pest control. Agricultural scientists have developed crop plants with enhanced insect resistance by genetically engineering crop plants to produce insecticidal proteins from *Bacillus*. For example, corn and cotton plants genetically engineered to produce Cry toxins (see, e.g., Aronson (2002) *Cell Mol. Life Sci.* 59(3):417-425; Schnepf et al. (1998) *Microbiol. Mol. Biol. Rev.* 62(3):775-806) are now widely used in American agriculture and have provided the farmer with an alternative to traditional insect-control methods. However, these Bt insecticidal proteins only protect plants from a relatively narrow range of pests. Moreover, these modes of insecticidal activity provided varying levels of specificity and, in some cases, caused significant environmental consequences.

Previous control of stinkbugs relied on broad spectrum insecticides. With the adoption of transgenic controls for major lepidopteran pests in several crops, these insecticides are no longer used and stinkbugs have become a major secondary pest. No successful use of transgenic control of stinkbugs has been described or adopted. This may be due in part to the extra oral digestion employed by stinkbugs where digestive enzymes are injected into the host plant prior to feeding. This makes it difficult to find proteins that survive long enough to manifest activity against these insects. RNAi may overcome that feeding behavior by relying on double stranded RNAs rather than proteins. Thus, there is an immediate need for alternative methods to control pests.

BRIEF SUMMARY OF THE INVENTION

Methods and compositions are provided which employ a silencing element that, when ingested by a pest, such as a *Pentatomidae* plant pest including for example, a *N. viridula* (southern green stink bug), *Acrosternum hilare* (green stinkbug), *Piezodorus guildini* (redbanded stinkbug), and/or *Halymorpha halys* (Brown marmorated stinkbug). plant pest, is capable of decreasing the expression of a target sequence in the pest. In specific embodiments, the decrease in expression of the target sequence controls the pest and thereby the methods and compositions are capable of limiting damage to a plant. The present invention provides various target polynucleotides as set forth in SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 302, 303 or 304 or active variants or fragments thereof, wherein a decrease in expression of one or more the sequences in the target pest controls the pest (i.e., has insecticidal activity). Further provided are silencing elements, which when ingested by the pest, decrease the level of expression of one or more of the target polynucleotides. Plants, plant parts, plant cells, bacteria and other host cells comprising the silencing elements or an active variant or fragment thereof are also provided.

In another embodiment, a method for controlling a pest, such as a *Pentatomidae* plant pest, such as, for example, a *N. viridula, Acrosternum hilare, Piezodorus guildini*, and/or *Halymorpha halys* plant pest, is provided. The method comprises feeding to a pest a composition comprising a silencing element, wherein the silencing element, when ingested by the pest, reduces the level of a target sequence in the pest and thereby controls the pest. Further provided are methods to protect a plant from a pest. Such methods comprise introducing into the plant or plant part a silencing element of the invention. When the plant expressing the silencing element is ingested by the pest, the level of the target sequence is decreased and the pest is controlled.

BRIEF DESCRIPTION OF THE DRAWINGS

FIG. 1 shows the Southern Green Stinkbug feeding assay results with soybean embryo tissue transformed with hairpin RNA silencing contructs.

FIG. 2 shows the Southern Green Stinkbug feeding assay results with soybean embryo tissue transformed with amiRNA silencing constructs.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I. Overview

Frequently, RNAi discovery methods rely on evaluation of known classes of sensitive genes (transcription factors, housekeeping genes etc.). In contrast, the target polynucleotide set forth herein were identified based solely on high throughput screens of a library of over 1000 expressed sequence tags from *N. viridula*. This screen allowed for the discovery of many novel sequences, many of which have extremely low or no homology to known sequences. This method provided the advantage of having no built in bias to genes that are frequently highly conserved across taxa. As a result, many novel targets for RNAi as well as known genes not previously shown to be sensitive to RNAi have been identified.

As such, methods and compositions are provided which employ a silencing element that, when ingested by a pest, such as a *Pentatomidae* plant pest or, for example, a *N. viridula, Acrosternum hilare, Piezodorus guildini*, and/or *Halymorpha halys* plant pest, is capable of decreasing the expression of a target sequence in the pest. In specific embodiments, the decrease in expression of the target sequence controls the pest and thereby the methods and compositions are capable of limiting damage to a plant or plant part. The present invention provides target polynucleotides as set forth in SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 302, 303, or 304. or active variants and fragments thereof. Silencing elements designed in view of these target polynucleotides are provided which, when ingested by the pest, decrease the expression of one or more of the target sequences and thereby controls the pest (i.e., has insecticidal activity).

As used herein, by "controlling a pest" or "controls a pest" is intended any affect on a pest that results in limiting the damage that the pest causes. Controlling a pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack, or deterring the pests from eating the plant.

Reducing the level of expression of the target polynucleotide or the polypeptide encoded thereby, in the pest results in the suppression, control, and/or killing the invading pathogenic organism. Reducing the level of expression of the target sequence of the pest will reduce the disease symptoms resulting from pathogen challenge by at least about 2% to at least about 6%, at least about 5% to about 50%, at least about 10% to about 60%, at least about 30% to about 70%, at least about 40% to about 80%, or at least about 50% to about 90% or greater. Hence, the methods of the invention can be utilized to control pests, particularly, *Pentatomidae* plant pest or a *N. viridula, Acrosternum hilare, Piezodorus guildini*, and/or *Halymorpha halys* plant pest.

Assays that measure the control of a pest are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. See, for example, Thomma et al. (1998) *Plant Biology* 95:15107-15111, herein incorporated by reference. See, also Baum et al. (2007) *Nature Biotech* 11:1322-1326 and WO 2007/035650 which proved both whole plant feeding assays and corn root feeding assays. Both of these references are herein incorporated by reference in their entirety. See, also the examples below.

The invention is drawn to compositions and methods for protecting plants from a plant pest, such as *Pentatomidae* plant pests or *N. viridula, Acrosternum hilare, Piezodorus guildini*, and/or *Halymorpha halys* plant pests or inducing resistance in a plant to a plant pest, such as *Pentatomidae* plant pests or *N. viridula, Acrosternum hilare, Piezodorus guildini*, and/or *Halymorpha halys* plant pests. As used herein "*Pentatomidae* plant pest" is used to refer to any member of the *Pentatomidae* family. Accordingly, the compositions and methods are also useful in protecting plants against any *Pentatomidae* plant pest including representative genera and species such as, but not limited to, *Acrocorisellus* (*A. serraticollis*), *Acrosternum* (*A. adelpha, A. hilare, A. herbidum, A. scutellatum*), *Agonoscelis* (*A. nubila*), *Alcaeorrhynchus* (*A. grandis, A. phymatophorus*), *Amaurochrous* (*A. brevitylus*), *Apateticus* (*A. anatarius, A. bracteatus, A. cynicus, A. lineolatus, A. marginiventris*), *Apoecilus, Arma* (*A. custos*), *Arvelius, Bagrada, Banasa* (*B. calva, B. dimiata, B. grisea, B. induta, B. sordida*), *Brochymena* (*B. affinis, B. cariosa, B. haedula, B. hoppingi, B. sulcata*), *Carbula* (*C. obtusangula, C. sinica*), *Chinavia, Chlorochroa* (*C. belfragii, C. kanei, C. norlandi, C. senilis, C. viridicata*), *Chlorocoris* (*C. distinctus, C. flaviviridis, C. hebetatus, C. subrugosus, C. tau*), *Codophila* (*C. remota, C. sulcata, C. varius*), *Coenus* (*C. delius, C. inermis, C. tarsalis*), *Cosmopepla* (*C. bimaculata, C. binotata, C. carnifex, C. decorata, C. intergressus*), *Dalpada* (*D. oculata*), *Dendrocoris* (*D. arizonesis, D. fruticicola, D. humeralis, D. parapini, D. reticulatus*), *Dolycoris* (*D. baccarum* (sloe bug)), *Dybowskyia* (*D. reticulata*), *Edessa, Erthesina* (*E. fullo*), *Eurydema* (*E. dominulus, E. gebleri* (shield bug), *E. pulchra, E. rugosa*), *Euschistus* (*E. biformis, E. integer, E. quadrator, E. servus, E. tristigma*), *Euthyrhynchus* (*E. floridanus, E. macronemis*), *Gonopsis* (*G. coccinea*), *Graphosoma* (*G. lineatum* (stink bug), *G. rubrolineatum*), *Halyomorpha* (*H. halys* (brown marmorated stink bug)), *Halys* (*H. sindillus, H. sulcatus*), *Holcostethus* (*H. abbreviatus, H. fulvipes, H. limbolarius, H. piceus, H. sphacelatus*), *Homalogonia* (*H. obtusa*), *Hymenarcys* (*H. aequalis, H. crassa, H. nervosa, H. perpuncata, H. reticulata*), *Lelia* (*L. decempunctata*), *Lineostethus, Loxa* (*L. flavicollis, L. viridis*), *Mecidea* (*M. indicia, M. major, M. minor*), *Megarrhamphus* (*M. hastatus*), *Menecles* (*M. insertus, M. portacrus*), Mormidea (*M. cubrosa, M. lugens, M. pama, M. pictiventris, M. ypsilon*), *Moromorpha* (*M. tetra*), *Murgantia* (*M. angularis, M. tessellata, M. varicolor, M. violascens*), *Neottiglossa* (*N. californica, N. cavifrons, N. coronaciliata, N. sulcifrons, N. undata*), *Nezara* (*N. smaragdulus, N. viridula* (southern green stink bug)), *Oebalus* (*O. grisescens, O. insularis, O. mexicanus, O. pugnax, O. typhoeus*), *Oechalia* (*O. schellenbergii* (spined predatory shield bug)), *Okeanos* (*O. quelpartensis*), *Oplomus* (*O. catena, O. dichrous, O. tripustulatus*), *Palomena* (*P. prasina* (green shield bug)), *Parabrochymena, Pentatoma* (*P. angulata, P. illuminata, P. japonica, P. kunmingensis, P. metallifera, P. parataibaiensis, P. rufipes, P. semiannulata, P. viridicornuta*), *Perillus* (*P. bioculatus, P. confluens, P. strigipes*), *Picromerus* (*P. griseus*), *Piezodorus* (*P. degeeri, P. guildinii, P. lituratus* (gorse shield bug)), *Pinthaeus* (*P. humeralis*), *Plautia* (*P. crossota, P. stali* (brown-winged green bug)), *Podisus* (*P. maculiventris*), *Priassus* (*P. testaceus*), *Prionosoma, Proxys* (*P. albopunctulatus, P. punctulatus, P. victor*), *Rhaphigaster* (*R. nebulosa*), *Scotinophara* (*S. horvathi*), *Stiretrus* (*S. anchorago, S. fimbriatus*), *Thyanta* (*T. accerra, T. calceata, T. casta, T. perditor, T. pseudocasta*), *Trichopepla* (*T. aurora, T. dubia, T. pilipes, T. semivittata, T. vandykei*), *Tylospilus*, and *Zicrona*.

II. Target Sequences

As used herein, a "target sequence" or "target polynucleotide" comprises any sequence in the pest that one desires to reduce the level of expression. In specific embodiments, decreasing the level of the target sequence in the pest controls the pest. For instance, the target sequence can be essential for growth and development. While the target sequence can be expressed in any tissue of the pest, in specific embodiments, the sequences targeted for suppression in the pest are expressed in cells of the gut tissue of the pest, cells in the midgut of the pest, and cells lining the gut lumen or the midgut. Such target sequences can be involved in, for example, gut cell metabolism, growth or differentiation. Non-limiting examples of target sequences of the invention include a polynucleotide set forth in SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 302, 303, or 304. As exemplified elsewhere herein, decreasing the level of expression of one or more of these target sequences in a *Pentatomidae* plant pest or a *N. viridula, Acrosternum hilare, Piezodorus guildini*, and/or *Halymorpha halys* plant pest controls the pest.

III. Silencing Elements

By "silencing element" is intended a polynucleotide which when ingested by a pest, is capable of reducing or eliminating the level or expression of a target polynucleotide or the polypeptide encoded thereby. The silencing element employed can reduce or eliminate the expression level of the target sequence by influencing the level of the target RNA transcript or, alternatively, by influencing translation and thereby affecting the level of the encoded polypeptide. Methods to assay for functional silencing elements that are capable of reducing or eliminating the level of a sequence of interest are disclosed elsewhere herein. A single polynucleotide employed in the methods of the invention can comprise one or more silencing elements to the same or different target polynucleotides. The silencing element can be produced in vivo (i.e., in a host cell such as a plant or microorganism) or in vitro.

In specific embodiments, the target sequence is not endogenous to the plant. In other embodiments, while the silencing element controls pests, preferably the silencing element has no effect on the normal plant or plant part.

As discussed in further detail below, silencing elements can include, but are not limited to, a sense suppression element, an antisense suppression element, a double stranded RNA, a siRNA, an amiRNA, a miRNA, or a hairpin suppression element. Non-limiting examples of silencing elements that can be employed to decrease expression of these target *Pentatomidae* plant pest sequences or *N. viridula, Acrosternum hilare, Piezodorus guildini*, and/or *Halymorpha halys* plant pest sequences comprise fragments and variants of the sense or antisense sequence or consists of the sense or antisense sequence of the sequence set forth in SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 302, 303, or 304 or a biologically active variant or fragment thereof. Additional sequences that can be employed as silencing elements include, for example, SEQ ID NOS: 284, 285, 286, 287, 288, 289, 290, 291, 292, 293, 294, 295, 296, 297, 298, 299, 300, 301, 305, 306, 307, 308, 309, 310, 311, 312, 321, 322, 323, 324, 325, 326, 327, 328, 329, 330, 331, 332, 333, 334, 335, or 336 or active variants or fragments thereof. The silencing element can further comprise additional sequences that advantageously effect transcription and/or the stability of a resulting transcript. For example, the silencing elements can comprise at least one thymine residue at the 3' end. This can aid in stabilization. Thus, the silencing elements can have at least 1, 2, 3, 4, 5, 6, 7, 8, 9, 10 or more thymine residues at the 3' end. As discussed in further detail below, enhancer suppressor elements can also be employed in conjunction with the silencing elements disclosed herein.

By "reduces" or "reducing" the expression level of a polynucleotide or a polypeptide encoded thereby is intended to mean, the polynucleotide or polypeptide level of the target sequence is statistically lower than the polynucleotide level or polypeptide level of the same target sequence in an appropriate control pest which is not exposed to (i.e., has not ingested) the silencing element. In particular embodiments of the invention, reducing the polynucleotide level and/or the polypeptide level of the target sequence in a pest according to the invention results in less than 95%, less than 90%, less than 80%, less than 70%, less than 60%, less than 50%, less than 40%, less than 30%, less than 20%, less than 10%, or less than 5% of the polynucleotide level, or the level of the polypeptide encoded thereby, of the same target sequence in an appropriate control pest. Methods to assay for the level of the RNA transcript, the level of the encoded polypeptide, or the activity of the polynucleotide or polypeptide are discussed elsewhere herein.

i. Sense Suppression Elements

As used herein, a "sense suppression element" comprises a polynucleotide designed to express an RNA molecule corresponding to at least a part of a target messenger RNA in the "sense" orientation. Expression of the RNA molecule comprising the sense suppression element reduces or eliminates the level of the target polynucleotide or the polypeptide encoded thereby. The polynucleotide comprising the sense suppression element may correspond to all or part of the sequence of the target polynucleotide, all or part of the 5' and/or 3' untranslated region of the target polynucleotide, all or part of the coding sequence of the target polynucleotide, or all or part of both the coding sequence and the untranslated regions of the target polynucleotide.

Typically, a sense suppression element has substantial sequence identity to the target polynucleotide, typically greater than about 65% sequence identity, greater than about 85% sequence identity, about 90%, 91%, 92%, 93%, 94%, 95%, 96%, 97%, 98% or 99% sequence identity. See, U.S. Pat. Nos. 5,283,184 and 5,034,323; herein incorporated by reference. The sense suppression element can be any length so long as it allows for the suppression of the targeted sequence. The sense suppression element can be, for example, 15, 16, 17, 18 19, 20, 22, 25, 30, 50, 100, 150, 200, 250, 300, 350, 400, 450, 500, 600, 700, 900, 1000, 1100, 1200, 1300 nucleotides or longer of the target polynucleotides set forth in any of SEQ ID NO:1-292 or 302-304. In other embodiments, the sense suppression element can be, for example, about 15-25, 25-100, 100-150, 150-200, 200-250, 250-300, 300-350, 350-400, 450-500, 500-550, 550-600, 600-650, 650-700, 700-750, 750-800, 800-850, 850-900, 900-950, 950-1000, 1000-1050, 1050-1100, 1100-1200, 1200-1300, 1300-1400, 1400-1500, 1500-1600, 1600-1700, 1700-1800 nucleotides or longer of the target polynucleotides set forth in any of SEQ ID NO: 1-292 or 302-304.

ii. Antisense Suppression Elements

As used herein, an "antisense suppression element" comprises a polynucleotide which is designed to express an RNA molecule complementary to all or part of a target messenger RNA. Expression of the antisense RNA suppression element reduces or eliminates the level of the target polynucleotide. The polynucleotide for use in antisense suppression may correspond to all or part of the complement of the sequence encoding the target polynucleotide, all or part of the complement of the 5' and/or 3' untranslated region of the target polynucleotide, all or part of the complement of the coding sequence of the target polynucleotide, or all or part of the complement of both the coding sequence and the untranslated regions of the target polynucleotide. In addition, the antisense suppression element may be fully complementary (i.e., 100% identical to the complement of the target sequence) or partially complementary (i.e., less than 100% identical to the complement of the target sequence) to the target polynucleotide. In specific embodiments, the antisense suppression element comprises at least 85%, 90%, 91%, 92%, 93%, 94%, 95%, 96%, 97%, 98%, or 99% sequence complementarity to the target polynucleotide. Antisense suppression may be used to inhibit the expression of multiple proteins in the same plant. See, for example, U.S. Pat. No. 5,942,657. Furthermore, the antisense suppression element can be complementary to a portion of the target polynucleotide. Generally, sequences of at least 15, 20, 22, 25, 50, 100, 200, 300, 400, 450 nucleotides or greater of the sequence set forth in any of SEQ ID NO: 1-292 or 302-304 may be used. Methods for using antisense suppression to inhibit the expression of endogenous genes in plants are described, for example, in Liu et at (2002) *Plant Physiol.* 129:1732-1743 and U.S. Pat. Nos. 5,759,829 and 5,942,657, each of which is herein incorporated by reference.

iii. Double Stranded RNA Suppression Element

A "double stranded RNA silencing element" or "dsRNA" comprises at least one transcript that is capable of forming a dsRNA either before or after ingestion by a pest. Thus, a "dsRNA silencing element" includes a dsRNA, a transcript or polyribonucleotide capable of forming a dsRNA or more than one transcript or polyribonucleotide capable of forming a dsRNA. "Double stranded RNA" or "dsRNA" refers to a polyribonucleotide structure formed either by a single self-complementary RNA molecule or a polyribonucleotide structure formed by the expression of least two distinct RNA strands. The dsRNA molecule(s) employed in the methods and compositions of the invention mediate the reduction of expression of a target sequence, for example, by mediating RNA interference "RNAi" or gene silencing in a sequence-specific manner. In the context of the present invention, the dsRNA is capable of reducing or eliminating the level or expression of a target polynucleotide or the polypeptide encoded thereby in a pest.

The dsRNA can reduce or eliminate the expression level of the target sequence by influencing the level of the target RNA transcript, by influencing translation and thereby affecting the level of the encoded polypeptide, or by influencing expression at the pre-transcriptional level (i.e., via the modulation of chromatin structure, methylation pattern, etc., to alter gene expression). See, for example, Verdel et al. (2004) *Science* 303:672-676; Pal-Bhadra et al. (2004) *Science* 303:669-672; Allshire (2002) *Science* 297:1818-1819; Volpe et al. (2002) *Science* 297:1833-1837; Jenuwein (2002) *Science* 297:2215-2218; and Hall et al. (2002) *Science* 297:2232-2237. Methods to assay for functional dsRNA that are capable of reducing or eliminating the level of a sequence of interest are disclosed elsewhere herein. Accordingly, as used herein, the term "dsRNA" is meant to encompass other terms used to describe nucleic acid molecules that are capable of mediating RNA interference or gene silencing, including, for example, short-interfering RNA (siRNA), double-stranded RNA (dsRNA), micro-RNA (miRNA), hairpin RNA, short hairpin RNA (shRNA), post-transcriptional gene silencing RNA (ptgsRNA), and others.

In specific embodiments, at least one strand of the duplex or double-stranded region of the dsRNA shares sufficient sequence identity or sequence complementarity to the target polynucleotide to allow for the dsRNA to reduce the level of expression of the target sequence. As used herein, the strand that is complementary to the target polynucleotide is the "antisense strand" and the strand homologous to the target polynucleotide is the "sense strand."

In another embodiment, the dsRNA comprises a hairpin RNA. A hairpin RNA comprises an RNA molecule that is capable of folding back onto itself to form a double stranded structure. Multiple structures can be employed as hairpin elements. In specific embodiments, the dsRNA suppression element comprises a hairpin element which comprises in the following order, a first segment, a second segment, and a third segment, where the first and the third segment share sufficient complementarity to allow the transcribed RNA to form a double-stranded stem-loop structure.

The "second segment" of the hairpin comprises a "loop" or a "loop region." These terms are used synonymously herein and are to be construed broadly to comprise any nucleotide sequence that confers enough flexibility to allow self-pairing to occur between complementary regions of a polynucleotide (i.e., segments 1 and 3 which form the stem of the hairpin). For example, in some embodiments, the loop region may be substantially single stranded and act as a spacer between the self-complementary regions of the hairpin stem-loop. In some embodiments, the loop region can comprise a random or nonsense nucleotide sequence and thus not share sequence identity to a target polynucleotide. In other embodiments, the loop region comprises a sense or an antisense RNA sequence or fragment thereof that shares identity to a target polynucleotide. See, for example, International Patent Publication No. WO 02/00904, herein incorporated by reference. In specific embodiments, the loop region can be optimized to be as short as possible while still providing enough intramolecular flexibility to allow the formation of the base-paired stem region. Accordingly, the loop sequence is generally less than 1000, 900, 800, 700, 600, 500, 400, 300, 200, 100, 50, 25, 20, 15, 10 nucleotides or less.

The "first" and the "third" segment of the hairpin RNA molecule comprise the base-paired stem of the hairpin structure. The first and the third segments are inverted repeats of one another and share sufficient complementarity to allow the formation of the base-paired stem region. In specific embodiments, the first and the third segments are fully complementary to one another. Alternatively, the first and the third segment may be partially complementary to each other so long as they are capable of hybridizing to one another to form a base-paired stem region. The amount of complementarity between the first and the third segment can be calculated as a percentage of the entire segment. Thus, the first and the third segment of the hairpin RNA generally share at least 50%, 60%, 70%, 80%, 85%, 90%, 91%, 92%, 93%, 94%, 95%, 96%, 97%, 98%, 99%, up to and including 100% complementarity.

The first and the third segment are at least about 1000, 500, 400, 300, 200, 100, 50, 40, 30, 25, 22, 20, 19, 18, 17, 16, 15 or 10 nucleotides in length. In specific embodiments, the length of the first and/or the third segment is about 10-100 nucleotides, about 10 to about 75 nucleotides, about 10 to about 50 nucleotides, about 10 to about 40 nucleotides, about 10 to about 35 nucleotides, about 10 to about 30 nucleotides, about 10 to about 25 nucleotides, about 10 to about 19 nucleotides, about 50 nucleotides to about 100 nucleotides, about 100 nucleotides to about 150 nucleotides, about 150 nucleotides to about 200 nucleotides, about 200 nucleotides to about 250 nucleotides, about 250 nucleotides to about 300 nucleotides, about 300 nucleotides to about 350 nucleotides, about 350 nucleotides to about 400 nucleotides, about 400 nucleotide to about 500 nucleotides, about 600 nt, about 700 nt, about 800 nt, about 900 nt, about 1000 nt, about 1100 nt, about 1200 nt, 1300 nt, 1400 nt, 1500 nt, 1600 nt, 1700 nt, 1800 nt, 1900 nt, 2000 nt or longer. In other embodiments, the length of the first and/or the third segment comprises at least 10-19 nucleotides; 19-35 nucleotides; 30-45 nucleotides; 40-50 nucleotides; 50-100 nucleotides; 100-300 nucleotides; about 500-700 nucleotides; about 700-900 nucleotides; about 900-1100 nucleotides; about 1300-1500 nucleotides; about 1500-1700 nucleotides; about 1700-1900 nucleotides; about 1900-2100 nucleotides; about 2100-2300 nucleotides; or about 2300-2500 nucleotides. See, for example, International Publication No. WO 0200904. In specific embodiments, the first and the third segment comprise at least 19 nucleotides having at least 85% complementary to the first segment. In still other embodiments, the first and the third segments which form the stem-loop structure of the hairpin comprises 3' or 5' overhang regions having unpaired nucleotide residues.

In specific embodiments, the sequences used in the first, the second, and/or the third segments comprise domains that are designed to have sufficient sequence identity to a target polynucleotide of interest and thereby have the ability to decrease the level of expression of the target polynucleotide. The specificity of the inhibitory RNA transcripts is therefore generally conferred by these domains of the silencing element. Thus, in some embodiments of the invention, the first, second and/or third segment of the silencing element comprise a domain having at least 10, at least 15, at least 19, at least 20, at least 21, at least 22, at least 23, at least 24, at least 25, at least 30, at least 40, at least 50, at least 100, at least 200, at least 300, at least 500, at least 1000, or more than 1000 nucleotides that share sufficient sequence identity to the target polynucleotide to allow for a decrease in expression levels of the target polynucleotide when expressed in an appropriate cell. In other embodiments, the domain is between about 15 to 50 nucleotides, about 19-35 nucleotides, about 25-50 nucleotides, about 19 to 75 nucleotides, about 40-90 nucleotides about 15-100 nucleotides 10-100 nucleotides, about 10 to about 75 nucleotides, about 10 to about 50 nucleotides, about 10 to about 40 nucleotides, about 10 to about 35 nucleotides, about 10 to about 30 nucleotides, about 10 to about 25 nucleotides, about 10 to about 19 nucleotides, about 50 nucleotides to about 100 nucleotides, about 100 nucleotides to about 150 nucleotides, about 150 nucleotides to about 200 nucleotides, about 200 nucleotides to about 250 nucleotides, about 250 nucleotides to about 300 nucleotides, about 300 nucleotides to about 350 nucleotides, about 350 nucleotides to about 400 nucleotides, about 400 nucleotide to about 500 nucleotides or longer. In other embodiments, the length of the first and/or the third segment comprises at least 10-19 nucleotides, 19-35 nucleotides, 30-45 nucleotides, 40-50 nucleotides, 50-100 nucleotides, or about 100-300 nucleotides.

In specific embodiments, the domain of the first, the second, and/or the third segment has 100% sequence identity to the target polynucleotide. In other embodiments, the domain of the first, the second and/or the third segment having homology to the target polypeptide have at least 50%, 60%, 70%, 80%, 85%, 90%, 91%, 92%, 93%, 94%, 95%, 96%, 97%, 98%, 99%, or greater sequence identity to a region of the target polynucleotide. The sequence identity of the domains of the first, the second and/or the third segments to the target polynucleotide need only be sufficient to decrease expression of the target polynucleotide of interest. See, for example, Chuang and Meyerowitz (2000) *Proc. Natl. Acad. Sci. USA* 97:4985-4990; Stoutjesdijk et al. (2002) *Plant Physiol.* 129:1723-1731; Waterhouse and Helliwell (2003) *Nat. Rev. Genet.* 4:29-38; Pandolfini et al. *BMC Biotechnology* 3:7, and U.S. Patent Publication No. 20030175965; each of which is herein incorporated by reference. A transient assay for the efficiency of hpRNA constructs to silence gene expression in vivo has been described by Panstruga et al. (2003) *Mol. Biol. Rep.* 30:135-140, herein incorporated by reference.

The amount of complementarity shared between the first, second, and/or third segment and the target polynucleotide or the amount of complementarity shared between the first segment and the third segment (i.e., the stem of the hairpin structure) may vary depending on the organism in which gene expression is to be controlled. Some organisms or cell types may require exact pairing or 100% identity, while other organisms or cell types may tolerate some mismatching. In some cells, for example, a single nucleotide mismatch in the targeting sequence abrogates the ability to suppress gene expression. In these cells, the suppression cassettes of the invention can be used to target the suppression of mutant genes, for example, oncogenes whose transcripts comprise point mutations and therefore they can be specifically targeted using the methods and compositions of the invention without altering the expression of the remaining wild-type allele.

Any region of the target polynucleotide can be used to design the domain of the silencing element that shares sufficient sequence identity to allow expression of the hairpin transcript to decrease the level of the target polynucleotide. For instance, the domain can be designed to share sequence identity to the 5' untranslated region of the target polynucleotide(s), the 3' untranslated region of the target polynucleotide(s), exonic regions of the target polynucleotide(s), intronic regions of the target polynucleotide(s), and any combination thereof. In specific embodiments, a domain of the silencing element shares sufficient homology to at least about 15, 16, 17, 18, 19, 20, 22, 25 or 30 consecutive nucleotides from about nucleotides 1-50, 25-75, 75-125, 50-100, 125-175, 175-225, 100-150, 150-200, 200-250, 225-275, 275-325, 250-300, 325-375, 375-425, 300-350, 350-400, 425-475, 400-450, 475-525, 450-500, 525-575, 575-625, 550-600, 625-675, 675-725, 600-650, 625-675, 675-725, 650-700, 725-825, 825-875, 750-800, 875-925, 925-975, 850-900, 925-975, 975-1025, 950-1000, 1000-1050, 1025-1075, 1075-1125, 1050-1100, 1125-1175, 1100-1200, 1175-1225, 1225-1275, 1200-1300, 1325-1375, 1375-1425, 1300-1400, 1425-1475, 1475-1525, 1400-1500, 1525-1575, 1575-1625, 1625-1675, 1675-1725, 1725-1775, 1775-1825, 1825-1875, 1875-1925, 1925-1975, 1975-2025, 2025-2075, 2075-2125, 2125-2175, 2175-2225, 1500-1600, 1600-1700, 1700-1800, 1800-1900, 1900-2000 of the target sequence. In some instances to optimize the siRNA sequences employed in the hairpin, the synthetic oligodeoxyribonucleotide/RNAse H method can be used to determine sites on the target mRNA that are in a conformation that is susceptible to RNA silencing. See, for example, Vickers et al. (2003) *J. Biol. Chem* 278:7108-7118 and Yang et al. (2002) *Proc. Natl. Acad. Sci. USA* 99:9442-9447, herein incorporated by reference. These studies indicate that there is a significant correlation between the RNase-H-sensitive sites and sites that promote efficient siRNA-directed mRNA degradation.

The hairpin silencing element may also be designed such that the sense sequence or the antisense sequence do not correspond to a target polynucleotide. In this embodiment, the sense and antisense sequence flank a loop sequence that comprises a nucleotide sequence corresponding to all or part of the target polynucleotide. Thus, it is the loop region that determines the specificity of the RNA interference. See, for example, WO 02/00904, herein incorporated by reference.

In addition, transcriptional gene silencing (TGS) may be accomplished through use of a hairpin suppression element where the inverted repeat of the hairpin shares sequence identity with the promoter region of a target polynucleotide to be silenced. See, for example, Aufsatz et al. (2002) *PNAS* 99 (Suppl. 4):16499-16506 and Mette et al. (2000) *EMBO J* 19(19):5194-5201.

While the various target sequences disclosed herein can be used to design any silencing element that encodes a hairpin suppression construct, non-limiting examples of such hairpin constructs are set forth in SEQ ID NO: 293 which targets SEQ ID NO: 278; SEQ ID NOS: 294, 295 and 296 which target SEQ ID NO: 279; SEQ ID NOS: 297 and 298 which target SEQ ID NO:280; SEQ ID NO:299 which targets SEQ ID NO:281; SEQ ID NO: 300 which targets SEQ ID NO: 282; and SEQ ID NO: 301 which targets SEQ ID NO: 283; or active variants or fragments thereof.

In other embodiments, the dsRNA can comprise a small RNA (sRNA). sRNAs can comprise both micro RNA (miRNA) and short-interfering RNA (siRNA) (Meister and Tuschl (2004) *Nature* 431:343-349 and Bonetta et al. (2004) *Nature Methods* 1:79-86). “MicroRNAs” or “miRNAs” are regulatory agents comprising about 19 to about 24 nucleotides (nt) in length, which are highly efficient at inhibiting the expression of target polynucleotides. See, for example Javier et al. (2003) *Nature* 425: 257-263, herein incorporated by reference. For miRNA interference, the silencing element can be designed to express a dsRNA molecule that forms a hairpin structure containing a 21 nucleotide sequence that is complementary to the target polynucleotide of interest. The miRNA can be an "artificial miRNA" or "amiRNA" which comprises a miRNA sequence that is synthetically designed to silence a target sequence.

When expressing an miRNA, the final (mature) miRNA is present in a duplex in a precursor backbone structure, the two strands being referred to as the miRNA (the strand that will eventually basepair with the target) and miRNA* (star sequence). This final miRNA is a substrate for a form of dicer that removes the miRNA/miRNA* duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al. (2004) *Genes & Development* 18:2237-2242 and Guo et al. (2005) *Plant Cell* 17:1376-1386).

The silencing element for miRNA interference comprises a miRNA precursor backbone. The miRNA precursor backbone comprises a DNA sequence having the miRNA and star sequences. When expressed as an RNA, the structure of the miRNA precursor backbone is such as to allow for the formation of a hairpin RNA structure that can be processed into a miRNA. In some embodiments, the miRNA precursor backbone comprises a genomic miRNA precursor sequence, wherein said sequence comprises a native precursor in which an heterologous (artificial) miRNA and star sequence are inserted.

As used herein, a "star sequence" is the sequence within a miRNA precursor backbone that is complementary to the miRNA and forms a duplex with the miRNA to form the stem structure of a hairpin RNA. In some embodiments, the star sequence can comprise less than 100% complementarity to the miRNA sequence. Alternatively, the star sequence can comprise at least 99%, 98%, 97%, 96%, 95%, 90%, 85%, 80% or lower sequence complementarity to the miRNA sequence as long as the star sequence has sufficient complementarity to the miRNA sequence to form a double stranded structure. In still further embodiments, the star sequence comprises a sequence having 1, 2, 3, 4, 5 or more mismatches with the miRNA sequence and still has sufficient complementarity to form a double stranded structure with the miRNA sequence resulting in production of miRNA and suppression of the target sequence.

The miRNA precursor backbones can be from any plant. In some embodiments, the miRNA precursor backbone is from a monocot. In other embodiments, the miRNA precursor backbone is from a dicot. In further embodiments, the backbone is from maize or soybean. MicroRNA precursor backbones have been described previously. For example, US20090155910A1 (WO 2009/079532) discloses the following soybean miRNA precursor backbones: 156c, 159, 166b, 168c, 396b and 398b, and US20090155909A1 (WO 2009/079548) discloses the following maize miRNA precursor backbones: 159c, 164h, 168a, 169r, and 396h. Each of these references is incorporated by reference in their entirety.

Thus, the miRNA precursor backbone can be altered to allow for efficient insertion of heterologous miRNA and star sequences within the miRNA precursor backbone. In such instances, the miRNA segment and the star segment of the miRNA precursor backbone are replaced with the heterologous miRNA and the heterologous star sequences, designed to target any sequence of interest, using a PCR technique and cloned into an expression construct. It is recognized that there could be alterations to the position at which the artificial miRNA and star sequences are inserted into the backbone. Detailed methods for inserting the miRNA and star sequence into the miRNA precursor backbone are described elsewhere herein (see, Example 8) and are also described in, for example, US Patent Applications 20090155909A1 and US20090155910A1, herein incorporated by reference in their entirety.

When designing a miRNA sequence and star sequence, various design choices can be made. See, for example, Schwab R, et al. (2005) *Dev Cell* 8: 517-27. In non-limiting embodiments, the miRNA sequences disclosed herein can have a "U" at the 5'-end, a "C" or "G" at the $19^{th}$ nucleotide position, and an "A" or "U" at the 10th nucleotide position. In other embodiments, the miRNA design is such that the miRNA have a high free delta-G as calculated using the ZipFold algorithm (Markham, N. R. & Zuker, M. (2005) *Nucleic Acids Res.* 33: W577-W581.) Optionally, a one base pair change can be added within the 5' portion of the miRNA so that the sequence differs from the target sequence by one nucleotide.

The methods and compositions of the invention employ silencing elements that when transcribed "form" a dsRNA molecule. Accordingly, the heterologous polynucleotide being expressed need not form the dsRNA by itself, but can interact with other sequences in the plant cell or in the pest gut after ingestion to allow the formation of the dsRNA. For example, a chimeric polynucleotide that can selectively silence the target polynucleotide can be generated by expressing a chimeric construct comprising the target sequence for a miRNA or siRNA to a sequence corresponding to all or part of the gene or genes to be silenced. In this embodiment, the dsRNA is "formed" when the target for the miRNA or siRNA interacts with the miRNA present in the cell. The resulting dsRNA can then reduce the level of expression of the gene or genes to be silenced. See, for example, US Application Publication 2007-0130653, entitled "Methods and Compositions for Gene Silencing", herein incorporated by reference. The construct can be designed to have a target for an endogenous miRNA or alternatively, a target for a heterologous and/or synthetic miRNA can be employed in the construct. If a heterologous and/or synthetic miRNA is employed, it can be introduced into the cell on the same nucleotide construct as the chimeric polynucleotide or on a separate construct. As discussed elsewhere herein, any method can be used to introduce the construct comprising the heterologous miRNA.

While the various target sequences disclosed herein can be used to design any silencing element that encodes a miRNA, non-limiting examples of such miRNA constructs include SEQ ID NOS: 311, 312, 327, 328, 335 or 336 which target SEQ ID NO: 304; SEQ ID NOS: 307, 308, 323, 324, 331 or 332 which target SEQ ID NO: 278; SEQ ID NOS: 309, 310, 325, 326, 333 or 334 which target SEQ ID NO: 303; and SEQ ID NOS: 305, 306, 321, 322, 329 or 330 which target SEQ ID NO: 302; or active variants or fragments thereof.

IV. Variants and Fragments

By "fragment" is intended a portion of the polynucleotide or a portion of the amino acid sequence and hence protein encoded thereby. Fragments of a polynucleotide may encode protein fragments that retain the biological activity of the native protein. Alternatively, fragments of a polynucleotide that are useful as a silencing element do not need to encode fragment proteins that retain biological activity. Thus, fragments of a nucleotide sequence may range from at least about 10, about 15, about 16, about 17, about 18, about 19, about 20 nucleotides, about 22 nucleotides, about 50 nucleotides, about 75 nucleotides, about 100 nucleotides, 200 nucleotides, 300 nucleotides, 400 nucleotides, 500 nucleotides, 600 nucleotides, 700 nucleotides and up to the full-length polynucleotide employed in the invention. Alternatively, fragments of a nucleotide sequence may range from 1-50, 25-75, 75-125, 50-100, 125-175, 175-225, 100-150, 150-200, 200-250, 225-275, 275-325, 250-300, 325-375, 375-425, 300-350, 350-400, 425-475, 400-450, 475-525, 450-500, 525-575, 575-625, 550-600, 625-675, 675-725, 600-650, 625-675, 675-725, 650-700, 725-825, 825-875, 750-800, 875-925, 925-975, 850-900, 925-975, 975-1025, 950-1000, 1000-1050, 1025-1075, 1075-1125, 1050-1100, 1125-1175, 1100-1200, 1175-1225, 1225-1275, 1200-1300, 1325-1375, 1375-1425, 1300-1400, 1425-1475, 1475-1525, 1400-1500, 1525-1575, 1575-1625, 1625-1675, 1675-1725, 1725-1775, 1775-1825, 1825-1875, 1875-1925, 1925-1975, 1975-2025, 2025-2075, 2075-2125, 2125-2175, 2175-2225, 1500-1600, 1600-1700, 1700-1800, 1800-1900, 1900-2000 of any one of SEQ ID NOS: 1-304 or 321-336. Methods to assay for the activity of a desired silencing element are described elsewhere herein.

Encompassed herein are fragments of the various target sequences (i.e. SEQ ID NOS: 1-292 and 302-304) which are useful as silencing elements and fragments of the various silencing elements provided herein (i.e. SEQ ID NOS:293-301 or 321-336). Thus, fragments of a nucleotide sequence that are useful as silencing elements may range from at least about 10, about 15, about 16, about 17, about 18, about 19, about 20 nucleotides, about 22 nucleotides, about 50 nucleotides, about 75 nucleotides, about 100 nucleotides, 200 nucleotides, 300 nucleotides, 400 nucleotides, 500 nucleotides, 600 nucleotides, 700 nucleotides and up to the full-length polynucleotide sequences of SEQ ID NOS: 1-304 or 321-336. Alternatively, fragments of a nucleotide sequence that are useful as silencing elements may range from 1-50, 25-75, 75-125, 50-100, 125-175, 175-225, 100-150, 150-200, 200-250, 225-275, 275-325, 250-300, 325-375, 375-425, 300-350, 350-400, 425-475, 400-450, 475-525, 450-500, 525-575, 575-625, 550-600, 625-675, 675-725, 600-650, 625-675, 675-725, 650-700, 725-825, 825-875, 750-800, 875-925, 925-975, 850-900, 925-975, 975-1025, 950-1000, 1000-1050, 1025-1075, 1075-1125, 1050-1100, 1125-1175, 1100-1200, 1175-1225, 1225-1275, 1200-1300, 1325-1375, 1375-1425, 1300-1400, 1425-1475, 1475-1525, 1400-1500, 1525-1575, 1575-1625, 1625-1675, 1675-1725, 1725-1775, 1775-1825, 1825-1875, 1875-1925, 1925-1975, 1975-2025, 2025-2075, 2075-2125, 2125-2175, 2175-2225, 1500-1600, 1600-1700, 1700-1800, 1800-1900, 1900-2000 of any one of SEQ ID NOS: 1-304 or 321-336. Methods to assay for the activity of a desired silencing element are described elsewhere herein. Various, non-limiting examples of fragments of SEQ ID NOS: 1-292 or 302-304 are provided herein and include, for example, SEQ ID NOS: 284-292 or 305-312.

"Variants" is intended to mean substantially similar sequences. Thus, further provided are variants of the various sequences set forth in SEQ ID NOS: 1-336. For polynucleotides, a variant comprises a deletion and/or addition of one or more nucleotides at one or more internal sites within the native polynucleotide and/or a substitution of one or more nucleotides at one or more sites in the native polynucleotide. A variant of a polynucleotide that is useful as a silencing element will retain the ability to reduce expression of the target polynucleotide and, in some embodiments, thereby control a pest of interest. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the polypeptides employed in the invention. Variant polynucleotides also include synthetically derived polynucleotide, such as those generated, for example, by using site-directed mutagenesis, but continue to retain the desired activity. Generally, variants of a particular polynucleotide of the invention (i.e., a silencing element) will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and parameters described elsewhere herein. Where any given pair of polynucleotides employed in the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

A method is further provided for identifying a silencing element from the target polynucleotides set froth in SEQ ID NO: 1-292 or 302-304. Such methods comprise obtaining a candidate fragment of any one of SEQ ID NO: 1-292 or 302-304 which is of sufficient length to act as a silencing element and thereby reduce the expression of the target polynucleotide and/or control a desired pest; expressing said candidate polynucleotide fragment in an appropriate expression cassette to produce a candidate silencing element and determining is said candidate polynucleotide fragment has the activity of a silencing element and thereby reduce the expression of the target polynucleotide and/or controls a desired pest. Methods of identifying such candidate fragments based on the desired pathway for suppression are known. For example, various bioinformatics programs can be employed to identify the region of the target polynucleotides that could be exploited to generate a silencing element. See, for example, Elbahir et al. (2001) *Genes and Development* 15:188-200, Schwartz et al. (2003) *Cell* 115:199-208, Khvorova et al. (2003) *Cell* 115:209-216. See also, siRNA at Whitehead (jura.wi.mit.edu/bioc/siRNAext/) which calculates the binding energies for both sense and antisense siRNAs. See, also genscript.com/ssl-bin/app/rnai?op=known; Block-iT™ RNAi designer from Invitrogen and GenScript siRNA Construct Builder.

V. DNA Constructs

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The polynucleotide encoding the silencing element or in specific embodiments employed in the methods and compositions of the invention can be provided in expression cassettes for expression in a plant or organism of interest. It is recognized that multiple silencing elements including multiple identical silencing elements, multiple silencing elements targeting different regions of the target sequence, or multiple silencing elements from different target sequences can be used. In this embodiment, it is recognized that each silencing element can be contained in a single or separate cassette, DNA construct, or vector. As discussed, any means of providing the silencing element is contemplated. A plant or plant cell can be transformed with a single cassette comprising DNA encoding one or more silencing elements or separate cassettes comprising each silencing element can be used to transform a plant or plant cell or host cell. Likewise, a plant transformed with one component can be subsequently transformed with the second component. One or more silencing elements can also be brought together by sexual crossing. That is, a first plant comprising one component is crossed with a second plant comprising the second component. Progeny plants from the cross will comprise both components.

The expression cassette can include 5' and 3' regulatory sequences operably linked to the polynucleotide of the invention. "Operably linked" is intended to mean a functional linkage between two or more elements. For example, an operable linkage between a polynucleotide of the invention and a regulatory sequence (i.e., a promoter) is a functional link that allows for expression of the polynucleotide of the invention. Operably linked elements may be contiguous or non-contiguous. When used to refer to the joining of two protein coding regions, by operably linked is intended that the coding regions are in the same reading frame. The cassette may additionally contain at least one additional polynucleotide to be cotransformed into the organism. Alternatively, the additional polypeptide(s) can be provided on multiple expression cassettes. Expression cassettes can be provided with a plurality of restriction sites and/or recombination sites for insertion of the polynucleotide to be under the transcriptional regulation of the regulatory regions. The expression cassette may additionally contain selectable marker genes.

The expression cassette can include in the 5'-3' direction of transcription, a transcriptional and translational initiation region (i.e., a promoter), a polynucleotide comprising the silencing element employed in the methods and compositions of the invention, and a transcriptional and translational termination region (i.e., termination region) functional in plants. In other embodiment, the double stranded RNA is expressed from a suppression cassette. Such a cassette can comprise two convergent promoters that drive transcription of an operably linked silencing element. "Convergent promoters" refers to promoters that are oriented on either terminus of the operably linked silencing element such that each promoter drives transcription of the silencing element in opposite directions, yielding two transcripts. In such embodiments, the convergent promoters allow for the transcription of the sense and anti-sense strand and thus allow for the formation of a dsRNA.

The regulatory regions (i.e., promoters, transcriptional regulatory regions, and translational termination regions) and/or the polynucleotides employed in the invention may be native/analogous to the host cell or to each other. Alternatively, the regulatory regions and/or the polynucleotide employed in the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

The termination region may be native with the transcriptional initiation region, may be native with the operably linked polynucleotide encoding the silencing element, may be native with the plant host, or may be derived from another source (i.e., foreign or heterologous) to the promoter, the polynucleotide comprising silencing element, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The polynucleotide encoding the silencing element can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026); soybean elongation factor 1A (ACUP01009998), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

An inducible promoter, for instance, a pathogen-inducible promoter could also be employed. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression within a particular plant tissue. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254 (3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

In one embodiment, the various silencing elements disclosed herein are expressed using a seed-preferred promoter. "Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Ciml (cytokinin-induced message); Kunitz trypsin inhibitor 3 (kti3) (Genbank accession AF233296); glycinin-1 genes (Genbank accession AB353075.1); cZ19B1 (maize 19 kDa zein); milps (myo-inositol-1-phosphate synthase) (see WO 00/11177 and U.S. Pat. No. 6,225,529; herein incorporated by reference). Gamma-zein is an endosperm-specific promoter. Globulin 1 (Glb-1) is a representative embryo-specific promoter. For dicots, seed-preferred promoters include, but are not limited to, bean β-phaseolin, napin, β-conglycinin alpha (Genbank accession GU723691), soybean lectin, cruciferin, and the like. For monocots, seed-preferred promoters include, but are not limited to, maize 15 kDa zein, 22 kDa zein, 27 kDa zein, gamma-zein, waxy, shrunken 1, shrunken 2, Globulin 1, etc. See also WO 00/12733, where seed-preferred promoters from end1 and end2 genes are disclosed; herein incorporated by reference.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

In one embodiment of this invention the plant-expressed promoter is a vascular-specific promoter such as a phloem-specific promoter. A "vascular-specific" promoter, as used herein, is a promoter which is at least expressed in vascular cells, or a promoter which is preferentially expressed in vascular cells. Expression of a vascular-specific promoter need not be exclusively in vascular cells, expression in other cell types or tissues is possible. A "phloem-specific promoter" as used herein, is a plant-expressible promoter which is at least expressed in phloem cells, or a promoter which is preferentially expressed in phloem cells.

Expression of a phloem-specific promoter need not be exclusively in phloem cells, expression in other cell types or tissues, e.g., xylem tissue, is possible. In one embodiment of this invention, a phloem-specific promoter is a plant-expressible promoter at least expressed in phloem cells, wherein the expression in non-phloem cells is more limited (or absent) compared to the expression in phloem cells. Examples of suitable vascular-specific or phloem-specific promoters in accordance with this invention include but are not limited to the promoters selected from the group consisting of: the SCSV3, SCSV4, SCSV5, and SCSV7 promoters (Schunmann et al. (2003) *Plant Functional Biology* 30:453-60; the rolC gene promoter of *Agrobacterium rhizogenes*(Kiyokawa et al. (1994) *Plant Physiology* 104:801-02; Pandolfini et al. (2003) *BioMedCentral* (BMC) Biotechnology 3:7, (biomedcentral.com/1472-6750/3/7, which can be accessed by adding the prefix "www."); Graham et al. (1997) *Plant Mol. Biol.* 33:729-35; Guivarc'h et al. (1996); Almon et al. (1997) *Plant Physiol.* 115:1599-607; the rolA gene promoter of *Agrobacterium rhizogenes* (Dehio et al. (1993) *Plant Mol. Biol.* 23:1199-210); the promoter of the *Agrobacterium tumefaciens* T-DNA gene 5 (Korber et al. (1991) *EMBO J.* 10:3983-91); the rice sucrose synthase RSs1 gene promoter (Shi et al. (1994) *J. Exp. Bot.* 45:623-31); the CoYMV or Commelina yellow mottle badnavirus promoter (Medberry et al. (1992) *Plant Cell* 4:185-92; Zhou et al. (1998) Chin. J. Biotechnol. 14:9-16); the CFDV or coconut foliar decay virus promoter (Rohde et al. (1994) *Plant Mol. Biol.* 27:623-28; Hehn and Rhode (1998) *J. Gen. Virol.* 79:1495-99); the RTBV or rice tungro bacilliform virus promoter (Yin and Beachy (1995) *Plant J.* 7:969-80; Yin et al. (1997) *Plant J.* 12:1179-80); the pea glutamin synthase GS3A gene (Edwards et al. (1990) *Proc. Natl. Acad. Sci. USA* 87:3459-63; Brears et al. (1991) *Plant J.* 1:235-44); the inv CD111 and inv CD141 promoters of the potato invertase genes (Hedley et al. (2000) *J. Exp. Botany* 51:817-21); the promoter isolated from Arabidopsis shown to have phloem-specific expression in tobacco by Kertbundit et al. (1991) *Proc. Natl. Acad. Sci. USA* 88:5212-16); the VAHOX1 promoter region (Tornero et al. (1996) *Plant J.* 9:639-48); the pea cell wall invertase gene promoter (Zhang et al. (1996) *Plant Physiol.* 112:1111-17); the promoter of the endogenous cotton protein related to chitinase of US published patent application 20030106097, an acid invertase gene promoter from carrot (Ramloch-Lorenz et al. (1993) *The Plant J.* 4:545-54); the promoter of the sulfate transporter geneSultr1; 3 (Yoshimoto et al. (2003) *Plant Physiol.*

131:1511-17); a promoter of a sucrose synthase gene (Nolte and Koch (1993) *Plant Physiol.* 101:899-905); and the promoter of a tobacco sucrose transporter gene (Kuhn et al. (1997) *Science* 275-1298-1300).

Possible promoters also include the Black Cherry promoter for Prunasin Hydrolase (PH DL1.4 PRO) (U.S. Pat. No. 6,797,859), Thioredoxin H promoter from cucumber and rice (Fukuda A et al. (2005). *Plant Cell Physiol.* 46(11): 1779-86), Rice (RSs1) (Shi, T. Wang et al. (1994). *J. Exp. Bot.* 45(274): 623-631) and maize sucrose synthese −1 promoters (Yang, N-S. et al. (1990) *PNAS* 87:4144-4148), PP2 promoter from pumpkin Guo, H. et al. (2004) *Transgenic Research* 13:559-566), At SUC2 promoter (Truernit, E. et al. (1995) *Planta* 196(3):564-70, At SAM-1 (S-adenosylmethionine synthetase) (Mijnsbrugge K V. et al. (1996) *Planr. Cell. Physiol.* 37(8): 1108-1115), and the Rice tungro bacilliform virus (RTBV) promoter (Bhattacharyya-Pakrasi et al. (1993) *Plant J.* 4(1):71-79).

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Sci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used in the present invention.

VI. Compositions Comprising Silencing Elements

One or more of the polynucleotides comprising the silencing element can be provided as an external composition such as a spray or powder to the plant, plant part, seed, a pest, or an area of cultivation. In another example, a plant is transformed with a DNA construct or expression cassette for expression of at least one silencing element. In either composition, the silencing element, when ingested by an insect, can reduce the level of a target pest sequence and thereby control the pest (i.e., a *Pentatomidae* plant pest including a *N. viridula, Acrosternum hilare, Piezodorus guildini*, and/or *Halymorpha halys*. It is recognized that the composition can comprise a cell (such as plant cell or a bacterial cell), in which a polynucleotide encoding the silencing element is stably incorporated into the genome and operably linked to promoters active in the cell. Compositions comprising a mixture of cells, some cells expressing at least one silencing element are also encompassed. In other embodiments, compositions comprising the silencing elements are not contained in a cell. In such embodiments, the composition can be applied to an area inhabited by a pest. In one embodiment, the composition is applied externally to a plant (i.e., by spraying a field or area of cultivation) to protect the plant from the pest.

The composition of the invention can further be formulated as bait. In this embodiment, the compositions comprise a food substance or an attractant which enhances the attractiveness of the composition to the pest.

The composition comprising the silencing element can be formulated in an agriculturally suitable and/or environmentally acceptable carrier. Such carriers can be any material that the animal, plant or environment to be treated can tolerate. Furthermore, the carrier must be such that the composition remains effective at controlling a pest. Examples of such carriers include water, saline, Ringer's solution, dextrose or other sugar solutions, Hank's solution, and other aqueous physiologically balanced salt solutions, phosphate buffer, bicarbonate buffer and Tris buffer. In addition, the composition may include compounds that increase the half-life of a composition.

It is recognized that the polynucleotides comprising sequences encoding the silencing element can be used to transform organisms to provide for host organism production of these components, and subsequent application of the host organism to the environment of the target pest(s). Such host organisms include baculoviruses, bacteria, and the like. In this manner, the combination of polynucleotides encoding the silencing element may be introduced via a suitable vector into a microbial host, and said host applied to the environment, or to plants or animals.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be stably incorporated into the genome of the cell (e.g., chromosome, plasmid, plastid, or mitochondrial DNA), converted into an autonomous replicon, or transiently expressed (e.g., transfected mRNA).

Microbial hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the sequences encoding the silencing element, and desirably, provide for improved protection of the components from environmental degradation and inactivation.

Such microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*, fungi, particularly yeast, e.g., *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinlandir*, and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae*, and *Aureobasidium pollulans*. Of particular interest are the pigmented microorganisms.

A number of ways are available for introducing the polynucleotide comprising the silencing element into the microbial host under conditions that allow for stable maintenance and expression of such nucleotide encoding sequences. For example, expression cassettes can be constructed which include the nucleotide constructs of interest operably linked with the transcriptional and translational regulatory signals for expression of the nucleotide constructs, and a nucleotide sequence homologous with a sequence in the host organism, whereby integration will occur, and/or a replication system that is functional in the host, whereby integration or stable maintenance will occur.

Transcriptional and translational regulatory signals include, but are not limited to, promoters, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook et al. (2000); *Molecular Cloning: A Laboratory Manual* (3rd ed.; Cold Spring Harbor Laboratory Press, Plainview, N.Y.); Davis et al. (1980) *Advanced Bacterial Genetics* (Cold Spring Harbor Laboratory, Cold Spring Harbor, N.Y.); and the references cited therein.

Suitable host cells include the prokaryotes and the lower eukaryotes, such as fungi. Illustrative prokaryotes, both Gram-negative and Gram-positive, include Enterobacteriaceae, such as *Escherichia, Erwinia, Shigella, Salmonella*, and *Proteus*; Bacillaceae; Rhizobiceae, such as *Rhizobium*; Spirillaceae, such as photobacterium, *Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae and Nitrobacteraceae. Among eukaryotes are fungi, such as Phycomycetes and Ascomycetes, which includes yeast, such as *Saccharomyces* and *Schizosaccharomyces*; and Basidiomycetes yeast, such as *Rhodotorula, Aureobasidium, Sporobolomyces*, and the like.

Characteristics of particular interest in selecting a host cell for purposes of the invention include ease of introducing the coding sequence into the host, availability of expression systems, efficiency of expression, stability in the host, and the presence of auxiliary genetic capabilities. Characteristics of interest for use as a pesticide microcapsule include protective qualities, such as thick cell walls, pigmentation, and intracellular packaging or formation of inclusion bodies; leaf affinity; lack of mammalian toxicity; attractiveness to pests for ingestion; and the like. Other considerations include ease of formulation and handling, economics, storage stability, and the like.

Host organisms of particular interest include yeast, such as *Rhodotorula* spp., *Aureobasidium* spp., *Saccharomyces* spp., and *Sporobolomyces* spp., phylloplane organisms such as *Pseudomonas* spp., *Erwinia* spp., and *Flavobacterium* spp., and other such organisms, including *Pseudomonas aeruginosa, Pseudomonas fluorescens, Saccharomyces cerevisiae, Bacillus thuringiensis, Escherichia coli, Bacillus subtilis*, and the like.

The sequences encoding the silencing elements encompassed by the invention can be introduced into microorganisms that multiply on plants (epiphytes) to deliver these components to potential target pests. Epiphytes, for example, can be gram-positive or gram-negative bacteria.

The silencing element can be fermented in a bacterial host and the resulting bacteria processed and used as a microbial spray in the same manner that *Bacillus thuringiensis* strains have been used as insecticidal sprays. Any suitable microorganism can be used for this purpose. *Pseudomonas* has been used to express *Bacillus thuringiensis* endotoxins as encapsulated proteins and the resulting cells processed and sprayed as an insecticide Gaertner et al. (1993), in *Advanced Engineered Pesticides*, ed. L. Kim (Marcel Decker, Inc.).

Alternatively, the components of the invention are produced by introducing heterologous genes into a cellular host. Expression of the heterologous sequences results, directly or indirectly, in the intracellular production of the silencing element. These compositions may then be formulated in accordance with conventional techniques for application to the environment hosting a target pest, e.g., soil, water, and foliage of plants. See, for example, EPA 0192319, and the references cited therein.

In the present invention, a transformed microorganism can be formulated with an acceptable carrier into separate or combined compositions that are, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors, or other preparations that influence plant growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention (i.e., at least one silencing element) are normally applied in the form of compositions and can be applied to the crop area, plant, or seed to be treated. For example, the compositions may be applied to grain in preparation for or during storage in a grain bin or silo, etc. The compositions may be applied simultaneously or in succession with other compounds. Methods of applying an active ingredient or a composition that contains at least one silencing element include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; carboxylate of a long chain fatty acid; an N-acylsarcosinate; mono- or di-esters of phosphoric acid with fatty alcohol ethoxylates or salts of such esters; fatty alcohol sulfates such as sodium dodecyl sulfate, sodium octadecyl sulfate, or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphthalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitan fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include, but are not limited to, inorganic minerals such as kaolin, phyllosilicates, carbonates, sulfates, phosphates, or botanical materials such as cork, powdered corncobs, peanut hulls, rice hulls, and walnut shells.

The compositions comprising the silencing element can be in a suitable form for direct application or as a concentrate of primary composition that requires dilution with a suitable quantity of water or other dilutent before application.

The compositions (including the transformed microorganisms) can be applied to the environment of an insect pest (such as a *Pentatomidae* plant pest or a *N. viridula, Acrosternum hilare, Piezodorus guildini*, and/or *Halymorpha halys* plant pest) by, for example, spraying, atomizing, dusting, scattering, coating or pouring, introducing into or on the soil, introducing into irrigation water, by seed treatment or general application or dusting at the time when the pest has begun to appear or before the appearance of pests as a protective measure. For example, the composition(s) and/or transformed microorganism(s) may be mixed with grain to protect the grain during storage. It is generally important to obtain good control of pests in the early stages of plant growth, as this is the time when the plant can be most severely damaged. The compositions can conveniently contain another insecticide if this is thought necessary. In an embodiment of the invention, the composition(s) is applied directly to the soil, at a time of planting, in granular form of a composition of a carrier and dead cells of a *Bacillus* strain or transformed microorganism of the invention. Another embodiment is a granular form of a composition comprising an agrochemical such as, for example, a herbicide, an insecticide, a fertilizer, in an inert carrier, and dead cells of a *Bacillus* strain or transformed microorganism of the invention.

VII. Plants, Plant Parts, and Methods of Introducing Sequences into Plants

The methods of the invention involve introducing a polynucleotide into a plant. In one embodiment, a plant cell is provided having stably incorporated into its genome a heterologous polynucleotide comprising any of the various silencing elements provided herein. It is recognized that the silencing element, when ingested by a *Pentatomidae* plant pest, can reduce the level of expression of any of the target sequences described herein (i.e. SEQ ID NOS: 1-292 or 302-304). "Introducing" is intended to mean presenting to the plant the polynucleotide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. No. 5,563,055 and U.S. Pat. No. 5,981,840), direct gene transfer (Paszkowski et al. (1984) *EMBO J.* 3:2717-2722), and ballistic particle acceleration (see, for example, U.S. Pat. No. 4,945,050; U.S. Pat. No. 5,879,918; U.S. Pat. No. 5,886,244; and, U.S. Pat. No. 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lecl transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P: 175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (*London*) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the silencing element sequences of the invention can be provided to a plant using a variety of transient transformation methods. Such transient transformation methods include, but are not limited to, the introduction of the protein or variants and fragments thereof directly into the plant or the introduction of the transcript into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, polynucleotides can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use of particles coated with polyethylimine (PEI; Sigma #P3143).

In other embodiments, the polynucleotide of the invention may be introduced into plants by contacting plants with a virus or viral nucleic acids. Generally, such methods involve incorporating a nucleotide construct of the invention within a viral DNA or RNA molecule. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

As used herein, the term plant also includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants and sugarcane plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

In specific embodiments, the plants/plant cells and/or seeds comprising an expression construct comprise a silencing element directed to a target sequence provided herein (i.e. SEQ ID NOS: 1-292 or 302-304) operably linked to a seed-preferred promoter.

VIII. Methods of Use

The methods of the invention comprise methods for controlling a pest (i.e., a *Pentatomidae* plant pest, such as, *N. viridula, Acrosternum hilare, Piezodorus guildini*, and/or *Halymorpha halys* plant pest). The method comprises feeding to a pest a composition comprising a silencing element of the invention, wherein said silencing element, when ingested by a pest (i.e., a *Pentatomidae* plant pest including *N. viridula, Acrosternum hilare, Piezodorus guildini*, and/or *Halymorpha halys*), reduces the level of a target polynucleotide of the pest and thereby controls the pest. The pest can be fed the silencing element in a variety of ways. For example, in one embodiment, the polynucleotide comprising the silencing element is introduced into a plant. As the *Pentatomidae* plant pest or *N. viridula, Acrosternum hilare, Piezodorus guildini*, and/or *Halymorpha halys* plant pest feeds on the plant or part thereof expressing these sequences, the silencing element is delivered to the pest. When the silencing element is delivered to the plant in this manner, it is recognized that the silencing element can be expressed constitutively or alternatively, it may be produced in a stage-specific manner by employing the various inducible or tissue-preferred or developmentally regulated promoters that are discussed elsewhere herein. In one embodiment, the silencing element is operably linked to a seed-preferred promoter. In specific embodiments, the silencing element expressed in the roots, stalk or stem, leaf including pedicel, xylem and phloem, fruit or reproductive tissue, silk, flowers and all parts therein or any combination thereof.

In another method, a composition comprising at least one silencing element of the invention is applied to a plant. In such embodiments, the silencing element can be formulated in an agronomically suitable and/or environmentally acceptable carrier, which is preferably, suitable for dispersal in fields. In addition, the carrier can also include compounds that increase the half life of the composition. In specific embodiments, the composition comprising the silencing element is formulated in such a manner such that it persists in the environment for a length of time sufficient to allow it to be delivered to a pest. In such embodiments, the composition can be applied to an area inhabited by a pest. In one embodiment, the composition is applied externally to a plant (i.e., by spraying a field) to protect the plant from pests.

In certain embodiments, the constructs of the present invention can be stacked with any combination of polynucleotide sequences of interest in order to create plants with a desired trait. A trait, as used herein, refers to the phenotype derived from a particular sequence or groups of sequences. For example, the polynucleotides of the present invention may be stacked with any other polynucleotides encoding polypeptides having pesticidal and/or insecticidal activity, such as other *Bacillus thuringiensis* toxic proteins (described in U.S. Pat. Nos. 5,366,892; 5,747,450; 5,737,514; 5,723,756; 5,593,881; and Geiser et al. (1986) *Gene* 48:109), lectins (Van Damme et al. (1994) *Plant Mol. Biol.* 24:825, pentin (described in U.S. Pat. No. 5,981,722), and the like. The combinations generated can also include multiple copies of any one of the polynucleotides of interest. The polynucleotides of the present invention can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122) and high methionine proteins (Pedersen et al. (1986) *J. Biol. Chem.* 261:6279; Kirihara et al. (1988) *Gene* 71:359; and Musumura et al. (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference.

The polynucleotides of the present invention can also be stacked with traits desirable for disease or herbicide resistance (e.g., fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Methods and compositions are further provided which allow for an increase in RNAi produced from the silencing element. In such embodiments, the methods and compositions employ a first polynucleotide comprising a silencing element for a target pest sequence operably linked to a promoter active in the plant cell; and, a second polynucleotide comprising a suppressor enhancer element comprising the target pest sequence or an active variant or fragment thereof operably linked to a promoter active in the plant cell. The combined expression of the silencing element with suppressor enhancer element leads to an increased amplification of the inhibitory RNA produced from the silencing element over that achievable with only the expression of the silencing element alone. In addition to the increased amplification of the specific RNAi species itself, the methods and compositions further allow for the production of a diverse population of RNAi species that can enhance the effectiveness of disrupting target gene expression. As such, when the suppressor enhancer element is expressed in a plant cell in combination with the silencing element, the methods and composition can allow for the systemic production of RNAi throughout the plant; the production of greater amounts of RNAi than would be observed with just the silencing element construct alone; and, the improved loading of RNAi into the phloem of the plant, thus providing better control of phloem feeding insects by an RNAi approach. Thus, the various methods and compositions provide improved methods for the delivery of inhibitory RNA to the target organism. See, for example, U.S. application Ser. No. 12/351,093, entitled "Compositions and Methods for the Suppression of Target Polynucleotides", filed Jan. 9, 2009 and herein incorporated by reference in its entirety.

As used herein, a "suppressor enhancer element" comprises a polynucleotide comprising the target sequence to be suppressed or an active fragment or variant thereof. It is recognize that the suppressor enhancer element need not be identical to the target sequence, but rather, the suppressor enhancer element can comprise a variant of the target sequence, so long as the suppressor enhancer element has sufficient sequence identity to the target sequence to allow for an increased level of the RNAi produced by the silencing element over that achievable with only the expression of the silencing element. Similarly, the suppressor enhancer element can comprise a fragment of the target sequence, wherein the fragment is of sufficient length to allow for an increased level of the RNAi produced by the silencing element over that achievable with only the expression of the silencing element. Thus, in specific embodiments, the suppressor enhancer element comprises a polynucleotide set forth in SEQ ID NO: 1-292, or 302-304 or an active variant or fragment thereof.

It is recognized that multiple suppressor enhancer elements from the same target sequence or from different target sequences, or from different regions of the same target sequence can be employed. For example, the suppressor enhancer elements employed can comprise fragments of the target sequence derived from different region of the target sequence (i.e., from the 3'UTR, coding sequence, intron, and/or 5'UTR). Further, the suppressor enhancer element can be contained in an expression cassette, as described elsewhere herein, and in specific embodiments, the suppressor enhancer element is on the same or on a different DNA vector or construct as the silencing element. The suppressor enhancer element can be operably linked to a promoter as disclosed herein. It is recognized that the suppressor enhancer element can be expressed constitutively or alternatively, it may be produced in a stage-specific manner employing the various inducible or tissue-preferred or developmentally regulated promoters that are discussed elsewhere herein.

In specific embodiments, employing both a silencing element and the suppressor enhancer element the systemic production of RNAi occurs throughout the entire plant. In further embodiments, the plant or plant parts of the invention have an improved loading of RNAi into the phloem of the plant than would be observed with the expression of the silencing element construct alone and, thus provide better control of phloem feeding insects by an RNAi approach. In specific embodiments, the plants, plant parts, and plant cells of the invention can further be characterized as allowing for the production of a diversity of RNAi species that can enhance the effectiveness of disrupting target gene expression.

In specific embodiments, the combined expression of the silencing element and the suppressor enhancer element increases the concentration of the inhibitory RNA in the plant cell, plant, plant part, plant tissue or phloem over the level that is achieved when the silencing element is expressed alone.

As used herein, an "increased level of inhibitory RNA" comprises any statistically significant increase in the level of RNAi produced in a plant having the combined expression when compared to an appropriate control plant. For example, an increase in the level of RNAi in the plant, plant part or the plant cell can comprise at least about a 1%, about a 1%-5%, about a 5%-10%, about a 10%-20%, about a 20%-30%, about a 30%-40%, about a 40%-50%, about a 50%-60%, about 60-70%, about 70%-80%, about a 80%-90%, about a 90%-100% or greater increase in the level of RNAi in the plant, plant part, plant cell, or phloem when compared to an appropriate control. In other embodiments, the increase in the level of RNAi in the plant, plant part, plant cell, or phloem can comprise at least about a 1 fold, about a 1 fold-5 fold, about a 5 fold-10 fold, about a 10 fold-20 fold, about a 20 fold-30 fold, about a 30 fold-40 fold, about a 40 fold-50 fold, about a 50 fold-60 fold, about 60 fold-70 fold, about 70 fold-80 fold, about a 80 fold-90 fold, about a 90 fold-100 fold or greater increase in the level of RNAi in the plant, plant part, plant cell or phloem when compared to an appropriate control. Methods to assay for an increase in the level of RNAi are discussed elsewhere herein.

Non-limiting examples of methods and compositions disclosed herein are as follows:

1. An isolated polynucleotide comprising a nucleotide sequence selected from the group consisting of:

(a) the nucleotide sequence comprising any one of SEQ ID NOS: 279, 302, 281, 304, 280, 283, 282, 303, 278, 284, 285, 286, 287, 288, 289, 290, 291, 292, 14, 18, 263, 17, 30, 34, 337, 338, 339, 340, 341, 342, 343, 344, 305, 306, 307, 308, 309, 310, 311, 312, 293, 294, 295, 296, 297, 298, 299, 300, 301, 321, 322, 323, 324, 325, 326, 327 or 328 or a complement thereof;

(b) the nucleotide sequence comprising at least 90% sequence identity to any one of SEQ ID NOS: 279, 302, 281, 304, 280, 283, 282, 303, 278, 284, 285, 286, 287, 288, 289, 290, 291, 292, 14, 18, 263, 17, 30, 34, 337, 338, 339, 340, 341, 342, 343, 344, 305, 306, 307, 308, 309, 310, 311, 312, 293, 294, 295, 296, 297, 298, 299, 300, 301, 321, 322, 323, 324, 325, 326, 327 or 328 or a complement thereof, wherein said polynucleotide encodes a silencing element having insecticidal activity against a *Pentatomidae* plant pest;

(c) the nucleotide sequence comprising at least 19 consecutive nucleotides of any one of SEQ ID NOS: 279, 302, 281, 304, 280, 283, 282, 303, 278, 284, 285, 286, 287, 288, 289, 290, 291, 292, 17, 30, 34, 14, 18 or 263 or a complement thereof, wherein said polynucleotide encodes a silencing element having insecticidal activity against a *Pentatomidae* plant pest; and, (d) the nucleotide sequence that hybridizes under stringent conditions to the full length complement of the nucleotide sequence of a), wherein said stringent conditions comprise hybridization in 50% formamide, 1 M NaCl, 1% SDS at 37° C., and a wash in 0.1×SSC at 60° C. to 65° C., wherein said polynucleotide encodes a silencing element having insecticidal activity against a *Pentatomidae* plant pest.

2. The isolated polynucleotide of embodiment 1, wherein said *Pentatomidae* plant pest is a *N. viridula* plant pest.

3. An expression cassette comprising a heterologous polynucleotide of embodiment 1 or 2 operably linked to a seed-preferred promoter.

4. The expression cassette of embodiment 3, wherein said polynucleotide is expressed as a double stranded RNA.

5. The expression cassette of embodiment 3, wherein said polynucleotide comprise a silencing element which is expressed as a hairpin RNA.

6. The expression cassette of embodiment 5, wherein the silencing element comprises, in the following order, a first segment, a second segment, and a third segment, wherein a) said first segment comprises at least about 19 nucleotides having at least 90% sequence complementarity to a target sequence set forth in SEQ ID NOS: 279, 302, 281, 304, 280, 283, 282, 303, 278, 284, 285, 286, 287, 288, 289, 290, 291, 292, 17, 30, 34, 14, 18 or 263;

b) said second segment comprises a loop of sufficient length to allow the silencing element to be transcribed as a hairpin RNA; and, c) said third segment comprises at least about 19 nucleotides having at least 85% complementarity to the first segment.

7. The expression cassette of embodiment 6, wherein said target sequence comprises the sequences set forth any one of SEQ ID NOS: 284, 285, 286, 287, 288, 289, 290, 291, 292, 337, 338, 339, 340, 341, 342, 343 or 344 or a sequence having at least 90% sequence identity to SEQ ID NOS: 284, 285, 286, 287, 288, 289, 290, 291, 292, 337, 338, 339, 340, 341, 342, 343 or 344.

8. The expression cassette of embodiment 6, wherein said expression cassette comprises any one of SEQ ID NOS: 293, 294, 295, 296, 297, 298, 299, 300, 301, 321, 322, 323, 324, 325, 326, 327 or 328.

9. The expression cassette of embodiment 3, wherein said polynucleotide is flanked by a first operably linked convergent promoter at one terminus of the polynucleotide and a second operably linked convergent promoter at the opposing terminus of the polynucleotide, wherein the first and the second convergent promoters are capable of driving expression of the polynucleotide.

10. A host cell comprising a heterologous expression cassette of any one of embodiments 3-9.

11. A plant cell having stably incorporated into its genome a heterologous polynucleotide comprising a silencing element operably linked to a seed-preferred promoter, wherein said silencing element, when ingested by a *Pentatomidae* plant pest, reduces the level of expression of any one of the target sequences set forth in SEQ ID NOS: 279, 302, 281, 304, 280, 283, 282, 303, 278, 284, 285, 286, 287, 288, 289, 290, 291, 292, 14, 18, 263, 17, 30, 34, 337, 338, 339, 340, 341, 342, 343, 344, 305, 306, 307, 308, 309, 310, 311, 312, 293, 294, 295, 296, 297, 298, 299, 300, 301, 321, 322, 323, 324, 325, 326, 327 or 328 in said *Pentatomidae* plant pest and thereby controls the *Pentatomidae* plant pest.

12. The plant cell of embodiment 11, wherein said silencing element comprises a) a fragment of at least 19 consecutive nucleotides of SEQ ID NOS: 279, 302, 281, 304, 280, 283, 282, 303, 278, 284, 285, 286, 287, 288, 289, 290, 291, 292, 17, 30, 34, 14, 18 or 263 or a complement thereof; or, b) the nucleotide sequence comprising at least 90% sequence identity to any one of SEQ ID NOS: 279, 302, 281, 304, 280, 283, 282, 303, 278, 284, 285, 286, 287, 288, 289, 290, 291, 292, 14, 18, 263, 17, 30, 34, 337, 338, 339, 340, 341, 342, 343, 344, 305, 306, 307, 308, 309, 310, 311, 312, 293, 294, 295, 296, 297, 298, 299, 300, 301, 321, 322, 323, 324, 325, 326, 327 or 328 or a complement thereof, wherein said silencing element, when ingested by a *Pentatomidae* plant pest, reduces the level of a target sequence in said *Pentatomidae* plant pest and thereby controls the *Pentatomidae* plant pest.

13. The plant cell of embodiment 12, wherein the *Pentatomidae* plant pest is a *N. viridula* plant pest.

14. The plant cell of any one of embodiment 11, 12 or 13, wherein said silencing element comprises the sequences set forth in any one of SEQ ID NOS: 284, 285, 286, 287, 288, 289, 290, 291, 292, 305, 306, 307, 308, 309, 310, 311, 312, 17, 30, 34, 337, 338, 339, 340, 341, 342, 343 or 344 or a complement thereof.

15. The plant cell of embodiment 11-14, wherein said plant cell comprises the expression cassette of embodiment 9.

16. The plant cell of any one of embodiments 11-14, wherein said silencing element expresses a double stranded RNA.

17. The plant cell of any one of embodiments 11-15, wherein said silencing element expresses a hairpin RNA.

18. The plant cell of embodiment 17, wherein said polynucleotide comprising the silencing element comprises, in the following order, a first segment, a second segment, and a third segment, wherein a) said first segment comprises at least about 19 nucleotides having at least 90% sequence complementarity to a target sequence set forth in SEQ ID NOS: 279, 302, 281, 304, 280, 283, 282, 303, 278, 284, 285, 286, 287, 288, 289, 290, 291, 292, 14, 18, 263, 17, 30, 34, 337, 338, 339, 340, 341, 342, 343, 344, 305, 306, 307, 308, 309, 310, 311, 312, 293, 294, 295, 296, 297, 298, 299, 300, 301, 321, 322, 323, 324, 325, 326, 327 or 328;

b) said second segment comprises a loop of sufficient length to allow the silencing element to be transcribed as a hairpin RNA; and, c) said third segment comprises at least about 19 nucleotides having at least 85% complementarity to the first segment.

19. The plant cell of any one of embodiments 11-18, wherein said plant cell is from a monocot.
20. The plant cell of embodiment 19, wherein said monocot is maize, barley, millet, wheat or rice.
21. The plant cell of any one of embodiments 11-18, wherein said plant cell is from a dicot.
22. The plant cell of embodiment 21, wherein said plant is soybean, canola, alfalfa, sunflower, safflower, tobacco, *Arabidopsis*, or cotton.
23. A plant or plant part comprising a plant cell of any one of embodiments 11-22.
24. A transgenic seed from the plant of embodiment 23, wherein said transgenic seed comprises said heterologous polynucleotide comprising said silencing element.
25. A method of controlling a *Pentatomidae* plant pest comprising feeding to a *Pentatomidae* plant pest a composition comprising a silencing element, wherein said silencing element, when ingested by said *Pentatomidae* plant pest, reduces the level of expression of any one of the target *Pentatomidae* plant pest sequences set forth in SEQ ID NOS: 279, 302, 281, 304, 280, 283, 282, 303, 278, 284, 285, 286, 287, 288, 289, 290, 291, 292, 17, 30, 34, 14, 18 or 263 and thereby controls the *Pentatomidae* plant pest.
26. The method of embodiment 25, wherein said silencing element comprises a) a fragment of at least 19 consecutive nucleotides of SEQ ID NOS: 279, 302, 281, 304, 280, 283, 282, 303, 278, 284, 285, 286, 287, 288, 289, 290, 291, 292, 17, 30, 34, 14, 18 or 263 or a complement thereof; or, b) the nucleotide sequence comprising at least 90% sequence identity to any one of SEQ ID NOS: 279, 302, 281, 304, 280, 283, 282, 303, 278, 284, 285, 286, 287, 288, 289, 290, 291, 292, 14, 18, 263, 17, 30, 34, 337, 338, 339, 340, 341, 342, 343, 344, 305, 306, 307, 308, 309, 310, 311, 312, 293, 294, 295, 296, 297, 298, 299, 300, 301, 321, 322, 323, 324, 325, 326, 327 or 328 or a complement thereof, wherein said silencing element, when ingested by a *Pentatomidae* plant pest, reduces the level of a target sequence in said *Pentatomidae* plant pest and thereby controls the *Pentatomidae* plant pest.
27. The method of embodiment 26, wherein said *Pentatomidae* plant pest comprises a *N. viridula* plant pest.
28. The method of any one of embodiments 26 or 27, wherein said silencing element comprises the sequence set forth in any one of SEQ ID NOS: 284, 285, 286, 287, 288, 289, 290, 291, 292, 305, 306, 307, 308, 309, 310, 311, 312, 17, 30, 34, 337, 338, 339, 340, 341, 342, 343 or 344 or a complement thereof.
29. The method of any one of embodiments 25-28, wherein said composition comprises a plant or plant part having stably incorporated into its genome a polynucleotide comprising said silencing element, wherein said silencing element is operably linked to a seed-preferred promoter.
30. The method of any one of embodiments 25-29, wherein said silencing element comprises a) a polynucleotide comprising the sense or antisense sequence of the sequence set forth in SEQ ID NOS: 284, 285, 286, 287, 288, 289, 290, 291, 292, 17, 30, 34, 14, 18, 263, 337, 338, 339, 340, 341, 342, 343, 344, 305, 306, 307, 308, 309, 310, 311 or 312 or a complement thereof; or, b) a polynucleotide comprising the sense or antisense sequence of a sequence having at least 95% sequence identity to the sequence set forth in SEQ ID NOS: 284, 285, 286, 287, 288, 289, 290, 291, 292, 17, 30, 34, 14, 18, 263, 337, 338, 339, 340, 341, 342, 343, 344, 305, 306, 307, 308, 309, 310, 311 or 312 or a complement thereof;
31. The method of any one of embodiments 25-30, wherein said silencing element expresses a double stranded RNA.
32. The method of any one of embodiments 25-30, wherein said silencing element comprises a hairpin RNA.
33. The method of embodiment 32, wherein said polynucleotide comprising the silencing element comprises, in the following order, a first segment, a second segment, and a third segment, wherein a) said first segment comprises at least about 20 nucleotides having at least 90% sequence complementarity to the target polynucleotide;

b) said second segment comprises a loop of sufficient length to allow the silencing element to be transcribed as a hairpin RNA; and, c) said third segment comprises at least about 20 nucleotides having at least 85% complementarity to the first segment.
34. The method of any one of embodiments 29-30, wherein said silencing element is flanked by a first operably linked convergent promoter at one terminus of the silencing element and a second operably linked convergent promoter at the opposing terminus of the polynucleotide, wherein the first and the second convergent promoters are capable of driving expression of the silencing element.
35. The method of embodiment 29, wherein said plant is a monocot.
36. The method of embodiment 35, wherein said monocot is maize, barley, millet, wheat or rice.
37. The method of embodiment 29, wherein said plant is a dicot.
38. The method of embodiment 37, wherein said plant is soybean, canola, alfalfa, sunflower, safflower, tobacco, *Arabidopsis*, or cotton.

The following examples are offered by way of illustration and not by way of limitation.

EXPERIMENTAL

Example 1

In Vitro Transcription dsRNA Screening Method

A high throughput survey of candidate genes from the stinkbug *Nezara viridula* was performed for their potential utility as a target for RNAi leading to mortality (insecticidal activity of RNAi). A library of over 1000 expressed sequence tags was subjected to in vitro transcription and individual samples tested against 2nd instar nymphs of *N. viridula*. The insects were fed the sample in an insect assay format. After 6 days, the number of dead nymphs was recorded. Table 1 provides the blast homology (Gene ID) of the various silencing elements (clone name) disclosed herein and also provides bioassay data demonstrating the insecticidal activity of the various sequences when fed to *N. viridula*.

TABLE 1

| clone name | Gene ID | 6 day score #dead/10 |
|---|---|---|
| inv1c.pk008.f8.f | no hits | 10 |
| inv1c.pk003.n13.f | conserved hypothetical protein | 10 |
| inv1c.pk003.o24.f | conserved hypothetical protein | 7 |
| inv1c.pk004.a3.f | cathepsin L1 precursor | 9 |
| inv1c.pk004.a23.f | no hits | 9 |
| inv1c.pk004.b4.f | forked protein | 8 |
| inv1c.pk004.b6.f | ribosomal protein L24e | 9 |

TABLE 1-continued

| clone name | Gene ID | 6 day score #dead/10 |
|---|---|---|
| inv1c.pk004.b17.f | no hits | 8 |
| inv1c.pk004.b23.f | nonspecific lipid transfer protein/sterol carrier protein | 9 |
| inv1c.pk004.c11.f | soldier specific protein | 7 |
| inv1c.pk004.c12.f | no hits | 10 |
| inv1c.pk004.d4.f | no hits | 8 |
| inv1c.pk004.d16.f | oligomycin sensitivity conferral protein//ATP synthase | 10 |
| inv1c.pk004.d17.f | no hits | 10 |
| inv1c.pk004.d19.f | no hits | 7 |
| inv1c.pk004.d20.f | no hits | 9 |
| inv1c.pk004.e6.f | mitochondrial protein PTCD3 | 10 |
| inv1c.pk004.e11.f | adapter molecule Crk | 10 |
| inv1c.pk004.e24.f | cytochrome P450 | 10 |
| inv1c.pk004.f2.f | no hits | 8 |
| inv1c.pk004.f10.f | no hits | 7 |
| inv1c.pk004.f12.f | no hits | 8 |
| inv1c.pk004.f17.f | similar to dipteran sequences | 7 |
| inv1c.pk004.f24.f | no hits | 8 |
| inv1c.pk004.g13.f | no hits | 8 |
| inv1c.pk004.g20.f | vertebrate homology | 9 |
| inv1c.pk004.g22.f | no hits | 10 |
| inv1c.pk004.g23.f | no hits | 8 |
| inv1c.pk004.h18.f | salivary protein | 10 |
| inv1c.pk004.h20.f | lin-52 homolog | 8 |
| inv1c.pk004.h21.f | cyclin t | 10 |
| inv1c.pk004.h23.f | similar to complement component 1 q subcomponent binding protein-like protein | 9 |
| inv1c.pk004.h24.f | similar to prefoldin subunit | 10 |
| inv1c.pk004.i1.f | hsp70 | 10 |
| inv1c.pk004.i4.f | serine/threonine kinase | 9 |
| inv1c.pk004.i7.f | no hits | 9 |
| inv1c.pk004.i14.f | cytochrome P450 | 10 |
| inv1c.pk005.f6.f | U6 snRNA-associated Sm-like protein | 7 |
| inv1c.pk005.f8.f | NADH dehydrogenase subunit 2 | 10 |
| inv1c.pk005.f20.f | apolipprotein D | 7 |
| inv1c.pk005.h1.f | similar to Gag protein | 10 |
| inv1c.pk005.i21.f | no hits | 8 |
| inv1c.pk005.j11.f | no hits | 8 |
| inv1c.pk005.j17.f | *Homo sapiens* 3 BAC RP11-666A9 | 9 |
| inv1c.pk005.k12.f | no hits | 7 |
| inv1c.pk005.l13.f | no hits | 10 |
| inv1c.pk005.m5.f | no hits | 10 |
| inv1c.pk005.m16.f | similar to translation initiation factor 3, subunit S8 | 8 |
| inv1c.pk006.j24.f | no hits | 9 |
| inv1c.pk006.k4.f | no hits | 7 |
| inv1c.pk006.k18.f | acyl-CoA binding protein | 7 |
| inv1c.pk006.k20.f | E3 ubiquitin ligase/zinc finger protein | 9 |
| inv1c.pk006.k21.f | no hits | 8 |
| inv1c.pk006.l7.f | nervana 3/similar to sodium/potassium-dependent atpase beta-2 subunit | 7 |
| inv1c.pk006.m2.f | no hits | 10 |
| inv1c.pk006.m13.f | no hits | 10 |
| inv1c.pk006.o14.f | no hits | 10 |
| inv1c.pk006.p4.f | ubiquinol-cytochrome c reductase | 10 |
| inv1c.pk006.p8.f | complex 11 kDa protein similar to ATPase inhibitor-like protein | 10 |
| inv1c.pk006.p11.f | 40S ribosomal protein S7 | 9 |
| inv1c.pk006.p14.f | similar to *Drosophila* and pea aphid sequences | 10 |
| inv1c.pk007.a5.f | homology to insect sequences (*Nasonia, Tribolium, Drosophila* | 8 |
| inv1c.pk007.b6.f | no hits | 9 |
| inv1c.pk007.c6.f | no hits | 10 |
| inv1c.pk007.c9.f | conserved hypothetical protein | 10 |
| inv1c.pk007.d17.f | putative ferritin | 10 |
| inv1c.pk007.e5.f | fatty acyl-CoA elongase | 10 |
| inv1c.pk007.e21.f | aldehyde dehydrogenase | 9 |
| inv1c.pk007.f1.f | no hits | 10 |
| inv1c.pk007.f9.f | beta-tubulin | 10 |
| inv1c.pk007.f12.f | no hits | 10 |
| inv1c.pk007.f19.f | mitochondrial import receptor subunit tom40 [*Aedes aegypti*] | 10 |

TABLE 1-continued

| clone name | Gene ID | 6 day score #dead/10 |
|---|---|---|
| inv1c.pk007.f24.f | no hits | 9 |
| inv1c.pk007.g6.f | no hits | 10 |
| inv1c.pk007.g17.f | putative odorant-binding protein precursor | 10 |
| inv1c.pk007.h7.f | no hits | 7 |
| inv1c.pk007.h11.f | no hits | 8 |
| inv1c.pk007.h19.f | no hits | 7 |
| inv1c.pk007.i7.f | transposase | 10 |
| inv1c.pk007.i16.f | venom prophenoloxidase-activating protease | 10 |
| inv1c.pk007.j14.f | no hits | 10 |
| inv1c.pk007.j19.f | no hits | 10 |
| inv1c.pk007.j21.f | conserved hypothetical protein | 9 |
| inv1c.pk007.j23.f | succinate dehydrogenase, cytochrome B small subunit | 7 |
| inv1c.pk007.j24.f | no hits | 8 |
| inv1c.pk007.k17.f | conserved hypothetical protein | 9 |
| inv1c.pk007.l5.f | no hits | 9 |
| inv1c.pk007.l8.f | transmembrane protein, putative | 9 |
| inv1c.pk007.l11.f | no hits | 10 |
| inv1c.pk007.m6.f | conserved hypothetical protein | 10 |
| inv1c.pk007.m21.f | no hits | 9 |
| inv1c.pk007.o14.f | proteasome beta subunit | 7 |
| inv1c.pk007.p17.f | no hits | 7 |
| inv1c.pk008.c8.f | ribosomal protein L35Ae | 7 |
| inv1c.pk008.c15.f | similar to prohibitin | 8 |
| inv1c.pk008.c17.f | no hits | 7 |
| inv1c.pk008.d1.f | conserved hypothetical protein | 9 |
| inv1c.pk008.d3.f | conserved hypothetical protein | 7 |
| inv1c.pk008.e11.f | no hits | 10 |
| inv1c.pk008.e15.f | no hits | 10 |
| inv1c.pk008.f3.f | conserved hypothetical protein | 9 |
| inv1c.pk008.f5.f | no hits | 8 |
| inv1c.pk008.f8.f | no hits | 10 |
| inv1c.pk008.f23.f | no hits | 10 |
| inv1c.pk008.g7.f | no hits | 7 |
| inv1c.pk008.g22.f | no hits | 7 |
| inv1c.pk008.h23.f | putative ribosomal protein S26 | 10 |
| inv1c.pk008.h24.f | similar to mevalonate kinase | 10 |
| inv1c.pk008.i10.f | no hits | 9 |
| inv1c.pk008.i21.f | putative accessory gland protein | 9 |
| inv1c.pk008.j20.f | similar to eukaryotic translation initiation factor 3 subunit 2 beta | 8 |
| inv1c.pk008.k24.f | no hits | 7 |
| inv1c.pk008.l11.f | similar to phosphatase and actin regulator | 9 |
| inv1c.pk008.p18.f | no hits | 9 |
| inv1c.pk009.b14.f | no hits | 8 |
| inv1c.pk009.b21.f | ribosomal protein S20 | 7 |
| inv1c.pk009.e9.f | no hits | 9 |
| inv1c.pk009.e10.f | similar to sarco(endo)plasmic reticulum-type calcium ATPase | 7 |
| inv1c.pk009.e17.f | similar to serine/threonine protein kinase death domain protein, pelle-like | 9 |
| inv1c.pk009.f12.f | no hits | 10 |
| inv1c.pk009.f17.f | no hits | 7 |
| inv1c.pk009.f19.f | no hits | 9 |
| inv1c.pk009.g2.f | no hits | 8 |
| inv1c.pk009.g21.f | no hits | 8 |
| inv1c.pk009.h21.f | no hits | 10 |
| inv1c.pk009.i13.f | no hits | 10 |
| inv1c.pk009.i24.f | no hits | 7 |
| inv1c.pk009.k4.f | no hits | 8 |
| inv1c.pk009.k8.f | conserved hypothetical protein | 10 |
| inv1c.pk010.a13.f | no hits | 7 |
| inv1c.pk010.a16.f | arginyl-tRNA synthetase | 7 |
| inv1c.pk010.b7.f | similar to tar RNA binding protein | 10 |
| inv1c.pk010.e5.f | no hits | 7 |
| inv1c.pk010.n9.f | no hits | 7 |
| inv1c.pk010.n24.f | no hits | 10 |
| inv1c.pk010.p16.f | cytochrome c oxidase subunit II | 7 |
| inv1c.pk010.p20.f | no hits | 8 |
| inv1c.pk011.a20.f | no hits | 7 |
| inv1c.pk011.b11.f | no hits | 7 |

Sequences displaying insecticidal activity are advanced to confirmation and further evaluation of activity against other stinkbug pests. The assay is scored for activity 6 days post infestation. The possible scores are dead, severely stunted (little or now growth but alive), stunted (growth to second instar but not equivalent to controls), or no activity. Samples demonstrating mortality or severe stunting are advanced to confirmation.

Following confirmation, a simple dose response assay is performed with *N. viridula*. Samples for dose response assays is produced in the same manner with the following modification; samples is further purified using column purification prior to enzymatic treatment. Samples is also normalized to 0.5 ug/ul and all samples are evaluated by gel electrophoresis. Dose response assays is performed with the following rates; 50, 25, 12, 6, 3, and 1.5 ppm

Example 2

Sequences Having Insecticidal Activity

DNA sequences which encode double stranded RNAs which were shown to have insecticidal activity against *N. viridula* using the assay described in Example 1 are set forth in SEQ ID NOS: 1-139.

Example 3

Transformation of Maize

Immature maize embryos from greenhouse donor plants are bombarded with a plasmid containing the silencing element of the invention operably linked to either a tissue specific, tissue selective, or constitutive promoter and the selectable marker gene PAT (Wohlleben et al. (1988) *Gene* 70:25-37), which confers resistance to the herbicide Bialaphos. In one embodiment, the promoter employed is a seed-preferred promoter. In one embodiment, the constructs will express a long double stranded RNA or a miRNA of the target sequence set forth in SEQ ID NOS: 1-292 or 302-304 or a fragment thereof. In specific embodiments, the target sequence comprises the sequences set forth in SEQ ID NOS: 278, 279, 280, 281, 282, 283, 302, 303 or 304. Such a construct can be linked to a promoter active in maize. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

A plasmid vector comprising the silencing element of interest operably linked to either the tissue specific, tissue selective, or constitutive promoter is made. This plasmid DNA plus plasmid DNA containing a PAT selectable marker is precipitated onto 1.1 μm (average diameter) tungsten pellets using a $CaCl_2$ precipitation procedure as follows: 100 μl prepared tungsten particles in water; 10 μl (1 μg) DNA in Tris EDTA buffer (1 μg total DNA); 100 μl 2.5 M $CaCl_2$; and, 10 μl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macro carrier and allowed to dry about 2 minutes before bombardment.

The sample plates are bombarded at level #4 in a particle gun. All samples receive a single shot at 650 PSI, with a total of ten aliquots taken from each tube of prepared particles/DNA.

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity.

Plants are monitored and scored for the appropriate marker, such as the control of a *Pentatomidae* plant pest, such as a *N. viridula* plant pest. For example, $R_0$ maize plants are fed to *N. viridula* 2nd instar nymphs. Contamination and larval quality are monitored. Larval mass and survivorship are recorded for analysis. A one-way ANOVA analysis and a Dunnett's test is performed on the larval mass data to look for statistical significance compared to an untransformed negative control maize plant diet. *N. viridula* $2^{nd}$ instar nymph stunting is measured after feeding on two events and compared to growth of larvae fed on negative control plants.

In other assays, transgenic corn plants ($R_o$) generated are planted into 10-inch pots containing Metromix soil after reaching an appropriate size. After allowing the *N. viridula* $2^{nd}$ instar nymphs to feed on the plant, plants are removed from the soil and washed so that the relevant plant parts can be evaluated for larval feeding. Plant damage is rated using routine methods to score the level of damage.

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCl, 0.10 g/l pyridoxine HCl, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCl, 0.10 g/l pyridoxine HCl, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

Example 4

*Agrobacterium*-Mediated Transformation of Maize

For *Agrobacterium*-mediated transformation of maize with a silencing element of the invention, the method of Zhao is employed (U.S. Pat. No. 5,981,840, and PCT patent publication WO98/32326; the contents of which are hereby incorporated by reference). Such a construct can, for example, express a long double stranded RNA or a miRNA of the target sequence set forth in SEQ ID NOS: 1-292 or 302-304. In one embodiment, the promoter employed is a seed-preferred promoter. In specific embodiments, the target sequence comprises the sequence set forth in SEQ ID NOS: 278, 279, 280, 281, 282, 283, 302, 303 or 304. Such a construct can be linked to the dMMB promoter. Briefly, immature embryos are isolated from maize and the embryos contacted with a suspension of *Agrobacterium*, where the bacteria are capable of transferring the polynucleotide comprising the silencing element to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants. Assays for insecticidal activity can be performed as described above in Example 3.

Example 5

Soybean Embryo Transformation

Culture Conditions

Soybean embryogenic suspension cultures (cv. Jack) are maintained in 35 ml liquid medium SB196 (see recipes below) on rotary shaker, 150 rpm, 26° C. with cool white fluorescent lights on 16:8 hr day/night photoperiod at light intensity of 60-85 μE/m2/s. Cultures are subcultured every 7 days to two weeks by inoculating approximately 35 mg of tissue into 35 ml of fresh liquid SB196 (the preferred subculture interval is every 7 days).

Soybean embryogenic suspension cultures are transformed with a plasmid containing the silencing element of the invention operably linked to either a tissue specific, tissue selective, or constitutive promoter by the method of particle gun bombardment (Klein et al. (1987) *Nature,* 327:70). In one embodiment, the promoter employed is a seed-preferred promoter. In one embodiment, the constructs will express a long double stranded RNA or a miRNA of the target sequence set forth in SEQ ID NOS: 1-292 or 302-304 or a fragment thereof. In specific embodiments, the target sequence comprises the sequences set forth in SEQ ID NOS: 278, 279, 280, 281, 282, 283, 302, 303 or 304.

Soybean Embryogenic Suspension Culture Initiation

Soybean cultures are initiated twice each month with 5-7 days between each initiation.

Pods with immature seeds from available soybean plants 45-55 days after planting are picked, removed from their shells and placed into a sterilized magenta box. The soybean seeds are sterilized by shaking them for 15 minutes in a 5% Clorox solution with 1 drop of ivory soap (95 ml of autoclaved distilled water plus 5 ml Clorox and 1 drop of soap). Mix well. Seeds are rinsed using 2 1-liter bottles of sterile distilled water and those less than 4 mm are placed on individual microscope slides. The small end of the seed are cut and the cotyledons pressed out of the seed coat. Cotyledons are transferred to plates containing SB1 medium (25-30 cotyledons per plate). Plates are wrapped with fiber tape and stored for 8 weeks. After this time secondary embryos are cut and placed into SB 196 liquid media for 7 days.

Preparation of DNA for Bombardment

Either an intact plasmid or a DNA plasmid fragment containing the genes of interest and the selectable marker gene are used for bombardment. Plasmid DNA for bombardment are routinely prepared and purified using the method described in the Promega™ Protocols and Applications Guide, Second Edition (page 106). Fragments of the plasmids carrying the silencing element of interest are obtained by gel isolation of double digested plasmids. In each case, 100 ug of plasmid DNA is digested in 0.5 ml of the specific enzyme mix that is appropriate for the plasmid of interest. The resulting DNA fragments are separated by gel electrophoresis on 1% SeaPlaque GTG agarose (BioWhitaker Molecular Applications) and the DNA fragments containing silencing element of interest are cut from the agarose gel. DNA is purified from the agarose using the GELase digesting enzyme following the manufacturer's protocol.

A 50 μl aliquot of sterile distilled water containing 3 mg of gold particles (3 mg gold) is added to 5 μl of a 1 μg/μl DNA solution (either intact plasmid or DNA fragment prepared as described above), 50 μl 2.5M $CaCl_2$ and 20 μl of 0.1 M spermidine. The mixture is shaken 3 min on level 3 of a vortex shaker and spun for 10 sec in a bench microfuge. After a wash with 400 μl 100% ethanol the pellet is suspended by sonication in 40 μl of 100% ethanol. Five μl of DNA suspension is dispensed to each flying disk of the Biolistic PDS 1000/HE instrument disk. Each 5 μl aliquot contains approximately 0.375 mg gold per bombardment (i.e. per disk).

Tissue Preparation and Bombardment with DNA

Approximately 150-200 mg of 7 day old embryonic suspension cultures are placed in an empty, sterile 60×15 mm petri dish and the dish covered with plastic mesh. Tissue is bombarded 1 or 2 shots per plate with membrane rupture pressure set at 1100 PSI and the chamber evacuated to a vacuum of 27-28 inches of mercury. Tissue is placed approximately 3.5 inches from the retaining/stopping screen.

Selection of Transformed Embryos

Transformed embryos were selected either using hygromycin (when the hygromycin phosphotransferase, HPT, gene was used as the selectable marker) or chlorsulfuron (when the acetolactate synthase, ALS, gene was used as the selectable marker).

Hygromycin (HPT) Selection

Following bombardment, the tissue is placed into fresh SB196 media and cultured as described above. Six days post-bombardment, the SB196 is exchanged with fresh SB196 containing a selection agent of 30 mg/L hygromycin. The selection media is refreshed weekly. Four to six weeks post selection, green, transformed tissue may be observed growing from untransformed, necrotic embryogenic clusters. Isolated, green tissue is removed and inoculated into multiwell plates to generate new, clonally propagated, transformed embryogenic suspension cultures.

Chlorsulfuron (ALS) Selection

Following bombardment, the tissue is divided between 2 flasks with fresh SB196 media and cultured as described above. Six to seven days post-bombardment, the SB196 is exchanged with fresh SB196 containing selection agent of 100 ng/ml Chlorsulfuron. The selection media is refreshed weekly. Four to six weeks post selection, green, transformed tissue may be observed growing from untransformed, necrotic embryogenic clusters. Isolated, green tissue is removed and inoculated into multiwell plates containing SB196 to generate new, clonally propagated, transformed embryogenic suspension cultures.

Regeneration of Soybean Somatic Embryos into Plants

In order to obtain whole plants from embryogenic suspension cultures, the tissue must be regenerated.

Embryo Maturation

Embryos are cultured for 4-6 weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 uE/m2 s. After this time embryo clusters are removed to a solid agar media, SB166, for 1-2 weeks. Clusters are then subcultured to medium SB103 for 3 weeks. During this period, individual embryos can be removed from the clusters and screened for the appropriate marker or the ability of the plant, when injected with the silencing elements, to control the *Pentatomidae* plant pest or the *N. viridula* plant pest.

Embryo Desiccation and Germination

Matured individual embryos are desiccated by placing them into an empty, small petri dish (35×10 mm) for approximately 4-7 days. The plates are sealed with fiber tape (creating a small humidity chamber). Desiccated embryos are planted into SB71-4 medium where they were left to germinate under the same culture conditions described above. Germinated plantlets are removed from germination medium and rinsed thoroughly with water and then planted in Redi-Earth in 24-cell pack tray, covered with clear plastic dome. After 2 weeks the dome is removed and plants hardened off for a further week. If plantlets looked hardy they are transplanted to 10" pot of Redi-Earth with up to 3 plantlets per pot.

Media Recipes

| SB 196-FN Lite liquid proliferation medium (per liter) | |
|---|---|
| MS FeEDTA - 100x Stock 1 | 10 ml |
| MS Sulfate - 100x Stock 2 | 10 ml |
| FN Lite Halides - 100x Stock 3 | 10 ml |
| FN Lite P, B, Mo - 100x Stock 4 | 10 ml |
| B5 vitamins (1 ml/L) | 1.0 ml |
| 2,4-D (10 mg/L final concentration) | 1.0 ml |
| KNO3 | 2.83 gm |
| (NH4)2SO4 | 0.463 gm |
| Asparagine | 1.0 gm |
| Sucrose (1%) | 10 gm |
| pH 5.8 | |

FN Lite Stock Solutions

| Stock # | | 1000 ml | 500 ml |
|---|---|---|---|
| 1 | MS Fe EDTA 100x Stock | | |
| | $Na_2$ EDTA* | 3.724 g | 1.862 g |
| | $FeSO_4$—$7H_2O$ | 2.784 g | 1.392 g |
| 2 | MS Sulfate 100x stock | | |
| | $MgSO_4$—$7H_2O$ | 37.0 g | 18.5 g |
| | $MnSO_4$—$H_2O$ | 1.69 g | 0.845 g |
| | $ZnSO_4$—$7H_2O$ | 0.86 g | 0.43 g |
| | $CuSO_4$—$5H_2O$ | 0.0025 g | 0.00125 g |
| 3 | FN Lite Halides 100x Stock | | |
| | $CaCl_2$—$2H_2O$ | 30.0 g | 15.0 g |
| | KI | 0.083 g | 0.0715 g |
| | $CoCl_2$—$6H_2O$ | 0.0025 g | 0.00125 g |
| 4 | FN Lite P, B, Mo 100x Stock | | |
| | $KH_2PO_4$ | 18.5 g | 9.25 g |
| | $H_3BO_3$ | 0.62 g | 0.31 g |
| | $Na_2MoO_4$—$2H_2O$ | 0.025 g | 0.0125 g |

*Add first, dissolve in dark bottle while stirring

SB1 solid medium (per liter) comprises: 1 pkg. MS salts (Gibco/BRL—Cat#11117-066); 1 ml B5 vitamins 1000× stock; 31.5 g sucrose; 2 ml 2,4-D (20 mg/L final concentration); pH 5.7; and, 8 g TC agar.

SB 166 solid medium (per liter) comprises: 1 pkg. MS salts (Gibco/BRL—Cat#11117-066); 1 ml B5 vitamins 1000× stock; 60 g maltose; 750 mg MgCl2 hexahydrate; 5 g activated charcoal; pH 5.7; and, 2 g gelrite.

SB 103 solid medium (per liter) comprises: 1 pkg. MS salts (Gibco/BRL—Cat#11117-066); 1 ml B5 vitamins 1000× stock; 60 g maltose; 750 mg MgCl2 hexahydrate; pH 5.7; and, 2 g gelrite.

SB 71-4 solid medium (per liter) comprises: 1 bottle Gamborg's B5 salts w/ sucrose (Gibco/BRL—Cat#21153-036); pH 5.7; and, 5 g TC agar.

2,4-D stock is obtained premade from Phytotech cat# D 295—concentration is 1 mg/ml.

B5 Vitamins Stock (per 100 ml) which is stored in aliquots at −20 C comprises: 10 g myo-inositol; 100 mg nicotinic acid; 100 mg pyridoxine HCl; and, 1 g thiamine. If the solution does not dissolve quickly enough, apply a low level of heat via the hot stir plate. Chlorsulfuron Stock comprises 1 mg/ml in 0.01 N Ammonium Hydroxide

Example 6

Expression of Silencing Elements Comprising siRNAs

SiRNAs were generated to target the cDNA sequence set forth in SEQ ID NOS: 140, 143, 146, 149, 152, 155, 158, 161, 164, 167, 170, 173, 176, 179, 182, 185, 188, 191, 194, 197, 200, 203, 206, 209, 212, 215, 218, 221, 224, 227, 230, 233, 236, 239, 242, 245, 248, 251, 254, 257, 260, 263, 266, 269, 273, and 276. Table 2 provides the clone name of the silencing element and the closest homology for the target sequence (gene name). Table 3 provides the clone name, the target cDNA, the sense and antisense siRNA sequence, and the respective SEQ ID NOS. Table 4 provides the bioassays for each of the siRNAs shown in Table 3.

TABLE 2

| Query Sequence Title (ID) | gene name |
|---|---|
| inv1c.pk003.j16.f | conserved protein of unknown function |
| inv1c.pk003.j16.f | conserved protein of unknown function |
| inv1c.pk004.b7.f | cathepsin L |
| inv1c.pk004.b7.f | cathepsin L |
| inv1c.pk004.b7.f | cathepsin L |
| inv1c.pk004.b7.f | cathepsin L |
| inv1c.pk004.c4.f | mitochondrial porin |
| inv1c.pk004.c4.f | mitochondrial porin |
| inv1c.pk004.c4.f | mitochondrial porin |
| inv1c.pk004.c4.f | mitochondrial porin |
| inv1c.pk004.c4.f | mitochondrial porin |
| inv1c.pk004.c4.f | mitochondrial porin |
| inv1c.pk004.c4.f | mitochondrial porin |
| inv1c.pk004.c4.f | mitochondrial porin |
| inv1c.pk004.c4.f | mitochondrial porin |
| inv1c.pk004.c4.f | mitochondrial porin |
| inv1c.pk004.f4.f | reverse transcriptase |
| inv1c.pk004.f4.f | reverse transcriptase |

TABLE 2-continued

| Query Sequence Title (ID) | gene name |
|---|---|
| inv1c.pk004.f4.f | reverse transcriptase |
| inv1c.pk004.j14.f | sugar transporter |
| inv1c.pk004.k9.f | glutathione s transferase |
| inv1c.pk004.k9.f | glutathione s transferase |
| inv1c.pk004.k9.f | glutathione s transferase |
| inv1c.pk005.a24.f | cathepsin L-like protease |
| inv1c.pk005.a24.f | cathepsin L-like protease |
| inv1c.pk005.b16.f | synapsin |
| inv1c.pk005.b16.f | synapsin |
| inv1c.pk005.b16.f | synapsin |
| inv1c.pk005.b16.f | synapsin |
| inv1c.pk005.b16.f | synapsin |
| inv1c.pk005.f20.f | Apolipoprotein D precursor |
| inv1c.pk005.f20.f | Apolipoprotein D precursor |
| inv1c.pk005.f20.f | Apolipoprotein D precursor |
| inv1c.pk005.f20.f | Apolipoprotein D precursor |
| inv1c.pk005.h1.f | nucleic acid binding protein |
| inv1c.pk005.h1.f | nucleic acid binding protein |
| inv1c.pk005.h1.f | nucleic acid binding protein |
| inv1c.pk005.h1.f | nucleic acid binding protein |
| inv1c.pk005.h1.f | nucleic acid binding protein |
| inv1c.pk005.h1.f | nucleic acid binding protein |
| inv1c.pk005.h1.f | nucleic acid binding protein |
| inv1c.pk005.h23.f | chitin synthase 1 |
| inv1c.pk005.j19.f | conserved hypothetical protein |
| inv1c.pk005.j19.f | conserved hypothetical protein |
| inv1c.pk005.k24.f | cathepsin B |
| inv1c.pk005.k24.f | cathepsin B |

TABLE 3

(Note: the sense RNA primer sequence and the antisense RNA primer sequences shown in table 3 were generated having 2 thymine residues at the 3' end.)

| siRNA number | Query Sequence Title (ID) | No. Bases | Target Location | Approx. Target Location (thirds) | Target cDNA Sequence |
|---|---|---|---|---|---|
| 1 | inv1c.pk003.j16.f | 656 | 227 | 2 | AATCAAGGTGTGGA CTGAAAATT |
| 2 | inv1c.pk003.j16.f | 656 | 490 | 3 | AATTGGTTGCTACAT ATTCTCTT |
| 3 | inv1c.pk004.b7.f | 603 | 150 | 1 | AAGAACGTCTTAGG ATGCATATT |
| 4 | inv1c.pk004.b7.f | 603 | 317 | 2 | AAGCAAGCACCTAC CTTCACATT |
| 5 | inv1c.pk004.b7.f | 603 | 412 | 3 | AAACCAAGGTAGCT GTGGATCTT |
| 6 | inv1c.pk004.b7.f | 603 | 545 | 3 | AATAATGGATGTGG TGGCGGATT |
| 7 | inv1c.pk004.c4.f | 688 | 133 | 1 | AAAAGGATACCACT TTGGACTTT |
| 8 | inv1c.pk004.c4.f | 688 | 134 | 1 | AAAGGATACCACTT TGGACTTTT |
| 9 | inv1c.pk004.c4.f | 688 | 171 | 1 | AAACCAAGACCCAG ACTGGAGTT |
| 10 | inv1c.pk004.c4.f | 688 | 176 | 1 | AAGACCCAGACTGG AGTTGAATT |
| 11 | inv1c.pk004.c4.f | 688 | 218 | 1 | AACCAAGAAACTGG GAAAGTGTT |
| 12 | inv1c.pk004.c4.f | 688 | 226 | 1 | AACTGGGAAAGTGT TCGGAAATT |

TABLE 3-continued (Note: the sense RNA primer sequence and the antisense RNA primer sequences shown in table 3 were generated having 2 thymine residues at the 3' end.)

| | | | | | |
|---|---|---|---|---|---|
| 13 | inv1c.pk004.c4.f | 688 | 322 | 2 | AACTGAAATTGCCCT CACTGATT |
| 14 | inv1c.pk004.c4.f | 688 | 359 | 2 | AAGCTTTCTTGTGAT ACCTCATT |
| 15 | inv1c.pk004.c4.f | 688 | 431 | 2 | AATGATACGTGTGCT TTGAACTT |
| 16 | inv1c.pk004.c4.f | 688 | 619 | 3 | AAGCATTAATGATG GACGTGTTT |
| 17 | inv1c.pk004.f4.f | 696 | 368 | 2 | AAAACTTTCTCAAA GAACCAGTT |
| 18 | inv1c.pk004.f4.f | 696 | 379 | 2 | AAAGAACCAGTTCC AAATGCATT |
| 19 | inv1c.pk004.f4.f | 696 | 394 | 2 | AATGCATTCCCTTCA ATCTCATT |
| 20 | inv1c.pk004.j14.f | 687 | 533 | 3 | AACCTCTCCTCGTCT GGAGTCTT |
| 21 | inv1c.pk004.k9.f | 663 | 212 | 1 | AAAGAATTCACCTG GTCCTACTT |
| 22 | inv1c.pk004.k9.f | 663 | 531 | 3 | AATTCTGGAAGAAA TGGACCATT |
| 23 | inv1c.pk004.k9.f | 663 | 641 | 3 | AACGTCTAGAAATG GTGAGAGTT |
| 24 | inv1c.pk005.a24.f | 443 | 198 | 2 | AATAAGAAACACGA AGCAGGCTT |
| 25 | inv1c.pk005.a24.f | 443 | 271 | 2 | AAATGAAGAGCCAT TTAGGCTTT |
| 26 | inv1c.pk005.b16.f | 680 | 17 | 1 | AACTTCGAACCATCT CCCCGGTT |
| 27 | inv1c.pk005.b16.f | 680 | 119 | 1 | AAGCTTCCTTCACTA CAAATGTT |
| 28 | /inv1c.pk005.b16.f | 680 | 156 | 1 | AAGGTTCAGCTCCG GGGATCTTT |
| 29 | inv1c.pk005.b16.f | 680 | 540 | 3 | AATCGACGACCAAA ATACTGATT |
| 30 | inv1c.pk005.b16.f | 680 | 569 | 3 | AATACTTCAGAGTA CGGCGTATT |
| 31 | inv1c.pk005.f20.f | 662 | 46 | 1 | AAAATGAGAGCTAC GTACTGCTT |
| 32 | inv1c.pk005.f20.f | 662 | 316 | 2 | AAATACCATTACAC AGGACATTT |
| 33 | inv1c.pk005.f20.f | 662 | 387 | 2 | AAGTGTTGCTGG CATCAAGTT |
| 34 | inv1c.pk005.f20.f | 662 | 605 | 3 | AATGCCCAGCAGAA ACCAACCTT |
| 35 | inv1c.pk005.h1.f | 628 | 143 | 1 | AAATACCACAGCCA GCAATAATT |
| 36 | inv1c.pk005.h1.f | 628 | 144 | 1 | AATACCACAGCCAG CAATAATTT |
| 37 | inv1c.pk005.h1.f | 628 | 192 | 1 | AAGCCTCCGGTACCT CAAGGTTT |

TABLE 3-continued (Note: the sense RNA primer sequence and the antisense RNA primer sequences shown in table 3 were generated having 2 thymine residues at the 3' end.)

| | | | | | |
|---|---|---|---|---|---|
| 38 | inv1c.pk005.h1.f | 628 | 28 | 2 | AATCTTATCGGACA AACCAGTTT |
| 39 | inv1c.pk005.h1.f | 628 | 556 | 3 | AAAAATATCCATTG CCACTGTTT |
| 40 | inv1c.pk005.h1.f | 628 | 557 | 3 | AAAATATCCATTGCC ACTGTTTT |
| 41 | inv1c.pk005.h1.f | 628 | 558 | 3 | AAATATCCATTGCCA CTGTTTTT |
| 42 | inv1c.pk005.h23.f | 647 | 301 | 2 | AAGGATGGGATGTG TTCCGAGTT |
| 43 | inv1c.pk005.j19.f | 597 | 172 | 1 | AAGATGGGGGGATG ATGTACGTT |
| 44 | inv1c.pk005.j19.f | 597 | 377 | 2 | AAGAACATCCACAG GAGAACCTT |
| 45 | inv1c.pk005.k24.f | 593 | 27 | 1 | AAGACTCTATTAATA TCCAGCTT |
| 46 | inv1c.pk005.k24.f | 593 | 132 | 1 | AAATGGAAAGCTGG GCAGAACTT |

| siRNA number | % CG | Sense Strand siRNA | Antisense siRNA Sequence | SEQ ID NOS Target cDNA/sense siRNA/antisense siRNA |
|---|---|---|---|---|
| 1 | 34.8 | UCAAGGUGUG GACUGAAAA | UUUUCAGUCCA CACCUUGA | 140/141/142 |
| 2 | 30.4 | UUGGUUGCUA CAUAUUCUC | GAGAAUAUGUA GCAACCAA | 143/144/145 |
| 3 | 34.8 | GAACGUCUUA GGAUGCAUA | UAUGCAUCCUA AGACGUUC | 146/147/148 |
| 4 | 43.5 | GCAAGCACCU ACCUUCACA | UGUGAAGGUAG GUGCUUGC | 149/150/151 |
| 5 | 43.5 | ACCAAGGUAG CUGUGGAUC | GAUCCACAGCU ACCUUGGU | 152/153/154 |
| 6 | 43.5 | UAAUGGAUGU GGUGGCGGA | UCCGCCACCACA UCCAUUA | 155/156/157 |
| 7 | 34.8 | AAGGATTACCA CUUUGGACU | AGUCCAAAGUG GUAUCCUU | 158/159/160 |
| 8 | 34.8 | AGGAUACCAC UUUGGACUU | AAGUCCAAAGU GGUAUCCU | 161/162/163 |
| 9 | 47.8 | ACCAAGACCC AGACUGGAG | CUCCAGUCUGG GUCUUGGU | 164/165/166 |
| 10 | 43.5 | GACCCAGACU GGAGUUGAA | UUCAACUCCAG UCUGGGUC | 167/168/169 |
| 11 | 39.1 | CCAAGAAACU GGGAAAGUG | CACUUUCCCAG UUUCUUGG | 170/171/172 |
| 12 | 39.1 | CUGGGAAAGU GUUCGGAAA | UUUCCGAACAC UUUCCCAG | 173/174/175 |
| 13 | 39.1 | CUGAAAUUGC CCUCACUGA | UCAGUGAGGGC AAUUUCAG | 176/177/178 |
| 14 | 34.8 | GCUUUCUUGU GAUACCUCA | UGAGGUAUCAC AAGAAAGC | 179/180/181 |
| 15 | 34.8 | UGAUACGUGU GCUUUGAAC | GUUCAAAGCAC ACGUAUCA | 182/183/184 |

TABLE 3-continued (Note: the sense RNA primer sequence and the antisense RNA primer sequences shown in table 3 were generated having 2 thymine residues at the 3' end.)

| | | | | |
|---|---|---|---|---|
| 16 | 34.8 | GCAUUAAUGA UGGACGUGU | ACACGUCCAUC AUUAAUGC | 185/186/187 |
| 17 | 30.4 | AACUUUCUCA AAGAACCAG | CUGGUUCUUUG AGAAAGUU | 188/189/190 |
| 18 | 34.8 | AGAACCAGUU CCAAAUGCA | UGCAUUUGGAA CUGGUUCU | 191/192/193 |
| 19 | 34.8 | UGCAUUCCCU UCAAUCUCA | UGAGAUUGAAG GGAAUGCA | 194/195/196 |
| 20 | 52.2 | CCUCUCCUCG UCUGGAGUC | GACUCCAGACG AGGAGAGG | 197/198/199 |
| 21 | 39.1 | AGAAUUCACC UGGUCCUAC | GUAGGACCAGG UGAAUUCU | 200/201/202 |
| 22 | 34.8 | UUCUGGAAGA AAUGGACCA | UGGUCCAUUUC UUCCAGAA | 203/204/205 |
| 23 | 39.1 | CGUCUAGAAA UGGUGAGAG | CUCUCACCAUU UCUAGACG | 206/207/208 |
| 24 | 39.1 | UAAGAAACAC GAAGCAGGC | GCCUGCUUCGU GUUUCUUA | 209/210/211 |
| 25 | 34.8 | AUGAAGAGCC AUUUAGGCU | AGCCUAAAUGG CUCUUCAU | 212/213/214 |
| 26 | 52.2 | CUUCGAACCA UCUCCCCGG | CCGGGGAGAUG GUUCGAAG | 215/216/217 |
| 27 | 34.8 | GCUUCCUUCA CUACAAAUG | CAUUUGUAGUG AAGGAAGC | 218/219/220 |
| 28 | 52.2 | GGUUCAGCUC CGGGGAUCU | AGAUCCCCGGA GCUGAACC | 221/222/223 |
| 29 | 34.8 | UCGACGACCA AAAUACUGA | UCAGUAUUUUG GUCGUCGA | 224/225/226 |
| 30 | 39.1 | UACUUCAGAG UACGGCGUA | UACGCCGUACU CUGAAGUA | 227/228/229 |
| 31 | 39.1 | AAUGAGAGCU ACGUACUGC | GCAGUACGUAG CUCUCAUU | 230/231/232 |
| 32 | 30.4 | AUACCAUUAC ACAGGACAU | AUGUCCUGUGU AAUGGUAU | 233/234/235 |
| 33 | 39.1 | GUGUUGCUGG AACAUCAAG | CUUGAUGUUCC AGCAACAC | 236/237/238 |
| 34 | 47.8 | UGCCCAGCAG AAACCAACC | GGUUGGUUUCU GCUGGGCA | 239/240/241 |
| 35 | 34.8 | AUACCACAGC CAGCAAUAA | UUAUUGCUGGC UGUGGUAU | 242/243/244 |
| 36 | 34.8 | UACCACAGCC AGCAAUAAU | AUUAUUGCUGG CUGUGGUA | 245/246/247 |
| 37 | 52.2 | GCCUCCGGUA CCUCAAGGU | ACCUUGAGGUA CCGGAGGC | 248/249/250 |
| 38 | 34.8 | UCUUAUCGGA CAAACCAGU | ACUGGUUUGUC CGAUAAGA | 251/252/253 |
| 39 | 30.4 | AAAUAUCCAU UGCCACUGU | ACAGUGGCAAU GGAUAUUU | 254/255/256 |
| 40 | 30.4 | AAUAUCCAUU GCCACUGUU | AACAGUGGCAA UGGAUAUU | 257/258/259 |

TABLE 3-continued (Note: the sense RNA primer sequence and the antisense RNA primer sequences shown in table 3 were generated having 2 thymine residues at the 3' end.)

| | | | | |
|---|---|---|---|---|
| 41 | 30.4 | AUAUCCAUUG CCACUGUUU | AAACAGUGGCA AUGGAUAU | 260/261/262 |
| 42 | 47.8 | GGAUGGGAUG UGUUCCGAG | CUCGGAACACA UCCCAUCC | 263/264/265 |
| 43 | 47.8 | GAUGGGGGGA UGAUGUACG | CGUACAUCAUC CCCCCAUC | 266/267/268 |
| 44 | 43.5 | GAACAUCCAC AGGAGAACC | GGUUCUCCUGU GGAUGUUC | 269/270/271 |
| 45 | 30.4 | GACUCUAUUA AUAUCCAGC | GCUGGAUAUUA AUAGAGUC | 272/273/274 |
| 46 | 43.5 | AUGGAAAGCU GGGCAGAAC | GUUCUGCCCAG CUUUCCAU | 275/276/277 |

TABLE 4

| siRNA number | Query Sequence Title (ID) | Bioassay-1 100 ppm (4 day score) | Bioassay-1 100 ppm (5 day score) | Bioassay-2 100 ppm (5 day score) | Comment | Bioassay-3 100 ppm (5 day score) | Bioassay-4 25 ppm 5 day | Bioassay-5 25 ppm | Bioassay-6 50 ppm |
|---|---|---|---|---|---|---|---|---|---|
| 1 | inv1c.pk003.j16.f | 3/9 | | 10/10 | | 8/10 | ND | | |
| 2 | inv1c.pk003.j16.f | 4/11 | | 10/10 | | 1/10 | ND | | |
| 3 | inv1c.pk004.b7.f | 11/12 | | 10/10 | | ND | ND | | |
| 4 | inv1c.pk004.b7.f | 7/11 | | 10/10 | | | 0/10 | | |
| 5 | inv1c.pk004.b7.f | 6/9 | | 9/10 | | | 0/10 | | |
| 6 | inv1c.pk004.b7.f | 5/11 | | 3/10 | | | | | |
| 7 | inv1c.pk004.c4.f | 3/9 | | 1/10 | | | | | |
| 8 | inv1c.pk004.c4.f | 3/10 | | 0/10 | | | | | |
| 9 | inv1c.pk004.c4.f | 4/10 | | 4/10 (5 stunted) | | | 0/10 | | |
| 10 | inv1c.pk004.c4.f | 3/10 | | 5/10 (3 stunted) | | | 1/10 | | |
| 11 | inv1c.pk004.c4.f | 4/10 | | 2/10 | | | | | |
| 12 | inv1c.pk004.c4.f | 5/9 | | 0/10 | | | | | |
| 13 | inv1c.pk004.c4.f | 7/10 | | 1/10 | | | | | |
| 14 | inv1c.pk004.c4.f | 4/10 | | 2/10 | | | | | |
| 15 | inv1c.pk004.c4.f | 5/9 | | 1/10 | | | | | |
| 16 | inv1c.pk004.c4.f | 6/10 | | 0/10 | | | | | |
| 17 | inv1c.pk004.f4.f | 5/10 | | 3/10 (2 stunted) | | | | | |
| 18 | inv1c.pk004.f4.f | 2/11 | | 3/10 (2 stunted) | | | | | |
| 19 | inv1c.pk004.f4.f | 6/9 | | 0/10 | | | | | |
| 20 | inv1c.pk004.j14.f | 6/10 | | 0/10 | | | | | |
| 21 | inv1c.pk004.k9.f | | 10/10 | | | 0/10 | | | |
| 22 | inv1c.pk004.k9.f | | 6/11 | | | 1/10 | | | |
| 23 | inv1c.pk004.k9.f | | 3/10 | | | 2/10 | | | |
| 24 | inv1c.pk005.a24.f | | 10/10 | 0/10 | | | | | |
| 25 | inv1c.pk005.a24.f | | | 0/10 | | | | | |
| 26 | inv1c.pk005.b16.f | | | 0/10 | Significant growth in survivors | | | | |
| 27 | inv1c.pk005.b16.f | | | 5/10 | Significant growth in survivors | | | | |
| 28 | inv1c.pk005.b16.f | | | 5/10 | Significant growth in survivors | | | | |
| 29 | inv1c.pk005.b16.f | | | 4/10 | Significant growth in survivors | | | | |
| 30 | inv1c.pk005.b16.f | | | 0/10 | | | | | |
| 31 | inv1c.pk005.f20.f | | | 9/10 | No growth | | 1/10 | | |
| 32 | inv1c.pk005.f20.f | | | 10/10 | Some growth before death | | 1/10 | | |
| 33 | inv1c.pk005.f20.f | | | 10/10 | Growth before death | | 2/10 (survivors stunted) | 4/10 | 8/10 |
| 34 | inv1c.pk005.f20.f | | | 4/10 | Growth before death | | | | |
| 35 | inv1c.pk005.h1.f | | | 7/10 | Growth before death | | 1/10 (some stunting) | | |
| 36 | inv1c.pk005.h1.f | | | 10/10 | some growth before death | | 1/10 | | |
| 37 | inv1c.pk005.h1.f | | | 10/10 | Growth before death | | 0/10 | | |
| 38 | inv1c.pk005.h1.f | | | 10/10 | no growth | | 1/10 | | |

TABLE 4-continued

| siRNA number | Query Sequence Title (ID) | Bioassay-1 100 ppm (4 day score) | Bioassay-1 100 ppm (5 day score) | Bioassay-2 100 ppm (5 day score) | Comment | Bioassay-3 100 ppm (5 day score) | Bioassay-4 25 ppm 5 day | Bioassay-5 25 ppm | Bioassay-6 50 ppm |
|---|---|---|---|---|---|---|---|---|---|
| 39 | inv1c.pk005.h1.f | | | 1/10 | | | | | |
| 40 | inv1c.pk005.h1.f | | | 8/10 | little growth | | 0/10 | | |
| 41 | inv1c.pk005.h1.f | | | 6/10 | some growth | | | | |
| 42 | inv1c.pk005.h23.f | | | 7/10 | No growth | | 0/10 | | |
| 43 | inv1c.pk005.j19.f | | | 10/10 | No growth | | 2/10 | | |
| 44 | inv1c.pk005.j19.f | | | | | | 1/10 | | |
| 45 | inv1c.pk005.k24.f | | | | | | 0/10 | | |
| 46 | inv1c.pk005.k24.f | | | | | | 0/10 | 5/10 | |

Example 7

Constructs Expressing siRNAs siRNAs designed to target the cDNA sequence set forth in SEQ ID NOS: 140, 143, 146, 149, 152, 155, 158, 161, 164, 167, 170, 173, 176, 179, 182, 185, 188, 191, 194, 197, 200, 203, 206, 209, 212, 215, 218, 221, 224, 227, 230, 233, 236, 239, 242, 245, 248, 251, 254, 257, 260, 263, 266, 269, 272, and 275 can be engineered to be expressed in planta. The construct can comprise, for example, the maize ubiquitin promoter/5'UTR/1$^{st}$ intron operably linked to a sequence comprising SEQ ID NO: 141 which is operably linked to the ADH1 intron followed by the sequence comprising SEQ ID NO: 142. It is recognized that any of the siRNA described in Example 6 can be generated employing a similar construct design.

Example 8

Generation of Silencing Constructs for In Vivo Testing Experiments

The activity of 9 dsRNAs listed in Table 1, was confirmed on repeated testing and the target genes advanced for further evaluation in in planta assays. For this purpose, 2 different types of constructs were assembled. In one, 2 SGSB target gene fragments, separated by a spiceosomal intron, were assembled in opposite orientations with respect to each other to produce a hairpin RNA. In planta produced hairpin RNAs are expected to be processed to yield siRNAs which upon uptake into insects, mediate RNAi inhibition of SGSB target gene expression. In the second, small 21-mer SGSB gene sequences are incorporated into a micro RNA backbone to produce an artificial pre-miRNA. Processing of the pre-miRNA in vivo releases the 21-nt miRNA that targets the SGSB gene for silencing. Hairpin constructs for in vivo expression and testing of dsRNAs were assembled via Gateway technology using procedures and practices well known to those skilled in the art of molecular biology. Target gene fragments were generated by PCR using gene specific sense and antisense primers containing Gateway attB4 (CAACTTTGTATAGAAAAGTTG (SEQ ID NO: 345)) and attB3 (CAACTTTGTATAATAAAGTTG (SEQ ID NO: 346)) sequences, respectively. The amplified DNA fragments were recombined into the pDONR vector, PHP36164 containing attP4-attP3 sites in a reaction catalyzed by BP Clonase. The resultant entry clones containing target gene fragments flanked by attL 4 and attL3 sites were then used to generate an expression construct by performing 2 sequential LR recombination reactions, first with the vector pKB499 and then with the vector PHP25224. The former destination vector contains the 193 bp intron2 fragment of the potato LS 1 gene flanked by attR4-R3 sites at the 5' end and attR3-R4 sites at the 3' end. LR recombination yields a hairpin segment comprised of sense and antisense target gene fragments separated by an intron loop. In planta expression is regulated by placement of the appropriate regulatory elements, promoter sequences upstream and termination sequences downstream, of the hairpin segment. In this particular example, promoter sequences are provided by a 1946 bp soybean ubiquitin promoter-5' UTR-Intron1 fragment and termination sequences are provided by an 888 bp 3' fragment of the *Arabidopsis* ubiquitin10 gene. Other promoter sequences providing constitutive or appropriate tissue specific expression may additionally be used. The final plant expression construct is produced by a second LR reaction in which the entire hairpin cassette is moved into a vector (PHP25224) which provides a plant selectable marker (herbicide resistant acetolactate synthase gene) for stable transformation experiments. In Table 5, the 9 entries correspond to hairpin constructs that were assembled and tested in soybean embryos for efficacy against Southern Green Stinkbug (SGSB).

TABLE 5

Hairpin constructs for SGSB target gene silencing

| Gene ID | SEQ length (bp) | SEQ ID NO | Fragment Location | Fragment SEQ ID NO | Construct | Construct SEQ ID NO (without promoter) |
|---|---|---|---|---|---|---|
| inv1c.pk004.e6.f:fis | 1054 | 278 | 2-537 | 284 | PHP49713 | 293 |
| inv1c.pk004.h20.f:fis | 861 | 279 | 72-677 | 285 | PHP48181 | 294 |
| inv1c.pk004.h20.f:fis | 861 | 279 | 72-834 | 286 | pKB505 | 295 |
| inv1c.pk004.h20.f:fis | 861 | 279 | 72-439 | 287 | pKB506 | 296 |
| inv1c.pk004.i1.f:fis | 992 | 280 | 27-511 | 288 | PHP48183 | 297 |
| inv1c.pk004.i1.f:fis | 992 | 280 | 488-938 | 289 | pKB508 | 298 |
| inv1c.pk008.m9.f:fis | 858 | 281 | 2-800 | 290 | PHP49450 | 299 |
| inv1c.pk011.f6.f:fis | 792 | 282 | 19-594 | 291 | PHP49451 | 300 |
| inv1c.pk010.g13.f:fis | 643 | 283 | 4-785 | 292 | PHP49480 | 301 |

Silencing constructs encoding artificial microRNAs (amiRNAs) that would have the ability to silence Southern Green Stinkbug genes were designed largely according to rules described in Schwab R, et al. (2005) *Dev Cell* 8: 517-27. To summarize, microRNA sequences are 21 nucleotides in length, start at their 5'-end with a "U", display 5' instability relative to their star sequence which is achieved by including a C or G at position 19, and their 10th nucleotide is either an "A" or an "U". An additional requirement for artificial microRNA design was that the amiRNA have a high free delta-G as calculated using the ZipFold algorithm (Markham, N. R. & Zuker, M. (2005) *Nucleic Acids Res.* 33: W577-W581.) Optionally, a one base pair change was added to the 5' portion of the amiRNA so that the sequence differed from the target sequence by one nucleotide. The amiRNAs that were used to silence SGSB genes are given in Table 6.

TABLE 6

| amiRNA Sequences | | | | |
|---|---|---|---|---|
| amiRNA precursor | GENE ID | Target SEQ ID NO | amiRNA Sequence | amiRNA SEQ ID NO |
| Nv-MCS Frg1 | inv1c.pk005.h23.f | 302 | taagtaccatgtccaacgcca | 305 |
| Nv-MCS Frg2 | inv1c.pk005.h23.f | 302 | tattacaataactgaccaccc | 306 |
| Nv-MMitpro2 | inv1c.pk004.e6.f:fis | 278 | tcctactacatatttccaccc | 307 |
| Nv-MitprotCD3 | inv1c.pk004.e6.f:fis | 278 | tattccttctatcttctccca | 308 |
| Nv-Madapmol2 | inv1c.pk004.e11.f:fis | 303 | taaagtatattaataattctt | 309 |
| Nv-MadadapCRK1 | inv1c.pk004.e11.f:fis | 303 | ttactatcttcccttacacaa | 310 |
| Nv-MNH1A | inv1c.pk004.d17.f:fis | 304 | tacgaagagataacacaagat | 311 |
| Nv-MNH1B | inv1c.pk004.d17.f:fis | 304 | taacaaaacaaaaaaaaactg | 312 |

"Star sequences" are those that base pair with the amiRNA sequences in the precursor RNA, to form imperfect stem structures. To form a perfect stem structure the star sequence would be the exact reverse complement of the amiRNA. The soybean precursor sequence miR159 as described in Zhang, B. at al. (2008) Planta 229:161-182 was folded with MFold (M. Zuker (2003) *Nucleic Acids Res.* 31: 3406-15; and D. H. Mathews, J. et al. (1999) *J. Mol. Biol.* 288: 911-940). The miRNA sequence was then replaced with the amiRNA sequence and the endogenous star sequence was replaced with the exact reverse complement of the amiRNA. Changes in the artificial star sequence were introduced so that the structure of the stem would remain the same as the endogenous structure. The altered sequence was then folded with mfold and the original and altered structures were compared by eye. If necessary, further alternations to the artificial star sequence were introduced to maintain the original structure. The DNA sequences corresponding to the artificial star sequences that were used to silence the desired target genes are shown in Table 7.

TABLE 7

| amiRNA Star Sequences | | | |
|---|---|---|---|
| amiRNA precursor | GENE ID | amiRNA Sequence | SEQ ID NO |
| Nv-MCS Frg1-Star | inv1c.pk005.h23.f | tggcgttggactaggtacttt | 313 |
| Nv-MCS Frg2-Star | inv1c.pk005.h23.f | gggtggtcagtatttgtaatt | 314 |
| Nv-MMitpro2-Star | inv1c.pk004.e6.f:fis | gggtggaaataattagtaggt | 315 |
| Nv-MitprotCD3-Star | inv1c.pk004.e6.f:fis | tgggagaagatcaaaggaatt | 316 |
| Nv-Madapmol2-Star | inv1c.pk004.e11.f:fis | aagaattattataatactttt | 317 |
| Nv-MadadapCRK1-Star | inv1c.pk004.e11.f:fis | ttgtgtaagggttgatagtat | 318 |
| Nv-MNH1A-Star | inv1c.pk004.d17.f:fis | atcttgtgttaaatcttcgtt | 319 |
| Nv-MNH1B-Star | inv1c.pk004.d17.f:fis | cagtttttttttgcttttgttt | 320 |

The soybean genomic miRNA precursor gene, miR159, was converted to amiRNA precursors by DNA synthesis (Genscript; Piscataway, N.J.). DNA fragments were synthesized with flanking AvrII and HpaI sites and were cloned by restriction enzyme digestion followed by DNA ligation downstream of the GmUbiquitin promoter-5'UTR-Intron1 fragment in the UBQ-Kozack OXOXalt7 vector. LR recombination reaction between this intermediate and the vector QC479i produced the eight final plant expression constructs given in Table 8.

TABLE 8 amiRNA Precursors and Expression Constructs

| GENE ID | amiRNA precursor length | amiRNA precursor SEQ ID NO | Target Sequence | Target Sequence SEQ ID NO | Expression Construct | Construct SEQ ID NO (with promoter) |
|---|---|---|---|---|---|---|
| inv1c.pk005.h23.f | 976 bp | 321 | tggcgttggacatggtactta | 337 | PHP44230 | 329 |
| inv1c.pk005.h23.f | 977 bp | 322 | gggtggtcagttattgtaata | 338 | PHP44231 | 330 |
| inv1c.pk004.e6.f:fis | 966 bp | 323 | gggtggaaatatgtagtagga | 339 | PHP44770 | 331 |
| inv1c.pk004.e6.f:fis | 966 bp | 324 | tgggagaagatagaaggaata | 340 | PHP44771 | 332 |
| inv1c.pk004.e11.f:fis | 966 bp | 325 | aagaattattaatatacttta | 341 | PHP44772 | 333 |
| inv1c.pk004.e11.f:fis | 966 bp | 326 | ttgtgtaagggaagatagtaa | 342 | PHP44773 | 334 |
| inv1c.pk004.d17.f:fis | 966 bp | 327 | atcttgtgttatctcttcgta | 343 | PHP44789 | 335 |
| inv1c.pk004.d17.f:fis | 966 bp | 328 | cagtttttttttgttttgtta | 344 | PHP44790 | 336 |

The SEQ ID NOS for the various target genes advanced for further evaluation in in planta assays are summarized in Table 9.

TABLE 9

| Clone | Target SEQ ID NO | Fragments of Target Sequences SEQ ID NO | Silencing Constructs for Target Sequence SEQ ID NO | Sequences Encoding Silencing Elements for Target Sequence SEQ ID NO |
|---|---|---|---|---|
| inv1c.pk004.d17.f:fis | 304 | 14, 343, 344 | 335 (amiRNA precursor sequence with promoter)<br>336 (amiRNA precursor sequence with promoter) | 311 (miRNA)<br>312 (miRNA)<br>327 (miRNA precursor sequence)<br>328 (miRNA precursor sequence) |
| inv1c.pk004.e6.f:fis | 278 | 17, 284, 339, 340 | 293 (hairpin RNA construct without promoter)<br>331(amiRNA precursor sequence with promoter)<br>332 (amiRNA precursor sequence with promoter) | 284 (hairpin RNA)<br>307 (miRNA)<br>308 (miRNA)<br>323 (miRNA precursor sequence)<br>324 (miRNA precursor sequence) |
| inv1c.pk004.e11.f:fis | 303 | 18, 341, 342 | 333 (amiRNA precursor sequence with promoter)<br>334 (amiRNA precursor sequence with promoter) | 309 (miRNA)<br>310 (miRNA)<br>325 (miRNA precursor sequence)<br>326 (miRNA precursor sequence) |
| inv1c.pk004.h20.f:fis | 279 | 30, 285, 286, 287 | 294 (hairpin RNA construct without promoter)<br>295 (hairpin RNA construct without promoter)<br>296 (hairpin RNA construct without promoter) | 285 (hairpin RNA)<br>286 (hairpin RNA)<br>287 (hairpin RNA) |
| inv1c.pk004.i1.f:fis | 280 | 34, 288, 289 | 297 (hairpin RNA construct without promoter)<br>298 (hairpin RNA construct without promoter) | 288 (hairpin RNA)<br>289 (hairpin RNA) |
| inv1c.pk005.h23.f | 302 | 263, 337, 338 | 329 (amiRNA precursor sequence with promoter)<br>330 (amiRNA precursor sequence with promoter) | 264 (sense siRNA, RNA sequence)<br>265 (anti-sense siRNA, RNA sequence)<br>305 (miRNA)<br>306 (miRNA)<br>321 (miRNA precursor sequence)<br>322 (miRNA precursor sequence) |
| inv1c.pk008.m9.f:fis | 281 | 290 | 299 (hairpin RNA construct without promoter) | 290 (hairpin RNA) |
| inv1c.pk010.g13.f:fis | 283 | 292 | 301 (hairpin RNA construct without promoter) | 292 (hairpin RNA) |
| inv1c.pk011.f6.f:fis | 282 | 291 | 300 (hairpin RNA construct without promoter) | 291 (hairpin RNA) |

Example 9

Transformation of Somatic Soybean Embryo Cultures

Culture Conditions:

Soybean embryogenic suspension cultures (cv. Jack) were maintained in 35 mL liquid medium SB196 (infra) on a rotary shaker, 150 rpm, 26° C. with cool white fluorescent lights on 16:8 hr day/night photoperiod at light intensity of 60-85 μE/m2/s. Cultures were sub-cultured every 7 days to two weeks by inoculating approximately 35 mg of tissue into 35 mL of fresh liquid SB196 (the preferred subculture interval is every 7 days).

Soybean embryogenic suspension cultures were transformed with the soybean expression plasmids described in Example 8 by the method of particle gun bombardment (Klein et al., *Nature,* 327:70 (1987)) using a DuPont Biolistic PDS1000/HE instrument (helium retrofit) for all transformations.

Soybean Embryogenic Suspension Culture Initiation:

Soybean cultures were initiated twice each month with 5-7 days between each initiation. Pods with immature seeds from available soybean plants 45-55 days after planting were picked, removed from their shells and placed into a sterilized magenta box. The soybean seeds were sterilized by shaking them for 15 min in a 5% Clorox solution with 1 drop of ivory soap (i.e., 95 mL of autoclaved distilled water plus 5 mL Clorox and 1 drop of soap, mixed well). Seeds were rinsed using 2 1-liter bottles of sterile distilled water and those less than 4 mm were placed on individual microscope slides. The small end of the seed was cut and the cotyledons pressed out of the seed coat. Cotyledons were transferred to plates containing SB199 medium (25-30 cotyledons per plate) for 2 weeks, then transferred to SB1 for 2-4 weeks. Plates were wrapped with fiber tape. After this time secondary embryos were cut and placed into SB 196 liquid media for 7 days.

Preparation of DNA for Bombardment:

Either an intact plasmid or a DNA plasmid fragment containing the genes of interest and the selectable marker gene may be used for bombardment. In the present example, pDNAs were isolated from bacterial transformants using a Qiagen mini-prep kit. DNA concentrations were determined by UV absorbance. Each silencing construct and hygromycin selectable marker plasmid (PHP18956) were combined in a 9:1 weight ratio to give a 1 ug/ul DNA solution.

A 50 μL aliquot of sterile distilled water containing 1 mg of gold particles was added to 5 μL of a 1 μg/μL DNA solution (intact silencing and selectable marker plasmids as described above), 50 μL 2.5M $CaCl_2$ and 20 μL of 0.1 M spermidine. The mixture was pulsed 5 times on level 4 of a vortex shaker and spun for 5 sec in a bench microfuge. After a wash with 150 μL of 100% ethanol, the pellet was suspended by sonication in 85 ul of 100% ethanol. Five μL of DNA suspension was dispensed to each flying disk of the Biolistic PDS1000/HE instrument disk. Each 5 μL aliquot contained approximately 0.058 mg gold particles per bombardment (i.e., per disk).

Tissue Preparation and Bombardment with DNA:

Approximately 100-150 mg of 7 day old embryonic suspension cultures were placed in an empty, sterile 60×15 mm petri dish and the dish was placed inside of an empty 150×25 mm Petri dish. Tissue was bombarded 1 shot per plate with membrane rupture pressure set at 650 PSI and the chamber was evacuated to a vacuum of 27-28 inches of mercury. Tissue was placed approximately 2.5 inches from the retaining/stopping screen.

Selection of Transformed Embryos:

Transformed embryos were selected using hygromycin as the selectable marker. Specifically, following bombardment, the tissue was placed into fresh SB196 media and cultured as described above. Six to eight days post-bombardment, the SB196 is exchanged with fresh SB196 containing 30 mg/L hygromycin. The selection media was refreshed bi-weekly. Four to six weeks post-selection, green, transformed tissue was observed growing from untransformed, necrotic embryogenic clusters. Isolated, green tissue was removed and inoculated into multi-well plates to generate new, clonally propagated, transformed embryogenic suspension cultures.

Embryo Maturation:

Transformed embryogenic clusters were cultured for 1-3 weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 μE/m² s. Embryo clusters were then removed to SB228 (SHaM) liquid media, 35 ml in 250 ml Erlenmeyer flask, for 2-3 weeks. Tissue cultured in SB228 was maintained on a rotary shaker, 130 rpm, 26° C. with cool white fluorescent lights on 16:8 hr day/night photoperiod at light intensity of 60-85 μE/m2/s. After this time, embryos were harvested and used in stinkbug feeding assays.

Media Recipes:

| SB 196-FN Lite Liquid Proliferation Medium, pH 5.8 (per liter) | |
|---|---|
| MS FeEDTA - 100x Stock 1 | 10 mL |
| MS Sulfate - 100x Stock 2 | 10 mL |
| FN Lite Halides - 100x Stock 3 | 10 mL |
| FN Lite P, B, Mo - 100x Stock 4 | 10 mL |
| B5 vitamins (1 mL/L) | 1.0 mL |
| 2,4-D (10 mg/L final concentration) | 1.0 mL |
| $KNO_3$ | 2.83 gm |
| $(NH_4)_2SO_4$ | 0.463 gm |
| asparagine | 1.0 gm |
| sucrose (1%) | 10 gm |

FN Lite Stock Solutions

| Stock Number | | 1000 mL | 500 mL |
|---|---|---|---|
| 1 | MS Fe EDTA 100x Stock | | |
| | $Na_2$ EDTA* | 3.724 g | 1.862 g |
| | $FeSO_4$—$7H_2O$ | 2.784 g | 1.392 g |
| 2 | MS Sulfate 100x stock | | |
| | $MgSO_4$—$7H_2O$ | 37.0 g | 18.5 g |
| | $MnSO_4$—$H_2O$ | 1.69 g | 0.845 g |
| | $ZnSO_4$—$7H_2O$ | 0.86 g | 0.43 g |
| | $CuSO_4$—$5H_2O$ | 0.0025 g | 0.00125 g |
| 3 | FN Lite Halides 100x Stock | | |
| | $CaCl_2$—$2H_2O$ | 30.0 g | 15.0 g |
| | KI | 0.083 g | 0.0715 g |
| | $CoCl_2$—$6H_2O$ | 0.0025 g | 0.00125 g |
| 4 | FN Lite P, B, Mo 100x Stock | | |
| | $KH_2PO_4$ | 18.5 g | 9.25 g |
| | $H_3BO_3$ | 0.62 g | 0.31 g |
| | $Na_2MoO_4$—$2H_2O$ | 0.025 g | 0.0125 g |

*Add first, dissolve in dark bottle while stirring

SB1 Solid Medium pH5.7 (Per Liter)

1 package MS salts (Gibco/BRL—Cat. No. 11117-066)
1 mL B5 vitamins 1000× stock
31.5 g glucose
2 mL 2,4-D (20 mg/L final concentration)
8 g TC agar SB199 Solid Medium (Per Liter)

1 package MS salts (Gibco/BRL—Cat. No. 11117-066)
1 mL B5 vitamins 1000× stock
30 g Sucrose
4 ml 2,4-D (40 mg/L final concentration)
pH 7.0
2 gm Gelrite SB 71-4 Solid Medium (Per Liter)

1 bottle Gamborg's B5 salts w/ sucrose (Gibco/BRL—Cat. No. 21153-036)
pH 5.7
5 g TC agar 2,4-D Stock Obtain premade from Phytotech Cat. No. D 295—concentration 1 mg/mL B5 Vitamins Stock (Per 100 mL)

Store aliquots at −20° C.
10 g myo-inositol
100 mg nicotinic acid
100 mg pyridoxine HCl
1 g thiamine If the solution does not dissolve quickly enough, apply a low level of heat via the hot stir plate.

| SB 228-Soybean Histodifferentiation & Maturation (SHaM) (per liter) | |
|---|---|
| DDI H2O | 600 ml |
| FN-Lite Macro Salts for SHaM 10X | 100 ml |
| MS Micro Salts 1000x | 1 ml |
| MS FeEDTA 100x | 10 ml |
| CaCl 100x | 6.82 ml |
| B5 Vitamins 1000x | 1 ml |
| L-Methionine | 0.149 g |
| Sucrose | 30 g |
| Sorbitol | 30 g |
| Adjust volume to 900 ml | |
| pH 5.8 | |
| Autoclave | |
| Add to cooled media (≤30° C.): | |
| *Glutamine (Final conc. 30 mM) 4% | 110 ml |

*Note:
Final volume will be 1010 ml after glutamine addition..

| FN-lite Macro for SHAM 10X-Stock #1 (per liter) | |
|---|---|
| $(NH_4)2SO_4$ (Ammonium Sulfate) | 4.63 g |
| $KNO_3$ (Potassium Nitrate) | 28.3 g |
| $MgSO_4$*$7H_20$ (Magnesium Sulfate Heptahydrate) | 3.7 g |
| $KH_2PO_4$ (Potassium Phosphate, Monobasic) | 1.85 g |
| Bring to volume | |
| Autoclave | |

| MS Micro 1000X-Stock #2 (per 1 liter) | |
|---|---|
| $H_3BO_3$ (Boric Acid) | 6.2 g |
| $MnSO_4$*$H_2O$ (Manganese Sulfate Monohydrate) | 16.9 g |
| ZnSO4*7H20 (Zinc Sulfate Heptahydrate) | 8.6 g |
| $Na_2MoO_4$*2H20 (Sodium Molybdate Dihydrate) | 0.25 g |
| $CuSO_4$*$5H_20$ (Copper Sulfate Pentahydrate) | 0.025 g |
| $CoCl_2$*$6H_20$ (Cobalt Chloride Hexahydrate) | 0.025 g |
| KI (Potassium Iodide) | 0.8300 g |
| Bring to volume | |
| Autoclave | |

| FeEDTA 100X-Stock #3 (per liter) | |
|---|---|
| $Na_2EDTA$* (Sodium EDTA) | 3.73 g |
| $FeSO_4$*$7H_20$ (Iron Sulfate Heptahydrate) | 2.78 g |
| Bring to Volume | |
| Solution is photosensitive. Bottle(s) should be wrapped in foil to omit light. | |
| Autoclave | |

*EDTA must be completely dissolved before adding iron

| Ca 100X-Stock #4 (per liter) | |
|---|---|
| $CaCl_2$*$2H_20$ (Calcium Chloride Dihydrate) | 44 g |
| Bring to Volume | |
| Autoclave | |

| B5 Vitamin 1000X-Stock #5 (per liter) | |
|---|---|
| Thiamine*HCl | 10 g |
| Nicotinic Acid | 1 g |
| Pyridoxine*HCl | 1 g |
| Myo-Inositol | 100 g |
| Bring to Volume | |
| Store frozen | |

| 4% Glutamine-Stock #6 (per liter) | |
|---|---|
| DDI water heated to 30° C. | 900 ml |
| L-Glutamine | 40 g |
| Gradually add while stirring and applying low heat. | |
| Do not exceed 35° C. | |
| Bring to Volume | |
| Filter Sterilize | |
| Store frozen * | |

* Note:
Warm thawed stock in 31° C. bath to fully dissolve crystals

It is recognized that the experiments set forth in example 9 can be employed with silencing elements operably linked to a seed-preferred promoter, such as, for example, those provided by the b-conglycinin-alpha (Genbank accession GU723691), Kunitz trypsin inhibitor 3 (AF233296), or the glycinin-1 (AB353075.1) genes.

Example 10

Assay of Transgenic Soybean Embryos for Efficacy Against Southern Green Stinkbug Cultures of SHaM maturated embryos, as described in Example 9, were harvested by filtration and used in feeding bioassays with $2^{nd}$ instar southern green stinkbugs. A typical soy embryo transformation experiment yielded 20 to 30 independent events that were each evaluated in 4 replicate assays. Each assay was set up in a 35 mm petri dish that contained a moistened Whatman filter disc and a $H_2O$ soaked cotton pellet along with 450-500 mg of soy embryo tissue. Embryo samples were infested with 5-2$^{nd}$ instar SGSBs, and the petri plate was covered and incubated at 27 C, 65% RH for 4 days. At this time, the sample was replenished with fresh tissue and the incubation was continued for 4 additional days at which time, the assays were scored for insect stunting and mortality.

FIGS. 1 and 2 show the results of insect feeding assays performed using embryo tissue transformed with the silencing construct DNAs listed in Tables 5 and 8. Each symbol corresponds to insect mortality scores averaged over the 4 replicate assays for each event. Controls correspond to feeding assays conducted using non-transgenic soybean embryo tissue. For all of the constructs, several transgenic events could be found which gave insect mortality scores greater than the controls. For some constructs, more than 50% of the events produced insect mortality at a rate significantly greater than controls. Variation in apparent efficacy from event to event is to be expected due to variation in construct expression with random integration of the construct DNA in the soybean genome.

Example 11

Assay of Transgenic Soybean Plants for Efficacy Against Southern Green Stinkbug Silencing constructs can be stably expressed in insect feeding tissue for efficacy testing of transgenic plants against southern green stinkbug. The DNA constructs described in Example 8 can be used for this purpose. These consist of trait gene hairpin or miRNA gene cassettes both of which are constitutively regulated by a soybean ubiquitin promoter-5'UTR-Intron1 fragment. Similar constructs can be built using other constitutive promoters as provided for example by soybean elongation factor 1 alpha (ACUP01009998) or *arabidopsis* ubiquitin (LO5399.1) genes. Alternatively, tissue specific expression and in some embodiments seed-preferred promoters can be produced by the use of seed storage protein promoters including those provided by the beta-conglycinin-alpha (Genbank accession GU723691), Kunitz trypsin inhibitor 3 (AF233296), or the glycinin-1 (AB353075.1) genes. To produce seed specific hairpin constructs (i.e. long dsRNA constructs and miRNA constructs), entry clones, generated as described in Example 8 above, are combined in an LR clonase reaction with a variant of the destination vector, pKB499, modified to contain a seed storage protein promoter in place of the Gm-Ubiquitin promoter. This first LR reaction generates the promoter-hairpin-terminator cassette. The final plant expression construct is produced by a second LR reaction in which the entire hairpin cassette is moved into a vector (PHP25224) which provides a plant selectable marker gene (herbicide resistant acetolactate synthase) for stable transformation experiments. For assembly of tissue specific miRNA constructs, the procedure outlined in Example 8 would be followed with final cloning of the artificial miR159 segment into a suitable plant expression vector that provides regulatory sequences of any one of the above seed storage protein promoters.

For biolistic transformation of soybean embryos as described in Example 5, a single DNA fragment containing both the trait gene and the plant selectable marker gene is prepared by restriction enzyme digestion followed by gel purification of restricted pDNA. In the case of both constitutive and tissue specific silencing constructs, 10 μg of plasmid DNA is used in 0.15 mL of the specific enzyme mix described below. Plasmids are digested with AscI (100 units) in NEBuffer 4 (20 mM Tris-acetate, 10 mM magnesium acetate, 50 mM potassium acetate, 1 mM dithiothreitol, pH 7.9), 100 μg/mL BSA, and 5 mM beta-mercaptoethanol at 37° C. for 3 hrs. The resulting DNA fragments are separated by gel electrophoresis on 1% agarose gel and the DNA fragment containing the trait gene-selectable marker gene cassettes are cut from the agarose gel. DNA is purified from the agarose using Qiagen's Quick Spin extraction method following the manufacturer's suggested protocol. Gold particles are coated with purified DNA fragments and used for biolistic introduction of DNA into soybean embryo cultures using the procedure outlined in Example 5.

First generation transgenic plants can be assayed for insecticidal activity in individual plant cages. When the plant has started to produce green pods approximately 1-2 inches in length, plants are removed to individual bug tent cages (BioQuip, CA). The cage is infested with 50 newly emerged second instar southern green stinkbugs (*Nezara viridula*). The nymphs are allowed to feed for 1 week at which time a count of surviving insects is performed. Counts are facilitated by using an aspirating device with removable vials and caps to collect insects and a hand held counting device to count each insect as it is aspirated. Counts can later be verified by freezing the sample and counting again under magnification where a measure of growth can also be performed on collected insects. Fully grown insects equivalent to controls are given a score of 0. Insects demonstrating 20-60% stunting are given a score of 1. Insects demonstrating 60-100% stunting (size equivalent to original infested insects) are given a score of 2 and dead insects are scored 3. Selected plants demonstrating high insecticidal activity are recovered from the tents, treated with Marathon insecticide, and returned to growth chambers or greenhouses to complete the reproductive phase and seed production.

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated polynucleotide operably linked to a heterologous promoter comprising a nucleotide sequence selected from the group consisting of:

(a) a nucleotide sequence comprising any one of SEQ ID NOS: 302, 263, 337, 338, 305, 306, 321, 322, or a complement thereof;

(b) a nucleotide sequence comprising at least 95% sequence identity to any one of SEQ ID NOS: 302, 263, 305, 306, 321, 322 or a complement thereof; and (c) a nucleotide sequence comprising at least 21 consecutive nucleotides of any one of SEQ ID NOS: 302, 263, or a complement thereof;

wherein said polynucleotide encodes a double stranded RNA having insecticidal activity against a *Pentatomidae* plant pest.

2. The isolated polynucleotide of claim 1, wherein said *Pentatomidae* plant pest is a *N. viridula* plant pest.

3. An expression cassette comprising the polynucleotide of claim 1.

4. The expression cassette of claim 3, wherein said polynucleotide is expressed as a hairpin RNA.

5. The expression cassette of claim 4, wherein the double stranded RNA comprises, a first segment, a second segment, and a third segment, wherein a) said first segment comprises at least 21 consecutive nucleotides having complementarity to a target sequence set forth in SEQ ID NOS: 302, or 263;

b) said second segment comprises a loop of sufficient length to allow the silencing element to be transcribed as a hairpin RNA; and, c) said third segment comprises at least 21 consecutive nucleotides complementary to the first segment.

6. The expression cassette of claim 5, wherein said expression cassette targets a sequence comprising the sequences set forth in any one of SEQ ID NOS: 337, 338, or a sequence having at least 95% sequence identity to SEQ ID NO: 337 or 338.

7. The expression cassette of claim 4, wherein said expression cassette comprises any of SEQ ID NO: 321 or 322, or the complement thereof.

8. The expression cassette of claim 3, wherein said polynucleotide is flanked by a first operably linked convergent promoter at one terminus of the polynucleotide and a second operably linked convergent promoter at the opposing terminus of the polynucleotide, wherein the first and the second convergent promoters are capable of driving expression of the double stranded RNA.

9. A host cell comprising the heterologous expression cassette of claim 3.

10. A plant cell having stably incorporated into its genome a polynucleotide operably linked to a heterologous promoter, wherein said polynucleotide comprises any one of the sequences set forth in SEQ ID NOS: 302, 263, 305, 306, 321 or 322 or a complement thereof, wherein said polynucleotide encodes a double stranded RNA having insecticidal activity against a *Pentatomidae* plant pest.

11. The plant cell of claim 10, wherein the *Pentatomidae* plant pest is a *N. viridula* plant pest.

12. The plant cell of claim 10, wherein said plant cell comprises an expression cassette, wherein the expression cassette comprises the polynucleotide flanked by a first operably linked convergent promoter at one terminus of the polynucleotide and a second operably linked convergent promoter at the opposing terminus of the polynucleotide, wherein the first and the second convergent promoters are capable of driving expression of the double stranded RNA.

13. The plant cell of claim 10, wherein said double stranded RNA comprises a hairpin RNA.

14. The plant cell of claim 13, wherein said hairpin RNA comprises, in the following order, a first segment, a second segment, and a third segment, wherein a) said first segment comprises at least 21 consecutive nucleotides complementary to any one of SEQ ID NOS: 302, 263, 305, 306, 321, or 322;

b) said second segment comprises a loop of sufficient length to allow the silencing element to be transcribed as a hairpin RNA; and, c) said third segment comprises at least 21 nucleotides complementary to the first segment.

15. The plant cell of claim 10, wherein said plant cell is from a monocot.

16. The plant cell of claim 15, wherein said monocot is maize, barley, millet, wheat or rice.

17. The plant cell of claim 10, wherein said plant cell is from a dicot.

18. The plant cell of claim 17, wherein said plant is soybean, canola, alfalfa, sunflower, safflower, tobacco, *Arabidopsis*, or cotton.

19. A plant or plant part comprising the plant cell of claim 10.

20. A transgenic seed from the plant of claim 19, wherein said transgenic seed comprises said heterologous polynucleotide encoding said double stranded RNA.

21. A method of controlling a *Pentatomidae* plant pest comprising feeding to a *Pentatomidae* plant pest a composition comprising a double stranded RNA, wherein said double stranded RNA comprises any one of the sequences set forth in SEQ ID NOS: 302, or 263 or the complement thereof and thereby controls the *Pentatomidae* plant pest.

22. The method of claim 21, wherein said *Pentatomidae* plant pest comprises a *N. viridula* plant pest.

23. The method of claim 21, wherein said composition comprises a plant or plant part having stably incorporated into its genome a polynucleotide encoding said double stranded RNA, wherein said polynucleotide is operably linked to a promoter.

24. The method of claim 23, wherein said polynucleotide sequence comprises:

a) the sequence of the sequence set forth in SEQ ID NOS: 337, 338, or a complement thereof; or, b) a sequence having at least 95% sequence identity to the sequence set forth in SEQ ID NOS: 337, 338, or a complement thereof.

25. The method of claim 21, wherein said double stranded RNA comprises a hairpin RNA.

26. The method of claim 25, wherein said double stranded RNA comprises a first segment, a second segment, and a third segment, wherein:

a) said first segment comprises at least 21 consecutive nucleotides;

b) said second segment comprises a loop of sufficient length to allow the double stranded RNA to be transcribed as a hairpin RNA; and, c) said third segment comprises at least 21 consecutive nucleotides complementary to the first segment.

27. The method of claim 23, wherein said polynucleotide is flanked by a first operably linked convergent promoter at one terminus of the polynucleotide and a second operably linked convergent promoter at the opposing terminus of the polynucleotide, wherein the first and the second convergent promoters are capable of driving expression of the double stranded RNA.

28. The method of claim 23, wherein said plant is a monocot.

29. The method of claim 28, wherein said monocot is maize, barley, millet, wheat or rice.

30. The method of claim 23, wherein said plant is a dicot.

31. The method of claim 30, wherein said plant is soybean, canola, alfalfa, sunflower, safflower, tobacco, *Arabidopsis*, or cotton.

* * * * *